United States Patent [19]
Gallatin et al.

[11] Patent Number: 5,831,029
[45] Date of Patent: Nov. 3, 1998

[54] HUMAN β2 INTEGRIN α SUBUNIT

[75] Inventors: W. Michael Gallatin, Mercer Island; Monica Van der Vieren, Seattle, both of Wash.

[73] Assignee: ICOS Corporation, Bothell, Wash.

[21] Appl. No.: 482,293

[22] Filed: Jun. 7, 1995

Related U.S. Application Data

[63] Continuation-in-part of Ser. No. 362,652, Dec. 21, 1994, which is a continuation-in-part of Ser. No. 286,889, Aug. 5, 1994, Pat. No. 5,470,953, which is a continuation-in-part of Ser. No. 173,497, Dec. 23, 1993, Pat. No. 5,437,958.

[51] Int. Cl.$^6$ ............................. C07K 16/28; C12P 21/08
[52] U.S. Cl. .................................... 530/387.2; 530/387.9; 530/388.1; 530/388.22; 530/388.7; 530/389.6; 435/331; 435/334; 435/346
[58] Field of Search ............................. 530/387.1, 387.2, 530/387.9, 388.1, 388.22, 388.7, 389.1, 389.6; 435/350, 331, 334, 346

[56] References Cited

U.S. PATENT DOCUMENTS 4,271,139 6/1981 Hart .
4,568,649 2/1986 Bertoglio-Matte .

OTHER PUBLICATIONS

Anderson, D.C. et al. J. Immunol. 137 (1): 15–27, Jul. 1986.
Diamond, M. S. et al. J. Cell Biol. 111: 3129–3139, Dec. 1990.
Hildreth, J. E. et al. Molecular Immunology 26 (12): 1155–1167, Dec. 1989.
Adams, et al., "Experimental graft arteriosclerosis: II. Immunocytochemical analysis of lesion development," *Transplantation*, 56:794–799 (1993).
Adams, et al., "Experimental graft arteriosclerosis: 1. The Lewis–to–F–444 Allograft Model," *Transplantation*, 53:1115–1119 (1992).
Anderson, et al., "Exact Definition of Species–specific and Cross–reactive Epitopes of the 65–kilodalton Protein of *Mycobacterium leprae* Using Synthetic Peptides", *J.Immunol.* 141:607–613 (1988).
Arfors, et al., "A monoclonal antibody to the membrane glycoprotein complex CD18 inhibits polymorphonuclear leukocyte accumulation and plasma leakage in vivo," *Blood* 69:338–340 (1987).
Arnaout, "Structure and function of the leukocyte adhesion molecules CD11/CD18," *Blood* 75:1037–1050 (1990).
Berman, et al., "Biosynthesis and function of membrane bound and secreted forms of recombinant CD11b/CD18 (Mac–1)," *J.Cell, Biochem* 52:183–195 (1993).
Burnett, et al., "The IgA heavy–chain gene family in rabbits: cloning and sequence analysis of 13 Cα genes," *EMBO J.* 8:4041–4047 (1989).
Capecchi, "Altering the genome by homologous recombination," *Science* 244:1288–1292 (1989).
Chang, et al., "A general method for facilitating heterodimeric pairing between two proteins: Application to expression of α and β T–cell receptor extracellular segments", *Proc.Natl.Acad.Sci (USA)* 91:11408–11412 (1994).
Collins, The HL–60 Promyelocytic Leukemia Cell Line: Proliferation, Differentiation, and Cellular Oncogene Expression, *Blood*, 0:1233–1244 (1987).
Corbi, et al., "cDNA cloning and complete primary structure of the α subunit of a leukocyte adhesion glycoprotein, p150,95,"*EMBO J.* 6:4023–4028 (1987).
Corbi, et al., "The human leukocyte adhesion glycoprotein Mac–1 (complement receptor type 3, CD11b α subunit," *J.Bio.Chem. 263*:12403–12411 (1988).
Cromartie, et al., "Arthritis in rats after systemic injection of Streptococcal cells or cell walls." *J.Exp.Med. 146*:1585–1602 (1977).
Chisaka, et al., "Developmental defects of the ear, cranial nerves and hindbrain resulting from targeted disruption of the mouse homeobox gene Hox–1.6." :*Nature 355*516–520 (1992).
Dana, et al., "Deficiency of a surface membrane glycoprotein (Mo1) in man," *J.Clin.Invest.73*:153–159 (1984).
Diamond, et al., "The I domain is a major recognition site on the leukocyte integrin Mac–1 (CD11b/CD18) for four distinct adhesion ligands," *J.Cell, Biol. 120*:1031–1043 (1993).
Danilenko, et al., "Canine leukocyte cell adhesion molecules (LeuCAMS): characterization of the CD11/CD18 family," *Tissue Antigens 40*:13–21 (1992).
Deng, et al., "Location of crossovers during gene targeting with insertion and replacement vectors," *Mol.Cell.Biol. 13*:2134–2140 (1993).
Frohman, "RACE: Rapid amplification of cDNA ends" in *PCR Protocols: A Guide to Methods and Applications*, Innis, et al. (eds.) Academic press:New York (1990) pp. 28–38.
Greve, et al., "The major human rhinovirus receptor is ICAM–1," *Cell 56*:839–847 (1989).
Hanenberg et al., "Macrophage infiltration precedes and is a prerequisite for lymphocytic insulitis in pancreatic islets of prediabetic BB rats," *Diatetologia 32* :126–134 (1989).
Hart and Greenwald, "Scintillation proximity assay (SPA) —a new method of immunoassay", *Molecular Immunol. 16*:265–267, (1979).

(List continued on next page.)

*Primary Examiner*—Frank C. Eisenschenk
*Assistant Examiner*—Evelyn Rabin
*Attorney, Agent, or Firm*—Marshall, O'Toole, Gerstein, Murray & Borun

[57] ABSTRACT

DNA encoding a novel human $\beta_2$ integrin α subunit polypeptide, designated $\alpha_d$, is disclosed along with methods and materials for production of the same by recombinant procedures. Fusion proteins are also disclosed which include extracellular $\alpha_d$ protein fragments, $\alpha_d$ I domain fragments or full length $\alpha_d$ polypeptides and human immunoglobulin constant regions. Binding molecules specific for $\alpha_d$ are also disclosed as useful for modulating the biological activities of $\alpha_d$. DNA from other species which show homology to human $\alpha_d$ encoding sequences are also disclosed.

10 Claims, 4 Drawing Sheets

OTHER PUBLICATIONS

Hart and Greenwald, "Scintillation proximity assay of antigen–antibody binding kinetics: concise communication, " *J.Nuc.Med* 20:1062–1065 (1979).

Hildreth & Orentas, "Involvement of a leukocyte adhesion receptor (LFA–1) in HIV–induced syncytium formation," *Science* 244:1075–1078 (1989).

Huitinga, et al., "Treatment with anti–CR3 antibodies ED7 and ED8 suppresses experimental allergic encephalomyelitis in Lewis rats," *Eur.J.Immunol* 23:709–715 (1993).

Hynes, Integrins, Versatility, Modulation, and Signaling in Cell Adhesion, *Cell* 69:11–25 (1992).

Jutila, et al., "In vivo distribution and characterization of two novel mononuclear phagocyte differentiation antigens in mice," *J.Leukocyte Biol.* 54:30–39 (1993).

Karin and Richards, "Human metallothionein genes—primary structure of the metallothionein–II gene and a related processed protein," *Nature* 299:797–802 (1982).

Kishimoto, et al., "Heterogeneous mutations in the βsubunit common to the LFA–1, Mac–1 and p150,95 glycoproteins cause leukocyte adhesion deficency," *Cell* 50:193–202 (1987).

Kishimoto, et al., "Cloning of the β subunit of the leukocyte adhesion proteins:homology to an extracellular matrix receptor defines a novel supergene family," *Cell* 48:681–690 (1987).

Kröncke, et al., "Activated Macrophages Kill Pancreatic Syngeneic Islet Cells Via Arginine–Dependant Nitric Oxide Generation", *Biochemical and Biophysical Research Communications*, 175:752–758 (1991).

Landis, et al., "A novel LFA–1 activation epitope maps to the I domain," *J.Cell.Biol.* 120:1519–1527 (1993).

Larson, et al., "Primary structure of the leukocyte function–associated molecule–1 α subunit: an integrin with an embedded domian defining a protein superfamily," *J.Cell.Biol.* 108:703–712 (1989).

Larson and Springer, "Structure and function of leukocyte integrins," *Immunol.Rev.* 114:181–217 (1990).

Letvin, et al., "Conservation of myeloid surface antigens on primary granulocytes," *Blood* 61 :408–410 (1983).

MacMicking, et al., "Altered Responses to Bacterial Infection and Endotoxic Shock in Mice Lacking inducible Nitric Oxide Synthase", *Cell* 81:641–650 (1995).

McCabe, "Production of single–stranded DNA by asymmetric PCR," in *PCR Protocols: A Guide to Methods and Applications*, Innis et al. (ed) Academic Press: New York (1990) pp. 76–83.

Merrill, et al., "Microglial Cell Cytotoxicity of Oligodendrocytes Is Mediated through Nitric Oxide", *Jour. of Immunol.* 151:2132–2141 (1993).

Metlay, et al., "The distinct leukocyte integrins of mouse spleen dendritic cells as identified with new hamster monoclonal antibodies ," *J.Exp.Med.* 171:1753–1771 (1990).

Michishita, et al., "A novel divalent cation–binding site in the A domain of the β2 integrin CR3 (CD11b/CD18) is essential for ligand binding," *Cell* 72: 857–867 (1993).

Moore, et al., "Canine leukocyte integrins: characterization of a CD18 homologue," *Tissue Antigens* 36:211–220 (1990).

Mulligan, et al., "Tissue injury caused by deposition of immune complexes is L–arginine dependent", *Proc.Natl.Acad.Sci.* (*USA*) 88:6338–6342 (1991).

Nourshargh, et al., "Accumulation of $^{111}$In–neutrophils in rabbit skin in allergic and non–allergic inflammatory reactions in vivo," *J.Immunol.* 142:3193–3198 (1989).

Patarroyo, et al., "Leukocyte–cell adhesion: a molecular process fundamental in leukocyte physiology," *Immunol. Rev.* 114:67–108 (1990).

Price, et al., "In vivo inhibition of neutrophil function in the rabbis using monoclonal antibody to CD18," *J.Immunol.* 139:4174–4177 (1987).

Randi and Hogg, "I domain of $\beta_2$ integrin lymphocyte function–associated antigen–1 contains a binding site for ligand intercellular adhesion molecule–1," *J.Biol.Chem* 269:12395–12398 (1994).

Rojiani et al., "In vitro interaction of a polypeptide homologous to human Ro/SS–A antigen (calreticulin) with a highly conserved amino acid sequence in the cytoplasmic domain of integrin α subunits" *Biochemistry* 30:9859–9866 (1991).

Rosenfeld, et al., "Fatty streak initiation in watanabe heritable hyperlipemic and comparably hypercholesterolemic fat–fed rabbits" *Arteriosclerosis* 7:9–23 (1987).

Rosenfeld, et al., "Fatty streak expansion and maturation in watanabe heritable hyperlipemic and hypercholesterolemic fat–fed rabbits" *Arteriosclerosis* 7:24–34 (1987).

Sambrook, et al.,(eds), "Immobilization of Bacteriophage λ plaques on nitrocellulose filters or nylon membranes" in *Molecular Cloning: a laboratory manual*, Cold Spring Harbor Press:ColdSring Harbor, NY (1989) p. 2.110.

Sanchez–Madrid, et al., "A human leukocyte differentiation antigen family with distinct α–subunits and a common β–subunit," *J.Exp.Med.* 154:1785–1803 (1981).

Schneiderman, et al., "Expression of 12 rabbit IgA Cα genes as chimeric rabbit–mouse IgA antibodies," *Proc.Natl.Acad..Sci.* (*USA*) 86:7561–7565 (1989).

Schwab, et al., "Pro–and anti–inflammatory roles of interleukin–1 in recurrence of bacterial cell wall–induced arthritis in rats," *Infection and Immunity* 59:4436–4442 (1991).

Searle, et al., "Regulation, linkage, and sequence of mouse metallothiionein I and II genes," *Mol.Cell.Biol.* 4:1221–1230 (1984).

Shaw, et al., "Molecular cloning of the human mucosal lymphocyte integrin $\alpha^E$ subunit," *J.Biol.Chem.* 269:6016–6025 (1994).

Smith, et al., "Cooperative interactions of LFA–1 and Mac–1 with intercellular adhesion molecule–1 in facilitating adherence and transendothelial migration of human meutrophils in vitro," *J.Clin.Invest.* 83:2008–2017 (1989).

Springer, "Adhesion molecules of the immune system," *Nature* 346:425–434 (1990).

Tamura, et al., "Epithelial integrin$\alpha_6\beta_4$: complete primary structure of $\alpha_6$ and variant forms of $\beta_4$," *J.Cell.Biol.* 111:1593–1604 (1990).

Ueda, et al., "Identification of the complement iC3b binding site in the β2 integrin CR3 (CD11b/CD18)," *Proc.Natl.Acad.Sci.* (*USA*) 91:10680–10684 (1994).

Varshney, et al., "Structure, organization, and regulation of human metallothionein $I_F$ gene: differential and cell–type–specific expression in response to heavy metals and glucocorticoids," *Mol.Cell.Biol.* 6:26–36 (1986).

Yamada, et al., "Mucosal injury and inflammation in a model of chronic granulumatous colitis in rats," *Gastroenterology* 104:759–771 (1993).

Zhou, et al., "Differential ligand binding specificites of recombinant CD11b/CD8 integrin I–domain" *J.Biol.Chem.* 269;17075–17079 (1994).

|       |            |            |            |            |            |            |     |
|-------|------------|------------|------------|------------|------------|------------|-----|
| αD    | TF-GT--VLL | LSVLASYHGF | NLDVEEPTIF | QEDAGGFGQS | VVQFGGSRLV |            | 47  |
| CD11B | MA-LR--VLL | LTALTLCHGF | NLDTENAMTF | QENARGFGQS | VVQLQGSRVV |            | 47  |
| CD11C | MTRTRAALLL | FTALATSLGF | NLDTEELTAF | RVDSAGFGDS | VVQYANSWVV |            | 50  |
|       |            |            |            |            |            |            |     |
| αD    | VGAPLEVVAA | NQTGRLYDCA | AATGMCQPIP | LHIRPEAVNM | SLGLTLAAST |            | 97  |
| CD11B | VGAPQEIVAA | NQRGSLYQCD | YSTGSCEPIR | LQVPVEAVNM | SLGLSLAATT |            | 97  |
| CD11C | VGAPQKIIAA | NQIGGLYQCG | YSTGACEPIG | LQVPPEAVNM | SLGLSLASTT |            | 100 |
|       |            |            |            |            |            |            |     |
| αD    | NGSRLLACGP | TLHRVCGENS | YSKGSCLLLG | SR-WEIIQTV | PDATPECPHQ |            | 146 |
| CD11B | SPPQLLACGP | TVHQTCSENT | YVKGLCFLFG | SNLRQQPQKF | PEALRGCPQE |            | 147 |
| CD11C | SPSQLLACGP | TVHHECGRNM | YLTGLCFLLG | PT--QLTQRL | PVSRQECPRQ |            | 148 |
|       |            |            |            |            |            |            |     |
| αD    | EMDIVFLIDG | SGSIDQNDFN | QMKGFVQAVM | GQFEGTDTLF | ALMQYSNLLK |            | 196 |
| CD11B | DSDIAFLIDG | SGSIIPHDFR | RMKEFVSTVM | EQLKKSKTLF | SLMQYSEEFR |            | 197 |
| CD11C | EQDIVFLIDG | SGSISSRNFA | TMMNFVRAVI | SQFQRPSTQF | SLMQFSNKFQ |            | 198 |
|       |            |            |            |            |            |            |     |
| αD    | IHFTFTQFRT | SPSQQSLVDP | IVQLKGLTFT | ATGILTVVTQ | LFHHKNGARK |            | 246 |
| CD11B | IHFTFKEFQN | NPNPRSLVKP | ITQLLGRTHT | ATGIRKVVRE | LFNITNGARK |            | 247 |
| CD11C | THFTFEEFRR | TSNPLSLLAS | VHQLQGFTYT | ATAIQNVVHR | LFHASYGARR |            | 248 |
|       |            |            |            |            |            |            |     |
| αD    | SAKKILIVIT | DGQKYKDPLE | YSDVIPQAEK | AGIIRYAIGV | GHAFQGPTAR |            | 296 |
| CD11B | NAFKILVVIT | DGEKFGDPLG | YEDVIPEADR | EGVIRYVIGV | GDAFRSEKSR |            | 297 |
| CD11C | DAIKILIVIT | DGKKEGDSLD | YKDVIPMADA | AGIIRYAIGV | GLAFQNRNSW |            | 298 |

FIGURE 1A

```
αD    QELNTISSAP PQDIIVFKVDN FAALGSIQKQ LQEKIYAVEG TQSRASSSFQ   346
CD11B QELNTIASKP PRDHVFQVNN FEALKTIQNQ LREKIFAIEG TQTGSSSSFE   347
CD11C KELNDIASKP SQEHIFKVED FDALKDIQNQ LKEKIFAIEG TETISSSSFE   348

αD    HEMSQEGFST ALTMDGLFLG AVGSFSWSGG AFLYPPNMSP TFINMSQENV   396
CD11B HEMSQEGFSA AITSNGPLLS TVGSYDWAGG VFLYTSKEKS TFINMTRVDS   397
CD11C LEMAQEGFSA VFTPDGPVLG AVGSFTWSGG AFLYPPNMSP TFINMSQENV   398

αD    DMRDSYLGYS TELALWKGVQ NLVLGAPRYQ HTGKAVIFTQ VSRQWRKKAE   446
CD11B DMNDAYLGYA AAIILRNRVQ SLVLGAPRYQ HIGLVAMFRQ NTGMWESNAN   447
CD11C DMRDSYLGYS TELALWKGVQ SLVLGAPRYQ HIGKAVIFIQ VSRQWRMKAE   448

αD    VTGTQIGSYF GASLCSVDVD SDGSTDLILI GAPHYYEQTR GGQVSVCPLP   496
CD11B VKGTQIGAYF GASLCSVDVD SNGSTDLVLI GAPHYYEQTR GGQVSVCPLP   497
CD11C VIGTQIGSYF GASLCSVDVD TDGSTDLVLI GAPHYYEQTR GGQVSVCPLP   498

αD    RGQRVQWQCD AVLRGEQGHP WGRFGAALTV LGDVNEDKLI DVAIGAPGEQ   546
CD11B RGQRARWQCD AVLYGEQGQP WGRFGAALTV LGDVNGDKLT DVAIGAPGEE   547
CD11C RGWRRWW-CD AVLYGEQGHP WGRFGAALTV LGDVNGDKLT DVVIGAPGEE   547

αD    ENRGAVYLFH GASESGISPS HSQRIASSQL SPRLQYFGQA LSGGQDLTQD   596
CD11B DNRGAVYLFH GTSGSGISPS HSQRIAGSKL SPRLQYFGQS LSGGQDLTMD   597
CD11C ENRGAVYLFH GVLGPSISPS HSQRIAGSQL SSRLQYFGQA LSGGQDLTQD   597
```

FIGURE 1B

```
αD     GLMDLAVGAR GQVLLLRSLP VLKVGVAMRF SPVEVAKAVY RCWEEKPSAL    646
CD11B  GLVDLTVGAQ GHVLLLRSQP VLRVKAIMEF NPREVARNVF ECNDQVVKGK    647
CD11C  GLVDLAVGAR GQVLLLRTRP VLWVGVSMQF IPAEIPRSAF ECREQVVSEQ    647

αD     EAGDATVCLT IQKSSLDQL- -GDIQSSVRF DLALDPGRLT SRAIFNETKN    694
CD11B  EAGEVRVCLH VQKSTRDRLR EGQIQSVVTY DLALDSGRPH SRAVFNETKN    697
CD11C  TLVQSNICLY IDKRSKNLLG SRDLQSSVTL DLALAPGRLS PRAIFQETKN    697

αD     PTLTTRKTLG LGIHCETLKL LLPDCVEDVV SPIILHLNFS LVREPIPSPQ    744
CD11B  STRRQTQVLG LTQTCETLKL QLPNCIEDPV SPIVLRLNFS LVGTPLSAFG    747
CD11C  RSLSRVRVLG LKAHCENFNL LLPSCVEDSV IPIILRLNFT LVGKPLLAFR    747

αD     NLRPVLAVGS QDLFTASLPF EKNCGQDGLC EGDLGVTLSF SGLQTLTVGS    794
CD11B  NLRPVLAEDA QRLFTALFPF EKNCGNDNIC QDDLSITFSF MSLDCLVVGG    797
CD11C  NLRPMLAALA QRYFTASLPF EKNCGADHIC QDNLGISFSF PGLKSLLVGS    797

αD     SLELNVIVTV WNAGEDSYGT VVSLYYPAGL SHRRVSGAQK QPHQSALRLA    844
CD11B  PREFNVTVTV RNDGEDSYRT QVTFFFPLDL SYRKVSTLQN QRSQRSWRLA    847
CD11C  NLELNAEVMV WNDGEDSYGT TITFSHPAGL SYRYVAEGQK QGQLRSLHLT    847

αD     CETVPTED-- EGLRSSRCSV NHPIFHEGSN GTFIVTFDVS Y----KATLG    888
CD11B  CESASSTEVS GALKSTSCSI NHPIFPENSE ----VTFNIT FDVDSKASLG    893
CD11C  CCSA-PVGSQ GTW-STSCRI NHLIFRGGAQ ----ITFLAT FDVSPKAVGL    891
```

FIGURE 1C

```
αD     DRMLMRASAS SENNKASSSK ATFQLELPVK YAVYTMISRQ EESTKYFNFA   938
CD11B  NKLLLKANVT SENNMPRTNK TEFQLELPVK YAVYMVVTSH GVSTKYLNFT   943
CD11C  DRLLLIANVS SENNIPRTSK TIFQLELPVK YAVYIVVSSH EQFTKYLNFS   941

αD     TS-DEKKMKE AEHRYRVNNL SQRDLAISIN FWVPVLLNGV AVWDVVMEAP   987
CD11B  AS-ENTS-RV MQHQYQVSNL GQRSLPISLV FLVPVRLNQT VIWDRPQVTF   991
CD11C  ESEEKES-HV AMHRYQVNNL GQRDLPVSIN FWVPVELNQE AVWMDVEVSH   990

αD     SQSLP--CVS ERKPPQHSDF LTQISRSPML DCSIADCLQF RCDVPSFSVQ   1035
CD11B  SENLSSTCHT KERLPSHSDF LAELRKAPVV NCSIAVCQRI QCDIPFFGIQ   1041
CD11C  PQNPSLRCSS EKIAPPASDF LAHIQKNPVL DCSIAGCLRF RCDVPSFSVQ   1040

αD     EELDFTLKGN LSFGWVRETL QKKVLVVSVA EITFDTSVYS QLPGQEAFMR   1085
CD11B  EEFNATLKGN LSFDWYIKTS HNHLLIVSTA EILFNDSVFT LLPGQGAFVR   1091
CD11C  EELDFTLKGN LSFGWVRQIL QKKVSVVSVA EIIFDTSVYS QLPGQEAFMR   1090

αD     AQMEMVLEED EVYNAIPIIM GSSVGALLLL ALITATLYKL GFFKRHYKEM   1135
CD11B  SQTETKVEPF EVPNPLPLIV GSSVGGLLLL ALITAALYKL GFFKRQYKDM   1141
CD11C  AQTITVLEKY KVHNPIPLIV GSSIGGLLLL ALITAVLYKV GFFKRQYKEM   1140

αD     LEDKPED--- -----TATFS GDDFSCVAPN VPLS                   1161
CD11B  M---SEG--- -----GP--P GAE-----PQ ----                   1153
CD11C  M---EEANGQ IAPENGT--Q TPS-----PP SEK                    1163
```

FIGURE 1D

HUMAN β2 INTEGRIN α SUBUNIT

This application is a continuation-in-part of U.S. application Ser. No. 08/362,652, filed Dec. 21, 1994, which is pending, which is a continuation-in-part of U.S. application Ser. No. 08/286,889, filed Aug. 5, 1994, U.S. Pat. No. 5,470,953, which in turn is a continuation-in-part of U.S. application Ser. No. 08/173,497, filed Dec. 23, 1993, U.S. Pat. No. 5,437,958.

FIELD OF THE INVENTION

The present invention relates to the cloning and expression of polynucleotides encoding a novel human $\beta_2$ integrin $\alpha$ subunit, designated $\alpha_d$, which is structurally related to the known human $\beta_2$ integrin $\alpha$ subunits, CD11a, CD11b and CD11c. The present invention also relates to polynucleotides isolated from other species which show homology to human $\alpha_d$ encoding sequences.

BACKGROUND OF THE INVENTION

The integrins are a class of membrane-associated molecules which actively participate in cellular adhesion. Integrins are transmembrane heterodimers comprising an a subunit in noncovalent association with a β subunit. To date, at least fourteen a subunits and eight β subunits have been identified [reviewed in Springer, Nature 346:425–434 (1990)]. The β subunits are generally capable of association with more than one α subunit and the heterodimers sharing a common β subunit have been classified as subfamilies within the integrin population.

One class of human integrins, restricted to expression in white blood cells, is characterized by a common $\beta_2$ subunit. As a result of this cell-specific expression, these integrins are commonly referred to as the leukocyte integrins, Leu-CAMs or leukointegrins. Because of the common $\beta_2$ subunit, an alternative designation of this class is the $\beta_2$ integrins. The $\beta_2$ subunit (CD18) has previously been isolated in association with one of three distinct α subunits, CD11a, CD11b or CD11c. The isolation of a cDNA encoding human CD18 is described in Kishimoto, et al., Cell 48:681–690 (1987). In official WHO nomenclature, the heterodimeric proteins are referred to as CD11a/CD18, CD11b/CD18, and CD11c/CD18; in common nomenclature they are referred to as LFA-1, Mac-1 or Mo1 and p150,95 or LeuM5, respectively [Cobbold, et al., in Leukocyte Typing III, McMichael (ed), Oxford Press, p.788 (1987)]. The human $\beta_2$ integrin α subunits CD11a, CD11b and CD11c have been demonstrated to migrate under reducing condition in electrophoresis with apparent molecular weights of approximately 180 kD, 155 kD and 150 kD, respectively, and DNAs encoding these subunits have been cloned [CD11a, Larson, et al., J. Cell Biol. 108:703–712 (1989); CD11b, Corbi, et al., J. Biol. Chem. 263:12403–12411 (1988) and CD11c, Corbi, et al. EMBO J. 6:4023–4028 (1987)]. Putative homologs of the human $\beta_2$ integrin α and β chains, defined by approximate similarity in molecular weight, have been variously identified in other species including monkeys and other primates [Letvin, et al., Blood 61:408–410 (1983)], mice [Sanchez-Madrid, et al., J. Exp. Med. 154:1517 (1981)], and dogs [Moore, et al., Tissue Antigens 36:211–220 (1990)].

The absolute molecular weights of presumed homologs from other species have been shown to vary significantly [see, e.g., Danilenko et al., Tissue Antigens 40:13–21 (1992)], and in the absence of sequence information, a definitive correlation between human integrin subunits and those identified in other species has not been possible. Moreover, variation in the number of members in a protein family has been observed between different species. Consider, for example, that more IgA isotypes have been isolated in rabbits than in humans [Burnett, et al., EMBO J. 8:4041–4047 (1989) and Schneiderman, et al., Proc. Natl. Acad. Sci. (USA) 86:7561–7565 (1989)]. Similarly, in humans, at least six variants of the metallothionine protein have been previously identified [Karin and Richards, Nature 299:797–802 (1982) and Varshney, et al., Mol. Cell. Biol. 6:26–37, (1986)], whereas in the mouse, only two such variants are in evidence [Searle, et al., Mol. Cell. Biol. 4:1221–1230 (1984)]. Therefore, existence of multiple members of a protein family in one species does not necessarily imply that corresponding family members exist in another species.

In the specific context of $\beta_2$ integrins, in dogs it has been observed that the presumed canine $\beta_2$ counterpart to the human CD18 is capable of dimer formation with as many as four potentially distinct α subunits [Danilenko, et al., supra]. Antibodies generated by immunizing mice with canine splenocytes resulted in monoclonal antibodies which immunoprecipitated proteins tentatively designated as canine homologs to human CD18, CD11a, CD11b and CD11c based mainly on similar, but not identical, molecular weights. Another anti-canine splenocyte antibody, Ca11.8H2, recognized and immunoprecipitated a fourth α-like canine subunit also capable of association with the $\beta_2$ subunit, but having a unique molecular weight and restricted in expression to a subset of differentiated tissue macrophages.

Antibodies generated by immunization of hamsters with murine dendritic cells resulted in two anti-integrin antibodies [Metlay, et al., J. Exp. Med. 171:1753–1771 (1990)]. One antibody, 2E6, immunoprecipitated a predominant heterodimer with subunits having approximate molecular weights of 180 kD and 90 kD in addition to minor bands in the molecular weight range of 150–160 kD. The second antibody, N418, precipitated another apparent heterodimer with subunits having approximate molecular weights of 150 kD and 90 Kd. Based on cellular adhesion blocking studies, it was hypothesized that antibody 2E6 recognized a murine counterpart to human CD18. While the molecular weight of the N418 antigen suggested recognition of a murine homolog to human CD11c/CD18, further analysis indicated that the murine antigen exhibited a tissue distribution pattern which was inconsistent with that observed for human CD11c/CD18.

The antigens recognized by the canine Ca11.8H2 antibody and the murine N418 antibody could represent a variant species (e.g., a glycosylation or splice variant) of a previously identified canine or murine α subunit. Alternatively, these antigens may represent unique canine and murine integrin α subunits. In the absence of specific information regarding primary structure, these alternatives cannot be distinguished.

In humans, CD11a/CD18 is expressed on all leukocytes. CD11b/CD18 and CD11c/CD18 are essentially restricted to expression on monocytes, granulocytes, macrophages and natural killer (NK) cells, but CD11c/CD18 is also detected on some B-cell types. In general, CD11a/CD18 predominates on lymphocytes, CD11b/CD18 on granulocytes and CD11c/CD18 on macrophages [see review, Arnaout, Blood 75:1037–1050 (1990)]. Expression of the α chains, however, is variable with regard to the state of activation and differentiation of the individual cell types [See review, Larson and Springer, Immunol. Rev. 114:181–217 (1990).]

The involvement of the $\beta_2$ integrins in human immune and inflammatory responses has been demonstrated using monoclonal antibodies which are capable of blocking $\beta_2$ integrin-associated cell adhesion. For example, CD11a/CD18, CD11b/CD18 and CD11c/CD18 actively participate in natural killer (NK) cell binding to lymphoma and adenocarcinoma cells [Patarroyo, et al., *Immunol. Rev.* 114:67–108 (1990)], granulocyte accumulation [Nourshargh, et al., *J. Immunol.* 142:3193–3198 (1989)], granulocyte-independent plasma leakage [Arfors, et al., *Blood* 69:338–340 (1987)], chemotactic response of stimulated leukocytes [Arfors, et al., supra] and leukocyte adhesion to vascular endothelium [Price, et al., *J. Immunol.* 139:4174–4177 (1987) and Smith, et al., *J. Clin. Invest.* 83:2008–2017 (1989)]. The fundamental role of $\beta_2$ integrins in immune and inflammatory responses is made apparent in the clinical syndrome referred to as leukocyte adhesion deficiency (LAD), wherein clinical manifestations include recurrent and often life threatening bacterial infections. LAD results from heterogeneous mutations in the $\beta_2$ subunit [Kishimoto, et al., *Cell* 50:193–202 (1987)] and the severity of the disease state is proportional to the degree of the deficiency in $\beta_2$ subunit expression. Formation of the complete integrin heterodimer is impaired by the $\beta_2$ mutation [Kishimoto, et al., supra].

Interestingly, at least one antibody specific for CD18 has been shown to inhibit human immunodeficiency virus type-1 (HIV-1) syncytia formation in vitro, albeit the exact mechanism of this inhibition is unclear [Hildreth and Orentas, *Science* 244:1075–1078 (1989)]. This observation is consistent with the discovery that a principal counter-receptor of CD11a/CD18, ICAM-1, is also a surface receptor for the major group of rhinovirus serotypes [Greve, et al., *Cell* 56:839 (1989)].

The significance of $\beta_2$ integrin binding activity in human immune and inflammatory responses underscores the necessity to develop a more complete understanding of this class of surface proteins. Identification of yet unknown members of this subfamily, as well as their counterreceptors, and the generation of monoclonal antibodies or other soluble factors which can alter biological activity of the $\beta_2$ integrins will provide practical means for therapeutic intervention in $\beta_2$ integrin-related immune and inflammatory responses.

BRIEF DESCRIPTION OF THE INVENTION

In one aspect, the present invention provides novel purified and isolated polynucleotides (e.g., DNA and RNA transcripts, both sense and anti-sense strands) encoding a novel human $\beta_2$ integrin $\alpha$ subunit, $\alpha_d$, and variants thereof (i.e., deletion, addition or substitution analogs) which possess binding and/or immunological properties inherent to $\alpha_d$. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide of SEQ ID NO: 2. Also provided are recombinant plasmid and viral DNA constructions (expression constructs) which include $\alpha_d$ encoding sequences, wherein the $\alpha_d$ encoding sequence is operatively linked to a homologous or heterologous transcriptional regulatory element or elements.

Also provided by the present invention are isolated and purified mouse and rat polynucleotides which exhibit homology to polynucleotides encoding human $\alpha_d$. A preferred mouse polynucleotide is set forth in SEQ ID NO: 52; a preferred rat polynucleotide is set forth in SEQ ID NO: 54.

As another aspect of the invention, prokaryotic or eukaryotic host cells transformed or transfected with DNA sequences of the invention are provided which express $\alpha_d$ polypeptide or variants thereof. Host cells of the invention are particularly useful for large scale production of $\alpha_d$ polypeptide, which can be isolated from either the host cell itself or from the medium in which the host cell is grown. Host cells which express $\alpha_d$ polypeptide on their extracellular membrane surface are also useful as immunogens in the production of $\alpha_d$-specific antibodies. Preferably, host cells transfected with $\alpha_d$ will be co-transfected to express a $\beta_2$ integrin subunit in order to allow surface expression of the heterodimer.

Also provided by the present invention are purified and isolated $\alpha_d$ polypeptides, fragments and variants thereof. Preferred $\alpha_d$ polypeptides are as set forth in SEQ ID NO: 2. Novel $\alpha_d$ products of the invention may be obtained as isolates from natural sources, but, along with $\alpha_d$ variant products, are preferably produced by recombinant procedures involving host cells of the invention. Completely glycosylated, partially glycosylated and wholly deglycosylated forms of the $\alpha_d$ polypeptide may be generated by varying the host cell selected for recombinant production and/or post-isolation processing. Variant $\alpha_d$ polypeptides of the invention may comprise water soluble and insoluble $\alpha_d$ polypeptides including analogs wherein one or more of the amino acids are deleted or replaced: (1) without loss, and preferably with enhancement, of one or more biological activities or immunological characteristics specific for $\alpha_d$; or (2) with specific disablement of a particular ligand/receptor binding or signalling function. Fusion polypeptides are also provided, wherein $\alpha_d$ amino acid sequences are expressed contiguously with amino acid sequences from other polypeptides. Such fusion polypeptides may possess modified biological, biochemical, and/or immunological properties in comparison to wild-type $\alpha_d$. Analog polypeptides including additional amino acid (e.g., lysine or cysteine) residues that facilitate multimer formation are contemplated.

Also comprehended by the present invention are polypeptides and other non-peptide molecules which specifically bind to $\alpha_d$. Preferred binding molecules include antibodies (e.g., monoclonal and polyclonal antibodies), counterreceptors (e.g., membrane-associated and soluble forms) and other ligands (e.g., naturally occurring or synthetic molecules), including those which competitively bind $\alpha_d$ in the presence of $\alpha_d$ monoclonal antibodies and/or specific counterreceptors. Binding molecules are useful for purification of $\alpha_d$ polypeptides and identifying cell types which express $\alpha_d$. Binding molecules are also useful for modulating (i.e., inhibiting, blocking or stimulating) of in vivo binding and/or signal transduction activities of $\alpha_d$.

Assays to identify $\alpha_d$ binding molecules are also provided, including immobilized ligand binding assays, solution binding assays, scintillation proximity assays, di-hybrid screening assays, and the like.

In vitro assays for identifying antibodies or other compounds that modulate the activity of $\alpha_d$ may involve, for example, immobilizing $\alpha_d$ or a natural ligand to which $\alpha_d$ binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of $\alpha_d$ binding.

Another type of assay for identifying compounds that modulate the interaction between $\alpha_d$ and a ligand involves immobilizing $\alpha_d$ or a fragment thereof on a solid support coated (or impregnated with) a fluorescent agent, labelling the ligand with a compound capable of exciting the fluorescent agent, contacting the immobilized $\alpha_d$ with the labelled ligand in the presence and absence of a putative modulator compound, detecting light emission by the fluorescent agent, and identifying modulating compounds as those compounds that affect the emission of light by the fluorescent agent in comparison to the emission of light by the fluorescent agent in the absence of a modulating compound. Alternatively, the $\alpha_d$ ligand may be immobilized and $\alpha_d$ may be labelled in the assay.

Yet another method contemplated by the invention for identifying compounds that modulate the interaction between $\alpha_d$ and a ligand involves transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a second hybrid DNA sequence encoding part or all of the ligand and the DNA binding domain or activating domain of the transcription factor which is not incorporated in the first fusion, evaluating the effect of a putative modulating compound on the interaction between $\alpha_d$ and the ligand by detecting binding of the ligand to $\alpha_d$ in a particular host cell by measuring the production of reporter gene product in the host cell in the presence or absence of the putative modulator, and identifying modulating compounds as those compounds altering production of the reported gene product in comparison to production of the reporter gene product in the absence of the modulating compound. Presently preferred for use in the assay are the lexA promoter, the lexA DNA binding domain, the GAL4 transactivation domain, the lacZ reporter gene, and a yeast host cell.

A modified version of the foregoing assay may be used in isolating a polynucleotide encoding a protein that binds to $\alpha_d$ by transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a library of second hybrid DNA sequences encoding second fusions of part or all of putative $\alpha_d$ binding proteins and the DNA binding domain or activating domain of the transcription factor which is not incorporated in the first fusion, detecting binding of an $\alpha_d$ binding protein to $\alpha_d$ in a particular host cell by detecting the production of reporter gene product in the host cell, and isolating second hybrid DNA sequences encoding $\alpha_d$ binding protein from the particular host cell.

Hybridoma cell lines which produce antibodies specific for $\alpha_d$ are also comprehended by the invention. Techniques for producing hybridomas which secrete monoclonal antibodies are well known in the art. Hybridoma cell lines may be generated after immunizing an animal with purified $\alpha_d$, variants of $\alpha_d$ or cells which express $\alpha_d$ or a variant thereof on the extracellular membrane surface. Immunogen cell types include cells which express $\alpha_d$ in vivo, or transfected prokaryotic or eukaryotic cell lines which normally do not normally express $\alpha_d$ in vivo.

The value of the information contributed through the disclosure of the DNA and amino acid sequences of $\alpha_d$ is manifest. In one series of examples, the disclosed $\alpha_d$ cDNA sequence makes possible the isolation of the human $\alpha_d$ genomic DNA sequence, including transcriptional control elements for the genomic sequence. Identification of $\alpha_d$ allelic variants and heterologous species (e.g., rat or mouse) DNAs is also comprehended. Isolation of the human $\alpha_d$ genomic DNA and heterologous species DNAs can be accomplished by standard DNA/DNA hybridization techniques, under appropriately stringent conditions, using all or part of the $\alpha_d$ cDNA sequence as a probe to screen an appropriate library. Alternatively, polymerase chain reaction (PCR) using oligonucleotide primers that are designed based on the known cDNA sequence can be used to amplify and identify genomic $\alpha_d$ DNA sequences. Synthetic DNAs encoding the $\alpha_d$ polypeptide, including fragments and other variants thereof, may be produced by conventional synthesis methods.

DNA sequence information of the invention also makes possible the development, by homologous recombination or "knockout" strategies [see, e.g., Kapecchi, *Science* 244:1288–1292 (1989)], to produce rodents that fail to express a functional $\alpha_d$ polypeptide or that express a variant $\alpha_d$ polypeptide. Such rodents are useful as models for studying the activities of $\alpha_d$ and $\alpha_d$ modulators in vivo.

DNA and amino acid sequences of the invention also make possible the analysis of $\alpha_d$ epitopes which actively participate in counterreceptor binding as well as epitopes which may regulate, rather than actively participate in, binding. Identification of epitopes which may participate in transmembrane signal transduction is also comprehended by the invention.

DNA of the invention is also useful for the detection of cell types which express $\alpha_d$ polypeptide. Standard DNA/RNA hybridization techniques which utilize $\alpha_d$ DNA to detect $\alpha_d$ RNA may be used to determine the constitutive level of $\alpha_d$ transcription within a cell, as well as changes in the level of transcription in response to internal or external agents. Identification of agents which modify transcription and/or translation of $\alpha_d$ can, in turn, be assessed for potential therapeutic or prophylactic value. DNA of the invention also makes possible in situ hybridization of $\alpha_d$ DNA to cellular RNA to determine the cellular localization of $\alpha_d$ specific messages within complex cell populations and tissues.

DNA of the invention is also useful for identification of non-human polynucleotide sequences which display homology to human $\alpha_d$ sequences. Possession of non-human $\alpha_d$ DNA sequences permits development of animal models (including, for example, transgenic models) of the human system.

As another aspect of the invention, monoclonal or polyclonal antibodies specific for $\alpha_d$ may be employed in immunohistochemical analysis to localize $\alpha_d$ to subcellular compartments or individual cells within tissues. Immunohistochemical analyses of this type are particularly useful when used in combination with in situ hybridization to localize both $\alpha_d$ mRNA and polypeptide products of the $\alpha_d$ gene.

Identification of cell types which express $\alpha_d$ may have significant ramifications for development of therapeutic and prophylactic agents. It is anticipated that the products of the invention related to $\alpha_d$ can be employed in the treatment of diseases wherein macrophages are an essential element of the disease process. Animal models for many pathological conditions associated with macrophage activity have been described in the art. For example, in mice, macrophage recruitment to sites of both chronic and acute inflammation is reported by Jutila, et al., *J. Leukocyte Biol.* 54:30–39

(1993). In rats, Adams, et al., [Transplantation 53:1115–1119(1992) and *Transplantation* 56:794–799 (1993)] describe a model for graft arteriosclerosis following heterotropic abdominal cardiac allograft transplantation. Rosenfeld, et al., [*Arteriosclerosis* 7:9–23 (1987) and *Arteriosclerosis* 7:24–34 (1987)] describe induced atherosclerosis in rabbits fed a cholesterol supplemented diet. Hanenberg, et al., [*Diabetologia* 32:126–134 (1989)] report the spontaneous development of insulin-dependent diabetes in BB rats. Yamada et al., [*Gastroenterology* 104:759–771 (1993)] describe an induced inflammatory bowel disease, chronic granulomatous colitis, in rats following injections of streptococcal peptidoglycan-polysaccharide polymers. Cromartie, et al., [*J. Exp. Med.* 146:1585–1602 (1977)] and Schwab, et al., [*Infection and Immunity* 59:4436–4442 (1991)] report that injection of streptococcal cell wall protein into rats results in an arthritic condition characterized by inflammation of peripheral joints and subsequent joint destruction. Finally, Huitinga, et al., [*Eur. J. Immunol* 23:709–715 (1993) describe experimental allergic encephalomyelitis, a model for multiple sclerosis, in Lewis rats. In each of these models, $\alpha_d$ antibodies, other $\alpha_d$ binding proteins, or soluble forms of $\alpha_d$ are utilized to attenuate the disease state, presumably through inactivation of macrophage activity.

Pharmaceutical compositions for treatment of these and other disease states are provided by the invention. Pharmaceutical compositions are designed for the purpose of inhibiting interaction between $\alpha_d$ and its ligand(s) and include various soluble and membrane-associated forms of $\alpha_d$ (comprising the entire $\alpha_d$ polypeptide, or fragments thereof which actively participate in $\alpha_d$ binding), soluble and membrane-associated forms of $\alpha_d$ binding proteins (including antibodies, ligands, and the like), intracellular or extracellular modulators of $\alpha_d$ binding activity, and/or modulators of $\alpha_d$ and/or $\alpha_d$-ligand polypeptide expression, including modulators of transcription, translation, post-translational processing and/or intracellular transport.

The invention also comprehends methods for treatment of disease states in which $\alpha_d$ binding, or localized accumulation of cells which express $\alpha_d$, is implicated, wherein a patient suffering from said disease state is provided an amount of a pharmaceutical composition of the invention sufficient to modulate levels of $\alpha_d$ binding or to modulate accumulation of cell types which express $\alpha_d$. The method of treatment of the invention is applicable to disease states such as, but not limited to, Type I diabetes, atherosclerosis, multiple sclerosis, asthma, psoriasis, lung inflammation, acute respiratory distress syndrome and rheumatoid arthritis.

BRIEF DESCRIPTION OF THE DRAWING

Numerous other aspects and advantages of the present invention will be apparent upon consideration of the following description thereof, reference being made to the drawing wherein:

FIGS. 1A through 1D comprises an alignment of the human amino acid sequences of CD11b (SEQ ID NO: 3), CD11c (SEQ ID NO: 4) and $\alpha_d$ (SEQ ID NO: 2).

DETAILED DESCRIPTION OF THE INVENTION

The present invention is illustrated by the following examples relating to the isolation of a cDNA clone encoding $\alpha_d$ from a human spleen cDNA library. More particularly, Example 1 illustrates the use of anti-canine $\alpha_{TM1}$ antibody in an attempt to detect a homologous human protein. Example 2 details purification of canine $\alpha_{TM1}$ and N-terminal sequencing of the polypeptide to design oligonucleotide primers for PCR amplification of the canine $\alpha_{TM1}$ gene. Example 3 addresses large scale purification of canine $\alpha_{TM1}$ for internal sequencing in order to design additional PCR primers. Example 4 describes use of the PCR and internal sequence primers to amplify a fragment of the canine $\alpha_{TM1}$ gene. Example 5 addresses cloning of the human $\alpha_d$-encoding cDNA sequence. Example 6 describes Northern blot hybridization analysis of human tissues and cells for expression of $\alpha_d$ mRNA. Example 7 details the construction of human $\alpha_d$ expression plasmids and transfection of COS cells with the resulting plasmids. Example 8 addresses ELISA analysis of $\alpha_d$ expression in transfected COS cells. Example 9 describes FACS analysis of COS cells transfected with human $\alpha_d$ expression plasmids. Example 10 addresses immunoprecipitation of CD18 in association with $\alpha_d$ in co-transfected COS cells. Example 11 relates to stable transfection of $\alpha_d$ expression constructs in Chinese hamster ovary cells. Example 12 addresses CD18-dependent binding of $\alpha_d$ to the intercellular adhesion molecule, ICAM-R. Example 13 describes scintillation proximity screening assays to identify inhibitors of $\alpha_d$ ligand/anti-ligand binding interactions. Example 14 addresses construction of expression plasmids which encode soluble forms of $\alpha_d$. Example 15 relates to production of $\alpha_d$-specific monoclonal antibodies. Example 16 describes analysis of $\alpha_d$ tissue distribution using polyclonal anti-serum. Example 17 describes isolation of rat cDNA sequences which show homology to human $\alpha_d$ gene sequences. Example 18 relates to construction of rat $\alpha_d$ I domain expression plasmids, including I domain/IgG fusion proteins, and production of monoclonal antibodies to I domain fusion proteins. Example 19 addresses isolation of mouse cDNA sequences which show homology to human $\alpha_d$ gene sequences. Example 20 describes isolation of additional mouse $\alpha_d$ cDNA clones used to confirm sequence analysis. Example 21 relates to in situ hybridization analysis of various mouse tissues to determine tissue and cell specific expression of the putative mouse homolog to human $\alpha_d$. Example 22 describes generation of expression constructs which encode the putative mouse homolog of human $\alpha_d$. Example 23 addresses design of a "knock-out" mouse wherein the gene encoding the putative mouse homolog of human $\alpha_d$ is disrupted. Example 24 describes isolation of rabbit cDNA clones which show homology to human $\alpha_d$ encoding sequences. Example 25 describes animal models of human disease states wherein modulation of $\alpha_d$ is assayed for therapeutic capabilities.

EXAMPLE 1

Attempt to Detect a Human Homolog of Canine $\alpha_{TM1}$

The monoclonal antibody Ca11.8H2 [Moore, et al., supra] specific for canine $\alpha_{TM1}$ was tested for cross-reactivity on human peripheral blood leukocytes in an attempt to identify a human homolog of canine $\alpha_{TM1}$. Cell preparations (typically 1×10⁶ cells) were incubated with undiluted hybridoma supernatant or a purified mouse IgG-negative control antibody (10 µg/ml) on ice in the presence of 0.1% sodium azide. Monoclonal antibody binding was detected by subsequent incubation with FITC-conjugated horse anti-mouse IgG (Vector Laboratories, Burlingame, Calif.) at 6 µg/ml. Stained cells were fixed with 2% w/v paraformaldehyde in phosphate buffered saline (PBS) and were analyzed with a Facstar Plus fluorescence-activated cell sorter (Becton Dickinson, Mountain View, Calif.). Typically, 10,000 cells were analyzed using logarithmic amplification for fluorescence intensity.

The results indicated that Ca11.8H2 did not cross-react with surface proteins expressed on human peripheral blood leukocytes, while the control cells, neoplastic canine peripheral blood lymphocytes, were essentially all positive for $\alpha_{TM1}$.

Because the monoclonal antibody Ca11.8H2 specific for the canine α subunit did not cross react with a human homolog, isolation of canine $\alpha_{TM1}$ DNA was deemed a necessary prerequisite to isolate a counterpart human gene if one existed.

EXAMPLE 2

Affinity Purification of Canine $\alpha_{TM1}$ For N-Terminal Sequencing

Canine $\alpha_{TM1}$ was affinity purified in order to determine N-terminal amino acid sequences for oligonucleotide probe/primer design. Briefly, anti-$\alpha_{TM1}$ monoclonal antibody Ca11.8H2 was coupled to Affigel 10 chromatographic resin (BioRad, Hercules, Calif.) and protein was isolated by specific antibody-protein interaction. Antibody was conjugated to the resin, according to the BioRad suggested protocol, at a concentration of approximately 5 mg antibody per ml of resin. Following the conjugation reaction, excess antibody was removed and the resin blocked with three volumes of 0.1M ethanolamine. The resin was then washed with thirty column volumes of phosphate buffered saline (PBS).

Twenty-five grams of a single dog spleen were homogenized in 250 ml of buffer containing 0.32M sucrose in 25 mM Tris-HCl, Ph 8.0, with protease inhibitors. Nuclei and cellular debris were pelleted with centrifugation at 1000 g for 15 minutes. Membranes were pelleted from the supernatant with centrifugation at 100,000 g for 30 minutes. The membrane pellet was resuspended in 200 ml lysis buffer (50 mM NaCl, 50 mM borate, pH 8.0, with 2% NP-40) and incubated for 1 hour on ice. Insoluble material was then pelleted by centrifugation at 100,000 g for 60 minutes. Ten milliliters of the cleared lysate were transferred to a 15 ml polypropylene tube with 0.5 ml Ca11.8H2-conjugated Affigel 10 resin described above. The tube was incubated overnight at 4° C. with rotation and the resin subsequently washed with 50 column volumes D-PBS. The resin was then transferred to a microfuge tube and boiled for ten minutes in 1 ml Laemmli (non-reducing) sample buffer containing 0.1M Tris-HCl, pH 6.8, 2% SDS, 20% glycerol and 0.002% bromophenol blue. The resin was pelleted by centrifugation and discarded; the supernatant was treated with ⅕ volume β-mercaptoethanol (Sigma, St. Louis, Mo.) and run on a 7% polyacrylamide gel. The separated proteins were transferred to Immobilon PVDF membrane (Millipore, Bedford, Mass.) as follows.

The gels were washed once in deionized, Millipore-filtered water and equilibrated for 15–45 minutes in 10 mM 3-[cyclohexylamino]-1-propanesulfonic acid (CAPS) transfer buffer, pH 10.5, with 10% methanol. Immobilon membranes were moistened with methanol, rinsed with filtered water, and equilibrated for 15–30 minutes in CAPS transfer buffer. The initial transfer was carried out using a Biorad transfer apparatus at 70 volts for 3 hours. The Immobilon membrane was removed after transfer and stained in filtered 0.1% R250 Coomassie stain for 10 minutes. Membranes were destained in 50% methanol/10% acetic acid three times, ten minutes each time. After destaining, the membranes were washed in filtered water and air-dried.

Protein bands of approximately 150 kD, 95 kD, 50 kD and 30 kD were detected. Presumably the 50 kD and 30 kD bands resulted from antibody contamination. N-terminal sequencing was then attempted on both the 150 kD and 95 kD bands, but the 95 kD protein was blocked, preventing sequencing. The protein band of 150 kD was excised from the membrane and directly sequenced with an Applied Biosystems (Foster City, Calif.) Model 473A protein sequencer according to the manufacturer's instructions. The resulting amino acid sequence is set in SEQ ID NO: 5 using single letter amino acid designations.

FNLDVEEPMVFQ (SEQ ID NO: 5)

The identified sequence included the FNLD sequence characteristic of α subunits of the integrin family [Tamura, et al., J. Cell. Biol. 111:1593–1604 (1990)].

Primer Design and Attempt to Amplify Canine $\alpha_{TM1}$ Sequences

From the N-terminal sequence information, three oligonucleotide probes were designed for hybridization: a) "Tommer," a fully degenerate oligonucleotide; b) "Patmer," a partially degenerate oligonucleotide; and c) "Guessmer," a nondegenerate oligonucleotide based on mammalian codon usage. These probes are set out below as SEQ ID NOS: 6, 7 and 8, respectively. Nucleic acid symbols are in accordance with 37 C.F.R. §1.882 for these and all other nucleotide sequences herein.

5'-TTrYAAYYTGGAYGTNGARGARCCNATGGTNTTY CA-3' (SEQ ID NO: 6)
5'-TTCAACCTGGACGTGGAGGAGCCCATGGTGTTCC AA-3' (SEQ ID NO: 7)
5'-TTCAACCTGGACGTNGAASANCCCATGGTCTTCC AA-3' (SEQ ID NO: 8)

Based on sequencing data, no relevant clones were detected using these oligonucleotides in several low stringency hybridizations to a canine spleen/peripheral blood macrophage cDNA library cloned into λZAP (Stratagene, La Jolla, Calif.).

Four other oligonucleotide primers, designated 5'Deg, 5'Spec, 3'Deg and 3'Spec (as set out in SEQ ID NOS: 9, 10, 11 and 12, respectively, wherein Deg indicates degenerate and Spec indicates non-degenerate) were subsequently designed based on the deduced N-terminal sequence for attempts to amplify canine $\alpha_{TM1}$ sequences by PCR from phage library DNA purified from plate lysates of the Stratagene library described above.

5'-TTrYAAYYTNGAYGTNGARGARCC-3' (SEQ ID NO: 9)
5 '-TTYAAYYTGGACGTNGAAGA-3' (SEQ ID NO: 10)
5'-TGRAANACCATNGGYTC-3' (SEQ ID NO: 11)
5'-TTGGAAGACCATNGGYTC-3' (SEQ ID NO: 12)

The $\alpha_{TM1}$ oligonucleotide primers were paired with T3 or T7 vector primers, as set out in SEQ ID NOS: 13 and 14, respectively, which hybridize to sequences flanking the polylinker region in the Bluescript phagemid found in λZAP.

5'-ATTAACCCTCACTAAAG-3' (SEQ ID NO: 13)
5'-AATACGACTCACTATAG-3' (SEQ ID NO: 14)

The PCR amplification was carried out in Taq buffer (Boehringer Mannheim, Indianapolis, Ind.) containing magnesium with 150 ng of library DNA, 1 μg of each primer, 200 μM dNTPs and 2.5 units Taq polymerase (Boehringer Mannheim) and the products were separated by electrophoresis on a 1% agarose gel in Tris-Acetate-EDTA (TAE) buffer with 0.25 μg/ml ethidium bromide. DNA was transferred to a Hybond (Amersham, Arlington Heights, Ill.) membrane by wicking overnight in 10×SSPE. After transfer, the immobilized DNA was denatured with 0.5M NaOH with 0.6M NaCl, neutralized with 1.0M Tris-HCl, pH 8.0, in 1.5M NaCl, and washed with 2×SSPE before UV crosslinking with a Stratalinker (Stratagene) crosslinking apparatus. The membrane was incubated in prehybridization buffer (5× SSPE, 4× Denhardts, 0.8% SDS, 30% formamide) for 2 hr at 50° C. with agitation.

Oligonucleotide probes 5'Deg, 5'Spec, 3'Deg and 3'Spec (SEQ ID NOS: 9, 10, 11 and 12, respectively) were labeled using a Boehringer Mannheim kinase buffer with 100–300 µCi γp$^{32}$-dATP and 1–3 units of polynucleotide kinase for 1–3 hr at 37° C. Unincorporated label was removed with Sephadex G-25 fine (Pharmacia, Piscataway, N.J.) chromatography using 10 mM Tris-HCl, pH 8.0, 1 mM EDTA (TE) buffer and the flow-through added directly to the prehybridization solution. Membranes were probed for 16 hr at 42° C. with agitation and washed repeatedly, with a final stringency wash of 1× SSPE/0.1% SDS at 50° C. for 15 min. The blot was then exposed to Kodak X-Omat AR film for 1–4 hours at −80° C.

The oligonucleotides 5'Deg, 5'Spec, 3'Deg and 3'Spec only hybridized to PCR products from the reactions in which they were used as primers and failed to hybridize as expected to PCR products from the reactions in which they were not used as primers. Thus, it was concluded that none of the PCR products were specific for $\alpha_{TM1}$ because no product hybridized with all of the appropriate probes.

EXAMPLE 3

Large Scale Affinity Purification of Canine $\alpha_{TM1}$ For Internal Sequencing In order to provide additional amino acid sequence for primer design, canine $\alpha_{TM1}$ was purified for internal sequencing. Three sections of frozen spleen (approximately 50 g each) and frozen cells from two partial spleens from adult dogs were used to generate protein for internal sequencing. Fifty grams of spleen were homogenized in 200–300 ml borate buffer with a Waring blender. The homogenized material was diluted with 1 volume of buffer containing 4% NP-40, and the mixture then gently agitated for at least one hour. The resulting lysate was cleared of large debris by centrifugation at 2000 g for 20 min, and then filtered through either a Corning (Corning, N.Y.) prefilter or a Corning 0.8 micron filter. The lysate was further clarified by filtration through the Corning 0.4 micron filter system.

Splenic lysate and the antibody-conjugated Affigel 10 resin described in Example 2 were combined at a 150:1 volume ratio in 100 ml aliquots and incubated overnight at 4° C. with rocking. The lysate was removed after centrifugation at 1000 g for 5 minutes, combined with more antibody-conjugated Affigel 10 resin and incubated overnight as above. The absorbed resin aliquots were then combined and washed with 50 volumes D-PBS/0.1% Tween 20 and the resin transferred to a 50 ml Biorad column. Adsorbed protein was eluted from the resin with 3–5 volumes of 0.1M glycine (pH 2.5); fractions of approximately 900 µl were collected and neutralized with 100 µl 1M Tris buffer, pH 8.0. Aliquots of 15 µl were removed from each fraction and boiled in an equal volume of 2× Laemmli sample buffer with ⅕ volume 1M dithiothreitol (DTF). These samples were electrophoresed on 8% Novex (San Diego, Calif.) polyacrylamide gels and visualized either by Coomassie stain or by silver stain using a Daiichi kit (Enprotech, Natick, Mass.) according to the manufacturer's suggested protocol. Fractions which contained the largest amounts of protein were combined and concentrated by vacuum. The remaining solution was diluted by 50% with reducing Laemmli sample buffer and run on 1.5 mm 7% polyacrylamide gels in Tris-glycine/SDS buffer. Protein was transferred from the gels to Immobilon membrane by the procedure described in Example 2 using the Hoefer transfer apparatus.

The protein bands corresponding to canine $\alpha_{TM1}$ were excised from 10 PVDF membranes and resulted in approximately 47 µg total protein. The bands were destained in 4 ml 50% methanol for 5 minutes, air dried and cut into 1×2 mm pieces. The membrane pieces were submerged in 2 ml 95% acetone at 4° C. for 30 minutes with occasional vortexing and then air dried.

Prior to proteolytic cleavage of the membrane bound protein, 3 mg of cyanogen bromide (CNBr) (Pierce, Rockford, Ill.) were dissolved in 1.25 ml 70% formic acid. This solution was then added to a tube containing the PVDF membrane pieces and the tube incubated in the dark at room temperature for 24 hours. The supernatant (S1) was then removed to another tube and the membrane pieces washed with 0.25 ml 70% formic acid. This supernatant (S2) was removed and added to the previous supernatant (S 1). Two milliliters of Milli Q water were added to the combined supernatants (S1 and S2) and the solution lyophilized. The PVDF membrane pieces were dried under nitrogen and extracted again with 1.25 ml 60% acetonitrile, 0.1% tetrafluoroacetic acid (TFA) at 42° C. for 17 hours. This supernatant (S3) was removed and the membrane pieces extracted again with 1.0 ml 80% acetonitrile with 0.08% TFA at 42° C. for 1 hour. This supernatant (S4) was combined with the previous supernatants (S1, S2 and S3) and vacuum dried.

The dried CNBr fragments were then dissolved in 63 µl 8M urea, 0.4M NH$_4$HCO$_3$. The fragments were reduced in 5 µl 45 mM dithiothreitol (DTT) and subsequently incubated at 50° C. for 15 minutes. The solution was then cooled to room temperature and the fragments alkylated by adding 5 µl 100 mM iodoacetamide (Sigma, St. Louis, Mo.). Following a 15 minute incubation at room temperature, the sample was diluted with 187 µl Milli Q water to a final urea concentration of 2.0M. Trypsin (Worthington, Freehold, N.J.) was then added at a ratio of 1:25 (w:w) of enzyme to protein and the protein digested for 24 hours at 37° C. Digestion was terminated with addition of 30 µl TFA.

The protein fragments were then separated with high performance liquid chromatography (HPLC) on a Waters 625 LC system (Millipore, Milford, Mass.) using a 2.1×250 mm, 5 micron Vydac C-18 column (Vydac, Hesperia, Calif.) equilibrated in 0.05% TFA and HPLC water (buffer A). The peptides were eluted with increasing concentration of 80% acetonitrile in 0.04% TFA (buffer B) with a gradient of 38–75% buffer B for 65–95 minutes and 75–98% buffer B for 95–105 minutes. Peptides were fractionated at a flow rate of 0.2 ml/minute and detected at 210 nm.

Following fractionation, the amino acid sequence of the peptides was analyzed by automated Edman degradation performed on an Applied Biosystems Model 437A protein sequencer using the manufacturer's standard cycles and the Model 610A Data Analysis software program, Version 1.2.1. All sequencing reagents were supplied by Applied Biosystems. The amino acid sequences of seven of the eight internal fragments are set out below wherein "X" indicates the identity of the amino acid was not certain.
VFQEXGAGFGQ (SEQ ID NO: 15)
LYDXVAATGLXQPI (SEQ ID NO: 16)
PLEYXDVIPQAE (SEQ ID NO: 17)
FQEGFSXVLX (SEQ ID NO: 18)
TSPTFIXMSQENVD (SEQ ID NO: 19)
LVVGAPLEVVAVXQTGR (SEQ ID NO: 20)
LDXKPXDTA (SEQ ID NO: 21)
Primer Design One internal amino acid sequence (set out in SEQ ID NO: 22) obtained was then used to design a fully degenerate oligonucleotide primer, designated p4(R) as set out in SEQ ID NO: 23.
FGEQFSE (SEQ ID NO: 22)
5'-RAANCCYTCYTGRAAACTYTC-3' (SEQ ID NO: 23)

EXAMPLE 4
PCR Cloning of A Canine $\alpha_{TM1}$ Fragment

The 5' portion of the canine $\alpha_{TM1}$ gene was amplified from double-stranded canine splenic cDNA by PCR.

A. Generation of Double Stranded Canine Spleen cDNA

One gram of frozen material from a juvenile dog spleen was ground in liquid nitrogen on dry ice and homogenized in 20 ml RNA-Stat 60 buffer (Tel-Test B, Inc, Friendswood, Tex.). Four ml chloroform were added, and the solution extracted by centrifugation at 12,000 g for 15 minutes. RNA was precipitated from the aqueous layer with 10 ml ethanol. Poly A+ RNA was then selected on Dynal Oligo dT Dynabeads (Dynal, Oslo, Norway). Five aliquots of 100 µg total RNA were combined and diluted with an equal volume of 2× binding buffer (20 mM Tris-HCl, pH 7.5, 1.0M LiCl, 1 mM EDTA, 0.1% SDS). RNA was then incubated 5 minutes with the Oligo dT Dynabeads (1.0 ml or 5 mg beads for all the samples). Beads were washed with buffer containing 10 mM Tris-HCl, pH 7.5, 0.15M LiCl, 1 mM EDTA and 0.1% SDS, according to the manufacturer's suggested protocol prior to elution of poly A+ mRNA with 2 mM EDTA, pH 7.5. Double-stranded cDNA was then generated using the eluted poly A+ mRNA and the Boehringer Mannheim cDNA Synthesis Kit according to the manufacturer's suggested protocol.

B. Isolation of a Partial Canine $\alpha_{TM1}$ cDNA

Oligonucleotide primers 5'Deg (SEQ ID NO: 9) and p4(R) (SEQ ID NO: 23) were employed in a standard PCR reaction using 150 ng double-stranded cDNA, 500 ng of each primer, 200 µM dNTPs and 1.5 units Taq polymerase (Boehringer Mannheim) in Taq buffer (Boehringer Mannheim) with magnesium. The resulting products (1 µl of the original reaction) were subjected to a second round of PCR with the same primers to increase product yield. This band was eluted from a 1% agarose gel onto Schleicher & Schuell (Keene, N.H.) NA45 paper in a buffer containing 10 mM Tris-HCl, pH 8, 1 mM EDTA, 1.5M NaCl at 65° C., precipitated, and ligated into the pCR™II vector (Invitrogen, San Diego, Calif.) using the TA cloning kit (Invitrogen) and the manufacturer's suggested protocol. The ligation mixture was transformed by electroporation into XL-1 Blue bacteria (Stratagene). One clone, 2.7, was determined to contain sequences corresponding to $\alpha_{TM1}$ peptide sequences which were not utilized in design of the primers.

Sequencing was performed with an Applied Biosystems 373A DNA sequencer (Foster City, Calif.) with a Dye-deoxy terminator cycle sequence kit (ABI) in which fluorescent-labeled dNTPs were incorporated in an asymmetric PCR reaction [McCabe, "Production of Single Stranded DNA by Asymmetric PCR," in *PCR Protocols: A Guide to Methods and Applications*, Innis, et al. (eds.) pp. 76–83 Academic Press: New York (1990)] as follows. Samples were held at 96° C. for 4 minutes and subjected to 25 cycles of the step sequence: 96° C., for 15 seconds; 50° C. for 1 second; 60° C. for 4 minutes. Sequence data was automatically downloaded into sample files on the computer that included chromatogram and text files. The sequence of the entire insert of clone 2.7 is set out in SEQ ID NO: 24.

Attempts to isolate the full length canine $\alpha_{TM1}$ cDNA from the Stratagene library (as described in Example 2) were unsuccessful. Approximately 1×10$^6$ phage plaques were screened by hybridization under low stringency conditions using 30% formamide with clone 2.7 as a probe, but no positive clones resulted. Attempts to amplify relevant sequences downstream from those represented in clone 2.7 using specific oligonucleotides derived from clone 2.7 or degenerate primers based on amino acid sequence from other peptide fragments paired with a degenerate oligonucleotide based on the conserved a subunit amino acid motif GFFKR [Tamura, et al., supra] were also unsuccessful.

EXAMPLE 5
Cloning of A Putative Human Homolog of Canine $\alpha_{TM1}$

To attempt the isolation of a human sequence homologous to canine $\alpha_{TM1}$ the approximately 1 kb canine $\alpha_{TM1}$ fragment from clone 2.7 was used as a probe. The probe was generated by PCR under conditions described in Example 2 using NT2 (as set out in SEQ ID NO: 25) and p4(R) (SEQ ID NO: 23) primers.

5'-GTNTTYCARGARGAYGG-3' (SEQ ID NO: 25)

The PCR product was purified using the Qiagen (Chatsworth, Ga.) Quick Spin kit and the manufacturer's suggested protocol. The purified DNA (200 ng) was labeled with 200 µCi $\alpha^{32}$PdCTP using the Boehringer Mannheim Random Prime Labelling kit and the manufacturer's suggested protocol. Unincorporated isotope was removed with Sephadex G25 (fine) gravity chromatography. The probe was denatured with 0.2 N NaOH and neutralized with 0.4M Tris-HCl, pH 8.0, before use.

Colony lifts on Hybond filters (Amersham) of a human spleen cDNA library in pCDNA/Amp (Invitrogen, San Diego, Calif.) were prepared. The filters were initially denatured and neutralized as described in Example 2 and subsequently incubated in a prehybridization solution (8 ml/filter) with 30% formamide at 50° C. with gentle agitation for 2 hours. Labeled probe as described above was added to this solution and incubated with the filters for 14 hours at 42° C. The filters were washed twice in 2× SSC/0.1% SDS at 37° C. and twice in 2× SSC/0.1% SDS at 50° C. Final stringency washes were 1× SSC/0.1% SDS, twice at 65° C. (1× SSC is 150 mM NaCl, 15 mM sodium citrate, pH 7.0). Filters were exposed to Kodak X-Omat AR film for six hours with an intensifying screen. Colonies giving signals on duplicate lifts were streaked on LB medium with magnesium (LBM)/carbenicillin plates and incubated overnight at 37° C. Resulting streaked colonies were lifted with Hybond filters and these filters were treated as above. The filters were hybridized under more stringent conditions with the 1 kb probe from clone 2.7, labeled as previously described, in a 50% formamide hybridization solution at 50° C. for 3 hours. Probed filters were washed with a final stringency of 0.1× SSC/0.1% SDS at 65° C. and exposed to Kodak X-Omat AR film for 2.5 hours at –80° C. with an intensifying screen. Positive colonies were identified and cultured in LBM/carbenicillin medium overnight. DNA from the cultures was prepared using the Promega Wizard miniprep kit according to the manufacturer's suggested protocol and the resulting DNA was sequenced.

The initial screening resulted in 18 positive clones, while the secondary screening under more stringent hybridization conditions produced one positive clone which was designated 19A2. The DNA and deduced amino acid sequences of the human $\alpha_d$ clone 19A2 are set out in SEQ ID NOS: 1 and 2, respectively.

Characteristics of The Human $\alpha_d$ cDNA and Predicted Polypeptide

Clone 19A2 encompasses the entire coding region for the mature protein, plus 48 bases (16 amino acid residues) of the 5' upstream signal sequence and 241 bases of 3' untranslated sequence which do not terminate in a polyadenylation sequence. The core molecular weight of the mature protein is predicted to be around 125 kD. The extracellular domain is predicted to encompass approximately amino acid residues 17 through 1108 of SEQ ID NO: 2. This extracellular region is contiguous with about a 20 amino acid region homologous to the human CD11c transmembrane region (residues 1109 through 1128 of SEQ ID NO: 2). The cytoplasmic domain comprises approximately 30 amino acids (about residues 1129 through 1161 of SEQ ID NO: 2). The protein also contains a region (around residues 150 through 352) of approximately 202 amino acids homologous to the I (insertion) domain common to CD11a, CD11b and CD11c [Larson and Springer, supra], $\alpha_E$ [Shaw, et al., *J. Biol. Chem.* 269:6016–6025 (1994)] and in VLA-1 and VLA-2, [Tamura, et al., supra]. The I domain in other integrins has been shown to participate in ICAM binding [Landis, et al., *J. Cell. Biol.* 120:1519–1527 (1993); Diamond, et al., *J. Cell. Biol.* 120:1031–1043 (1993)], suggesting that $\alpha_d$ may also bind members of the ICAM family of surface molecules. This region has not been demonstrated to exist in any other integrin subunits.

The deduced amino acid sequence of $\alpha_d$ shows approximately 36% identity to that of CD11a, approximately 60% identity to CD11b and approximately 66% identity to CD11c. An alignment of amino acid sequences for (CD11b SEQ ID NO: 3), CD11c (SEQ ID NO: 4) and $\alpha_d$ (SEQ ID NO: 2) is presented in FIG. 1.

The cytoplasmic domains of $\alpha$ subunits in $\beta_2$ integrins are typically distinct from one another within the same species, while individual $\alpha$ subunits show high degrees of homology across species boundaries. Consistent with these observations, the cytoplasmic region of $\alpha_d$ differs markedly from CD11a, CD11b, and CD11c except for a membrane proximal GFFKR amino acid sequence which has been shown to be conserved among all $\alpha$ integrins [Rojiani, et al., *Biochemistry* 30: 9859–9866 (1991)]. Since the cytoplasmic tail region of integrins has been implicated in "inside out" signaling and in avidity regulation [Landis et al., supra], it is possible that $\alpha_d$ interacts with cytosolic molecules distinct from those interacting with CD11a, CD11b, and CD11c, and, as a result, participates in signaling pathways distinct from those involving other $\beta_2$ integrins.

The extracellular domain of $\alpha_d$ contains a conserved DGSGS amino acid sequence adjacent the I-domain; in CD11b, the DGSGS sequence is a metal-binding region required for ligand interaction [Michishita, et al. *Cell* 72:857–867 (1993)]. Three additional putative cation binding sites in CD11b and CD11c are conserved in the $\alpha_d$ sequence at amino acids 465–474, 518–527, and 592–600 in clone 19A2 (SEQ ID NO: 1). The $\alpha_d$ I-domain is 36%, 62%, and 57% identical to the corresponding regions in CD11a, CD11b, and CD11c, respectively, and the relatively low sequence homology in this region suggests that $\alpha_d$ may interact with a set of extracellular proteins distinct from proteins with which other known $\beta_2$ integrins interact. Alternatively, the affinity of $\alpha_d$ for known $\beta_2$ integrin ligands, for example, ICAM-1, ICAM-2 and/or ICAM-R, may be distinct from that demonstrated for the other $\beta_2$ integrin/ICAM interactions. [See Example 12.]

Isolation of additional human $\alpha_d$ cDNA clones for sequence verification

In order to confirm the DNA sequence encoding human $\alpha_d$, additional human cDNAs were isolated by hybridization from a human splenic oligo dt-primed cDNA library (Invitrogen) in pcDNA/Amp (described in Example 5) which was size selected by agarose gel electrophoresis for cDNA greater than 3 kb in length. The probe for hybridization was derived from a 5' region of $\alpha_d$ as described below. Hybridization conditions were the same as described above for the isolation of the initial human $\alpha_d$ clone, except that following hybridization, filters were washed twice in 2× SSC/0.1% SDS at room temperature and once in 2× SSC/ 0.1% SDS at 42° C. Filters were exposed to Kodak X-Omat AR film overnight.

The 5' $\alpha_d$ hybridization probe was generated by PCR from the 19A2 clone using primers CD11c 5' For (SEQ ID NO: 94) and CD11c 5' Rev (SEQ ID NO: 95) under the following conditions. Samples were held at 94° C. for four minutes and subjected to 30 cycles of the temperature step sequence i) 94° C., for 15 seconds; ii) 5° C., for 30 seconds; and iii) 72° C., for 1 minute in a Perkin-Elmer 9600 thermocycler.

CD11c 5' For: (5')CTGGTCTGGAGGTGCCTTCCTG(3') (SEQ ID NO: 94)

CD11c 5' Rev: (5')CCTGAGCAGGAGCACCTGGCC(3') (SEQ ID NO: 95)

The amplification product was purified using the BioRad (Hercules, Calif.) Prep-A-Gene kit according to manufacturer's suggested protocol. The resulting 5' $\alpha_d$ probe was approximately 720 bases long, corresponding to the region from nucleotide 1121 to nucleotide 1839 in SEQ ID NO: 1. The purified DNA (approximately 50 ng) was labeled with $^{32}$P-dCTP using a Boehringer Mannheim (Indianapolis, Ind.) Random Prime Labeling kit according to manufacturer's suggested protocol. Unincorporated isotope was removed using Centrisep Spin Columns (Princeton Separations, Adelphia, N.J.) according to manufacturer's suggested protocol. Labeled probe was added to the filters in a prehybridization solution containing 45% formamide and incubation allowed to proceed overnight at 50° C. Following incubation, the filters were washed as described above.

Thirteen colonies gave signals on duplicate lifts. Positive colonies were picked from master plates, diluted in LBM and carbenicillin (100 $\mu$g/ml) and plated at varying dilutions onto Hybond (Amersham) filters. Duplicate filters were hybridized with the same solution from the primary hybridization and following hybridization, the filters were washed at a final stringency of 2× SSC/0.1% SDS at 42° C. and exposed to film.

Ten of the originally identified thirteen positive colonies were confirmed in the secondary screen. Of these ten clones, two (designated A7.Q and A8.Q) were sequenced and determined to encode human $\alpha_d$. Clone A7.Q was found to be approximately 2.5 kb in length, including a 5' leader, part of a coding region, and an additional 60 bases of 5' untranslated sequence. The incomplete coding region was determined to have resulted from an aberrantly spliced intron region at corresponding nucleotide 2152 of SEQ ID NO: 1. Clone A8.Q was determined to be approximately 4 kb in length, spanning the entire $\alpha_d$ coding region and also including an intron sequence at corresponding base 305 of SEQ ID NO: 1. In comparison to the originally isolated $\alpha_d$ clone (SEQ ID NO: 1), one difference was observed in that both A7.Q and A8.Q clones were determined to have a three base CAG codon insertion occurring at base 1495. Sequences for clones A7.Q AND A8.Q are set out in SEQ ID NOs: 96 and 97, respectively, and a composite human sequence derived from clones A7.Q and A8.Q, and its corresponding deduced amino acid sequence, are set out in SEQ ID NOs: 98 and 99, respectively.

EXAMPLE 6

Northern Analysis of Human $\alpha_d$ Expression in Tissues

In order to determine the relative level of expression and tissue specificity of $\alpha_d$, Northern analysis was performed using fragments from clone 19A2 as probes. Approximately 10 $\mu$g of total RNA from each of several human tissues or cultured cell lines were loaded on a formaldehyde agarose gel in the presence of 1 $\mu$g of ethidium bromide. After electrophoresis at 100 V for 4 hr, the RNA was transferred to a nitrocellulose membrane (Schleicher & Schuell) by wicking in 10× SSC overnight. The membrane was baked 1.5 hr at 80° C. under vacuum. Prehybridization solution containing 50% formamide in 3-(N-morpholino)propane sulfonic acid (MOPS) buffer was used to block the membrane for 3 hr at 42° C. Fragments of clone 19A2 were labeled with the Boehringer Mannheim Random Prime kit according to the manufacturer's instructions including both $\alpha P^{32}dCTP$ and $\alpha P^{32}dTTP$. Unincorporated label was removed on a Sephadex G25 column in TE buffer. The membrane was probed with $1.5 \times 10^6$ counts per ml of prehybridization buffer. The blot was then washed successively with 2× SSC/0.1% SDS at room temperature, 2× SSC/0.1% SDS at 42° C., 2× SSC/0.1% SDS at 50° C., 1× SSC/0.1% SDS at 50° C., 0.5× SSC/0.1% SDS at 50° C. and 0.1× SSC/0.1% SDS at 50° C. The blot was then exposed to film for 19 hr.

Hybridization using a BstXI fragment from clone 19A2 (corresponding to nucleotides 2011 to 3388 in SEQ ID NO: 1) revealed a weak signal in the approximately 5 kb range in liver, placenta, thymus, and tonsil total RNA. No signal was detected in kidney, brain or heart samples. The amount of RNA present in the kidney lane was minimal, as determined with ethidium bromide staining.

When using a second fragment of clone 19A2 (encompassing the region from bases 500 to 2100 in SEQ ID NO: 1), RNA transcripts of two different sizes were detected in a human multi-tissue Northern (MTN) blot using polyA$^+$ RNA (Clontech). An approximately 6.5 kb band was observed in spleen and skeletal muscle, while a 4.5 kb band was detected in lung and peripheral blood leukocytes. The variation in sizes observed could be caused by tissue specific polyadenylation, cross reactivity of the probe with other integrin family members, or hybridization with alternatively spliced mRNAs.

Northern analysis using a third fragment from clone 19A2, spanning nucleotides 2000 to 3100 in SEQ ID NO: 1, gave results consistent with those using the other clone 19A2 fragments.

RNA from three myeloid lineage cell lines was also probed using the fragments corresponding to nucleotides 500 to 2100 and 2000 to 3100 in SEQ ID NO: 1. A THP-1 cell line, previously stimulated with PMA, gave a diffuse signal in the same size range (approximately 5.0 kb), with a slightly stronger intensity than the tissue signals. RNA from unstimulated and DMSO-stimulated HL-60 cells hybridized with the $\alpha_d$ probe at the same intensity as the tissue samples, however, PMA treatment seemed to increase the signal intensity. Since PMA and DMSO drive HL-60 cell differentiation toward monocyte/macrophage and granulocyte pathways, respectively, this result suggests enhanced $\alpha_d$ expression in monocyte/macrophage cell types. U937 cells expressed the $\alpha_d$ message and this signal did not increase with PMA stimulation. No band was detected in Molt, Daudi, H9, JY, or Jurkat cells.

EXAMPLE 7

Transient Expression of Human $\alpha_d$ Constructs

A. Generation of expression constructs

The human clone 19A2 lacks an initiating methionine codon and possibly some of the 5' signal sequence. Therefore, in order to generate a human expression plasmid containing 19A2 sequences, two different strategies were used. In the first, two plasmids were constructed in which signal peptide sequences derived from genes encoding either CD11b or CD11c were spliced into clone 19A2 to generate a chimeric $\alpha_d$ sequence. In the second approach, a third plasmid was constructed in which an adenosine base was added at position 0 in clone 19A2 to encode an initiating methionine.

The three plasmids contained different regions which encoded the 5' portion of the $\alpha_d$ sequence or the chimeric $\alpha_d$ sequence. The $\alpha_d$ region was PCR amplified (see conditions in Example 2) with a specific 3' primer BamRev (set out below in SEQ ID NO: 26) and one of three 5' primers. The three 5' primers contained in sequence: (1) identical non-specific bases at positions 1–6 allowing for digestion, an EcoRI site from positions 7–12 and a consensus Kozak sequence from positions 13–18; (2) a portion of the CD11b (primer ER1B) or CD11c (primer ER1C) signal sequence, or an adenosine (primer ER1D); and (3) an additional 15–17 bases specifically overlapping 5' sequences from clone 19A2 to allow primer annealing. Primers ER1B, ER1C or ER1D are set out in SEQ ID NOS: 27, 28 or 29, respectively, where the initiating methionine codon is underlined and the EcoRI site is double underlined.

5'-CCACTGTCAGGATGCCCGTG-3' (SEQ ID NO: 26)
5'-AGTTACGAATTCGCCACCATGGCTCTACGGGTG CTTCTTCTG-3' (SEQ ID NO: 27)
5'-AGTTACGAATTCGCCACCATGACTCGGACTGTGC TTCTTCTG-3' (SEQ ID NO: 28)
5'-AGTTACGAATTCGCCACCATGACCTTCGGCAC TGTG-3' (SEQ ID NO: 29)

The resulting PCR product was digested with EcoRI and BamHI.

All three plasmids contained a common second $\alpha_d$ region (to be inserted immediately downstream from the 5' region described in the previous paragraph) including the 3' end of the $\alpha_d$ clone. The second $\alpha_d$ region, which extended from nucleotide 625 into the XbaI site in the vector 3' polylinker region of clone 19A2, was isolated by digestion of clone 19A2 with BamHI and XbaI.

Three ligation reactions were prepared in which the 3' $\alpha_d$ BamHI/XbaI fragment was ligated to one of the three 5' $\alpha_d$ EcoRI/BamHI fragments using Boehringer Mannheim ligase buffer and T4 ligase (1 unit per reaction). After a 4 hour incubation at 14° C., an appropriate amount of vector pcDNA.3 (Invitrogen) digested with EcoRI and XbaI was added to each reaction with an additional unit of ligase. Reactions were allowed to continue for another 14 hours. One tenth of the reaction mixture was then transformed into competent XL-1 Blue cells. The resulting colonies were cultured and the DNA isolated as in Example 5. Digestion with EcoRI identified three clones which were positive for that restriction site, and thus, the engineered signal sequences. The clones were designated pATM.B1 (CD11b/$\alpha_d$, from primer ER1B), pATM.C10 (CD11c/$\alpha_d$, from primer ER1C) and pATM.D12 (adenosine/$\alpha_d$ from primer ER1d). The presence of the appropriate signal sequences in each clone was verified by nucleic acid sequencing.

B. Transfection of COS Cells

Expression from the $\alpha_d$ plasmids discussed above was effected by cotransfection of COS cells with the individual plasmids and a CD18 expression plasmid, pRC.CD18. As a positive control, COS cells were also co-transfected with the plasmid pRC.CD18 and a CD11a expression plasmid, pDC.CD11A.

Cells were passaged in culture medium (DMEM/ 10%FBS/pen-strep) into 10 cm Corning tissue culture-treated petri dishes at 50% confluency 16 hours prior to transfection. Cells were removed from the plates with Versene buffer (0.5 mM NaEDTA in PBS) without trypsin for all procedures. Before transfection, the plates were washed once with serum-free DMEM. Fifteen micrograms of each plasmid were added to 5 ml transfection buffer (DMEM with 20 µg/ml DEAE-Dextran and 0.5 mM chloroquine) on each plate. After 1.5 hours incubation at 37° C., the cells were shocked for 1 minute with 5 ml DMEM/ 10% DMSO. This DMSO solution was then replaced with 10 ml/plate culture medium.

Resulting transfectants were analyzed by ELISA, FACS, and immunoprecipitation as described in Examples 8, 9, and 10.

EXAMPLE 8
ELISA Analysis of COS Transfectants

In order to determine if the COS cells co-transfected with CD18 expression plasmid pRC.CD 18 and an $\alpha_d$ plasmid expressed $\alpha_d$ on the cell surface in association with CD18, ELISAs were performed using primary antibodies raised against CD18 (e.g., TS1/18 purified from ATCC HB203). As a positive control, ELISAs were also performed on cells co-transfected with the CD18 expression plasmid and a CD11a expression plasmid, pDC.CD 11A. The primary antibodies in this control included CD18 antibodies and anti-CD11a antibodies (e.g., TS1/22 purified from ATCC HB202).

For ELISA, cells from each plate were removed with Versene buffer and transferred to a single 96-well flat-bottomed Corning tissue culture plate. Cells were allowed to incubate in culture media 2 days prior to assay. The plates were then washed twice with 150 µl/well D-PBS/0.5% teleost skin gelatin (Sigma) solution. This buffer was used in all steps except during the development. All washes and incubations were performed at room temperature. The wells were blocked with gelatin solution for 1 hour. Primary antibodies were diluted to 10 µl/ml in gelatin solution and 50 µl were then added to each well. Triplicate wells were set up for each primary antibody. After 1 hour incubation, plates were washed 3× with 150 µl/well gelatin solution. Secondary antibody (goat anti-mouse Ig/HRP-Fc specific [Jackson, West Grove, Pa.]) at a 1:3500 dilution was added at 50 µl/well and plates were incubated for 1 hour. After three washes, plates were developed for 20 minutes with 100 µl/well o-phenyldiamine (OPD) (Sigma) solution (1 mg/ml OPD in citrate buffer) before addition of 50 µl/well 15% sulfuric acid.

Analysis of transfectants in the ELISA format with anti-CD18 specific antibodies revealed no significant expression above background in cells transfected only with the plasmid encoding CD18. Cells co-transfected with plasmid containing CD11a and CD18 showed an increase in expression over background when analyzed with CD18 specific antibodies or with reagents specific for CD11a. Further analysis of cells co-transfected with plasmids encoding CD18 and one of the aid expression constructs (pATM.C10 or pATM.D12) revealed that cell surface expression of CD18 was rescued by concomitant expression of $\alpha_d$. The increase in detectable CD18 expression in COS cells transfected with pATM.C10 or pATM.D12 was comparable to that observed in co-transfected CD11a/CD18 positive control cells.

EXAMPLE 9
FACS Analysis of COS Transfectants

For FACS analysis, cells in petri dishes were fed with fresh culture medium the day after transfection and allowed to incubate 2 days prior to the assay. Transfectant cells were removed from the plates with 3 ml Versene, washed once with 5 ml FACS buffer (DMEM/2% FBS/0.2% sodium azide) and diluted to 500,000 cells/sample in 0.1 ml FACS buffer. Ten microliters of either 1 mg/ml FITC-conjugated CD18, CD11a, or CD11b specific antibodies (Becton Dickinson) or 800 µg/ml CFSE-conjugated murine 23F2G (anti-CD18) (ATCC HB11081) were added to each sample. Samples were then incubated on ice for 45 minutes, washed 3× with 5 ml/wash FACS buffer and resuspended in 0.2 ml FACS buffer. Samples were processed on a Becton Dickinson FACscan and the data analyzed using Lysys II software (Becton Dickinson).

COS cells transfected with CD18 sequences only did not stain for CD18, CD11a or CD11b. When co-transfected with CD11a/CD18, about 15% of the cells stained with antibodies to CD11a or CD18. All cells transfected with CD18 and any $\alpha_d$ construct resulted in no detectable staining for CD11a and CD11b. The pATM.B1, pATM.C10 and pATM.D12 groups stained 4%, 13% and 8% positive for CD18, respectively. Fluorescence of the positive population in the CD11a/CD18 group was 4-fold higher than background. In comparison, the co-transfection of $\alpha_d$ constructs with the CD18 construct produced a positive population that showed a 4-to 7-fold increase in fluorescence intensity over background.

EXAMPLE 10
Biotin-Labeled Immunoprecipitation of Human $\alpha_d$/CD18 Complexes from Co-transfected COS Cells Immunoprecipitation was attempted on cells co-transfected with CD18 and each of the $\alpha_d$ expression plasmids separately described in Example 7 in order to determine if $\alpha_d$ could be isolated as part of the $\alpha\beta$ heterodimer complex characteristic of integrins.

Transfected cells (1–3×10$^8$ cells/group) were removed from petri dishes with Versene buffer and washed 3 times in 50 ml/group D-PBS. Each sample was labeled with 2 mg Sulpho-NHS Biotin (Pierce, Rockford, Ill.) for 15 minutes at room temperature. The reaction was quenched by washing 3 times in 50 ml/sample cold D-PBS. Washed cells were resuspended in 1 ml lysis buffer (1% NP40, 50 mM Tris-HCl, pH 8.0, 0.2M NaCl, 2 mM Ca$^{++}$, 2 mM Mg$^{++}$, and protease inhibitors) and incubated 15 minutes on ice. Insoluble material was pelleted by centrifugation at 10,000 g for 5 minutes, and the supernatant removed to fresh tubes. In order to remove material non-specifically reactive with mouse immunoglobulin, a pre-clearance step was initially performed. Twenty-five micrograms of mouse immunoglobulin (Cappel, West Chester, Pa.) was incubated with supernatants at 4° C. After 2.5 hr, 100 µl (25 µg) rabbit anti-mouse Ig conjugated Sepharose (prepared from Protein A Sepharose 4B and rabbit anti-mouse IgG, both from Zymed, San Francisco, Calif.) was added to each sample; incubation was continued at 4° C. with rocking for 16 hours. Sepharose beads were removed from the supernatants by centrifugation. After pre-clearance, the supernatants were then treated with 20 µg anti-CD18 antibody (TS1.18) for 2 hours at 4° C. Antibody/antigen complexes were isolated from supernatants by incubation with 100 µl/sample rabbit anti-mouse/ Protein A-sepharose preparation described above. Beads were washed 4 times with 10 mM HEPES, 0.2M NaCl, and 1% Triton-X 100. Washed beads were pelleted and boiled for 10 minutes in 20 µl 2× Laemmli sample buffer with 2% β-mercaptoethanol. Samples were centrifuged and run on an 8% prepoured Novex polyacrylamide gel (Novex) at 100 V for 30 minutes. Protein was transferred to nitrocellulose membranes (Schleicher & Schuell) in TBS-T buffer at 200 mAmps for 1 hour. Membranes were blocked for 2 hr with 3% BSA in TBS-T. Membranes were treated with 1:6000 dilution of Strep-avidin horse radish peroxidase (POD) (Boehringer Mannheim) for 1 hour, followed by 3 washes in TBS-T. The Amersham Enhanced Chemiluminescence kit was then used according to the manufacturer's instructions to develop the blot. The membrane was exposed to Hyperfilm MP (Amersham) for 0.5 to 2 minutes.

Immunoprecipitation of CD18 complexes from cells transfected with pRC.CD18 and either pATM.B1, pATM.C10 or pATM.D12 revealed surface expression of a heterodimeric species consisting of approximately 100 kD β chain, consistent with the predicted size of CD18, and an α chain of approximately 150 kD, corresponding to $\alpha_d$.

EXAMPLE 11
Stable Transfection of Human $\alpha_d$ in Chinese Hamster Ovary Cells To determine whether $\alpha_d$ is expressed on the cell surface as a heterodimer in association with CD18, cDNAs encoding each chain were both transiently and stably transfected into a cell line lacking both $\alpha_d$ and CD18.

For these experiments, $\alpha_d$ cDNA was augmented with additional leader sequences and a Kozak consensus sequence, as described in Example 7, and subcloned into expression vector pcDNA3. The final construct, designated pATM.D12, was co-transfected with a modified commercial vector, pDC1.CD18 encoding human CD18 into dihydrofolate reductase (DHFR)⁻Chinese hamster ovary (CHO) cells. The plasmid pDC1.CD18 encodes a DHFR⁺ marker and transfectants can be selected using an appropriate nucleoside-deficient medium. The modifications which resulted in pDC1.CD18 are as follows.

The plasmid pRC/CMV (Invitrogen) is a mammalian expression vector with a cytomegalovirus promoter and ampicillin resistance marker gene. A DHFR gene from the plasmid pSC1190-DHFR was inserted into pRC/CMV 5' of the SV40 origin of replication. In addition, a polylinker from the 5' region of the plasmid pHF2G-DHF was ligated into the pRC/CMV/DHFR construct, 3' to the DHFR gene. CD18 encoding sequences are subsequently cloned into the resulting plasmid between the 5' flanking polylinker region and the bovine growth hormone poly A encoding region.

Surface expression of CD18 was analyzed by flow cytometry using the monoclonal antibody TS1/18. Heterodimer formation detected between $\alpha_d$ and CD18 in this cell line was consistent with the immunoprecipitation described in Example 10 with transient expression in COS cells.

EXAMPLE 12
Human $\alpha_d$ binds to ICAM-R in a CD18-dependent fashion

In view of reports that demonstrate interactions between the leukocyte integrins and intercellular adhesion molecules (ICAMs) which mediate cell-cell contact [Hynes, *Cell* 69:11–25 (1992)], the ability of CHO cells expressing $\alpha_d$/CD18 to bind ICAM-1, ICAM-R, or VCAM-1 was assessed by two methods.

In replicate assays, soluble ICAM-1, ICAM-R, or VCAM-1 IgG1 fusion proteins were immobilized on plastic and the ability of $\alpha_d$/CD18 CHO transfected cells to bind the immobilized ligand was determined. Transfected cells were labeled internally with calcein, washed in binding buffer (RPMI with 1% BSA), and incubated in either buffer only (with or without 10 ng/ml PMA) or buffer with anti-CD18 monoclonal antibodies at 10 μg/ml. Transfected cells were added to 96-well Immulon 4 microtiter plates previously coated with soluble ICAM-1/IgG1, ICAM-R/IgG1 or VCAM-1/IgG1 fusion protein, or bovine serum albumin (BSA) as a negative control. Design of the soluble forms of these adhesion molecules is described and fully disclosed in co-pending and co-owned U.S. patent application Ser. No. 08/102,852, filed Aug. 5, 1993. Wells were blocked with 1% BSA in PBS prior to addition of labeled cells. After washing the plates by immersion in PBS with 0.1% BSA for 20 minutes, total fluorescence remaining in each well was measured using a Cytofluor 2300 (Millipore, Milford, Mass.).

In experiments with immobilized ICAMs, $\alpha_d$/CD18 co-transfectants consistently showed a 3–5 fold increase in binding to ICAM-R/IgG1 wells over BSA coated wells. The specificity and CD18-dependence of this binding was demonstrated by the inhibitory effects of anti-CD18 antibody TS 1/18. The binding of cells transfected with CD11a/CD18 to ICAM-1/IgG1 wells was comparable to the binding observed with BSA coated wells. CD11a/CD18 transfected cells showed a 2–3 fold increase in binding to ICAM-1/IgG1 wells only following pretreatment with PMA. PMA treatment of $\alpha_d$/CD18 transfectants did not affect binding to ICAM-1/IgG1 or ICAM-R/IgG1 wells. No detectable binding of $\alpha_d$/CD18 transfectants to VCAM-1/IgG1 wells was observed.

Binding of $\alpha_d$/CD18-transfected cells to soluble ICAM-1/IgG1, ICAM-R/IgG1, or VCAM-1/IgG1 fusion proteins was determined by flow cytometry. Approximately one million $\alpha_d$/CD18-transfected CHO cells (grown in spinner flasks for higher expression) per measurement were suspended in 100 μl binding buffer (RPMI and 1% BSA) with or without 10 μg/ml anti-CD18 antibody. After a 20 minute incubation at room temperature, the cells were washed in binding buffer and soluble ICAM-1/IgG1 or ICAM-R/IgG1 fusion protein was added to a final concentration of 5 μg/ml. Binding was allowed to proceed for 30 minute at 37° C., after which the cells were washed three times and resuspended in 100 μl binding buffer containing FITC-conjugated sheep anti-human IgG1 at a 1:100 dilution. After a 30 minute incubation, samples were washed three times and suspended in 200 μl binding buffer for analysis with a Becton Dickinson FACScan.

Approximately 40–50% of the $\alpha_d$/CD18 transfectants indicated binding to ICAM-R/IgG1, but no binding to ICAM-1/IgG1 or VCAM-1/IgG1 proteins. Pretreatment of transfected cells with PMA has no effect on $\alpha_d$/CD18 binding to either ICAM-1/IgG1, ICAM-R/IgG1 or VCAM-1/IgG1, which was consistent with the immobilized adhesion assay. Binding by ICAM-R was reduced to background levels after treatment of $\alpha_d$/CD18 transfectants with anti-CD18 antibody TS1/18.

The collective data from these two binding assays illustrate that $\alpha_d$/CD18 binds to ICAM-R and does so preferentially as compared to ICAM-1 and VCAM-1. The $\alpha_d$/CD18 binding preference for ICAM-R over ICAM-1 is opposite that observed with CD11a/CD18 and CD11b/CD18. Thus modulation of $\alpha_d$/CD18 binding may be expected to selectively affect normal and pathologic immune function where ICAM-R plays a prominent role. Moreover, results of similar assays, in which antibodies immunospecific for various extracellular domains of ICAM-R were tested for their ability to inhibit binding of ICAM-R to $\alpha_d$/CD18 transfectants, indicated that $\alpha_d$/CD18 and CD11a/CD18 interact with different domains of ICAM-R.

The failure of CD11a/CD18 to bind ICAM-1/IgG1 or ICAM-R/IgG1 in solution suggests that the affinity of binding between CD11a/CD18 and ICAM-1 or ICAM-R is too low to permit binding in solution. Detection of $\alpha_d$/CD18 binding to ICAM-R/IgG 1, however, suggests an unusually high binding affinity.

$\alpha_d$ Binding to iC3b

Complement component C3 can be proteolytically cleaved to form the complex iC3b, which initiates the alternative pathway of complement activation and leads ultimately to cell-mediated destruction of a target. Both CD11b and CD11c have been implicated in iC3b binding and subsequent phagocytosis of iC3b-coated particles. A peptide fragment in the CD11b I domain has recently been identified as the site of iC3b interaction [Ueda, et al., *Proc. Natl. Acad. Sci.* (USA) 91:10680–10684 (1994)]. The region of iC3b binding is highly conserved in CD11b, CD11c, and $\alpha_d$, suggesting an $\alpha_d$/iC3b binding interaction.

Binding of $\alpha_d$ to iC3b is performed using transfectants or cell lines naturally expressing $\alpha_d$ (for example, PMA-stimulated HL60 cells) and iC3b-coated sheep red blood cells (sRBC) in a rosette assay [Dana, et al., *J. Clin. Invest.* 73:153–159 (1984)]. The abilities of $\alpha_d$/CD18 CHO transfectants, VLA4-CHO transfectants (negative control) and PMA-stimulated HL60 cells (positive control) to form rosettes are compared in the presence and absence of an anti-CD18 monoclonal antibody (for example TS1/18.1).

EXAMPLE 13
Screening by Scintillation Proximity Assay

Specific inhibitors of binding between the $\alpha_d$ ligands of the present invention and their binding partners ($\alpha_d$ ligand/anti-ligand pair) may be determined by a variety of means, such as scintillation proximity assay techniques as generally described in U.S. Pat. No. 4,271,139, Hart and Greenwald, *Mol. Immunol.* 12:265–267 (1979), and Hart and Greenwald, *J. Nuc. Med.* 20:1062–1065 (1979), each of which is incorporated herein by reference.

Briefly, one member of the $\alpha_d$ ligand/anti-ligand pair is bound to a solid support either directly or indirectly. Indirect capture would involve a monoclonal antibody, directly bound to the support, which recognizes a specific epitope at the C-terminus of the soluble integrin β chain protein. This epitope would be either the hemagglutinin protein or the mycobacterial IIIE9 epitope [Anderson, et al., *J. Immunol.* 141:607–613 (1988). A fluorescent agent is also bound to the support. Alternatively, the fluorescent agent may be integrated into the solid support as described in U.S. Pat. No. 4,568,649, incorporated herein by reference. The non-support bound member of the $\alpha_d$ ligand/anti-ligand pair is labeled with a radioactive compound that emits radiation capable of exciting the fluorescent agent. When the ligand binds the radiolabeled anti-ligand, the label is brought sufficiently close to the support-bound fluorescer to excite the fluorescer and cause emission of light. When not bound, the label is generally too distant from the solid support to excite the fluorescent agent, and light emissions are low. The emitted light is measured and correlated with binding between the ligand and the anti-ligand. Addition of a binding inhibitor to the sample will decrease the fluorescent emission by keeping the radioactive label from being captured in the proximity of the solid support. Therefore, binding inhibitors may be identified by their effect on fluorescent emissions from the samples. Potential anti-ligands to $\alpha_d$ may also be identified by similar means.

EXAMPLE 14
Soluble Human $\alpha_d$ Expression Constructs

The expression of full-length, soluble human $\alpha_d$/CD18 heterodimeric protein provides easily purified material for immunization and binding assays. The advantage of generating soluble protein is that it can be purified from supernatants rather than from cell lysates (as with full-length membrane-bound $\alpha_d$/CD18); recovery in therefore improved and impurities reduced.

The soluble $\alpha_d$ expression plasmid was constructed as follows. A nucleotide fragment corresponding to the region from bases 0 to 3161 in SEQ ID NO: 1, cloned into plasmid pATM.D12, was isolated by digestion with HindIII and AatII. A PCR fragment corresponding to bases 3130 to 3390 in SEQ ID NO: 1, overlapping the HindIII/AatII fragment and containing an addition MluI restriction site at the 3' terminus, was amplified from pATM.D12 with primers sHAD.5 and sHAD.3 set out in SEQ ID NOS: 30 and 31, respectively.

5'-TTGCTGACTGCCTGCAGTTC-3' (SEQ ID NO: 30)
5'-GTTCTGACGCGTAATGGCATTGTAGACCTCGTCT TC-3' (SEQ ID NO: 31)

The PCR amplification product was digested with AatII and MluI and ligated to the HindIII/AatII fragment. The resulting product was ligated into HindIII/MluI-digested plasmid pDC1.s.

This construct is co-expressed with soluble CD18 in stably transfected CHO cells, and expression is detected by autoradiographic visualization of immunoprecipitated CD18 complexes derived from $^{35}$S-methionine labeled cells. The construct is also co-expressed with CD18 in 293 cells [Berman, et al., *J. Cell. Biochem.* 52:183–195 (1993)].

Soluble full-length $\alpha_d$ construct

In order to facilitate expression and purification of an intact $\alpha_d$/CD18 heterodimer, soluble $\alpha_d$ and CD18 expression plasmids will be constructed to include a "leucine zipper" fusion sequence which should stabilize the heterodimer during purification [Chang, et al., *Proc. Natl. Acad. Sci.* (USA), 91:11408–11412 (1994)]. Briefly, DNA encoding the acidic and basic amino acid strands of the zipper have been generated by primer annealing using oligonucleotides described in Chang, et al. The DNA sequences have been further modified to include additional Mlu1 and Xba1 restriction sites at the 5' and 3' ends, respectively, of the DNA to facilitate subcloning into $\alpha_d$ or CD18 expression constructs previously described. In addition, sequences representing either hemagglutinin protein or a polyhistidine sequence have been added, as well as a stop codon inserted after the Xba1 site. The hemagglutinin or polyhistidine sequences are incorporated to facilitate affinity purification of the expressed protein. Sequences encoding the basic strand of the zipper are incorporated on the plasmid vector expressing CD18; the acidic strand is inserted on the α chain construct. Upon expression of the modified $\alpha_d$ and CD18 proteins in a host cell, it is presumed that interaction between the acidic and basic strands of the zipper structure will stabilize the heterodimer and permit isolation of the intact $\alpha_d$/CD 18 molecule by affinity purification as described above.

Soluble Human $\alpha_d$ I Domain Expression Constructs

It has previously been reported that the I domain in CD11a can be expressed as an independent structural unit that maintains ligand binding capabilities and antibody recognition [Randi and Hogg, *J. Biol. Chem.* 269:12395–12398 (1994); Zhout, et al., *J. Biol. Chem.* 269:17075–17079 (1994); Michishita, et al., *Cell* 72:857–867 (1993)]. To generate a soluble fusion protein comprising the $\alpha_d$ I domain and human IgG4, the $\alpha_d$ I domain is amplified by PCR using primers designed to add flanking BamHI and XhoI restriction sites to facilitate subcloning. These primers are set out in SEQ ID NOS: 32 and 33 with restriction sites underlined.

5'-ACGTATGCAGGATCCCATCAAGAGATGGACATC GCT-3' (SEQ ID NO: 32)
5'-ACTGCATGTCTCGAGGCTGAAGCCTTCTTGGG ACATC-3' (SEQ ID NO: 33)

The C nucleotide immediately 3' to the BamHI site in SEQ ID NO: 32 corresponds to nucleotide 435 in SEQ ID NO: 1; the G nucleotide 3' to the XhoI site in SEQ ID NO: 33 is complementary to nucleotide 1067 in SEQ ID NO: 1. The amplified I domain is digested with the appropriate enzymes, the purified fragment ligated into the mammalian expression vector pDCs and the prokaryotic expression vector pGEX-4T-3 (Pharmacia) and the I domain fragment sequenced. The fusion protein is then expressed in COS, CHO or E. coli cells transfected or transformed with an appropriate expression construct.

Given the affinity of $\alpha_d$ for ICAM-R, expression of the $\alpha_d$ I domain may be of sufficient affinity to be a useful inhibitor of cell adhesion in which $\alpha_d$ participates.

Analysis of Human $\alpha_d$ I Domain/IgG4 Fusion Proteins

Protein was resolved by SDS-PAGE under reducing and non-reducing conditions and visualized by either silver staining or Coomassie staining. Protein was then transferred to Immobilon PVDF membranes and subjected to Western blot analysis using anti-human IgG monoclonal antibodies or anti-bovine Ig monoclonal antibodies.

Protein detected was determined to migrate at about 120 kD under non-reducing conditions and at about 45 kD under reducing conditions. Minor bands were also detected on non-reducing gels at approximately 40–50 kD which were reactive with the anti-human, but not anti-bovine, antibodies. A 200 kD minor band was determined to be bovine Ig by Western blot.

Binding Assays Using I Domain Expression Products

The ability of the I domain to specifically recognize ICAM-R/IgG chimeric protein was tested in an ELISA format. Serial dilutions of $\alpha_d$ I domain IgG4 fusion protein ($I\alpha_d/IgG^4$) in TBS were incubated with ICAM-1/IgG, ICAM-R/IgG, VCAM-1/IgG, or an irrelevant IgG1 myeloma protein immobilized on Immulon IV RIA/EIA plates. CD11a I domain/IgG chimeric protein and human IgG4/kappa myeloma protein were used as negative controls. Bound IgG4 was detected with the biotinylated anti-IgG4 monoclonal antibody HP6023 followed by addition of strepavidin-peroxidase conjugate and development with substrate o-phenyldiamine.

In repeated assays, no binding of the CD11a/IgG4 protein or the IgG4 myeloma protein was detected with any of the immobilized proteins. The $I\alpha_d/IgG^4$ protein did not bind to fish skin gelatin or bovine serum albumin blocking agents, human IgG1, or ICAM-1/IgG. A two to three fold increase in binding signal over background was detected in ICAM-R/IgG protein coated wells using 1–5 µg/ml concentrations of $I\alpha_d/IgG4$ protein. The signal in VCAM-1/IgG protein coated wells was 7–10 fold higher than background. In previous assays, $\alpha_d/CD18$ transfected CHO cells did not bind VCAM-1/IgG protein, suggesting that VCAM-1 binding may be characteristic of isolated I domain amino acid sequences.

Additional $\alpha_d$ I domain constructs

Additional $\alpha_d$ I domain constructs are generated in the same fashion as the previous construct, but incorporating more amino acids around the $\alpha_d$ I domain. Specific constructs include: i) sequences from exon 5 (amino acids 127–353 in SEQ ID NO: 2), preceding the current construct, ii) the EF-hand repeats (amino acids 17–603 in SEQ ID NO: 2) following the I domain, and iii) the alpha chain truncated at the transmembrane region (amino acids 17–1029 in SEQ ID NO: 2), with an IgG4 tail for purification and detection purposes. These constructs are ligated into either the mammalian expression vector pDCS1 or the prokaryotic expression vector pGEX-4T-3 (Pharmacia) and the I domain sequenced. The fusion proteins are then be expressed in COS, CHO, or E. coli cells transformed or transfected with an appropriate expression construct. Protein are purified on a ProSepA column (Bioprocessing Limited, Durham, England), tested for reactivity with the anti-IgG4 monoclonal antibody HP6023 and visualized on polyacrylamide gels with Coomassie staining.

In order to construct an expression plasmid for the entire $\alpha_d$ polypeptide, pATM.D12, described supra, is modified to express an $\alpha_d$-IgG4 fusion protein by the following method. IgG4 encoding DNA is isolated from the vector pDCS1 by PCR using primers which individually incorporate a 5' AatII restriction site (SEQ ID NO: 89) and a 3' Xba1 restriction site (SEQ ID NO: 90).

5'-CGCTGTGACGTCAGAGTTGAGTCCAAATATGG-3' (SEQ ID NO: 89)

5'-GGTGACACTATAGAATAGGGC-3' (SEQ ID NO: 90)

Plasmid pATM.D12 is digested with AatII and Xba1, and the appropriately digested and purified IgG4 PCR product ligated into the linear vector.

EXAMPLE 15

Production of Human $\alpha_d$-Specific Antibodies

A. Production of Monoclonal Antibodies

1. Transiently transfected cells from Example 7 were washed three times in Dulbecco's phosphate buffered saline (D-PBS) and injected at $5\times10^6$ cells/mouse into Balb/c mice with 50 µg/mouse muramyl dipeptidase (Sigma) in PBS. Mice were injected two more times in the same fashion at two week intervals. The pre-bleed and immunized serum from the mice were screened by FACS analysis as outlined in Example 9 and the spleen from the mouse with the highest reactivity to cells transfected with $\alpha_d/CD18$ was fused. Hybridoma culture supernatants were then screened separately for lack of reactivity against COS cells transfected with CD11a/CD18 and for reactivity with cells co-transfected with an $\alpha_d$ expression plasmid and CD18.

This method resulted in no monoclonal antibodies.

2. As an alternative for production of monoclonal antibodies, soluble $\alpha_d$ I domain/IgG4 fusion protein was affinity purified from supernatant of stably transfected CHO cells and used to immunize Balb/c mice as described above. Hybridomas were established and supernatants from these hybridomas were screened by ELISA for reactivity against $\alpha_d$ I domain fusion protein. Positive cultures were then analyzed for reactivity with full length $\alpha_d/CD18$ complexes expressed on CHO transfectants.

Mouse 1908 received three initial immunizations of $\alpha_d/CD18$ transfected CHO cells and two subsequent boosts with soluble $\alpha_d/CD18$ heterodimer. Two final immunizations included 50 µg/mouse $\alpha_d$ I domain/IgG4 fusion protein. The fusion produced 270 IgG-producing wells. Supernatant from 45 wells showed at least 7-fold higher binding to $I\alpha_d/IgG^4$ fusion protein than to human IgG4 by ELISA. None of the supernatants reacted to $\alpha_d/CD18$ transfected CHO cells as determined by FACS analysis.

To determine whether the supernatants were able to recognize integrin alpha subunit proteins in another context, fresh frozen splenic sections were stained with supernatants from 24 of the 45 wells. Three supernatants were determined to be positive: one stained large cells in the red pulp, while two others stained scattered cells in the red pulp and also trabeculae.

These supernatants were further analyzed by their ability to immunoprecipitate biotinylated CD18 complexes from either $\alpha_d/CD18$ transfected CHO cells or PMA-stimulated HL60 cells. Fusion wells with supernatants that recognized protein in detergent lysates (which should not be as conformationally constrained as protein expressed as heterodimers) were selected for further subcloning. Monoclonal antibodies which recognize protein in detergent may be more useful in immunoprecipitation of heterodimeric complexes from transfectants, tissues, and cell lines.

3. As another alternative to monoclonal antibody production, CD18 complexes were immunoprecipitated from human spleen lysates with the anti-CD18 monoclonal antibody 23F2G after preclearance of CD11a/CD18 (using monoclonal antibody TS2/4) and CD11b/CD18 (using monoclonal antibody Mo-1). Five Balb/c mice, ten to twelve weeks old, were immunized by subcutaneous injection with approximately 30 μg of resulting protein in complete Freund's adjuvant on day 0, followed by two boosts of 30 ug immunogen/mouse on days 28 and 43 in incomplete Freund's adjuvant. Test sera were drawn ten days following the final boost and reactivity was assessed by using 1:500 dilution of each serum to detect 1 μg/lane immunogen in a Western blot. Sera from three mice detected bands of approximately 95 and 150 kD; no signal was seen in lanes treated with a 1:50 dilution of preimmune sera. The 150 kD band was presumed to represent $\alpha_d$ in an in vivo glycosylation state. In addition, all post immune sera immunoprecipitated protein from lysates of biotinylated $\alpha_d$/CD18 CHO cells that migrated at appropriate molecular weights on SDS-PAGE to represent the heterodimer. From these results, mouse #2212 was selected and was further immunized by intraperitoneal injection on day 64 with 30 μg immunogen in PBS. The mouse was sacrificed four days later, and the spleen was sterilely removed.

A single-cell suspension was formed by grinding the spleen between the frosted ends of two glass microscope slides submerged in serum-free RPMI 1640 supplemented with 2 mM L-glutamine, 1 mM sodium pyruvate, 100 units/ml penicillin, and 100 μg/ml streptomycin (RPMI) (Gibco, Canada). The cell suspension was filtered through a sterile 70-mesh Nitex cell strainer (Becton Dickinson, Parsippany, N.J.), and the filtrate washed twice by centrifugation at 200× g for 5 minutes. The resulting pellet was resuspended in 20 ml serum-free RPMI. Thymocytes taken from three naive Balb/c mice were prepared in a similar manner.

Prior to fusion, NS-1 myeloma cells, kept in log phase in RPMI with 10% Fetalclone serum (FBS) (Hyclone Laboratories, Inc., Logan, Utah) for three days prior to fusion, were pelleted by centrifugation at 200× g for 5 minutes, washed twice as described in the foregoing paragraph, and counted. Approximately $2 \times 10^8$ spleen cells were combined with $4 \times 10^7$ NS-1 cells, and the resulting mixture pelleted by centrifugation at 200× g. The supernatant was discarded. The cell pellet dislodged by tapping the tube and 2 ml of 50% PEG 1500 in 75 mM Hepes (pH 8.0, 37° C.) (Boehringer Mannheim) was added over the course of one minute with stirring. An additional 14 ml of serum-free RPMI was subsequently added over the next seven minutes, followed by immediate addition of 16 ml RPMI. The resulting mixture was centrifuged at 200× g for 10 minutes and the supernatant was discarded. The pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and $1.5 \times 10^6$ thymocytes/ml, and dispensed into ten 96-well flat bottom tissue culture plates (Corning, United Kingdom) at 200 μl/well. Cells were fed on days 2, 4, and 6 days post-fusion by aspirating approximately 100 μl from each well with an 18 G needle (Becton Dickinson), and adding 100 μl/well plating medium described above, except containing 10 units/ml IL-6 and lacking thymocytes.

On day 7–10 post-fusion, supernatant from each well was screened by antibody capture ELISA, testing for the presence of mouse IgG. Immulon 4 plates (Dynatech, Cambridge, Mass.) were coated with 50 μl/well goat anti-mouse IgA, IgG, or IgM (Organon Teknika) diluted 1:5000 in 50 mM carbonate buffer, pH 9.6, at 4° C. Plates were washed 3× with PBS containing 0.5% Tween 20 (PBST) and 50 μl culture supernatant from each well was added. After incubation at 37° C. for 30 minutes, wells were washed with PBST as above, and 50 μl of horseradish peroxidase conjugated goat anti-mouse IgG(fc) (Jackson ImmunoResearch, West Grove, Pa.) diluted 1:3500 in PBST was added to each well. Plates were incubated as above, washed 4× with PBST and 100 μl substrate, consisting of 1 mg/ml o-phenylene diamine (Sigma) and 0.1 μl/ml 30% $H_2O_2$ in 100 mM Citrate, pH 4.5, was added. The color reaction was stopped after five minutes with addition of 50 μl 15% $H2SO_4$. Absorbance at 490 nm was determined for each well using a plate reader (Dynatech).

Hybridomas were further characterized as follows. Supernatants from IgG-producing cultures were analyzed by flow cytometry for reactivity to $\alpha_d$/CD18-transformed CHO cells but not to JY cells (a B-cell line positive for LFA-1, but not other $\beta_2$ integrins as observed in previous in-house staining experiments). Briefly, $5 \times 10^5$ $\alpha_d$/CD18-transformed CHO or $\alpha_d$/CD18⁻ JY cells were suspended in 50 μl RPMI containing 2% FBS and 10 mM $NaN_3$ (FACS buffer). Individual cell suspensions were added to 50 μl IgG positive hybridoma culture supernatant in wells of 96-well round bottomed plates (Coming). After a 30 minute incubation on ice, cells were washed twice by pelleting in a clinical centrifuge, supernatant from each well was discarded, and pellets resuspended in 200–300 μl FACS buffer. The last wash was replaced with 50 μl/well of a 1:100 dilution of a $F(ab')_2$ fragment of sheep anti-mouse IgG (H+L)-FITC conjugate (Sigma, St. Louis, Miss.) prepared in FACS Buffer. After incubation as described above, cells were washed twice with Dulbecco's PBS (D-PBS) supplemented with 10 mM $NaN_3$, and finally resuspended in D-PBS containing 1% paraformaldehyde. Samples were then transferred to polystyrene tubes for flow cytometric analysis (FACS) with a Becton Dickinson FACsan analyzer.

The fusion yielded four cultures deemed positive by both criteria. When the secondary screen was repeated on expanded supernatants approximately four days later, three of the four cultures remained positive. The three wells, designated 169A, 169B, 169D were cloned two to three times, successively, by doubling dilution in RPMI, 15% FBS, 100 mM sodium hypoxanthine, 16 mM thymidine, and 10 units/ml IL-6. Wells of clone plates were scored visually after four days and the number of colonies in the least dense wells were recorded. Selected wells of the each cloning were assayed by FACS after 7–10 days. Activity was found in two of the cultures, 169A and 169B. In the final cloning, positive wells containing single colonies were expanded in RPMI with 11% FBS. Antibody from clonal supernatants of 169A and 169B were isotyped using IsoStrip kit (Boehringer Mannheim) according to manufacturer instructions and found to be of the IgG1 isotype.

Immunoprecipitation of $\alpha_d$/CD18 complexes from CHO transfectants and PMA-stimulated HL60 cells was used as a tertiary screen for specificity. Hybridomas 169A and 169B precipitated appropriate bands from CHO lines, and a single α chain species of 150–160 kD from HL60 cells as determined by SDS-PAGE. Hybridomas 169A and 169B were deposited May 31, 1995 with the American Type Culture Collection, 12301 Parklawn Drive, Rockville, Md. 20852 and assigned Accession Numbers HB11907 and HB11906, respectively.

4. As another alternative, monoclonal antibodies are generated as follows. Affinity purified $\alpha_d$/CD18 heterodimeric protein from detergent lysates of stably transfected CHO cells is used with 50 μg/ml muramyl dipeptidase to immunize Balb/c mice as described above. Mice receive three immunizations before serum reactivity against $\alpha_d$/CD18 is determined by immunoprecipitation of biotinylated complexes in the CHO transfectants. Hybridomas from positive animals are established according to standard protocols, after which hybridoma cultures are selected by flow cytometry using $\alpha_d$/CD18 transfectants. CD11a/CD18 transfectants are utilized to control for CD18-only reactivity.

5. As another alternative for monoclonal antibody production, Balb/c mice undergo an immunization/immunosuppression protocol designed to reduce reactivity to CHO cell determinants on transfectants used for immunization. This protocol involves immunization with untransfected CHO cells and subsequent killing of CHO-reactive B-cell blasts with cyclophosphamide treatment. After three rounds of immunization and cyclophosphamide treatment are performed, the mice are immunized with $\alpha_d$/CD18 CHO transfected cells as described above.

6. As another alternative, CD18 complexes from detergent lysates of PMA stimulated HL60 cells are enriched by preclearance as described above. Other β2 integrins are cleared on the same columns. Immunization with the resulting complexes, hybridoma production, and screening protocols are performed as described supra.

B. Production of Polyclonal Sera

Purified $\alpha_d$ I domain/IgG4 chimera (Example 14) was used to generate polyclonal anti-serum in rabbits. The $\alpha_d$ I domain/IgG4 antigen was injected at 100 μg/rabbit initially in complete Freund's adjuvant, followed by three boosts with the same amount of protein in incomplete Freund's adjuvant. Test bleeds were assayed after the third and fourth injections. Rabbit immunoglobulin (Ig) was purified from the serum on a protein A-sepharose column and precleared of anti-human IgG reactivity on a human IgG/Affigel column. Reactivity by ELISA to the I domain chimera, but not to human IgG, was used to confirm complete preclearance.

The precleared polyclonal sera was used to immunoprecipitate protein from detergent lysates of surface-biotinylated CHO cells previously transfected with $\alpha_d$ and CD18 expression vectors. Immunoprecipitation was carried out by the method previously described in Example 10. The precleared sera recognized a protein complex of the same molecular weight as that precipitated by anti-CD18 monoclonal antibody TS1.18. In addition, the sera recognized a single band of appropriate size in a Western blot of CD18 complexes from $\alpha_d$/CD18 transfected CHO cells. Affinity purified integrins CD11a/CD18, CD11b/CD18, and VLA4 from human spleen were not recognized by the rabbit polyclonal sera. The sera failed to react with $\alpha_d$-transfected CHO cells in solution, as determined by flow cytometry. It was therefore concluded that the polyclonal rabbit sera was only capable of recognizing denatured $\alpha_d$ I domain/IgG4 proteins.

In an attempt to produce polyclonal antisera against $\alpha_d$/CD18, a mouse was immunized 3 times with $\alpha_d$ transfected CHO cells (D6. CHO, $\alpha_d$/CD18) with adjuvant peptide and once with purified $\alpha_d$/CD18 heterodimer. A final boost included only $\alpha_d$/CD18 heterodimer. Approximately 100 μl immunized serum was precleared by addition of approximately $10^8$ LFA-1-transfected CHO cells for 2 hours at 4° C. The resulting serum was assayed for $\alpha_d$ reactivity at dilutions of 1/5000, 1/10000, 1/20000 and 1/40000 on normal human spleen. The polyclonal antibody was reactive at a dilution of 1/20000, while a 1/40000 dilution stained very weakly.

EXAMPLE 16

Analysis of $\alpha_d$ distribution

Tissue distribution of $\alpha_d$/CD18 was determined using polyclonal anti-serum generated as described in Example 15.

Purified rabbit polyclonal antibody was used at concentrations ranging between 120 ng/ml and 60 μg/ml for immunocytochemical analysis of frozen human spleen sections. Sections of 6 micron thickness were layered onto Superfrost Plus Slides (VWR) and stored at −70° C. Prior to use, slides were removed from −70° C. and placed at 55 ° C. for 5 minutes. Sections were then fixed in cold acetone for 2 minutes and air dried. Sections were blocked in a solution containing 1% BSA, 30% normal human sera and 5% normal rabbit sera for 30 minutes at room temperature. Primary antibody was applied to each section for 1 hour at room temperature. Unbound antibody was removed by washing the slides 3 times in TBS buffer for 5 minutes per wash. Next, a rabbit anti-mouse IgG link antibody was applied to each section in the same TBS buffer. A mouse alkaline phosphatase anti-alkaline phosphatase (APAAP) antibody, incubated for 30 minutes at room temperature, was used to detect the second antibody. Slides were then washed 3 times in TBS buffer. Fast Blue substrate (Vector Labs) was applied and color development stopped by immersion in water. Slides were counterstained in Nuclear Fast Red (Sigma) and rinsed in water before mounting with Aqua Mount (Baxter). Staining was detected in the splenic red pulp with this reagent, but not with an irrelevant rabbit polyclonal Ig preparation or the unpurified preimmune serum from the same animal.

Once mouse serum was determined to have specific $\alpha_d$ reactivity, it was used to stain various lymphoid and non-lymphoid tissues. Monoclonal antibodies recognizing CD18, CD11a, CD11b, and CD11c were used in the same experiment as controls. Staining of normal spleen sections with $\alpha_d$ polyclonal sera, and monoclonal antibodies to CD11a, CD11b, CD11c, and CD18 revealed the following results. The pattern observed with $\alpha_d$ polyclonal sera did not display the same pattern of labeling as CD11a, CD11b, CD11c, or CD18. There is a distinct pattern of labeling with some cells located in the marginal zone of the white pulp and a distinct labeling of cells peripheral to the marginal zone. This pattern was not observed with the other antibodies. Individual cells scattered throughout the red pulp were also labeled which may or may not be the same population or subset seen with CD11a and CD18.

Labeling with CD11c did display some cells staining in the marginal zone, but the antibody did not show the distinct ring pattern around the white pulp when compared to $\alpha_d$ polyclonal sera, nor did labeling in the red pulp give the same pattern of staining as $\alpha_d$ polyclonal sera.

Therefore, the labeling pattern seen with $\alpha_d$ polyclonal serum was unique compared to that seen using antibodies to the other $\beta_2$ integrins (CD11a, CD11b, CD11c, and CD18), and suggests that the in vivo distribution of $\alpha_d$ in man is distinct from that of other $\beta_2$ integrins.

Characterization of Human $\alpha_d$ Expression With Monoclonal Antibodies

Antibodies secreted by hybridomas 169A and 169B were used to analyze human $\alpha_d$ expression in frozen tissue sections by immunocytochemistry and on cell lines and peripheral blood leukocytes by flow cytometry. Hybridoma supernatants used in both sets of experiments were undiluted.

Tissue Staining

All stains were carried out as described above, except for liver sections which were stained in the following manner. After acetone fixation, sections were quenched in 1% $H_2O_2$ and 1% sodium azide in TBS for 15 minutes at room temperature. After primary antibody staining, a rabbit anti-mouse antibody directly conjugated to peroxidase was applied for 30 minutes at room temperature. Slides were washed 3 times in TBS buffer. A swine anti-rabbit antibody, directly conjugated to peroxidase, was incubated for 30 minutes at room temperature to detect the second antibody. Slides were then washed 3 times in TBS buffer and AEC substrate (Vector Labs) was applied and to allow color development. Slides were counterstained with Hematoxylin Gill's No. 2 (Sigma), and subsequently rinsed in water before dehydration and mounting.

In spleen sections, the majority of expression was localized to the splenic red pulp on cells identified by morphology as granulocytes and macrophages. A large number of granulocytes were stained, while only a subset of macrophages gave signal. A small number of follicular dendritic cells in the white pulp also were weakly stained by the $\alpha_d$ antibodies. CD11a and CD18 staining was detected throughout the red and white pulp. CD11c staining was more pronounced in large cells presumed to be macrophages in the splenic white pulp and in the marginal zone surrounding the white pulp; diffuse staining in the red pulp was also noted. CD11b appeared to have distribution overlapping with but not identical to $\alpha_d$ in the red pulp, with no white pulp involvement.

Integrin expression in normal and (rheumatoid) arthritic synovial tissue was compared. Minimal staining with all anti-integrin antibodies (including antibodies specifically immunoreactive with CD11a, CD11b, CD11c, CD18, as well as $\alpha_d$) was noted in normal tissue, with a widespread distribution on resident cells, presumably macrophages. In the inflamed synovium, expression of all integrins was more localized to cells clustered around lymphatic vessels. While $\alpha_d$ and CD11b expression patterns were similar, CD11c did not appear to be as strongly expressed and was restricted to a subset of leukocytes.

In the dog, CD11b, but not $\alpha_d$, expression was observed on liver macrophages, or Kuppfer cells. Staining of normal human liver sections (as previously described for staining of dog liver section, supra) confirmed the conservation of this staining pattern in humans. In addition, CD11c was detected at low levels. In sections from a hepatitis patient, all leukointegrin staining was higher than observed on normal liver, while $\alpha_d$ expression was detected on macrophages and granulocytes in these samples.

Minimal staining of normal human colon sections was observed with anti-$\alpha_d$ antibodies; faint smooth muscle staining and leukocyte staining was observed. All leukointegrins were detected at higher levels in sections from patients with Crohn's disease.

Normal lung showed a limited number of weakly $\alpha_d$-positive cells; these were determined by morphology to be macrophages and neutrophils. In lung tissue from a patent with emphysema, $\alpha_d$ staining was observed on neutrophils and on marophages containing hemisiderin, an iron-containing pigment, indicating red cell engulfment by these cells.

Sections of normal brain and plaque lesions from patients with multiple sclerosis (MS) were examined for integrin expression. In normal brain, $\alpha_d$ staining was less intense than that of CD11a, CD11b, and CD11c, and restricted to cells typed as microglial cells by morphology and CD68 staining. CD11b positive cells were located surrounding vessels and throughout the tissue. CD11c$^+$ cells appeared to be located within vessels, whereas $\alpha_d^+$ cells surrounded the vessels. In MS tissue sections, $\alpha_d$ expression was found on both microglial cells and on a non-macrophage leukocyte subset; $\alpha_d^+$ cells were located within plaque lesions, as well as throughout the cortex. The $\alpha_d$ signal was equivalent in intensity to CD11c, but lower than that of CD11b.

Both thoracic aorta and abdominal aorta sections from PDAY (Pathobiological Determinants of Atherosclerosis in Youth, LSU Medical Center) tissue samples were analyzed with anti-leukointegrin and anti-CAM antibodies. The lesions examined were consistent with aortic fatty streaks which consisted of subintimal aggregates of large foam cells (mostly macrophages with ingested lipid) and infiltrates of smaller leukocytes. Single label studies with monoclonal antibodies specific for $\alpha_d$ and the other $\beta_2$ integrin $\alpha$ chains (CD11a, CD11b, and CD11c), plus a macrophage marker (CD68) revealed that the majority of lipid-laden macrophages expressed a moderate level of $\alpha_d$ and CD18, while expressing CD11a and CD11c at weak or weak to moderate levels, respectively. CD11b was faintly expressed, and then by only a subset of macrophages.

Double label studies were conducted to determine the relative localization of $\alpha_d$ and ICAM-R antigens in the aortic sections. Since foam cells in these sections stained with the antibody Ham 56, specific for a macrophage marker, but not with antibodies to smooth muscle actin, it was determined that the foam cells were not derived from subintimal smooth muscle cells. CD68 positive macrophages expressing $\alpha_d$ were surrounded by and interspersed with small ICAM-R positive leukocytes. There appeared to be a limited number of small leukocytes which were CD68 negative but stained with both $\alpha_d$ and ICAM-R antibodies.

Distribution of $\alpha_d$ in normal tissues appeared to be on resident leukocytes in a pattern overlapping with but not identical to that of CD11b and CD11c, two other leukointegrin $\alpha$ chains which have previously been characterized as having restricted leukocyte distribution. Cellular morphology indicated that $\alpha_d$ staining is largely confined to macrophages and granulocytes, with limited lymphocyte staining. Generally, tissue inflammation appeared to increase the number and types of leukocytes observed in a particular tissue, along with increased staining of leukointegrins, including $\alpha_d$. Since the cellular and spatial distribution of the leukointegrins was not identical in pathologic tissues, it was inferred that distinct functions and ligands exist for each family member, including $\alpha_d$, in specific contexts.

Interestingly, $\alpha_d$ expression in early atherosclerotic lesions appeared to be more pronounced than that of CD11a, CD11b, and CD11c, suggesting that $\alpha_d$ may play a central role in the establishment of these lesions. The apposed distribution of $\alpha_d$ and ICAM-R positive cells, supported by evidence suggesting an interaction between $\alpha_d$ and ICAM-R, suggests that $\alpha_d$ may be involved in leukocyte recruitment or activation at early stages in these lesions.

Cell Line and Peripheral Blood Leukocyte Staining

The antibodies 169A and 169B stained a promyeolmonocytic cell line, HL60, by FACS. Surface expression of $\alpha_d$ in these cells is negatively affected by PMA stimulation, which is reported to induce differentiation along a macrophage pathway, but is unaffected by DMSO, which induces granulocyte differentiation [Collins, et al., Blood 70:1233–1244 (1987)]. The FACS profiles of 169A and 169B were antithetical with PMA stimulation to those observed with anti-CD11b and anti-CD11c monoclonal antibodies. A monocyte cell line, THP-1, also exhibited weak staining with 169A and 169B. In addition, a subset of cells in the lymphocyte and monocyte gates of peripheral blood leukocytes appeared to be weakly positive by FACS. A subset of peripheral blood monocytes stained weakly with 169A and 169B, while B lymphocytes were found to have no surface expression of $\alpha_d$. The CD8+ subset of T lymphocytes was $\alpha_d^+$. In addition, antibodies 169A and 169B failed to detect antigen on the B cell lines, JY, Ramos, a basophilic line, KU812, and T cell lines, Jurkat, SKW, and Molt 16.

In light of the results with HL60 cells, granulocytes were isolated from peripheral blood by ficoll/hypaque gradient centrifugation and subsequent red blood cells lysis. All preparations were found to be ≦90% PMNs by visualization of nuclear morphology in acetic acid. Separate populations were stimulated for 30 minutes with 50 ng/ml PMA or $10^{-8}$ M formyl peptide (fMLP) to release potential intracellular integrin stores. Unstimulated populations exhibited low, but significant expression of 169A and 169B antigens over an IgG1 control, with a detectable increase observed upon stimulation. On PMNs, levels of $\alpha_d$ and CD11c surface expression were more similar than that observed on HL60 cells. The antibody 169B was used subsequently to precipitate a heterodimeric molecule from a detergent lysate of biotinylated PMNs with subunit sizes of approximately 150 and 95 kD appropriate to $\alpha_d$ and CD18, respectively.

The presence of $\alpha_d$ on PMNs could not be anticipated from the information known about canine $\alpha_d$ expression. Canine neutrophils, unlike their human counterparts, express the T helper cell marker CD4, and also integrin VLA-4, and therefore may have different ligands and functions in the dog than in the human.

EXAMPLE 17
Isolation of Rat cDNA Clones

In view of the existence of both canine and human $\alpha_d$ subunits, attempts were made to isolate homologous genes in other species, including rat (this example) and mouse (Example 17, infra).

A partial sequence of a rat cDNA showing homology to the human $\alpha_d$ gene was obtained from a rat splenic λgt10 library (Clontech). The library was plated at 2×10⁴ pfu/plate onto 150 mm LBM/agar plates. The library was lifted onto Hybond membranes (Amersham), denatured 3 minutes, neutralized 3 minutes and washed 5 minutes with buffers as described in standard protocols [Sambrook, et al., *Molecular Cloning: a laboratory manual*, p.2.110]. The membranes were placed immediately into a Stratalinker (Stratagene) and the DNA crosslinked using the autocrosslinking setting. The membranes were prehybridized and hybridized in 30% or 50% formamide, for low and high stringency conditions, respectively. Membranes were initially screened with a ³²P-labeled probe generated from the human $\alpha_d$ cDNA, corresponding to bases 500 to 2100 in clone 19A2 (SEQ ID NO: 1). The probe was labeled using Boehringer Mannheim's Random Prime Kit according to manufacturer's suggested protocol. Filters were washed with 2× SSC at 55° C.

Two clones, designated 684.3 and 705.1, were identified which showed sequence homology to human $\alpha_d$, human CD11b, and human CD11c. Both clones aligned to the human $\alpha_d$ gene in the 3' region of the gene, starting at base 1871 and extending to base 3012 for clone 684.3, and bases 1551 to 3367 for clone 705.1.

In order to isolate a more complete rat sequence which included the 5' region, the same library was rescreened using the same protocol as employed for the initial screening, but using a mouse probe generated from clone A1160 (See Example 17, infra). Single, isolated plaques were selected from the second screening and maintained as single clones on LBM/agar plates. Sequencing primers 434FL and 434FR (SEQ ID NOS: 34 and 35, respectively) were used in a standard PCR protocol to generate DNA for sequencing.
5'-TATAGACTGCTGGGTAGTCCCCAC-3' (SEQ ID NO: 34)
5'-TGAAGATTGGGGGTAAATAACAGA-3' (SEQ ID NO: 35)
DNA from the PCR was purified using a Quick Spin Column (Qiagen) according to manufacturer's suggested protocol.

Two clones, designated 741,4 and 741.11, were identified which overlapped clones 684.3 and 705.1; in the overlapping regions, clones 741.1 and 741.11 were 100% homologous to clones 684.3 and 705.1. A composite rat cDNA having homology to the human $\alpha_d$ gene is set out in SEQ ID NO: 36; the predicted amino acid sequence is set forth in SEQ ID NO: 37.

Cloning of the 5' end of Rat $\alpha_d$

A 5' cDNA fragment for the rat $\alpha_d$ gene was obtained using a Clonetech rat spleen RACE cloning kit according to manufacturer's suggested protocol. The gene specific oligonucleotides used were designated 741.11#2R and 741.2#1R (SEQ ID NOS: 59 and 58, respectively).
5'-CCAAAGCTGGCTGCATCCTCTC-3' (SEQ ID NO: 59)
5'-GGCCTTGCAGCTGGACAATG-3' (SEQ ID NO: 58)
Oligo 741.11#2R encompasses base pairs 131–152 in SEQ ID NO: 36, in the reverse orientation and 741.2#1R encompasses bases pairs 696–715 in SEQ ID NO: 36, also in the reverse orientation. A primary PCR was carried out using the 3'-most oligo, 741.2#1R. A second PCR followed using oligo 741.11#2R and DNA generated from the primary reaction. A band of approximately 300 base pairs was detected on a 1% agarose gel.

The secondary PCR product was ligated into plasmid pCRTAII (Invitrogen) according to manufacturer's suggested protocol. White (positive) colonies were picked and added to 100 μl LBM containing 1 μl of a 50 mg/ml carbenicillin stock solution and 1 μl M13 K07 phage culture in individual wells in a round bottom 96 well tissue culture plate. The mixture was incubated at 37° C. for 30 minutes to one hour. Following the initial incubation period, 100 μl of LBM (containing 1 μl of 50 mg/ml carbenicillin and a 1:250 dilution of a 10 mg/ml kanamycin stock solution) were added and the incubation was continued overnight at 37° C.

Using a sterile 96 well metal transfer prong, supernatant from the 96 well plate was transferred to four Amersham Hybond nylon filters. The filters were denatured, neutralized and cross linked by standard protocols. The filters were prehybridized in 20 mls of prehybridization buffer (5× SSPE; 5× Denhardts; 1% SDS; 50 ugs/ml denatured salmon sperm DNA) at 50° C. for several hours while shaking.

Oligo probes 741.11#1 and 741.11#1R (SEQ ID NOS: 56 and 57, respectively), encompassing base pairs 86–105 (SEQ ID NO: 36) in the forward and reverse orientation respectively, were labeled as follows.
5'-CCTGTCATGGGTCTAACCTG-3' (SEQ ID NO: 56)
5'-AGGTTAGACCCATGACAGG-3' (SEQ ID NO: 57)
Approximately 65 ng oligo DNA in 12 μl dH₂O was heated to 65° C. for two minutes. Three μl of 10 mCi/ml γ-³²P-ATP were added to the tube along with 4 μl 5× Kinase Buffer (Gibco) and 1 μl T4 DNA Kinase (Gibco). The mixture was incubated at 37° C. for 30 minutes. Following incubation, 16 μl of each labeled oligo probe were added to the prehybridization buffer and filters and hybridization was continued overnight at 42° C. The filters were washed three times in 5× SSPE; 0.1% SDS for 5 minutes per wash at room temperature, and autoradiographed for 6 hours. Positive clones were expanded and DNA purified using the Magic Mini Prep Kit (Promega) according to manufacturer's suggested protocol. Clone 2F7 was selected for sequencing and showed 100% homology to clone 741.11 in the overlapping region. The complete rat $\alpha_d$ nucleic acid sequence is set out in SEQ ID NO: 54; the amino acid sequence is set out in SEQ ID NO: 55.

Characteristics of the Rat cDNA and Amino Acid Sequences

Neither nucleic acid nor amino acid sequences have previously been reported for rat α subunits in $\beta_2$ integrins. However sequence comparisons to reported human $\beta_2$ integrin α subunits suggests that the isolated rat clone and its predicted amino acid sequence are most closely related to $\alpha_d$ nucleotide and amino acid sequences.

At the nucleic acid level, the isolated rat cDNA clone shows 80% identity in comparison to the human $\alpha_d$ cDNA; 68% identity in comparison to human CD11b; 70% identity in comparison to human CD11c; and 65% identity in comparison to mouse CD11b. No significant identity is found in comparison to human CD11a and to mouse CD11a.

At the amino acid level, the predicted rat polypeptide encoded by the isolated cDNA shows 70% identity in comparison to human $\alpha_d$ polypeptide; 28% identity in comparison to human CD11a; 58% identity in comparison to human CD11b; 61% identity in comparison to human CD11c; 28% identity in comparison to mouse CD11a; and 55% identity in comparison to mouse CD11b.

EXAMPLE 18

Production and Characterization of Rodent $\alpha_d$-Specific Antibodies

A. Antibodies against Rat $\alpha_d$ I domain/Hu IgG4 Fusion Proteins

In view of the fact that the I domain of human $\beta_2$ integrins has been demonstrated to participate in ligand binding, it was assumed that the same would be true for rat $\alpha_d$ protein. Monoclonal antibodies immunospecific for the rat $\alpha_d$ I domain may therefore be useful in rat models of human disease states wherein $\alpha_d$ binding is implicated.

Oligos "rat alpha-DI5" (SEQ ID NO: 87) and "rat alpha-DI3" (SEQ ID NO: 88) were generated from the rat $\alpha_d$ sequence corresponding to base pairs 469–493 and base pairs 1101–1125 (in the reverse orientation), respectively, in SEQ ID NO: 54. The oligos were used in a standard PCR reaction to generate a rat $\alpha_d$ DNA fragment containing the I domain spanning base pairs 459–1125 in SEQ ID NO: 54. The PCR product was ligated into vector pCRTAII (Invitrogen) according to manufacturer's suggested protocol. A positive colony was selected and expanded for DNA purification using a Qiagen (Chatsworth, Ga.) Midi Prep kit according to manufacturer's protocol. The DNA was digested with XhoI and BgM in a standard restriction enzyme digest and a 600 base pair band was gel purified which was subsequently ligated into pDCS1/HuIgG4 expression vector. A positive colony was selected, expanded and DNA purified with a Quiagen Maxi Prep Kit.

COS cells were plated at half confluence on 1000mm culture dishes and grown overnight at 37° C. in 7% $CO_2$. Cells were rinsed once with 5 ml DMEM. To 5 ml DMEM, 50 μl DEAE-Dextran, 2 μl chloroquine and 15 μg rat $\alpha_d$ I domain/HuIgG4 DNA described above was added. The mixture was added to the COS cells and incubated at 37° C. for 3 hours. Media was then removed and 5 ml 10% DMSO in CMF-PBS was added for exactly one minute. The cells were gently rinsed once with DMEM. Ten ml DMEM containing 10% FBS was added to the cells and incubation continued overnight at 37° C. in 7% $CO_2$. The next day, media was replaced with fresh media and incubation continued for three additional days. The media was harvested and fresh media was added to the plate. After three days, the media was collected again and the plates discarded. The procedure was repeated until 2 liters of culture supernatant were collected.

Supernatant collected as described above was loaded onto a Prosep-A column (Bioprocessing Limited) and protein purified as described below.

The column was initially washed with 15 column volumes of Wash Buffer containing 35 mM Tris and 150 mM NaCl, pH 7.5. Supernatant was loaded at a slow rate of less than approximately 60 column volumes per hour. After loading, the column was washed with 15 column volumes of Wash Buffer, 15 column volumes of 0.55M diethanolamine, pH 8.5, and 15 column volumes 50 mM citric acid, pH 5.0. Protein was eluted with 50 mM citric acid, pH 3.0. Protein was neutralized with 1.0M Tris, pH 8.0, and dialyzed in sterile PBS.

The rat $\alpha_d$ I domain protein was analyzed as described in Example 14. The detected protein migrated in the same manner as observed with human I domain protein.

B. Production of Monoclonal Antibodies to Rat $\alpha_d$ I Domain/HuIgG4 Fusion Proteins Mice were individually immunized with 50 μg purified rat $\alpha_d$ I domain/HuIgG4 fusion protein previously emulsified in an equal volume of Freunds Complete Adjuvant (FCA) (Sigma). Approximately 200 μl of the antigen/adjuvant preparation was injected at 4 sites in the back and flanks of each of the mice. Two weeks later the mice were boosted with an injection of 100 μl rat $\alpha_d$ I domain/HuIgG4 antigen (50 μg/mouse) previously emulsified in an equal volume of Freunds Incomplete Adjuvant (FIA). After two additional weeks, the mice were boosted with 50 μg antigen in 200 μl PBS injected intravenously.

To evaluate serum titers in the immunized mice, retro-orbital bleeds were performed on the animals ten days following the third immunization. The blood was allowed to clot and serum isolated by centrifugation. The serum was used in an immunoprecipitation on biotinylated (BIP) rat splenocytes. Serum from each mouse immunoprecipitated protein bands of expected molecular weight for rat $\alpha_d$ and rat CD18. One mouse was selected for the fusion and was boosted a fourth time as described above for the third boost.

The hybridoma supernatants were screened by antibody capture, described as follows. Immulon 4 plates (Dynatech, Cambridge, Mass.) were coated at 4° C. with 50 μl/well goat anti-mouse IgA, IgG or IgM (Organon Teknika) diluted 1:5000 in 50 mM carbonate buffer, pH 9.6. Plates were washed 3× with PBS containing 0.05% Tween 20 (PBST) and 50 μl culture supernatant was added. After incubation at 37° C. for 30 minutes, and washing as described above, 50 μl horseradish peroxidase-conjugated goat anti-mouse IgG9 (Fc) (Jackson ImmunoResearch, West Grove, Pa.) diluted 1:3500 in PBST was added. Plates were incubated as described above and washed 4× with PBST. Immediately thereafter, 100 μl substrate, containing 1 mg/ml o-phenylene diamine (Sigma) and 0.1 μl/ml 30% $H_2O_2$ in 100 mM citrate, pH4.5, was added. The color reaction was stopped after 5 minutes with the addition of 50 μl 15% $H_2SO_4$. Absorbance at 490 nm was read on a Dynatech plate reader.

Supernatant from antibody-containing wells was also analyzed by ELISA with immobilized rat $\alpha_d$ I domain/HuIgG4 fusion protein. An ELISA with HuIgG4 antibody coated plates served as a control for reactivity against the IgG fusion partner. Positive wells were selected for further screening by BIP on rat splenocyte lysates using techniques described below.

C. Production of Polyclonal Sera To Rat $\alpha_d$ I domain/HuIgG4 Fusion Protein Two rabbits were prebled prior to immunization with 100 μg purified rat $\alpha_d$ I domain/HuIgG4 fusion protein in complete Freund's adjuvant. Injections were repeated at the same dose every three weeks in incomplete Freunds adjuvant (IFA). After three injections the rabbits were test bled and the collected sera used in a standard immunoprecipitation on rat splenocyte lysates. It was determined that sera from both rabbits were immunoreactive with rat $\alpha_d$. The rabbits were boosted again with 100 ug antigen in IFA, and the collected sera assayed for increased immunoreactivity with rat $\alpha_d$ by immunoprecipitation. The animals were given a final boost and 10 days later, bled out and sera collected.

Rat $\alpha_d$ Histology

Rabbit polyclonal sera generated against rat $\alpha_d$ "I" domain was used in immunohistochemical staining of rat tissue sections by the technique described in Example. 16. The staining pattern detected on frozen and on paraffin embedded rat spleen sections was essentially identical to that observed with the antibodies against human $\alpha_d$, with staining individual cells throughout the red pulp. The staining pattern differed from that observed with monoclonal antibodies against rat CD11a, CD11b and CD18. In addition, a positive staining pattern was seen in the thymus on individual cells throughout the cortex. Neither of these tissue gave any signal when stained with the rabbit preimmune sera.

D. Analysis of Antibody Specificity

Rats were sacrificed by asphyxiation with $CO_2$ and spleens were removed using standard surgical techniques. Splenocytes were harvested by gently pushing the spleen through a wire mesh with a 3 cc syringe plunger in 20 mls RPMI. Cells were collected into a 50 ml conical tube and washed in the appropriate buffer.

Cells were washed three times in cold D-PBS and resuspended at a density of $10^8$ to $10^9$ cells in 40 ml PBS. Four mg of NHS-Biotin (Pierce) was added to the cell suspension and the reaction was allowed to continue for exactly 15 minutes at room temperature. The cells were pelleted and washed three times in cold D-PBS.

Cells were resuspended at a density of $10^8$ cells/ml in cold lysis Buffer (1% NP40; 50 mM Tris-HCl, pH 8.0; 150 mM NaCl; 2 mM CaCl; 2 mM MgCl; 1:100 solution of pepstain, leupeptine, and aprotinin, added just before adding to cells; and 0.0001 g PMSF crystals, added just before adding to cells). Lysates were vortexed for approximately 30 seconds, incubated for 5 minute at room temperature, and further incubated for 15 minutes on ice. Lysates were centrifuged for 10 minutes at 10,000× g to pellet the insoluble material. Supernatant was collected into a new tube and stored at between 4° C. and −20° C.

One ml cell lysate was precleared by incubation with 200 μl of a protein A sepharose slurry (Zymed) overnight at 4° C. Precleared lysate was aliquoted into Eppendorf tubes at 50 μl/tube for each antibody to be tested. Twenty-five μl of polyclonal serum or 100 to 500 μl of monoclonal antibody supernatant were added to the precleared lysates and the resulting mixture incubated for 2 hours at 4° C. with rotation. One hundred μl rabbit anti-mouse IgG (Jackson) bound to protein A sepharose beads in a PBS slurry was then added and incubation continued for 30 minutes at room temperature with rotation. Beads were pelleted with gentle centrifugation, and washed three times with cold Wash Buffer (10 mM HEPES; 0.2M NaCl; 1% Triton X-100). Supernatant was removed by aspiration, and 20 μl 2× SDS sample buffer containing 10% β-mercaptoethanol was added. The sample was boiled for 2 minutes in a water bath, and the sample loaded onto a 5% SDS PAGE gel. Following separation, the proteins were transferred to nitrocellulose at constant current overnight. The nitrocellulose filters were blocked with 3% BSA in TBS-T for 1 hour at room temperature and the blocking buffer was removed. A 1:6000 dilution of Strepavidin-HRP conjugate (Jackson) in 0.1% BSA TBS-T was added and incubation continued for 30 minutes at room temperature. Filters were washed three times for 15 minutes each with TBS-T and autoradiographed using Amersham's ECL kit according to manufacturer's suggested protocol.

EXAMPLE 19

Isolation of Mouse cDNA Clones

Isolation of a mouse $\alpha_d$ homolog was attempted.

Cross-species hybridization was performed using two PCR-generated probes: a 1.5 kb fragment corresponding to bases 522 to 2047 from human clone 19A2 (SEQ ID NO: 1), and a 1.0 kb rat fragment which corresponds to bases 1900 to 2900 in human clone 19A2 (SEQ ID NO: 1). The human probe was generated by PCR using primer pairs designated ATM-2 and 9–10.1 set out in SEQ ID NOS: 38 and 39, respectively; the rat probe was generated using primer pairs 434L and 434R, set out in SEQ ID NOS: 34 and 35, respectively. Samples were incubated at 94° C. for 4 minutes and subjected to 30 cycles of the temperature step sequence: 94° C.; 50° C. 2 minutes; 72° C., 4 minutes.

5'-GTCCAAGCTGTCATGGGCCAG-3' (SEQ ID NO: 38)
5'-GTCCAGCAGACTGAAGAGCACGG-3' (SEQ ID NO: 39)

The PCR products were purified using the Qiagen Quick Spin kit according to manufacturer's suggested protocol, and approximately 180 ng DNA was labeled with 200 μCi [$^{32}$P]-dCTP using a Boehringer Mannheim Random Primer Labeling kit according to manufacturer's suggested protocol. Unincorporated isotope was removed using a Centri-sep Spin Column (Princeton Separations, Adelphia, N.J.) according to manufacturer's suggested protocol. The probes were denatured with 0.2 N NaOH and neutralized with 0.4M Tris-HCl, pH 8.0, before use.

A mouse thymic oligo dT-primed cDNA library in lambda ZAP II (Stratagene) was plated at approximately 30,000 plaques per 15 cm plate. Plaque lifts on nitrocellulose filters (Schleicher & Schuell, Keene, N.H.) were incubated at 50° C. with agitation for 1 hour in a prehybridization solution (8 ml/lift) containing 30% formamide. Labeled human and rat probes were added to the prehybridization solution and incubation continued overnight at 50° C. Filters were washed twice in 2× SSC/0.1% at room temperature, once in 2× SSC/0.1% SDS at 37° C., and once in 2× SSC/0.1% SDS at 42° C. Filters were exposed on Kodak X-Omat AR film at −80° C. for 27 hours with an intensifying screen.

Four plaques giving positive signals on duplicate lifts were restreaked on LB medium with magnesium (LBM)/carbenicillin (100 mg/ml) plates and incubated overnight at 37° C. The phage plaques were lifted with Hybond filters (Amersham), probed as in the initial screen, and exposed on Kodak X-Omat AR film for 24 hours at −80° C. with an intensifying screen.

Twelve plaques giving positive signals were transferred into low $Mg^{++}$ phage diluent containing 10 mM Tris-HCl and 1 mM $MgCl_2$. Insert size was determined by PCR amplification using T3 and T7 primers (SEQ ID NOS: 13 and 14, respectively) and the following reaction conditions. Samples were incubated at 94° C. for 4 minutes and subjected to 30 cycles of the temperature step sequence: 94° C., for 15 seconds; 50° C., for 30 seconds; and 72° C. for 1 minute.

Six samples produced distinct bands that ranged in size from 300 bases to 1 kb. Phagemids were released via co-infection with helper phage and recirculatized to generate Bluescript SK⁻(Stratagene). The resulting colonies were cultured in LBM/carbenicillin (100 mg/ml) overnight. DNA was isolated with a Promega Wizard miniprep kit (Madison, Wis.) according to manufacturer's suggested protocol. EcoRI restriction analysis of purified DNA confirmed the molecular weights which were detected using PCR. Insert DNA was sequenced with M13 and M13 reverse.1 primers set out in SEQ ID NOS: 40 and 41, respectively.
5'-TGTAAAACGACGGCCAGT-3' (SEQ ID NO: 40)
5'-GGAAACAGCTATGACCATG-3' (SEQ ID NO: 41)

Sequencing was performed as described in Example 4.

of the six clones, only two, designated 10.3–1 and 10.5–2, provided sequence information and were identical 600 bp fragments. The 600 bp sequence was 68% identical to a corresponding region of human $\alpha_d$, 40% identical to human CD11a, 58% identical to human CD11c, and 54% identical to mouse CD11b. This 600 bp fragment was then utilized to isolate a more complete cDNA encoding a putative mouse $\alpha_d$ homolog.

A mouse splenic cDNA library (oligo dT⁻and random-primed) in lambda Zap II (Stratagene) was plated at $2.5 \times 10^4$ phage/15 cm LBM plate. Plaques were lifted on Hybond nylon transfer membranes (Amersham), denatured with 0.5M NaOH/1.5M NaCl, neutralized with 0.5M Tris Base/1.5M NaCl/11.6 HCl, and washed in 2× SSC. The DNA was cross-linked to filters by ultraviolet irradiation.

Approximately 500,000 plaques were screened using probes 10.3–1 and 10.5–2 previously labeled as described supra. Probes were added to a prehybridization solution and incubated overnight at 50° C. The filters were washed twice in 2× SSC/0.1% SDS at room temperature, once in 2× SSC/0.1% SDS at 37° C., and once in 2× SSC/0.1% SDS at 42° C. Filters were exposed on Kodak X-Omat AR film for 24 hours at –80° C. with an intensifying screen. Fourteen plaques giving positive signals on duplicate lifts were subjected to a secondary screen identical to that for the initial screen except for additional final high stringency washes in 2× SSC/ 0.1% SDS at 50° C., in 0.5× SSC/0.1% SDS at 50° C., and at 55° C. in 0.2× SSC/0.1% SDS. The filters were exposed on Kodak X-Omat AR film at –80° C. for 13 hours with an intensifying screen.

Eighteen positive plaques were transferred into low Mg⁺⁺ phage diluent and insert size determined by PCR amplification as described above. Seven of the samples gave single bands that ranged in size from 600 bp to 4 kb. EcoRI restriction analysis of purified DNA confirmed the sizes observed from PCR and the DNA was sequenced with primers M13 and M13 reverse. 1 (SEQ ID NOS: 40 and 41, respectively).

One clone designated B3800 contained a 4 kb insert which corresponded to a region 200 bases downstream of the 5' end of the human $\alpha_d$ 19A2 clone and includes 553 bases of a 3' untranslated region. Clone B3800 showed 77% identity to a corresponding region of human $\alpha_d$, 44% identity to a corresponding region of human CD11a, 59% identity to a corresponding region of human CD11c, and 51% identity to a corresponding region of mouse CD11b. The second clone A1160 was a 1.2 kb insert which aligned to the 5' end of the coding region of human $\alpha_d$ approximately 12 nucleic acids downstream of the initiating methionine. Clone A1160 showed 75% identity to a corresponding region of human $\alpha_d$, 46% identity to a corresponding region of human CD11a, 62% identity to a corresponding region of human CD11c, and 66% identity to a corresponding region of mouse CD11b.

Clone A1160, the fragment closer to the 5' end of human clone 19A2, is 1160 bases in length, and shares a region of overlap with clone B3800 starting at base 205 and continuing to base 1134. Clone A1160 has a 110-base insertion (bases 704–814 of clone A1160) not present in the overlapping region of clone B3800. This insertion occurs at a probable exon-intron boundary [Fleming, et al., J. Immunol. 150:480–490 (1993)] and was removed before subsequent ligation of clones A1160 and B3800.

Rapid Amplification of 5' cDNA End of the Putative Mouse $\alpha_d$ Clone

RACE PCR [Frohman, "RACE: Rapid Amplification of cDNA Ends," in PCR Protocols: A Guide to Methods and Applications, Innis, et al. (eds.) pp. 28–38, Academic Press:New York (1990)] was used to obtain missing 5' sequences of the putative mouse $\alpha_d$ clone, including 5' untranslated sequence and initiating methionine. A mouse splenic RACE-Ready kit (Clontech, Palo Alto, Calif.) was used according to the manufacturer's suggested protocol. Two antisense, gene-specific primers, A1160 RACE1-primary and A1160 RACE2-nested (SEQ ID NOS: 42 and 43), were designed to perform primary and nested PCR.
5'-GGACATGTTCACTGCCTCTAGG-3' (SEQ ID NO: 42)
5'-GGCGGACAGTCAGACGACTGTCCTG-3' (SEQ ID NO: 43)

The primers, SEQ ID NOS: 42 and 43, correspond to regions starting 302 and 247 bases from the 5' end, respectively. PCR was performed as described, supra, using the 5' anchor primer (SEQ ID NO: 44) and mouse spleen cDNA supplied with the kit.
5'-CTGGTTCGGCCCACCTCTGAAGGTTCCAGAATC GATAG-3' (SEQ ID NO: 44)

Electrophoresis of the PCR product revealed a band approximately 280 bases in size, which was subcloned using a TA cloning kit (Invitrogen) according to manufacturer's suggested protocol. Ten resulting colonies were cultured, and the DNA isolated and sequenced. An additional 60 bases of 5' sequence were identified by this method, which correspond to bases 1 to 60 in SEQ ID NO: 45.

Characteristics of the Mouse cDNA and Predicted Amino Acid Sequence

A composite sequence of the mouse cDNA encoding a putative homolog of human $\alpha_d$ is set out in SEQ ID NO: 45. Although homology between the external domains of the human and mouse clones is high, homology between the cytoplasmic domains is only 30%. The observed variation may indicate C-terminal functional differences between the human and mouse proteins., Alternatively, the variation in the cytoplasmic domains may result from splice variation, or may indicate the existence of an additional $\beta_2$ integrin gene(s).

At the amino acid level, the mouse cDNA predicts a protein (SEQ ID NO: 46) with 28% identity to mouse CD11a, 53% identity to mouse CD11b, 28% identity to human CD11a, 55% identity to human CD11b, 59% identity to human CD11c, and 70% identity to human $\alpha_d$. Comparison of the amino acid sequences of the cytoplasmic domains of human $\alpha_d$ and the putative mouse homolog indicates regions of the same length, but having divergent primary structure. Similar sequence length in these regions suggests species variation rather than splice variant forms. When compared to the predicted rat polypeptide, Example 16, supra, mouse and rat cytoplasmic domains show greater than 60% identity.

EXAMPLE 20
Isolation of additional mouse $\alpha_d$ cDNA clones for sequence verification In order to verify the nucleic and amino acids sequences describe in Example 19 for mouse $\alpha_d$, additional mouse sequences were isolated for the purposes of confirmation.

Isolation of mouse cDNA by hybridization with two homologous $\alpha_d$ probes (3' and 5') was performed using both a mouse splenic random primed library and an oligo dT-primed cDNA library in lambda ZAP II (Strategene). The library was plated at $5\times10^5$ phage per 15 cm LBM plate. Plaques were lifted on Hybond nylon membranes (Amersham), and the membranes were denatured (0.5M NaOH/1.5M NaCl), neutralized (0.5M Tris Base/1.5M NaCl/11.6M HCl) and washed (2× SSC salt solution). DNA was cross-lined to filters by ultraviolet irradiation.

Probes were generated using primers described below in a PCR reaction under the following conditions. Samples were held at 94° C. for 4 minutes and then run through 30 cycles of the temperature step sequence (94° C. for 15 seconds; 50° C. for 30 seconds; 72° C. for 1 minute in a Perkin-Elmer 9600 thermocycler).

The 3' probe was approximately 900 bases long and spanned a region from nucleotides 2752 to 3651 (in SEQ ID NO: 1) (5'→3') and was produced with primers 11.b-1/2FOR11 and 11.b-1/2REV2 as shown in SEQ ID NOS: 69 and 74, respectively). This probe was used in a first set of lifts.

The 5' probe was approximately 800 bases long and spanned a region from nucleotides 149 to 946 (in SEQ ID NO: 1) (5'→3') and was produced with primers 11.b-1/2FOR1 and 11.a-1/1REV1 as shown in SEQ ID NOS: 50 and 85, respectively). This probe was used in a second set of lifts.

In a third set of lifts, both probes described above were used together on the same plates.

Approximately 500,000 plaques were screened using the two probes from above which were labeled in the same way as described in Example 17. Labeled probes were added to a prehybridization solution, containing 45% formamide, and incubated overnight at 50° C. Filters were washed twice in 2× SSC/0.1% SDS at room temperature (22° C.). A final wash was carried out in 2× SSC/0.1% SDS at 50° C. Autoradiography was for 19 hours at −80° C. on Kodak X-Omat AR film with an intensifying screen.

Thirteen plaques giving positive signals on at least duplicate lifts were subjected to a secondary screen performed as described for the initial screen except that both the 3' and 5' labeled probes were used for hybridization and an additional final wash was incorporated using 2× SSC/0.1% SDS at 65'C. Autoradiography was performed as described above for 2.5 hours.

Thirteen plaques (designated MS2P1 through MS2P13) giving positive signals were transferred into low $Mg^{++}$ phage diluent. Insert size was determined by PCR amplification (Perkin-Elmer 9600 thermocycler) using T3 and T7 primers which anneal to Bluescript phagemid in ZAP II (sequence previously described) under the same conditions shown above. Band sizes ranged from 500 bases to 4Kb. Phagemids were isolated, prepared, and sequenced with M13 and M13 reverse.1 primers (SEQ ID NOS: 40 and 41, respectively). Five of the thirteen clones; MS2P-3, MS2P-6, MS2P-9, MS2P-12, and MS2P-13, were sequenced, and together, represented a region from approximately base 200 at the 5' end to about 300 bases past a first stop codon at the 3' end.

Automated sequencing was performed as described in Example 4 by first using M13 and M13 reverse.1 primers (SEQ ID NOS: 40 and 41, respectively) to sequence the ends of each clone and to determine its position relative to construct #17 (SEQ ID NO: 45). Each clone was then completely sequenced using the appropriate primers (listed below) for that particular region.

11.b-1/2FOR1  5'-GCAGCCAGCTTCGGACAGAC-3' (SEQ ID NO: 50)
11.a-1/1FOR2  5'-CCGCCTGCCACTGGCGTGTGC-3' (SEQ ID NO: 60)
11.a-1/1FOR3  5'-CCCAGATGAAGGACTTCGTCAA-3' (SEQ ID NO: 61)
11.b-1/2FOR4  5'-GCTGGGATCATTCGCTATGC-3' (SEQ ID NO: 62)
11.b-1/2FOR5  5'-CAATGGATGGACCAGTTCTGG-3' (SEQ ID NO: 63)
11.b-1/2FOR6  5'-CAGATCGGCTCCTACTTTGG-3' (SEQ ID NO: 64)
11.b-1/2FOR7  5'-CATGGAGCCTCGAGACAGG-3' (SEQ ID NO: 65)
11.b-1/2FOR8  5'-CCACTGTCCTCGAAGCTGGAG-3' (SEQ ID NO: 66)
11.b-1/2FOR9  5'-CTTCGTCCTGTGCTGGCTGTGGGCTC-3 (SEQ ID NO: 67)
11.b-1/2FOR10  5'-CGCCTGGCATGTGAGGCTGAG-3' (SEQ ID NO: 68)
11.b-1/2FOR11  5'-CCGTGATCAGTAGGCAGGAAG-3' (SEQ ID NO: 69)
11.b-1/2FOR12  5-GTCACAGAGGGAACCTCC-3' (SEQ ID NO: 70)
11.b-1/2FOR13  5'-GCTCCTGAGTGAGGCTGAAATCA-3' (SEQ ID NO: 71)
11.b-1/2FOR14  5'-GAGATGCTGGATCTACCATCTGC-3' (SEQ ID NO: 72)
11.b-1/2FOR15  5'-CTGAGCTGGGAGAT =TrrATGG-3' (SEQ ID NO: 73)
11.b-1/2REV2  5'-GTGGATCAGCACTGAAATCTG-3' (SEQ ID NO: 74)
11.b-1/2REV3  5'-CGTlTGAAGAAGCCAAGCTTG-3' (SEQ ID NO: 75)
11.b-1/2REV4  5'-CACAGCGGAGGTGCAGGCAG-3' (SEQ ID NO: 76)
11.b-1/2REV5  5'-CTCACTGCTTGCGCTGGC-3' (SEQ ID NO: 77)
11.b-1/2REV6  5'-CGGTAAGATAGCTCTGCTGG-3' (SEQ ID NO: 78)
11.b-1/2REV7  5'-GAGCCCACAGCCAGCACAGG-3' (SEQ ID NO: 79)
11.b-1/2REV8  5'-GATCCAACGCCAGATCATACC-3' (SEQ ID NO: 80)
11.b-1/2REV9  5'-CACGGCCAGGTCCACCAGGC-3' (SEQ ID NO: 81)
11.b-1/2REV10  5'-CACGTCCCCTAGCACTGTCAG-3' (SEQ ID NO: 82)
11.b-1/2REV11  5'-CCATGTCCACAGAACAGAGAG-3' (SEQ ID NO: 51)
11.b-1/2REV12  5'-TTGACGAAGTCCTTCATCTGGG-3' (SEQ ID NO: 83)
11.b-1/2REV13  5'-GAACTGCAAGCTGGAGCCCAG-3' (SEQ ID NO: 84)
11.a-1/1REV1  5'-CTGGATGCTGCGAAGTGCTAC-3' (SEQ ID NO: 85)
11.a-1/1REV2  5'-GCCTTGGAGCTGGACGATGGC-3' (SEQ ID NO: 86)

Sequences were edited, aligned, and compared to a previously isolated mouse $\alpha_d$ sequence (construct #17, SEQ ID NO: 45).

Alignment of the new sequences revealed an 18 base deletion in construct #17 beginning at nucleotide 2308; the deletion did not cause a shift in the reading frame. Clone MS2P-9, sequenced as described above, also revealed the same 18 base deletion. The deletion has been observed to occur in 50% of mouse clones that include the region but has not been detected in rat or human $\alpha_d$ clones. The eighteen base deletion is characterized by a 12 base palindromic sequence AAGCAGGAGCTCCTGTGT (SEQ ID NO: 91). This inverted repeat in the nucleic acid sequence is self-complementary and may form a loop out, causing cleavage during reverse transcription. The mouse $\alpha_d$ sequence which includes the additional 18 bases is set forth in SEQ ID NO: 52; the deduced amino acid sequence is set forth in SEQ ID NO: 53.

EXAMPLE 21
In situ hybridizations in Mouse

Tissue distribution was then determined for mouse $\alpha_d$ in order to provide a comparison to that in humans, described in Example 6.

A single stranded 200 bp mRNA probe was generated from a DNA template, corresponding to nucleotides 3460 to 3707 in the cytoplasmic tail region of the murine cDNA, by in vitro RNA transcription incorporating $^{35}$S-UTP (Amersham).

Whole mouse embryos (harvested at days 11–18 after fertilization) and various mouse tissues, including spleen, kidney, liver, intestine, and thymus, were hybridized in situ with the radiolabeled single-stranded mRNA probe.

Tissues were sectioned at 6 µm thickness, adhered to Vectabond (Vector Laboratories, Inc., Burlingame, Calif.) coated slides, and stored at −70° C. Prior to use, slides were removed from −70° C. and placed at 50° C. for approximately 5 minutes. Sections were fixed in 4% paraformaldehyde for 20 minutes at 4° C., dehydrated with an increasing ethanol gradient (70–95–100%) for 1 minute at 4° C. at each concentration, and air dried for 30 minutes at room temperature. Sections were denatured for 2 minutes at 70° C. in 70% formamide/2x SSC, rinsed twice in 2x SSC, dehydrated with the ethanol gradient described supra and air dried for 30 minutes. Hybridization was carried out overnight (12–16 hours) at 55° C. in a solution containing $^{35}$S-labeled riboprobes at 6×10$^5$ cpm/section and diethylpyrocarbonate (DEPC)-treated water to give a final concentration of 50% formamide, 0.3M NaCl, 20 mM Tris-HCl, pH 7.5, 10% dextran sulfate, 1x Denhardt's solution, 100 mM dithiothreitol (DTT) and 5 mM EDTA. After hybridization, sections were washed for 1 hour at room temperature in 4x SSC/10 mM DTT, 40 minutes at 60° C. in 50% formamide/2x SSC/10 mM DTT, 30 minutes at room temperature in 2x SSC, and 30 minutes at room temperature in 0.1x SSC. The sections were dehydrated, air dried for 2 hours, coated with Kodak NTB2 photographic emulsion, air dried for 2 hours, developed (after storage at 4° C. in complete darkness) and counterstained with hematoxylin/eosin.

Spleen tissue showed a strong signal primarily in the red pulp. This pattern is consistent with that of tissue macrophage distribution in the spleen, but does not exclude other cell types.

EXAMPLE 22
Generation of Mouse Expression Constructs

In order to construct an expression plasmid including mouse cDNA sequences exhibiting homology to human $\alpha_d$, inserts from clones A1160 and B3800 were ligated. Prior to this ligation, however, a 5' leader sequence, including an initiating methionine, was added to clone A1160. A primer designated "5' PCR leader" (SEQ ID NO: 47) was designed to contain: (1) identical nonspecific bases at positions 1–6 allowing for digestion; (2) a BamHI site (underlined in SEQ ID NO: 47) from positions 7–12 to facilitate subcloning into an expression vector; (3) a consensus Kozak sequence from positions 13–18, (4) a signal sequence including a codon for an initiating methionine (bold in SEQ ID NO: 47), and (5) an additional 31 bases of specifically overlapping 5' sequence from clone A1160 to allow primer annealing. A second primer designated "3' end frag" (SEQ ID NO: 48) was used with primer "5' PCR leader" to amplify the insert from clone A1160.

| | |
|---|---|
| 5'-AGTTACGGATCCGGCACCATGAC- | |
| -CTTCGGCACTGTGATCCTCCTGTGTGTG-3' | (SEQ ID NO: 47) |
| 5'-GCTGGACGATGGCATCCAC-3' | (SEQ ID NO: 48) |

The resulting PCR product did not digest with BamHI, suggesting that an insufficient number of bases preceded the restriction site, prohibiting recognition by the enzyme. The length of the "tail" sequence preceding the BamHI site in the 5' primer (SEQ ID NO: 47) was increased and PCR was repeated on the amplification product from the first PCR. A 5' primer, designated mAD.5'.2 (SEQ ID NO: 49), was designed with additional nonspecific bases at positions 1–4 and an additional 20 bases specifically overlapping the previously employed "5' PCR leader" primer sequences.

5'-GTAGAGTTACGGATCCGGCACCAT-3' (SEQ ID NO: 49)

Primers "mAD.5'.2" and "3' end frag" were used together in PCR with the product from the first amplification as template. A resulting secondary PCR product was subcloned into plasmid pCRtmII (Invitrogen) according to manufacturer's suggested protocol and transformed into competent One shot cells (Invitrogen). One clone containing the PCR product was identified by restriction enzyme analysis using BamHI and EcoRI and sequenced. After the sequence was verified, the insert was isolated by digestion with BamHI and EcoRI and gel purified.

The insert from clone B3800 was isolated by digestion with EcoRI and NotI, gel purified, and added to a ligation reaction which included the augmented A1160 BamHI/EcoRI fragment. Ligation was allowed to proceed for 14 hours at 14° C. Vector pcDNA.3 (lnvitrogen), digested with BamHI and NotI, was added to the ligation reaction with additional ligase and the reaction was continued for another 12 hours. An aliquot of the reaction mixture was transformed into competent E. coli cells, the resulting colonies cultured, and one positive clone identified by PCR analysis with the primers 11.b-1/2FOR1 and 11.b-1/2REV11 (SEQ ID NOS: 50 and 51, respectively). These primers bridge the A1160 and B3800 fragments, therefore detection of an amplification product indicates the two fragments were ligated. The sequence of the positive clone was verified with the primers set out in SEQ ID NOS: 50 and 51, which amplify from base 100 to 1405 after the initiating methionine.

EXAMPLE 23
Construction of a Knock-out Mouse

In order to more accurately assess the immunological role of the protein encoded by the putative mouse $\alpha_d$ cDNA, a "knock-out" mouse is designed wherein the genomic DNA sequence encoding the putative $\alpha_d$ homolog is disrupted by homologous recombination. The significance of the protein encoded by the disrupted gene is thereby assessed by the absence of the encoded protein. Generation of "knock-out" mice is described in Deng, et al., *Mol. Cell. Biol.* 13:2134–2140 (1993).

Design of such a mouse begins with construction of a plasmid containing sequences to be "knocked out" by homologous recombination events. A 750 base pair fragment of the mouse cDNA (corresponding to nucleotides 1985 to 2733 in SEQ ID NO: 45) was used to identify a mouse genomic sequence encoding the putative mouse $\alpha_d$ homolog from a γFIXII genomic library. Primary screening resulted in 14 positive plaques, seven of which were confirmed by secondary screening. Liquid lysates were obtained from two of the plaques giving the strongest signal and the γ DNA was isolated by conventional methods. Restriction mapping and Southern analysis confirmed the authenticity of one clone, designated 14–1, and the insert DNA was isolated by digestion with NotI. This fragment was cloned into Bluescript SKII$^+$.

In order to identify a restriction fragment of approximately 9 to 14 kb, a length reported to optimize the probability of homologous recombination events, Southern hybridization was performed with the 750 bp cDNA probe. Prior to hybridization, a restriction map was constructed for clone 14–1. A 12 kb fragment was identified as a possible candidate and this fragment was subcloned into pBluescript SKII$^+$ in a position wherein the mouse DNA is flanked by thymidine kinase encoding cassettes. Further analysis of this clone with an I domain probe (corresponding to nucleotides 454–1064 in SEQ ID NO: 45) indicated that the clone did not contain I domain encoding sequences.

Using the same I domain probe, the γFIXII genomic library was rescreened. Initially, six positive clones were detected, one of which remained positive upon secondary screening. DNA isolated from this clone reacted strongly in Southern analysis with an I domain probe. No reactivity was detected using the original 750 bp probe, however, indicating that this clone included regions 5' to nucleotides 1985–2773 of SEQ ID NO: 45.

Alternatively, the lack of hybridization to the 750 bp probe may have suggested that the clone was another member of the integrin family of proteins. To determine if this explanation was plausible, the 13 kb insert was subcloned into pBluescript SKII$^+$. Purified DNA was sequenced using primers corresponding to $\alpha_d$ I domain nucleic acid sequences 441–461, 591–612, 717–739, and reverse 898–918 in SEQ ID NO: 52. Sequence information was obtained using only the first 4441–4461 primer, and only the 5'-most exon of the I domain was efficiently amplified. The remainder of the I domain was not amplified. The resulting clone therefore comprised exon 6 of the mouse $\alpha_d$ gene, and intronic sequences to the 3' and 5' end of the exon. Exon 7 was not represented in the clone. After sequencing, a construct is generated containing neomycin resistance and thymidine kinase genes.

The neomycin resistance (neo$^r$) gene is inserted into the resulting plasmid in a manner that interrupts the protein coding sequence of the genomic mouse DNA. The resulting plasmid therefore contains a neo$^r$ gene within the mouse genomic DNA sequences, all of which are positioned within a thymidine kinase encoding region. Plasmid construction in this manner is required to favor homologous recombination over random recombination [Chisaka, et al., *Nature* 355:516–520 (1992)].

EXAMPLE 24

Cloning of Rabbit $\alpha_d$ - Construction and Screening of the Rabbit cDNA Library Identification of human $\alpha_d$ homologs in rats and mice led to the investigation of the existence of a rabbit homolog which would be useful in rabbit models of human disease states described infra.

Poly A$^+$ RNA was prepared from a whole rabbit spleen using an Invitrogen FastTrack kit (San Diego, Calif.) according to manufacturer's suggested protocol and reagents supplied with the kit. From 1.65 g tissue, 73 μg poly A$^+$ RNA were isolated. The rabbit spleen RNA was used to construct a ZAP Express cDNA library using a kit from Stratagene (La Jolla, Calif.). Resulting cDNA was directionally cloned into EcoRI and XhoI sites in the lambda arms of a pBK-CMV phagemid vector. Gigapack II Gold (Stratagene) was used to package the lambda arms into phage particles. The resulting library titer was estimated to be approximately 8×10$^5$ particles, with an average insert size of 1.2 kb.

The library was amplified once by plating for confluent plaque growth and cell lysate was collected. The amplified library was plated at approximately 30,000 plaque forming units (pfu) per 150 mm plate with *E. coli* and the resulting mixture incubated for 12–16 hrs at 37° C. to allow plaque formation. Phage DNA was transferred onto Hybond N$^+$ nylon membranes (Amersham, Arlington Heights, Ill.). The membranes were hybridized with a mixture of two random primed radiolabeled mouse $\alpha_d$ PCR DNA probes. The first probe was generated from a PCR product spanning nucleotides 149–946 in SEQ ID NO: 52. The second probe was from a PCR product spanning nucleotides 2752–3651 in SEQ ID NO: 52. Probes were labeled by random priming (Boehringer Mannheim Random Primed DNA Labeling Kit) and the reaction mixture was passed over a Sephadex G-50 column to remove unincorporated nucleotides. The hybridization solution was composed of 5× SSPE, 5× Denhardts, 1% SDS, 40% Formamide and the labeled probes at 1×10$^6$ dpm/ml. Hybridization was carried out at 42° C. for 16–18 hours. Filters were washed extensively in 2× SSPE/0.1% SDS at room temperature and exposed to X-ray film to visualize any hybridizing plaques.

Two clones with significant sequence homology to human $\alpha_d$ were identified. Clone #2 was approximately 800 bp in length and mapped to the 5'end of human $\alpha_d$. Clone #2 includes an initiating methionine and complete leader sequence. Clone #7 was approximately 1.5 kb and includes an initiating methionine. The 5' end of clone #7 overlapped that of clone #2, while the 3' sequences terminated at a point beyond the I domain sequences. Clone #7 was completely sequenced by the primer walking method. The nucleotide and deduced amino acid sequences for clone #7 are set out in SEQ ID NOs: 100 and 101, respectively.

The predicted N terminal amino acid sequence for rabbit $\alpha_d$ as determined from clones #2 and #7 indicated a protein with 73% identity with human $\alpha_d$, 65% identity with mouse $\alpha_d$, and 58% identity with mouse CD11b, human CD11b, and human CD11c. The nucleic acid sequence for clone #2 is set out in SEQ ID NO: 92; the predicted amino acid sequence is set out in SEQ ID NO: 93

Isolation of a full length rabbit $\alpha_d$ cDNA was attempted using labeled rabbit clone # 7 and rescreening the cDNA library from which the fragment was derived. Twenty-five additional clones were identified with one, designated clone 49, determined to be the largest. Clone 49 was completely sequenced using the nested deletions technique. The nucleotide and amino acid sequences for clone 49 are set out in SEQ ID NOs: 102 and 103, respectively. Since clones #7 and #49 did not overlap, oligonucleotides were designed to be used as primers in a PCR with first strand rabbit spleen cDNA to isolate the missing sequence.

The relationship of the putative amino acid sequence of these two partial clones with that of other leukointegrins is described in Table 1.

TABLE 1

Percent identity of $\beta_2$ integrin family members on the amino acid level.

| | Human $\alpha_d$ | Rabbit #7 | Rabbit #49 |
|---|---|---|---|
| Human $\alpha_d$ | 100 | 74 | 80 |
| Mouse $\alpha_d$ | 70 | 67 | 74 |
| Rat $\alpha_d$ | 70 | 66 | 73 |
| Mouse CD11a | random* | 28 | 28 |
| Mouse CD11b | 55 | 59 | 53 |
| Human CD11a | 36 | 28 | 28 |
| Human CD11b | 60 | 58 | 55 |
| Human CD11c | 66 | 59 | 62 |

*If <25% identity, it is just random alingment and not significant.

Isolation of a rabbit $\alpha_d$ clone allows expression of the protein, either on the surface of transfectants or as a soluble full length or truncated form. This protein is then used as an immunogen for the production of monoclonal antibodies for use in rabbit models of human disease states.

EXAMPLE 25
Animal Models For Determining $\alpha_d$ Therapeutic Utility

Immunohistologic data in dog and in situ hybridization in rats and mice has determined that in spleen $\alpha_d$ is expressed primarily by macrophages present in red pulp and in lymph nodes, $\alpha_d$ is found in medullary cords and sinuses. The expression pattern is remarkably similar to what has been reported for two murine antigens defined by the monoclonal antibodies F4/80 and SK39. While biochemical characterization of these murine antigens has demonstrated that they are distinct from $\alpha_d$, it is highly probably that $\alpha_d$ defines the same macrophage subset as the murine F4/80 and SK39 antigens.

In mouse, SK39-positive macrophages have been identified in splenic red pulp where they may participate in the clearance of foreign materials from circulation, and in medulla of lymph nodes [Jutila, et al., *J. Leukocyte Biol.* 54:30–39 (1993)]. SK39-positive macrophages have also been reported at sites of both acute and chronic inflammation. Furthermore, monocytes recruited to thioglycolate-inflamed peritoneal cavities also express the SK39 antigen. Collectively, these findings suggest that, if SK39$^+$ cells are also $\alpha_d^+$, then these cells are responsible for the clearance of foreign materials in the spleen and participate in inflammation where macrophages play a significant role.

While the function of $\alpha_d$ remains unclear, other more well characterized $\beta_2$ integrins have been shown to participate in a wide variety of adhesion events that facilitate cell migration, enhance phagocytosis, and promote cell-cell interactions, events which all lead to upregulation of inflammatory processes. Therefore, it is highly plausible that interfering with the normal $\alpha_d$ function may also interfere with inflammation where macrophages play a significant role. Such an anti-inflammatory effect could result from: i) blocking macrophage recruitment to sites of inflammation, ii) preventing macrophage activation at the site of inflammation or iii) interfering with macrophage effector functions which damage normal host tissue through either specific autoimmune responses or as a result of bystander cell damage.

Disease states in which there is evidence of macrophages playing a significant role in the disease process include multiple sclerosis, arthritis, graft atherosclerosis, some forms of diabetes and inflammatory bowel disease. Animal models, discussed below, have been shown to reproduce many of the aspects of these human disorders. Inhibitors of $\alpha_d$ function are tested in these model systems to determine if the potential exists for treating the corresponding human diseases.

A. Graft Arteriosclerosis

Cardiac transplantation is now the accepted form of therapeutic intervention for some types of end-state heart disease. As the use of cyclosporin A has increased one year survival rates to 80%, the development of progressive graft arteriosclerosis has emerged as the leading cause of death in cardiac transplants surviving beyond the first year. Recent studies have found that the incidence of significant graft arteriosclerosis 3 years following a cardiac transplant is in the range of 36–44% [Adams, et al., *Transplantation* 53:1115–1119 (1992); Adams, et al., *Transplantation* 56:794–799 (1993)].

Graft arteriosclerosis typically consists of diffuse, occlusive, intimal lesions which affect the entire coronary vessel wall, and are often accompanied by lipid deposition. While the pathogenesis of graft arteriosclerosis remains unknown, it is presumably linked to histocompatibility differences between donor and recipient, and is immunologic in nature. Histologically, the areas of intimal thickening are composed primarily of macrophages, although T cells are occasionally seen. It is therefore possible that macrophages expressing $\alpha_d$ may play a significant role in the induction and/or development of graft arteriosclerosis. In such a case, monoclonal antibodies or small molecule inhibitors (for example, soluble ICAM-R) of $\alpha_d$ function could be given prophylactically to individuals who received heart transplants and are at risk of developing graft arteriosclerosis.

Although atherosclerosis in heart transplants presents the greatest threat to life, graft arteriosclerosis is also seen in other solid organ transplants, including kidneys and livers. Therapeutic use of $\alpha_d$ blocking agents could prevent graft arteriosclerosis in other organ transplants and reduce complications resulting from graft failure.

One model for graft arteriosclerosis in the rat involves heterotopic cardiac allografts transplanted across minor histocompatibility barriers. When Lewis cardiac allografts are transplanted into MHC class I and II compatible F-344 recipients, 80% of the allografts survive at least 3 weeks, while 25% of the grafts survive indefinitely. During this low-grade graft rejection, arteriosclerosis lesions form in the donor heart. Arterial lesions in 120 day old allografts typically have diffuse fibrotic intimal thickening indistinguishable in appearance from graft arteriosclerosis lesions found in rejecting human cardiac allografts.

Rats are transplanted with hearts mismatched at minor histocompatibility antigens, for example Lewis into F-344. Monoclonal antibodies specific for rat $\alpha_d$ or small molecule inhibitors of $\alpha_d$ are given periodically to transplant recipients. Treatment is expected to reduce the incidence of graft arteriosclerosis in non-rejecting donor hearts. Treatment of rats with $\alpha_d$ monoclonal antibodies or small molecule inhibitors may not be limited to prophylactic treatments. Blocking $\alpha_d$ function is also be expected to reduce macrophage mediated inflammation and allow reversal of arterial damage in the graft.

B. Atherosclerosis in Rabbits Fed Cholesterol

Rabbits fed an atherogenic diet containing a cholesterol supplement for approximately 12–16 weeks develop intimal lesions that cover most of the lumenal surface of the ascending aorta [Rosenfeld, et al., *Arteriosclerosis* 7:9–23 (1987); Rosenfeld, et al., *Arteriosclerosis* 7:24–34 (1987)]. The atherosclerotic lesions seen in these rabbits are simmer to those in humans. Lesions contain large numbers of T cells, most of which express CD45RO, a marker associated with memory T cells. Approximately half of the infiltrating T cells also express MHC class II antigen and some express the IL-2 receptor suggesting that many of the cells are in an activated state.

One feature of the atherosclerotic lesions found in cholesterol fed rabbits, but apparently absent in rodent models, is the accumulation of foam cell-rich lesions. Foam cell macrophages are believed to result from the uptake of oxidized low-density lipoprotein (LDL) by specific receptors. Oxidized LDL particles have been found to be toxic for some cell types including endothelial cells and smooth muscle cells. The uptake of potentially toxic, oxidized LDL particles by macrophages serves as an irritant and drives macrophage activation, contributing to the inflammation associated with atherosclerotic lesions.

Once monoclonal antibodies have been generated to rabbit $\alpha_d$, cholesterol fed rabbits are treated. Treatments include prophylactic administration of $\alpha_d$ monoclonal antibodies or small molecule inhibitors, to demonstrate that $\alpha_d^+$ macrophages are involved in the disease process. Additional studies would demonstrate that monoclonal antibodies to $\alpha_d$ or small molecule inhibitors are capable of reversing vessel damage detected in rabbits fed an atherogenic diet.

C. Insulin-dependent Diabetes

BB rats spontaneously develop insulin-dependent diabetes at 70–150 days of age. Using immunohistochemistry, MHC classII$^+$, ED1$^+$ macrophages can be detected infiltrating the islets early in the disease. Many of the macrophages appear to be engaged in phagocytosis of cell debris or normal cells. As the disease progresses, larger numbers of macrophages are found infiltrating the islets, although significant numbers of T cells, and later B cells, also appear to be recruited to the site [Hanenberg, et al., *Diabetologia* 32:126–134 (1989)].

Development of diabetes in BB rats appears to depend on both early macrophage infiltration and subsequent T cells recruitment. Treatment of BB rats with silica particles, which are toxic to macrophages, has been effective in blocking the early macrophage infiltration of the islets. In the absence of early macrophage infiltration, subsequent tissue damage by an autoaggressive lymphocyte population fails to occur. Administration of monoclonal antibody OX-19 (specific for rat CD5) or monoclonal antibody OX-8 (specific for rat CD8), which block the T cell-associated phase of the disease, is also effective in suppressing the development of diabetes.

The central role of macrophages in the pathology of this model makes it attractive for testing inhibitors of $\alpha_d$ function. Rats genetically predisposed to the development of insulin-dependent diabetes are treated with monoclonal antibodies to $\alpha_d$ or small molecule inhibitors and evaluated for the development of the disease. Preventing or delaying clinical onset is evidence that $\alpha_d$ plays a pivotal role in macrophage damage to the islet cells.

D. Inflammatory Bowel Disease (Crohn's Disease, Ulcerative Colitis)

Animal models used in the study of inflammatory bowel disease (IBD) are generally elicited by intrarectal administration of noxious irritants (e.g. acetic acid or trinitrobenzene sulfonic acid/ethanol). Colonic inflammation induced by these agents is the result of chemical or metabolic injury and lacks the chronic and spontaneously relapsing inflammation associated with human IBD. However, a recently described model using subserosal injections of purified peptidoglycan-polysaccharide (PG-PS) polymers from either group A or group D streptococci appears to be a more physiologically relevant model for human IBD [Yamada, et al., *Gastroenterology* 104:759–771 (1993)].

In this model PG-PS is injected into the subserosal layer of the distal colon. The resulting inflammatory response is biphasic with an initial acute episode three days after injection, which is followed by a spontaneous chronic phase three to four weeks later. The late phase response is granulomatous in nature, and results in colonic thickening, adhesions, colonic nodules and mucosal lesions. In addition to mucosal injury, PG-PS colitis frequently leads to arthritis anemia and granulomatous hepatitis. The extraintestinal manifestations of the disease make the model attractive for studying Crohn's colitis in that a significant number of patients with active Crohn's disease suffer from arthritic joint disease and hepatobillary inflammation.

Granulomatous lesions are the result of chronic inflammation which leads to the recruitment and subsequent activation of cells of the monocyte/macrophage lineage. Presence of granulomatous lesions in Crohn's disease and the above animal model make this an attractive clinical target for $\alpha_d$ monoclonal antibodies or other inhibitors of $\alpha_d$ function. Inhibitors of $\alpha_d$ function are expected to block the formation of lesions associated with IBD or even reverse tissue damage seen in the disease.

E. Arthritis

Arthritis appears to be a multi-factorial disease process involving a variety of inflammatory cell types including neutrophils, T lymphocytes and phagocytic macrophages. Although a variety of arthritis models exist, preparations of streptococcal cell wall proteoglycan produce a disorder most similar to the human disease.

In rats, streptococcal cell wall induces inflammation of peripheral joints characterized by repeated episodes of disease progression followed by remission and eventually resulting in joint destruction over a period of several months [Cromartie, et al., *J. Exp. Med.* 146:1585–1602 (1977); Schwab et al., *Infection and Immunity* 59:4436–4442 (1991)]. During the chronic phase of the disease, mononuclear phagocytes or macrophages are believed to play a major role in destruction of the synovium. Furthermore, agents which suppress the recruitment of macrophages into the synovium effectively reduce the inflammation and pathology characteristic of arthritis.

A central role for the macrophage in synovium destruction that leads to arthritis predicts that monoclonal antibodies to $\alpha_d$ or inhibitors of $\alpha_d$ function may have therapeutic potential in the treatment of this disease. As in other models previously described, $\alpha_d$ monoclonal antibodies or small molecule inhibitors administered prophylactically are expected to block or moderate joint inflammation and prevent destruction of the synovium. Agents that interfere with $\alpha_d$ function may also moderate ongoing inflammation by preventing the recruitment of additional macrophages to the joint or blocking macrophage activation. The net result would be to reverse ongoing destruction of the joint and facilitate tissue repair.

F. Multiple Sclerosis

Although pathogenesis of multiple sclerosis (MS) remains unclear, it is generally accepted that the disease is mediated by CD4$^+$ T cells which recognize autoantigens in the central nervous system and initiate an inflammatory cascade. The resulting immune response results in the recruitment of additional inflammatory cells, including activated macrophages which contribute to the disease. Experimental autoimmune encephalomyelitis (EAE) is an animal model which reproduces some aspects of MS. Recently, monoclonal antibodies reactive with CD11b/CD18 [Huitinga, et al., *Eur. J. Immunol.* 23:709–715 (1993)] present on inflammatory macrophages have been shown to block both clinical and histologic disease. The results suggest that monoclonal antibodies or small molecule inhibitors to $\alpha_d$ are likely to be effective in blocking the inflammatory response in EAE. Such agents also have important therapeutic applications in the treatment of MS.

G. Immune Complex Alveolitis

Alveolar macrophages located in the alveolar ducts, airways, connective tissue, and pleural spaces of the lung represent the lung's first line of defense against inhaled environmental agents. In response to stimulation by agents, including bacterial-derived LPS, IFN-γ and immune complexes, alveolar macrophages release a variety of potent inflammatory mediators, including highly reactive oxygen radicals and nitrogen intermediates. While superoxide anions, hydrogen peroxide and nitric oxide (NO.) have important functions in eradicating pathogens and lysing tumor targets, these agents can have injurious effects on normal tissues.

In a rat model of immune complex alveolitis, NO. release from alveolar macrophages has been shown to mediate much of the lung damage [Mulligan, et al., *Proc. Natl. Acad. Sci.* (USA) 88:638–6342 (1991)]. NO. has also been implicated as a mediator in other immune complex mediated injuries including dermal vasculitis [Mulligan, et al. supra] and could potentially play a role in diseases such as glomerulonephritis.

NO. mediated tissue damage is not limited to inflammation involving immune complexes. For example, microglial cell stimulated, by agents such as PMA, LPS or IFN-γ, produce NO. at levels capable of killing oligodendrocytes [Merrill, et al., *Immunol.* 151:2132 (1993)]. Pancreatic islet cells have also been found to be sensitive to NO., and macrophage release of this mediator has been implicated in the tissue damage which leads to diabetes [Kroncke, et al., *BBRC* 175:752–758 (1991)]. More recently, it was conclusively demonstrated that NO. release plays a role in endotoxic shock [MacMicking, et al., *Cell* 81:641–650 (1995)]. When administered lipopolysaccharide (LPS), normal wild-type mice experience a severe, progressive decline in arterial pressure resulting in death. Mice deficient in inducible nitric oxide, however, experience a much less severe decline in arterial pressure in response to LPS, and all survive the treatment.

In vitro assays indicate that blockage of $\alpha_d$ is effective at blocking some aspects of macrophage (or leukocyte which express $\alpha_d$, in general) activation, including NO. release. Alveolar macrophages stimulated with IFN-γ in the presence of anti-$\alpha_d$ polyclonal anti-serum (generated in rabbits against a rat $\alpha_d$ I domain polypeptide) were found to produce significantly less nitrite/nitrate—breakdown products of NO. than macrophages treated with control anti-serum. This finding indicates that monoclonal antibodies to $\alpha_d$, particularly to the I-domain, may be potent anti-inflammatory agents with potential uses in MS, diabetes, lung inflammation and endotoxic shock. Furthermore, in contrast to CD18, which effects the function of a wide variety of leukocyte types, the limited distribution of $\alpha_d$ may make this a more attractive target than CD18 for preventing macrophage (or leukocyte which express $\alpha_d$, in general) activation.

Rat IgG immune complex-induced alveolitis is a widely used experimental model important in understanding acute lung injury. The injury is elicited by instilling anti-bovine serum albumin (BSA) antibodies into lungs via tracheal cannulation, followed by an intravenous injection of BSA. The formation of immune complexes in the microvasculature of the lung leads to complement activation and the recruitment of neutrophils into the lung. Presumably, formation of immune complexes in the lung following extravasation of leukocytes from the blood and subsequent leukocyte movement across lung epithelium. The subsequent release of mediators, including radicals, TNF-α and nitric oxide (NO.), from activated endothelial cells, neutrophils and macrophages which participate in progression of the disease. Pathologic features of the disease include increased vascular permeability leading to edema and the presence of large numbers of erythrocytes and PMNs present in the alveolar spaces.

Polyclonal anti-serum specific for the I domain of $\alpha_d$ was tested in a rat model of immune complex-induced alveolitis. The anti-$\alpha_d$ polyclonal serum was administered via tracheal cannulation at the same time anti-BSA was introduced into the lungs. Lung injury was subsequently elicited by intravenous administration of BSA along with a trace amount of $^{125}$I-labeled BSA (approximately 800,000 cpm) to quantitate edema resulting from lung injury. Lung injury was allowed to proceed for four hours and damage was assessed using a lung permeability value, is defined as the ratio of $^{125}$I-labeled BSA in the lung compared to the amount of label present in the 1.0 ml of blood. Typically lung permeability values for positive control rates range between 0.6 and 0.8, while negative controls (rats not receiving BSA) have permeability index values in the range of 0.1–0.2.

Initial studies indicated that treatment with anti-$\alpha_d$ polyclonal anti-serum reduced lung permeability values by greater that 50%, representing a dramatic moderation of lung injury. Historically, treatments with anti-CD18 have reduced permeability values by 60%. These findings indicate that $\alpha_d$ may be the most important $\beta_2$ integrin during acute lung injury, however it cannot be precisely determined if the effect of the anti-sera prohibits leukocyte extravasation from the blood, or movement across lung epithelia.

As additional proof that $\alpha_d$ moderates lung injury, TNF-alpha levels in the bronchoalveolar lavage fluid were evaluated. Treatment with the anti-$\alpha_d$ anti-serum was found to reduce TNF-alpha levels approximately four-fold. TNF-alpha has long been viewed as an important mediator in acute lung inflammation, and responsible for the recruitment of inflammatory cells into sites of inflammation, cell activation and tissue damage. Presumably, anti-$\alpha_d$ anti-serum blocks activation of resident alveolar macrophages during the formation of immune complex alveolitis, and thereby moderates the release of TNF-α and NO., and reduces subsequent tissue damage caused by these agents and the recruitment of neutrophils.

Numerous modifications and variations in the invention as set forth in the above illustrative examples are expected to occur to those skilled in the art. Consequently only such limitations as appear in the appended claims should be placed on the invention.

What is claimed is:

1. An antibody which specifically binds $\alpha_d$.

2. An antibody according to claim 1 which is a monoclonal antibody.

3. An anti-idiotype antibody specific for the monoclonal antibody of claim 2.

4. A hybridoma cell line producing the monoclonal antibody according to claim 2.

5. A hybridoma designated 169A (A.T.C.C. Accession Number HB11907).

6. A monoclonal antibody secreted by hybridoma 169A.

7. A hybridoma designated 169B (A.T.C.C. Accession Number HB11906).

8. A monoclonal antibody secreted by hybridoma 169B.

9. An antibody which specifically binds $\alpha_d$ and which binds a polypeptide fragment comprising the $\alpha_d$ extracellular domain sequences of SEQ ID NO: 55.

10. An antibody according to claim 9 which is a monoclonal antibody.

* * * * *

UNITED STATES PATENT AND TRADEMARK OFFICE
CERTIFICATE OF CORRECTION

PATENT NO. : 5,831,029
DATED : November 3, 1998
INVENTOR(S) : Gallatin et al.

It is certified that error appears in the above-identified patent and that said Letters Patent is hereby corrected as shown below:

Title page,
Information disclosure statement, [C14], replace "Nature 355 516-520 (1992)" with "Nature 355:516-520 (1992)"

Information disclosure statement, [C29], back side of front page, replace "defiency" with "deficiency"

Information disclosure statement, [C54], replace "metallothiionein" with "metallothionein"

Information disclosure statement, [C56], back side of front page, replace "meutroph:is" with "neutroph:is"

Information disclosure statement, [C61], back side of front page, "gramulumatous" with "granulomatous"

Column 1,
Line 23, replace "an a subunit" with "an α subunit"
Line 25, replace "fourteen a subunits" with "fourteen α subunits"

Column 10,
Line 20, replace "5'-TTrYAA" with -- 5'TTYAA --
Line 39, replace "5'-TTrYAA" with -- 5'-TTYAA --

Column 11,
Line 35, replace "a Coming 0.8" with "a corning 0.8"
Line 51, replace "(DTF)" with "(DTT)"

Column 14,
Line 2, replace "a subunit amino" with "α subunit amio"
Line 22, replace "pCDNA/Amp" with "pcDNA/Amp"

Column 18,
Line 14, replace "codon is underlined" with "codon is underlined"
Line 17, "SEQ ID NO:27" does not have "ATG" underlined in the PTO form but it is in our document
Line 20, "SEQ ID NO:28" does not have "ATG" underlined in the sequence as seen in our copy of the patent

UNITED STATES PATENT AND TRADEMARK OFFICE
CERTIFICATE OF CORRECTION

PATENT NO.   : 5,831,029
DATED        : November 3, 1998
INVENTOR(S)  : Gallatin et al.

It is certified that error appears in the above-identified patent and that said Letters Patent is hereby corrected as shown below:

Column 19,
Line 30, replace "diluted to 10μl.ml" with "diluted to 10ug/ml"
Line 49, replace "aid expression" with "αd expression"

Column 24,
Line 57, the restriction site "GGATCC" of SEQ ID NO:32 is not underlined but it is in our copy of the patent
Line 59, the restriction site "CTCGAG" of SEQ ID NO:33 is not under lined but it is in our copy of the patent
Line 59, replace "CCTITCTTGGGACATC-3" with "CCTTCTTGGGACATC-3"

Column 25,
Line 61, "be" should be deleted from "are then be expressed"

Column 27,
Line 57, replace "200μI/well" with "200ul/well"

Signed and Sealed this

Eleventh Day of December, 2001

*Attest:*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 103

5,831,029

53 54

-continued ( 2 ) INFORMATION FOR SEQ ID NO:1:

( i ) SEQUENCE CHARACTERISTICS:
        ( A ) LENGTH: 3726 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..3485

( x i ) SEQUENCE DESCRIPTION: SEQ ID NO:1:

```
TG ACC TTC GGC ACT GTG CTT CTT CTG AGT GTC CTG GCT TCT TAT CAT        47
   Thr Phe Gly Thr Val Leu Leu Leu Ser Val Leu Ala Ser Tyr His
   1               5                   10                  15

GGA TTC AAC CTG GAT GTG GAG GAG CCT ACG ATC TTC CAG GAG GAT GCA       95
Gly Phe Asn Leu Asp Val Glu Glu Pro Thr Ile Phe Gln Glu Asp Ala
                20                  25                  30

GGC GGC TTT GGG CAG AGC GTG GTG CAG TTC GGT GGA TCT CGA CTC GTG       143
Gly Gly Phe Gly Gln Ser Val Val Gln Phe Gly Gly Ser Arg Leu Val
            35                  40                  45

GTG GGA GCA CCC CTG GAG GTG GTG GCG GCC AAC CAG ACG GGA CGG CTG       191
Val Gly Ala Pro Leu Glu Val Val Ala Ala Asn Gln Thr Gly Arg Leu
        50                  55                  60

TAT GAC TGC GCA GCT GCC ACC GGC ATG TGC CAG CCC ATC CCG CTG CAC       239
Tyr Asp Cys Ala Ala Ala Thr Gly Met Cys Gln Pro Ile Pro Leu His
    65                  70                  75

ATC CGC CCT GAG GCC GTG AAC ATG TCC TTG GGC CTG ACC CTG GCA GCC       287
Ile Arg Pro Glu Ala Val Asn Met Ser Leu Gly Leu Thr Leu Ala Ala
80                  85                  90                  95

TCC ACC AAC GGC TCC CGG CTC CTG GCC TGT GGC CCG ACC CTG CAC AGA       335
Ser Thr Asn Gly Ser Arg Leu Leu Ala Cys Gly Pro Thr Leu His Arg
                100                 105                 110

GTC TGT GGG GAG AAC TCA TAC TCA AAG GGT TCC TGC CTC CTG CTG GGC       383
Val Cys Gly Glu Asn Ser Tyr Ser Lys Gly Ser Cys Leu Leu Leu Gly
            115                 120                 125

TCG CGC TGG GAG ATC ATC CAG ACA GTC CCC GAC GCC ACG CCA GAG TGT       431
Ser Arg Trp Glu Ile Ile Gln Thr Val Pro Asp Ala Thr Pro Glu Cys
        130                 135                 140

CCA CAT CAA GAG ATG GAC ATC GTC TTC CTG ATT GAC GGC TCT GGA AGC       479
Pro His Gln Glu Met Asp Ile Val Phe Leu Ile Asp Gly Ser Gly Ser
    145                 150                 155

ATT GAC CAA AAT GAC TTT AAC CAG ATG AAG GGC TTT GTC CAA GCT GTC       527
Ile Asp Gln Asn Asp Phe Asn Gln Met Lys Gly Phe Val Gln Ala Val
160                 165                 170                 175

ATG GGC CAG TTT GAG GGC ACT GAC ACC CTG TTT GCA CTG ATG CAG TAC       575
Met Gly Gln Phe Glu Gly Thr Asp Thr Leu Phe Ala Leu Met Gln Tyr
                180                 185                 190

TCA AAC CTC CTG AAG ATC CAC TTC ACC TTC ACC CAA TTC CGG ACC AGC       623
Ser Asn Leu Leu Lys Ile His Phe Thr Phe Thr Gln Phe Arg Thr Ser
            195                 200                 205

CCG AGC CAG CAG AGC CTG GTG GAT CCC ATC GTC CAA CTG AAA GGC CTG       671
Pro Ser Gln Gln Ser Leu Val Asp Pro Ile Val Gln Leu Lys Gly Leu
        210                 215                 220

ACG TTC ACG GCC ACG GGC ATC CTG ACA GTG GTG ACA CAG CTA TTT CAT       719
Thr Phe Thr Ala Thr Gly Ile Leu Thr Val Val Thr Gln Leu Phe His
    225                 230                 235

CAT AAG AAT GGG GCC CGA AAA AGT GCC AAG AAG ATC CTC ATT GTC ATC       767
His Lys Asn Gly Ala Arg Lys Ser Ala Lys Lys Ile Leu Ile Val Ile
240                 245                 250                 255
```

| | | | | | | | | | | | | | | | | |
|---|---|---|---|---|---|---|---|---|---|---|---|---|---|---|---|---|
| ACA | GAT | GGG | CAG | AAG | TAC | AAA | GAC | CCC | CTG | GAA | TAC | AGT | GAT | GTC | ATC | 815 |
| Thr | Asp | Gly | Gln | Lys | Tyr | Lys | Asp | Pro | Leu | Glu | Tyr | Ser | Asp | Val | Ile | |
| | | | 260 | | | | | 265 | | | | | 270 | | | |
| CCC | CAG | GCA | GAG | AAG | GCT | GGC | ATC | ATC | CGC | TAC | GCT | ATC | GGG | GTG | GGA | 863 |
| Pro | Gln | Ala | Glu | Lys | Ala | Gly | Ile | Ile | Arg | Tyr | Ala | Ile | Gly | Val | Gly | |
| | | | 275 | | | | 280 | | | | | 285 | | | | |
| CAC | GCT | TTC | CAG | GGA | CCC | ACT | GCC | AGG | CAG | GAG | CTG | AAT | ACC | ATC | AGC | 911 |
| His | Ala | Phe | Gln | Gly | Pro | Thr | Ala | Arg | Gln | Glu | Leu | Asn | Thr | Ile | Ser | |
| | | 290 | | | | | 295 | | | | | 300 | | | | |
| TCA | GCG | CCT | CCG | CAG | GAC | CAC | GTG | TTC | AAG | GTG | GAC | AAC | TTT | GCA | GCC | 959 |
| Ser | Ala | Pro | Pro | Gln | Asp | His | Val | Phe | Lys | Val | Asp | Asn | Phe | Ala | Ala | |
| | 305 | | | | | 310 | | | | | 315 | | | | | |
| CTT | GGC | AGC | ATC | CAG | AAG | CAG | CTG | CAG | GAG | AAG | ATC | TAT | GCA | GTT | GAG | 1007 |
| Leu | Gly | Ser | Ile | Gln | Lys | Gln | Leu | Gln | Glu | Lys | Ile | Tyr | Ala | Val | Glu | |
| 320 | | | | | 325 | | | | | 330 | | | | | 335 | |
| GGA | ACC | CAG | TCC | AGG | GCA | AGC | AGC | TCC | TTC | CAG | CAC | GAG | ATG | TCC | CAA | 1055 |
| Gly | Thr | Gln | Ser | Arg | Ala | Ser | Ser | Ser | Phe | Gln | His | Glu | Met | Ser | Gln | |
| | | | | 340 | | | | | 345 | | | | | 350 | | |
| GAA | GGC | TTC | AGC | ACA | GCC | CTC | ACA | ATG | GAT | GGC | CTC | TTC | CTG | GGG | GCT | 1103 |
| Glu | Gly | Phe | Ser | Thr | Ala | Leu | Thr | Met | Asp | Gly | Leu | Phe | Leu | Gly | Ala | |
| | | | 355 | | | | | 360 | | | | | 365 | | | |
| GTG | GGG | AGC | TTT | AGC | TGG | TCT | GGA | GGT | GCC | TTC | CTG | TAT | CCC | CCA | AAT | 1151 |
| Val | Gly | Ser | Phe | Ser | Trp | Ser | Gly | Gly | Ala | Phe | Leu | Tyr | Pro | Pro | Asn | |
| | | 370 | | | | | 375 | | | | | 380 | | | | |
| ATG | AGC | CCC | ACC | TTC | ATC | AAC | ATG | TCT | CAG | GAG | AAT | GTG | GAC | ATG | AGG | 1199 |
| Met | Ser | Pro | Thr | Phe | Ile | Asn | Met | Ser | Gln | Glu | Asn | Val | Asp | Met | Arg | |
| | 385 | | | | | 390 | | | | | 395 | | | | | |
| GAC | TCT | TAC | CTG | GGT | TAC | TCC | ACC | GAG | CTA | GCC | CTG | TGG | AAG | GGG | GTA | 1247 |
| Asp | Ser | Tyr | Leu | Gly | Tyr | Ser | Thr | Glu | Leu | Ala | Leu | Trp | Lys | Gly | Val | |
| 400 | | | | | 405 | | | | | 410 | | | | | 415 | |
| CAG | AAC | CTG | GTC | CTG | GGG | GCC | CCC | CGC | TAC | CAG | CAT | ACC | GGG | AAG | GCT | 1295 |
| Gln | Asn | Leu | Val | Leu | Gly | Ala | Pro | Arg | Tyr | Gln | His | Thr | Gly | Lys | Ala | |
| | | | | 420 | | | | | 425 | | | | | 430 | | |
| GTC | ATC | TTC | ACC | CAG | GTG | TCC | AGG | CAA | TGG | AGG | AAG | AAG | GCC | GAA | GTC | 1343 |
| Val | Ile | Phe | Thr | Gln | Val | Ser | Arg | Gln | Trp | Arg | Lys | Lys | Ala | Glu | Val | |
| | | | 435 | | | | | 440 | | | | | 445 | | | |
| ACA | GGG | ACG | CAG | ATC | GGC | TCC | TAC | TTC | GGG | GCC | TCC | CTC | TGC | TCC | GTG | 1391 |
| Thr | Gly | Thr | Gln | Ile | Gly | Ser | Tyr | Phe | Gly | Ala | Ser | Leu | Cys | Ser | Val | |
| | | 450 | | | | | 455 | | | | | 460 | | | | |
| GAT | GTG | GAC | AGC | GAT | GGC | AGC | ACC | GAC | CTG | ATC | CTC | ATT | GGG | GCC | CCC | 1439 |
| Asp | Val | Asp | Ser | Asp | Gly | Ser | Thr | Asp | Leu | Ile | Leu | Ile | Gly | Ala | Pro | |
| | 465 | | | | | 470 | | | | | 475 | | | | | |
| CAT | TAC | TAT | GAG | CAG | ACC | CGA | GGG | GGC | CAG | GTG | TCC | GTG | TGT | CCC | TTG | 1487 |
| His | Tyr | Tyr | Glu | Gln | Thr | Arg | Gly | Gly | Gln | Val | Ser | Val | Cys | Pro | Leu | |
| 480 | | | | | 485 | | | | | 490 | | | | | 495 | |
| CCT | AGG | GGG | CAG | AGG | GTG | CAG | TGG | CAG | TGT | GAC | GCT | GTT | CTC | CGT | GGT | 1535 |
| Pro | Arg | Gly | Gln | Arg | Val | Gln | Trp | Gln | Cys | Asp | Ala | Val | Leu | Arg | Gly | |
| | | | | 500 | | | | | 505 | | | | | 510 | | |
| GAG | CAG | GGC | CAC | CCC | TGG | GGC | CGC | TTT | GGG | GCA | GCC | CTG | ACA | GTG | TTG | 1583 |
| Glu | Gln | Gly | His | Pro | Trp | Gly | Arg | Phe | Gly | Ala | Ala | Leu | Thr | Val | Leu | |
| | | | 515 | | | | | 520 | | | | | 525 | | | |
| GGG | GAT | GTG | AAT | GAG | GAC | AAG | CTG | ATA | GAC | GTG | GCC | ATT | GGG | GCC | CCG | 1631 |
| Gly | Asp | Val | Asn | Glu | Asp | Lys | Leu | Ile | Asp | Val | Ala | Ile | Gly | Ala | Pro | |
| | | 530 | | | | | 535 | | | | | 540 | | | | |
| GGA | GAG | CAG | GAG | AAC | CGG | GGT | GCT | GTC | TAC | CTG | TTT | CAC | GGA | GCC | TCA | 1679 |
| Gly | Glu | Gln | Glu | Asn | Arg | Gly | Ala | Val | Tyr | Leu | Phe | His | Gly | Ala | Ser | |
| | 545 | | | | | 550 | | | | | 555 | | | | | |
| GAA | TCC | GGC | ATC | AGC | CCC | TCC | CAC | AGC | CAG | CGG | ATT | GCC | AGC | TCC | CAG | 1727 |
| Glu | Ser | Gly | Ile | Ser | Pro | Ser | His | Ser | Gln | Arg | Ile | Ala | Ser | Ser | Gln | |
| 560 | | | | | 565 | | | | | 570 | | | | | 575 | |

-continued

| | | | | | | | | | | | | | | | | |
|---|---|---|---|---|---|---|---|---|---|---|---|---|---|---|---|---|
| CTC | TCC | CCC | AGG | CTG | CAG | TAT | TTT | GGG | CAG | GCG | CTG | AGT | GGG | GGT | CAG | 1775 |
| Leu | Ser | Pro | Arg 580 | Leu | Gln | Tyr | Phe | Gly | Gln 585 | Ala | Leu | Ser | Gly | Gly 590 | Gln | |
| GAC | CTC | ACC | CAG | GAT | GGA | CTG | ATG | GAC | CTG | GCC | GTG | GGG | GCC | CGG | GGC | 1823 |
| Asp | Leu | Thr | Gln 595 | Asp | Gly | Leu | Met | Asp 600 | Leu | Ala | Val | Gly | Ala 605 | Arg | Gly | |
| CAG | GTG | CTC | CTG | CTC | AGG | AGT | CTG | CCG | GTG | CTG | AAA | GTG | GGG | GTG | GCC | 1871 |
| Gln | Val | Leu 610 | Leu | Leu | Arg | Ser | Leu 615 | Pro | Val | Leu | Lys | Val 620 | Gly | Val | Ala | |
| ATG | AGA | TTC | AGC | CCT | GTG | GAG | GTG | GCC | AAG | GCT | GTG | TAC | CGG | TGC | TGG | 1919 |
| Met | Arg 625 | Phe | Ser | Pro | Val | Glu 630 | Val | Ala | Lys | Ala | Val 635 | Tyr | Arg | Cys | Trp | |
| GAA | GAG | AAG | CCC | AGT | GCC | CTG | GAA | GCT | GGG | GAC | GCC | ACC | GTC | TGT | CTC | 1967 |
| Glu 640 | Glu | Lys | Pro | Ser | Ala 645 | Leu | Glu | Ala | Gly | Asp 650 | Ala | Thr | Val | Cys | Leu 655 | |
| ACC | ATC | CAG | AAA | AGC | TCA | CTG | GAC | CAG | CTA | GGT | GAC | ATC | CAA | AGC | TCT | 2015 |
| Thr | Ile | Gln | Lys | Ser 660 | Ser | Leu | Asp | Gln | Leu 665 | Gly | Asp | Ile | Gln | Ser 670 | Ser | |
| GTC | AGG | TTT | GAT | CTG | GCA | CTG | GAC | CCA | GGT | CGT | CTG | ACT | TCT | CGT | GCC | 2063 |
| Val | Arg | Phe | Asp 675 | Leu | Ala | Leu | Asp | Pro 680 | Gly | Arg | Leu | Thr | Ser 685 | Arg | Ala | |
| ATT | TTC | AAT | GAA | ACC | AAG | AAC | CCC | ACT | TTG | ACT | CGA | AGA | AAA | ACC | CTG | 2111 |
| Ile | Phe | Asn 690 | Glu | Thr | Lys | Asn | Pro 695 | Thr | Leu | Thr | Arg | Arg 700 | Lys | Thr | Leu | |
| GGA | CTG | GGG | ATT | CAC | TGT | GAA | ACC | CTG | AAG | CTG | CTT | TTG | CCA | GAT | TGT | 2159 |
| Gly | Leu | Gly 705 | Ile | His | Cys | Glu | Thr 710 | Leu | Lys | Leu | Leu | Leu 715 | Pro | Asp | Cys | |
| GTG | GAG | GAT | GTG | GTG | AGC | CCC | ATC | ATT | CTG | CAC | CTC | AAC | TTC | TCA | CTG | 2207 |
| Val 720 | Glu | Asp | Val | Val | Ser 725 | Pro | Ile | Ile | Leu | His 730 | Leu | Asn | Phe | Ser | Leu 735 | |
| GTG | AGA | GAG | CCC | ATC | CCC | TCC | CCC | CAG | AAC | CTG | CGT | CCT | GTG | CTG | GCC | 2255 |
| Val | Arg | Glu | Pro | Ile 740 | Pro | Ser | Pro | Gln | Asn 745 | Leu | Arg | Pro | Val | Leu 750 | Ala | |
| GTG | GGC | TCA | CAA | GAC | CTC | TTC | ACT | GCT | TCT | CTC | CCC | TTC | GAG | AAG | AAC | 2303 |
| Val | Gly | Ser | Gln 755 | Asp | Leu | Phe | Thr | Ala 760 | Ser | Leu | Pro | Phe | Glu 765 | Lys | Asn | |
| TGT | GGG | CAA | GAT | GGC | CTC | TGT | GAA | GGG | GAC | CTG | GGT | GTC | ACC | CTC | AGC | 2351 |
| Cys | Gly | Gln | Asp 770 | Gly | Leu | Cys | Glu | Gly 775 | Asp | Leu | Gly | Val | Thr 780 | Leu | Ser | |
| TTC | TCA | GGC | CTG | CAG | ACC | CTG | ACC | GTG | GGG | AGC | TCC | CTG | GAG | CTC | AAC | 2399 |
| Phe | Ser 785 | Gly | Leu | Gln | Thr | Leu 790 | Thr | Val | Gly | Ser | Ser 795 | Leu | Glu | Leu | Asn | |
| GTG | ATT | GTG | ACT | GTG | TGG | AAC | GCA | GGT | GAG | GAT | TCC | TAC | GGA | ACC | GTG | 2447 |
| Val 800 | Ile | Val | Thr | Val | Trp 805 | Asn | Ala | Gly | Glu | Asp 810 | Ser | Tyr | Gly | Thr | Val 815 | |
| GTC | AGC | CTC | TAC | TAT | CCA | GCA | GGG | CTG | TCG | CAC | CGA | CGG | GTG | TCA | GGA | 2495 |
| Val | Ser | Leu | Tyr | Tyr 820 | Pro | Ala | Gly | Leu | Ser 825 | His | Arg | Arg | Val | Ser 830 | Gly | |
| GCC | CAG | AAG | CAG | CCC | CAT | CAG | AGT | GCC | CTG | CGC | CTG | GCA | TGT | GAG | ACA | 2543 |
| Ala | Gln | Lys | Gln 835 | Pro | His | Gln | Ser | Ala 840 | Leu | Arg | Leu | Ala | Cys 845 | Glu | Thr | |
| GTG | CCC | ACT | GAG | GAT | GAG | GGC | CTA | AGA | AGC | AGC | CGC | TGC | AGT | GTC | AAC | 2591 |
| Val | Pro | Thr | Glu 850 | Asp | Glu | Gly | Leu | Arg 855 | Ser | Ser | Arg | Cys | Ser 860 | Val | Asn | |
| CAC | CCC | ATC | TTC | CAT | GAG | GGC | TCT | AAC | GGC | ACC | TTC | ATA | GTC | ACA | TTC | 2639 |
| His | Pro | Ile 865 | Phe | His | Glu | Gly | Ser 870 | Asn | Gly | Thr | Phe | Ile 875 | Val | Thr | Phe | |
| GAT | GTC | TCC | TAC | AAG | GCC | ACC | CTG | GGA | GAC | AGG | ATG | CTT | ATG | AGG | GCC | 2687 |
| Asp 880 | Val | Ser | Tyr | Lys | Ala 885 | Thr | Leu | Gly | Asp | Arg 890 | Met | Leu | Met | Arg 895 | Ala | |

| | | | | | | | | | | | | | | | | |
|---|---|---|---|---|---|---|---|---|---|---|---|---|---|---|---|---|
| AGT | GCA | AGC | AGT | GAG | AAC | AAT | AAG | GCT | TCA | AGC | AGC | AAG | GCC | ACC | TTC | 2735 |
| Ser | Ala | Ser | Ser | Glu | Asn | Asn | Lys | Ala | Ser | Ser | Ser | Lys | Ala | Thr | Phe | |
| | | | | 900 | | | | 905 | | | | | | 910 | | |
| CAG | CTG | GAG | CTC | CCG | GTG | AAG | TAT | GCA | GTC | TAC | ACC | ATG | ATC | AGC | AGG | 2783 |
| Gln | Leu | Glu | Leu | Pro | Val | Lys | Tyr | Ala | Val | Tyr | Thr | Met | Ile | Ser | Arg | |
| | | | | 915 | | | | 920 | | | | | | 925 | | |
| CAG | GAA | GAA | TCC | ACC | AAG | TAC | TTC | AAC | TTT | GCA | ACC | TCC | GAT | GAG | AAG | 2831 |
| Gln | Glu | Glu | Ser | Thr | Lys | Tyr | Phe | Asn | Phe | Ala | Thr | Ser | Asp | Glu | Lys | |
| | | 930 | | | | | | 935 | | | | 940 | | | | |
| AAA | ATG | AAA | GAG | GCT | GAG | CAT | CGA | TAC | CGT | GTG | AAT | AAC | CTC | AGC | CAG | 2879 |
| Lys | Met | Lys | Glu | Ala | Glu | His | Arg | Tyr | Arg | Val | Asn | Asn | Leu | Ser | Gln | |
| | | 945 | | | | 950 | | | | | 955 | | | | | |
| CGA | GAT | CTG | GCC | ATC | AGC | ATT | AAC | TTC | TGG | GTT | CCT | GTC | CTG | CTG | AAC | 2927 |
| Arg | Asp | Leu | Ala | Ile | Ser | Ile | Asn | Phe | Trp | Val | Pro | Val | Leu | Leu | Asn | |
| 960 | | | | | 965 | | | | | 970 | | | | | 975 | |
| GGG | GTG | GCT | GTG | TGG | GAT | GTG | GTC | ATG | GAG | GCC | CCA | TCT | CAG | AGT | CTC | 2975 |
| Gly | Val | Ala | Val | Trp | Asp | Val | Val | Met | Glu | Ala | Pro | Ser | Gln | Ser | Leu | |
| | | | | 980 | | | | 985 | | | | | | 990 | | |
| CCC | TGT | GTT | TCA | GAG | AGA | AAA | CCT | CCC | CAG | CAT | TCT | GAC | TTC | CTG | ACC | 3023 |
| Pro | Cys | Val | Ser | Glu | Arg | Lys | Pro | Pro | Gln | His | Ser | Asp | Phe | Leu | Thr | |
| | | | 995 | | | | | 1000 | | | | | 1005 | | | |
| CAG | ATT | TCA | AGA | AGT | CCC | ATG | CTG | GAC | TGC | TCC | ATT | GCT | GAC | TGC | CTG | 3071 |
| Gln | Ile | Ser | Arg | Ser | Pro | Met | Leu | Asp | Cys | Ser | Ile | Ala | Asp | Cys | Leu | |
| | | | 1010 | | | | | 1015 | | | | | 1020 | | | |
| CAG | TTC | CGC | TGT | GAC | GTC | CCC | TCC | TTC | AGC | GTC | CAG | GAG | GAG | CTG | GAT | 3119 |
| Gln | Phe | Arg | Cys | Asp | Val | Pro | Ser | Phe | Ser | Val | Gln | Glu | Glu | Leu | Asp | |
| | | | 1025 | | | | | 1030 | | | | | 1035 | | | |
| TTC | ACC | CTG | AAG | GGC | AAT | CTC | AGT | TTC | GGC | TGG | GTC | CGC | GAG | ACA | TTG | 3167 |
| Phe | Thr | Leu | Lys | Gly | Asn | Leu | Ser | Phe | Gly | Trp | Val | Arg | Glu | Thr | Leu | |
| 1040 | | | | | 1045 | | | | | 1050 | | | | | 1055 | |
| CAG | AAG | AAG | GTG | TTG | GTC | GTG | AGT | GTG | GCT | GAA | ATT | ACG | TTC | GAC | ACA | 3215 |
| Gln | Lys | Lys | Val | Leu | Val | Val | Ser | Val | Ala | Glu | Ile | Thr | Phe | Asp | Thr | |
| | | | | 1060 | | | | | 1065 | | | | | 1070 | | |
| TCC | GTG | TAC | TCC | CAG | CTT | CCA | GGA | CAG | GAG | GCA | TTT | ATG | AGA | GCT | CAG | 3263 |
| Ser | Val | Tyr | Ser | Gln | Leu | Pro | Gly | Gln | Glu | Ala | Phe | Met | Arg | Ala | Gln | |
| | | | 1075 | | | | | 1080 | | | | | 1085 | | | |
| ATG | GAG | ATG | GTG | CTA | GAA | GAA | GAC | GAG | GTC | TAC | AAT | GCC | ATT | CCC | ATC | 3311 |
| Met | Glu | Met | Val | Leu | Glu | Glu | Asp | Glu | Val | Tyr | Asn | Ala | Ile | Pro | Ile | |
| | | | | 1090 | | | | | 1095 | | | | | 1100 | | |
| ATC | ATG | GGC | AGC | TCT | GTG | GGG | GCT | CTG | CTA | CTG | CTG | GCG | CTC | ATC | ACA | 3359 |
| Ile | Met | Gly | Ser | Ser | Val | Gly | Ala | Leu | Leu | Leu | Leu | Ala | Leu | Ile | Thr | |
| | | | | 1105 | | | | | 1110 | | | | | 1115 | | |
| GCC | ACA | CTG | TAC | AAG | CTT | GGC | TTC | TTC | AAA | CGC | CAC | TAC | AAG | GAA | ATG | 3407 |
| Ala | Thr | Leu | Tyr | Lys | Leu | Gly | Phe | Phe | Lys | Arg | His | Tyr | Lys | Glu | Met | |
| 1120 | | | | | 1125 | | | | | 1130 | | | | | 1135 | |
| CTG | GAG | GAC | AAG | CCT | GAA | GAC | ACT | GCC | ACA | TTC | AGT | GGG | GAC | GAT | TTC | 3455 |
| Leu | Glu | Asp | Lys | Pro | Glu | Asp | Thr | Ala | Thr | Phe | Ser | Gly | Asp | Asp | Phe | |
| | | | | 1140 | | | | | 1145 | | | | | 1150 | | |
| AGC | TGT | GTG | GCC | CCA | AAT | GTG | CCT | TTG | TCC | TAATAATCCA | CTTTCCTGTT | | | | | 3505 |
| Ser | Cys | Val | Ala | Pro | Asn | Val | Pro | Leu | Ser | | | | | | | |
| | | | | 1155 | | | | | 1160 | | | | | | | |

| | | | | |
|---|---|---|---|---|
| TATCTCTACC | ACTGTGGGCT | GGACTTGCTT | GCAACCATAA | ATCAACTTAC | ATGGAAACAA | 3565 |
| CTTCTGCATA | GATCTGCACT | GGCCTAAGCA | ACCTACCAGG | TGCTAAGCAC | CTTCTCGGAG | 3625 |
| AGATAGAGAT | TGTAATGTTT | TTACATATCT | GTCCATCTTT | TCAGCAATG | ACCCACTTTT | 3685 |
| TACAGAAGCA | GGCATGGTGC | CAGCATAAAT | TTTCATATGC | T | | 3726 |

( 2 ) INFORMATION FOR SEQ ID NO:2:

( i ) SEQUENCE CHARACTERISTICS:

(A) LENGTH: 1161 amino acids
(B) TYPE: amino acid
(D) TOPOLOGY: linear (ii) MOLECULE TYPE: protein (xi) SEQUENCE DESCRIPTION: SEQ ID NO:2:

```
Thr Phe Gly Thr Val Leu Leu Leu Ser Val Leu Ala Ser Tyr His Gly
  1               5                  10                  15

Phe Asn Leu Asp Val Glu Glu Pro Thr Ile Phe Gln Glu Asp Ala Gly
                 20                  25                  30

Gly Phe Gly Gln Ser Val Val Gln Phe Gly Gly Ser Arg Leu Val Val
             35                  40                  45

Gly Ala Pro Leu Glu Val Val Ala Ala Asn Gln Thr Gly Arg Leu Tyr
         50                  55                  60

Asp Cys Ala Ala Ala Thr Gly Met Cys Gln Pro Ile Pro Leu His Ile
 65                  70                  75                  80

Arg Pro Glu Ala Val Asn Met Ser Leu Gly Leu Thr Leu Ala Ala Ser
                     85                  90                  95

Thr Asn Gly Ser Arg Leu Leu Ala Cys Gly Pro Thr Leu His Arg Val
                100                 105                 110

Cys Gly Glu Asn Ser Tyr Ser Lys Gly Ser Cys Leu Leu Leu Gly Ser
             115                 120                 125

Arg Trp Glu Ile Ile Gln Thr Val Pro Asp Ala Thr Pro Glu Cys Pro
    130                 135                 140

His Gln Glu Met Asp Ile Val Phe Leu Ile Asp Gly Ser Gly Ser Ile
145                     150                 155                 160

Asp Gln Asn Asp Phe Asn Gln Met Lys Gly Phe Val Gln Ala Val Met
                    165                 170                 175

Gly Gln Phe Glu Gly Thr Asp Thr Leu Phe Ala Leu Met Gln Tyr Ser
                180                 185                 190

Asn Leu Leu Lys Ile His Phe Thr Phe Thr Gln Phe Arg Thr Ser Pro
            195                 200                 205

Ser Gln Gln Ser Leu Val Asp Pro Ile Val Gln Leu Lys Gly Leu Thr
    210                 215                 220

Phe Thr Ala Thr Gly Ile Leu Thr Val Val Thr Gln Leu Phe His His
225                     230                 235                 240

Lys Asn Gly Ala Arg Lys Ser Ala Lys Lys Ile Leu Ile Val Ile Thr
                    245                 250                 255

Asp Gly Gln Lys Tyr Lys Asp Pro Leu Glu Tyr Ser Asp Val Ile Pro
                260                 265                 270

Gln Ala Glu Lys Ala Gly Ile Ile Arg Tyr Ala Ile Gly Val Gly His
            275                 280                 285

Ala Phe Gln Gly Pro Thr Ala Arg Gln Glu Leu Asn Thr Ile Ser Ser
290                     295                 300

Ala Pro Pro Gln Asp His Val Phe Lys Val Asp Asn Phe Ala Ala Leu
305                     310                 315                 320

Gly Ser Ile Gln Lys Gln Leu Gln Glu Lys Ile Tyr Ala Val Glu Gly
                325                 330                 335

Thr Gln Ser Arg Ala Ser Ser Ser Phe Gln His Glu Met Ser Gln Glu
                340                 345                 350

Gly Phe Ser Thr Ala Leu Thr Met Asp Gly Leu Phe Leu Gly Ala Val
            355                 360                 365

Gly Ser Phe Ser Trp Ser Gly Gly Ala Phe Leu Tyr Pro Pro Asn Met
            370                 375                 380
```

| | | | | | | | | | | | | | | |
|---|---|---|---|---|---|---|---|---|---|---|---|---|---|---|
| Ser 385 | Pro | Thr | Phe | Ile | Asn 390 | Met | Ser | Gln | Glu 395 | Asn | Val | Asp | Met | Arg Asp 400 |
| Ser | Tyr | Leu | Gly | Tyr 405 | Ser | Thr | Glu | Leu 410 | Ala | Leu | Trp | Lys | Gly 415 | Val Gln |
| Asn | Leu | Val | Leu 420 | Gly | Ala | Pro | Arg | Tyr 425 | Gln | His | Thr | Gly 430 | Lys | Ala Val |
| Ile | Phe | Thr 435 | Gln | Val | Ser | Arg | Gln 440 | Trp | Arg | Lys | Lys 445 | Ala | Glu | Val Thr |
| Gly | Thr 450 | Gln | Ile | Gly | Ser | Tyr 455 | Phe | Gly | Ala | Ser | Leu 460 | Cys | Ser | Val Asp |
| Val 465 | Asp | Ser | Asp | Gly | Ser 470 | Thr | Asp | Leu | Ile | Leu 475 | Ile | Gly | Ala | Pro His 480 |
| Tyr | Tyr | Glu | Gln | Thr 485 | Arg | Gly | Gly | Gln | Val 490 | Ser | Val | Cys | Pro 495 | Leu Pro |
| Arg | Gly | Gln | Arg 500 | Val | Gln | Trp | Gln | Cys 505 | Asp | Ala | Val | Leu 510 | Arg | Gly Glu |
| Gln | Gly | His 515 | Pro | Trp | Gly | Arg | Phe 520 | Gly | Ala | Ala | Leu 525 | Thr | Val | Leu Gly |
| Asp | Val 530 | Asn | Glu | Asp | Lys | Leu 535 | Ile | Asp | Val | Ala | Ile 540 | Gly | Ala | Pro Gly |
| Glu 545 | Gln | Glu | Asn | Arg | Gly 550 | Ala | Val | Tyr | Leu | Phe 555 | His | Gly | Ala | Ser Glu 560 |
| Ser | Gly | Ile | Ser | Pro 565 | Ser | His | Ser | Gln | Arg 570 | Ile | Ala | Ser | Ser 575 | Gln Leu |
| Ser | Pro | Arg | Leu 580 | Gln | Tyr | Phe | Gly | Gln 585 | Ala | Leu | Ser | Gly 590 | Gly | Gln Asp |
| Leu | Thr | Gln 595 | Asp | Gly | Leu | Met | Asp 600 | Leu | Ala | Val | Gly | Ala 605 | Arg | Gly Gln |
| Val | Leu 610 | Leu | Leu | Arg | Ser | Leu 615 | Pro | Val | Leu | Lys | Val 620 | Gly | Val | Ala Met |
| Arg 625 | Phe | Ser | Pro | Val | Glu 630 | Val | Ala | Lys | Ala | Val 635 | Tyr | Arg | Cys | Trp Glu 640 |
| Glu | Lys | Pro | Ser | Ala 645 | Leu | Glu | Ala | Gly | Asp 650 | Ala | Thr | Val | Cys | Leu Thr 655 |
| Ile | Gln | Lys | Ser 660 | Ser | Leu | Asp | Gln | Leu 665 | Gly | Asp | Ile | Gln 670 | Ser | Ser Val |
| Arg | Phe | Asp 675 | Leu | Ala | Leu | Asp | Pro 680 | Gly | Arg | Leu | Thr 685 | Ser | Arg | Ala Ile |
| Phe | Asn 690 | Glu | Thr | Lys | Asn | Pro 695 | Thr | Leu | Thr | Arg | Arg 700 | Lys | Thr | Leu Gly |
| Leu 705 | Gly | Ile | His | Cys | Glu 710 | Thr | Leu | Lys | Leu | Leu 715 | Leu | Pro | Asp | Cys Val 720 |
| Glu | Asp | Val | Val | Ser 725 | Pro | Ile | Ile | Leu | His 730 | Leu | Asn | Phe | Ser | Leu Val 735 |
| Arg | Glu | Pro | Ile 740 | Pro | Ser | Pro | Gln | Asn 745 | Leu | Arg | Pro | Val 750 | Leu | Ala Val |
| Gly | Ser | Gln 755 | Asp | Leu | Phe | Thr | Ala 760 | Ser | Leu | Pro | Phe 765 | Glu | Lys | Asn Cys |
| Gly | Gln | Asp 770 | Gly | Leu | Cys | Glu | Gly 775 | Asp | Leu | Gly | Val 780 | Thr | Leu | Ser Phe |
| Ser 785 | Gly | Leu | Gln | Thr | Leu 790 | Thr | Val | Gly | Ser | Ser 795 | Leu | Glu | Leu | Asn Val 800 |
| Ile | Val | Thr | Val | Trp 805 | Asn | Ala | Gly | Glu | Asp 810 | Ser | Tyr | Gly | Thr | Val Val 815 |

| | | | | | | | | | | | | | |
|---|---|---|---|---|---|---|---|---|---|---|---|---|---|
| Ser | Leu | Tyr | Tyr 820 | Pro | Ala | Gly | Leu | Ser 825 | His | Arg | Arg | Val | Ser 830 | Gly | Ala |
| Gln | Lys | Gln 835 | Pro | His | Gln | Ser | Ala 840 | Leu | Arg | Leu | Ala 845 | Cys | Glu | Thr | Val |
| Pro | Thr 850 | Glu | Asp | Glu | Gly | Leu 855 | Arg | Ser | Ser | Arg | Cys 860 | Ser | Val | Asn | His |
| Pro 865 | Ile | Phe | His | Glu | Gly 870 | Ser | Asn | Gly | Thr | Phe 875 | Ile | Val | Thr | Phe | Asp 880 |
| Val | Ser | Tyr | Lys | Ala 885 | Thr | Leu | Gly | Asp | Arg 890 | Met | Leu | Met | Arg | Ala 895 | Ser |
| Ala | Ser | Ser | Glu 900 | Asn | Asn | Lys | Ala | Ser 905 | Ser | Ser | Lys | Ala | Thr 910 | Phe | Gln |
| Leu | Glu | Leu 915 | Pro | Val | Lys | Tyr | Ala 920 | Val | Tyr | Thr | Met | Ile 925 | Ser | Arg | Gln |
| Glu | Glu 930 | Ser | Thr | Lys | Tyr | Phe 935 | Asn | Phe | Ala | Thr | Ser 940 | Asp | Glu | Lys | Lys |
| Met 945 | Lys | Glu | Ala | Glu | His 950 | Arg | Tyr | Arg | Val | Asn 955 | Asn | Leu | Ser | Gln | Arg 960 |
| Asp | Leu | Ala | Ile | Ser 965 | Ile | Asn | Phe | Trp | Val 970 | Pro | Val | Leu | Leu | Asn 975 | Gly |
| Val | Ala | Val | Trp 980 | Asp | Val | Val | Met | Glu 985 | Ala | Pro | Ser | Gln | Leu 990 | Pro |
| Cys | Val | Ser 995 | Glu | Arg | Lys | Pro | Pro 1000 | Gln | His | Ser | Asp | Phe 1005 | Leu | Thr | Gln |
| Ile | Ser | Arg 1010 | Ser | Pro | Met | Leu | Asp 1015 | Cys | Ser | Ile | Ala | Asp 1020 | Cys | Leu | Gln |
| Phe 1025 | Arg | Cys | Asp | Val | Pro 1030 | Ser | Phe | Ser | Val | Gln 1035 | Glu | Glu | Leu | Asp | Phe 1040 |
| Thr | Leu | Lys | Gly | Asn 1045 | Leu | Ser | Phe | Gly | Trp 1050 | Val | Arg | Glu | Thr | Leu 1055 | Gln |
| Lys | Lys | Val | Leu 1060 | Val | Val | Ser | Val | Ala 1065 | Glu | Ile | Thr | Phe | Asp 1070 | Thr | Ser |
| Val | Tyr | Ser 1075 | Gln | Leu | Pro | Gly | Gln 1080 | Glu | Ala | Phe | Met | Arg 1085 | Ala | Gln | Met |
| Glu | Met 1090 | Val | Leu | Glu | Glu | Asp 1095 | Glu | Val | Tyr | Asn | Ala 1100 | Ile | Pro | Ile | Ile |
| Met 1105 | Gly | Ser | Ser | Val | Gly 1110 | Ala | Leu | Leu | Leu | Leu 1115 | Ala | Leu | Ile | Thr | Ala 1120 |
| Thr | Leu | Tyr | Lys | Leu 1125 | Gly | Phe | Phe | Lys | Arg 1130 | His | Tyr | Lys | Glu | Met 1135 | Leu |
| Glu | Asp | Lys | Pro 1140 | Glu | Asp | Thr | Ala | Thr 1145 | Phe | Ser | Gly | Asp | Asp 1150 | Phe | Ser |
| Cys | Val | Ala | Pro 1155 | Asn | Val | Pro | Lys 1160 | Ser |

(2) INFORMATION FOR SEQ ID NO:3:

(i) SEQUENCE CHARACTERISTICS:
        (A) LENGTH: 1153 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Ala Leu Arg Val Leu Leu Leu Thr Ala Leu Thr Leu Cys His Gly
1               5                   10                  15

Phe Asn Leu Asp Thr Glu Asn Ala Met Thr Phe Gln Glu Asn Ala Arg
            20              25              30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50              55                  60

Gln Cys Asp Tyr Ser Thr Gly Ser Cys Glu Pro Ile Arg Leu Gln Val
65              70              75                      80

Pro Val Glu Ala Val Asn Met Ser Leu Gly Leu Ser Leu Ala Ala Thr
                85              90                      95

Thr Ser Pro Pro Gln Leu Leu Ala Cys Gly Pro Thr Val His Gln Thr
            100             105             110

Cys Ser Glu Asn Thr Tyr Val Lys Gly Leu Cys Phe Leu Phe Gly Ser
        115             120             125

Asn Leu Arg Gln Gln Pro Gln Lys Phe Pro Glu Ala Leu Arg Gly Cys
    130             135             140

Pro Gln Glu Asp Ser Asp Ile Ala Phe Leu Ile Asp Gly Ser Gly Ser
145             150             155                     160

Ile Ile Pro His Asp Phe Arg Arg Met Lys Glu Phe Val Ser Thr Val
            165             170             175

Met Glu Gln Leu Lys Lys Ser Lys Thr Leu Phe Ser Leu Met Gln Tyr
            180             185             190

Ser Glu Glu Phe Arg Ile His Phe Thr Phe Lys Glu Phe Gln Asn Asn
        195             200             205

Pro Asn Pro Arg Ser Leu Val Lys Pro Ile Thr Gln Leu Leu Gly Arg
    210             215             220

Thr His Thr Ala Thr Gly Ile Arg Lys Val Val Arg Glu Leu Phe Asn
225             230             235             240

Ile Thr Asn Gly Ala Arg Lys Asn Ala Phe Lys Ile Leu Val Val Ile
            245             250             255

Thr Asp Gly Glu Lys Phe Gly Asp Pro Leu Gly Tyr Glu Asp Val Ile
            260             265             270

Pro Glu Ala Asp Arg Glu Gly Val Ile Arg Tyr Val Ile Gly Val Gly
        275             280             285

Asp Ala Phe Arg Ser Glu Lys Ser Arg Gln Glu Leu Asn Thr Ile Ala
    290             295             300

Ser Lys Pro Pro Arg Asp His Val Phe Gln Val Asn Asn Phe Glu Ala
305             310             315             320

Leu Lys Thr Ile Gln Asn Gln Leu Arg Glu Lys Ile Phe Ala Ile Glu
            325             330             335

Gly Thr Gln Thr Gly Ser Ser Ser Phe Glu His Glu Met Ser Gln
        340             345             350

Glu Gly Phe Ser Ala Ala Ile Thr Ser Asn Gly Pro Leu Leu Ser Thr
        355             360             365

Val Gly Ser Tyr Asp Trp Ala Gly Gly Val Phe Leu Tyr Thr Ser Lys
    370             375             380

Glu Lys Ser Thr Phe Ile Asn Met Thr Arg Val Asp Ser Asp Met Asn
385             390             395             400

Asp Ala Tyr Leu Gly Tyr Ala Ala Ala Ile Ile Leu Arg Asn Arg Val
            405             410             415

Gln Ser Leu Val Leu Gly Ala Pro Arg Tyr Gln His Ile Gly Leu Val
        420             425             430
```

```
Ala  Met  Phe  Arg  Gln  Asn  Thr  Gly  Met  Trp  Glu  Ser  Asn  Ala  Asn  Val
          435                      440                     445

Lys  Gly  Thr  Gln  Ile  Gly  Ala  Tyr  Phe  Gly  Ala  Ser  Leu  Cys  Ser  Val
          450                      455                     460

Asp  Val  Asp  Ser  Asn  Gly  Ser  Thr  Asp  Leu  Val  Leu  Ile  Gly  Ala  Pro
465                      470                     475                     480

His  Tyr  Tyr  Glu  Gln  Thr  Arg  Gly  Gly  Gln  Val  Ser  Val  Cys  Pro  Leu
                    485                     490                     495

Pro  Arg  Gly  Gln  Arg  Ala  Arg  Trp  Gln  Cys  Asp  Ala  Val  Leu  Tyr  Gly
          500                      505                     510

Glu  Gln  Gly  Gln  Pro  Trp  Gly  Arg  Phe  Gly  Ala  Ala  Leu  Thr  Val  Leu
          515                      520                     525

Gly  Asp  Val  Asn  Gly  Asp  Lys  Leu  Thr  Asp  Val  Ala  Ile  Gly  Ala  Pro
          530                      535                     540

Gly  Glu  Glu  Asp  Asn  Arg  Gly  Ala  Val  Tyr  Leu  Phe  His  Gly  Thr  Ser
545                      550                     555                     560

Gly  Ser  Gly  Ile  Ser  Pro  Ser  His  Ser  Gln  Arg  Ile  Ala  Gly  Ser  Lys
                    565                     570                     575

Leu  Ser  Pro  Arg  Leu  Gln  Tyr  Phe  Gly  Gln  Ser  Leu  Ser  Gly  Gly  Gln
          580                      585                     590

Asp  Leu  Thr  Met  Asp  Gly  Leu  Val  Asp  Leu  Thr  Val  Gly  Ala  Gln  Gly
          595                      600                     605

His  Val  Leu  Leu  Leu  Arg  Ser  Gln  Pro  Val  Leu  Arg  Val  Lys  Ala  Ile
          610                      615                     620

Met  Glu  Phe  Asn  Pro  Arg  Glu  Val  Ala  Arg  Asn  Val  Phe  Glu  Cys  Asn
625                      630                     635                     640

Asp  Gln  Val  Val  Lys  Gly  Lys  Glu  Ala  Gly  Glu  Val  Arg  Val  Cys  Leu
                    645                     650                     655

His  Val  Gln  Lys  Ser  Thr  Arg  Asp  Arg  Leu  Arg  Glu  Gly  Gln  Ile  Gln
          660                      665                     670

Ser  Val  Val  Thr  Tyr  Asp  Leu  Ala  Leu  Asp  Ser  Gly  Arg  Pro  His  Ser
          675                      680                     685

Arg  Ala  Val  Phe  Asn  Glu  Thr  Lys  Asn  Ser  Thr  Arg  Arg  Gln  Thr  Gln
          690                      695                     700

Val  Leu  Gly  Leu  Thr  Gln  Thr  Cys  Glu  Thr  Leu  Lys  Leu  Gln  Leu  Pro
705                      710                     715                     720

Asn  Cys  Ile  Glu  Asp  Pro  Val  Ser  Pro  Ile  Val  Leu  Arg  Leu  Asn  Phe
                    725                     730                     735

Ser  Leu  Val  Gly  Thr  Pro  Leu  Ser  Ala  Phe  Gly  Asn  Leu  Arg  Pro  Val
          740                      745                     750

Leu  Ala  Glu  Asp  Ala  Gln  Arg  Leu  Phe  Thr  Ala  Leu  Phe  Pro  Phe  Glu
          755                      760                     765

Lys  Asn  Cys  Gly  Asn  Asp  Asn  Ile  Cys  Gln  Asp  Asp  Leu  Ser  Ile  Thr
          770                      775                     780

Phe  Ser  Phe  Met  Ser  Leu  Asp  Cys  Leu  Val  Val  Gly  Gly  Pro  Arg  Glu
785                      790                     795                     800

Phe  Asn  Val  Thr  Val  Thr  Val  Arg  Asn  Asp  Gly  Glu  Asp  Ser  Tyr  Arg
                    805                     810                     815

Thr  Gln  Val  Thr  Phe  Phe  Phe  Pro  Leu  Asp  Leu  Ser  Tyr  Arg  Lys  Val
          820                      825                     830

Ser  Thr  Leu  Gln  Asn  Gln  Arg  Ser  Gln  Arg  Ser  Trp  Arg  Leu  Ala  Cys
          835                      840                     845

Glu  Ser  Ala  Ser  Ser  Thr  Glu  Val  Ser  Gly  Ala  Leu  Lys  Ser  Thr  Ser
```

|     | 850 |     |     |     | 855 |     |     |     | 860 |     |     |     |     |
| --- | --- | --- | --- | --- | --- | --- | --- | --- | --- | --- | --- | --- | --- |
| Cys 865 | Ser | Ile | Asn | His | Pro 870 | Ile | Phe | Pro | Glu | Asn 875 | Ser | Glu | Val | Thr | Phe 880 |
| Asn | Ile | Thr | Phe | Asp 885 | Val | Asp | Ser | Lys | Ala 890 | Ser | Leu | Gly | Asn | Lys 895 | Leu |
| Leu | Leu | Lys | Ala 900 | Asn | Val | Thr | Ser | Glu 905 | Asn | Asn | Met | Pro | Arg 910 | Thr | Asn |
| Lys | Thr | Glu 915 | Phe | Gln | Leu | Glu | Leu 920 | Pro | Val | Lys | Tyr | Ala 925 | Val | Tyr | Met |
| Val | Val 930 | Thr | Ser | His | Gly | Val 935 | Ser | Thr | Lys | Tyr | Leu 940 | Asn | Phe | Thr | Ala |
| Ser 945 | Glu | Asn | Thr | Ser | Arg 950 | Val | Met | Gln | His | Gln 955 | Tyr | Gln | Val | Ser | Asn 960 |
| Leu | Gly | Gln | Arg | Ser 965 | Leu | Pro | Ile | Ser | Leu 970 | Val | Phe | Leu | Val | Pro 975 | Val |
| Arg | Leu | Asn | Gln 980 | Thr | Val | Ile | Trp | Asp 985 | Arg | Pro | Gln | Val | Thr 990 | Phe | Ser |
| Glu | Asn | Leu 995 | Ser | Ser | Thr | Cys | His 1000 | Thr | Lys | Glu | Arg | Leu 1005 | Pro | Ser | His |
| Ser | Asp 1010 | Phe | Leu | Ala | Glu | Leu 1015 | Arg | Lys | Ala | Pro | Val 1020 | Val | Asn | Cys | Ser |
| Ile 1025 | Ala | Val | Cys | Gln | Arg 1030 | Ile | Gln | Cys | Asp | Ile 1035 | Pro | Phe | Phe | Gly | Ile 1040 |
| Gln | Glu | Glu | Phe | Asn 1045 | Ala | Thr | Leu | Lys | Gly 1050 | Asn | Leu | Ser | Phe | Asp 1055 | Trp |
| Tyr | Ile | Lys | Thr 1060 | Ser | His | Asn | His | Leu 1065 | Leu | Ile | Val | Ser | Thr 1070 | Ala | Glu |
| Ile | Leu | Phe 1075 | Asn | Asp | Ser | Val | Phe 1080 | Thr | Leu | Leu | Pro | Gly 1085 | Gln | Gly | Ala |
| Phe | Val 1090 | Arg | Ser | Gln | Thr | Glu 1095 | Thr | Lys | Val | Glu | Pro 1100 | Phe | Glu | Val | Pro |
| Asn 1105 | Pro | Leu | Pro | Leu | Ile 1110 | Val | Gly | Ser | Ser | Val 1115 | Gly | Gly | Leu | Leu | Leu 1120 |
| Leu | Ala | Leu | Ile | Thr 1125 | Ala | Ala | Leu | Tyr | Lys 1130 | Leu | Gly | Phe | Phe | Lys 1135 | Arg |
| Gln | Tyr | Lys | Asp 1140 | Met | Met | Ser | Glu | Gly 1145 | Gly | Pro | Pro | Gly | Ala 1150 | Glu | Pro |
| Gln |     |     |     |     |     |     |     |     |     |     |     |     |     |     |     |

(2) INFORMATION FOR SEQ ID NO:4:

(i) SEQUENCE CHARACTERISTICS:
        (A) LENGTH: 1163 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

| Met 1 | Thr | Arg | Thr | Arg 5 | Ala | Ala | Leu | Leu | Leu 10 | Phe | Thr | Ala | Leu | Ala 15 | Thr |
| --- | --- | --- | --- | --- | --- | --- | --- | --- | --- | --- | --- | --- | --- | --- | --- |
| Ser | Leu | Gly | Phe 20 | Asn | Leu | Asp | Thr | Glu 25 | Glu | Leu | Thr | Ala | Phe 30 | Arg | Val |
| Asp | Ser | Ala 35 | Gly | Phe | Gly | Asp | Ser 40 | Val | Val | Gln | Tyr | Ala 45 | Asn | Ser | Trp |

| | | | | | | | | | | | | | |
|---|---|---|---|---|---|---|---|---|---|---|---|---|---|
| Val | Val | Val | Gly | Ala | Pro | Gln | Lys | Ile | Ile | Ala | Ala | Asn | Gln | Ile | Gly |
| | 50 | | | | 55 | | | | | 60 | | | | | |
| Gly | Leu | Tyr | Gln | Cys | Gly | Tyr | Ser | Thr | Gly | Ala | Cys | Glu | Pro | Ile | Gly |
| 65 | | | | | 70 | | | | | 75 | | | | | 80 |
| Leu | Gln | Val | Pro | Pro | Glu | Ala | Val | Asn | Met | Ser | Leu | Gly | Leu | Ser | Leu |
| | | | | 85 | | | | | 90 | | | | | 95 | |
| Ala | Ser | Thr | Thr | Ser | Pro | Ser | Gln | Leu | Leu | Ala | Cys | Gly | Pro | Thr | Val |
| | | | 100 | | | | | 105 | | | | | 110 | | |
| His | His | Glu | Cys | Gly | Arg | Asn | Met | Tyr | Leu | Thr | Gly | Leu | Cys | Phe | Leu |
| | | 115 | | | | | 120 | | | | | 125 | | | |
| Leu | Gly | Pro | Thr | Gln | Leu | Thr | Gln | Arg | Leu | Pro | Val | Ser | Arg | Gln | Glu |
| | 130 | | | | | 135 | | | | | 140 | | | | |
| Cys | Pro | Arg | Gln | Glu | Gln | Asp | Ile | Val | Phe | Leu | Ile | Asp | Gly | Ser | Gly |
| 145 | | | | | 150 | | | | | 155 | | | | | 160 |
| Ser | Ile | Ser | Ser | Arg | Asn | Phe | Ala | Thr | Met | Met | Asn | Phe | Val | Arg | Ala |
| | | | | 165 | | | | | 170 | | | | | 175 | |
| Val | Ile | Ser | Gln | Phe | Gln | Arg | Pro | Ser | Thr | Gln | Phe | Ser | Leu | Met | Gln |
| | | | 180 | | | | | 185 | | | | | 190 | | |
| Phe | Ser | Asn | Lys | Phe | Gln | Thr | His | Phe | Thr | Phe | Glu | Glu | Phe | Arg | Arg |
| | | 195 | | | | | 200 | | | | | 205 | | | |
| Thr | Ser | Asn | Pro | Leu | Ser | Leu | Leu | Ala | Ser | Val | His | Gln | Leu | Gln | Gly |
| | 210 | | | | | 215 | | | | | 220 | | | | |
| Phe | Thr | Tyr | Thr | Ala | Thr | Ala | Ile | Gln | Asn | Val | Val | His | Arg | Leu | Phe |
| 225 | | | | | 230 | | | | | 235 | | | | | 240 |
| His | Ala | Ser | Tyr | Gly | Ala | Arg | Arg | Asp | Ala | Ile | Lys | Ile | Leu | Ile | Val |
| | | | | 245 | | | | | 250 | | | | | 255 | |
| Ile | Thr | Asp | Gly | Lys | Lys | Glu | Gly | Asp | Ser | Leu | Asp | Tyr | Lys | Asp | Val |
| | | | 260 | | | | | 265 | | | | | 270 | | |
| Ile | Pro | Met | Ala | Asp | Ala | Ala | Gly | Ile | Ile | Arg | Tyr | Ala | Ile | Gly | Val |
| | | 275 | | | | | 280 | | | | | 285 | | | |
| Gly | Leu | Ala | Phe | Gln | Asn | Arg | Asn | Ser | Trp | Lys | Glu | Leu | Asn | Asp | Ile |
| | 290 | | | | | 295 | | | | | 300 | | | | |
| Ala | Ser | Lys | Pro | Ser | Gln | Glu | His | Ile | Phe | Lys | Val | Glu | Asp | Phe | Asp |
| 305 | | | | | 310 | | | | | 315 | | | | | 320 |
| Ala | Leu | Lys | Asp | Ile | Gln | Asn | Gln | Leu | Lys | Glu | Lys | Ile | Phe | Ala | Ile |
| | | | | 325 | | | | | 330 | | | | | 335 | |
| Glu | Gly | Thr | Glu | Thr | Ile | Ser | Ser | Ser | Phe | Glu | Leu | Glu | Met | Ala | |
| | | | 340 | | | | | 345 | | | | | 350 | | |
| Gln | Glu | Gly | Phe | Ser | Ala | Val | Phe | Thr | Pro | Asp | Gly | Pro | Val | Leu | Gly |
| | | 355 | | | | | 360 | | | | | 365 | | | |
| Ala | Val | Gly | Ser | Phe | Thr | Trp | Ser | Gly | Gly | Ala | Phe | Leu | Tyr | Pro | Pro |
| | 370 | | | | | 375 | | | | | 380 | | | | |
| Asn | Met | Ser | Pro | Thr | Phe | Ile | Asn | Met | Ser | Gln | Glu | Asn | Val | Asp | Met |
| 385 | | | | | 390 | | | | | 395 | | | | | 400 |
| Arg | Asp | Ser | Tyr | Leu | Gly | Tyr | Ser | Thr | Glu | Leu | Ala | Leu | Trp | Lys | Gly |
| | | | | 405 | | | | | 410 | | | | | 415 | |
| Val | Gln | Ser | Leu | Val | Leu | Gly | Ala | Pro | Arg | Tyr | Gln | His | Ile | Gly | Lys |
| | | | 420 | | | | | 425 | | | | | 430 | | |
| Ala | Val | Ile | Phe | Ile | Gln | Val | Ser | Arg | Gln | Trp | Arg | Met | Lys | Ala | Glu |
| | | 435 | | | | | 440 | | | | | 445 | | | |
| Val | Ile | Gly | Thr | Gln | Ile | Gly | Ser | Tyr | Phe | Gly | Ala | Ser | Leu | Cys | Ser |
| | 450 | | | | | 455 | | | | | 460 | | | | |
| Val | Asp | Val | Asp | Thr | Asp | Gly | Ser | Thr | Asp | Leu | Val | Leu | Ile | Gly | Ala |
| 465 | | | | | 470 | | | | | 475 | | | | | 480 |

| | | | | | | | | | | | | | | |
|---|---|---|---|---|---|---|---|---|---|---|---|---|---|---|
| Pro | His | Tyr | Tyr | Glu<br>485 | Gln | Thr | Arg | Gly | Gly<br>490 | Gln | Val | Ser | Val | Cys<br>495 | Pro |
| Leu | Pro | Arg | Gly<br>500 | Trp | Arg | Arg | Trp<br>505 | Cys | Asp | Ala | Val | Leu<br>510 | Tyr | Gly |
| Glu | Gln | Gly<br>515 | His | Pro | Trp | Gly<br>520 | Arg | Phe | Gly | Ala | Ala<br>525 | Leu | Thr | Val | Leu |
| Gly | Asp<br>530 | Val | Asn | Gly | Asp | Lys<br>535 | Leu | Thr | Asp | Val | Val<br>540 | Ile | Gly | Ala | Pro |
| Gly<br>545 | Glu | Glu | Glu | Asn | Arg<br>550 | Gly | Ala | Val | Tyr | Leu<br>555 | Phe | His | Gly | Val | Leu<br>560 |
| Gly | Pro | Ser | Ile | Ser<br>565 | Pro | Ser | His | Ser | Gln<br>570 | Arg | Ile | Ala | Gly | Ser<br>575 | Gln |
| Leu | Ser | Ser | Arg<br>580 | Leu | Gln | Tyr | Phe | Gly<br>585 | Gln | Ala | Leu | Ser | Gly<br>590 | Gly | Gln |
| Asp | Leu | Thr<br>595 | Gln | Asp | Gly | Leu<br>600 | Val | Asp | Leu | Ala | Val<br>605 | Gly | Ala | Arg | Gly |
| Gln | Val<br>610 | Leu | Leu | Leu | Arg<br>615 | Thr | Arg | Pro | Val | Leu<br>620 | Trp | Val | Gly | Val | Ser |
| Met<br>625 | Gln | Phe | Ile | Pro<br>630 | Ala | Glu | Ile | Pro<br>635 | Arg | Ser | Ala | Phe | Glu<br>640 | Cys | Arg |
| Glu | Gln | Val | Val | Ser<br>645 | Glu | Gln | Thr | Leu | Val<br>650 | Gln | Ser | Asn | Ile | Cys<br>655 | Leu |
| Tyr | Ile | Asp | Lys<br>660 | Arg | Ser | Lys | Asn | Leu<br>665 | Leu | Gly | Ser | Arg | Asp<br>670 | Leu | Gln |
| Ser | Ser | Val<br>675 | Thr | Leu | Asp | Leu | Ala<br>680 | Leu | Ala | Pro | Gly | Arg<br>685 | Leu | Ser | Pro |
| Arg | Ala<br>690 | Ile | Phe | Gln | Glu | Thr<br>695 | Lys | Asn | Arg | Ser | Leu<br>700 | Ser | Arg | Val | Arg |
| Val<br>705 | Leu | Gly | Leu | Lys | Ala<br>710 | His | Cys | Glu | Asn | Phe<br>715 | Asn | Leu | Leu | Leu | Pro<br>720 |
| Ser | Cys | Val | Glu | Asp<br>725 | Ser | Val | Ile | Pro | Ile<br>730 | Ile | Leu | Arg | Leu | Asn<br>735 | Phe |
| Thr | Leu | Val | Gly<br>740 | Lys | Pro | Leu | Leu | Ala<br>745 | Phe | Arg | Asn | Leu | Arg<br>750 | Pro | Met |
| Leu | Ala | Ala<br>755 | Leu | Ala | Gln | Arg | Tyr<br>760 | Phe | Thr | Ala | Ser | Leu<br>765 | Pro | Phe | Glu |
| Lys | Asn<br>770 | Cys | Gly | Ala | Asp | His<br>775 | Ile | Cys | Gln | Asp | Asn<br>780 | Leu | Gly | Ile | Ser |
| Phe<br>785 | Ser | Phe | Pro | Gly | Leu<br>790 | Lys | Ser | Leu | Leu | Val<br>795 | Gly | Ser | Asn | Leu | Glu<br>800 |
| Leu | Asn | Ala | Glu | Val<br>805 | Met | Val | Trp | Asn | Asp<br>810 | Gly | Glu | Asp | Ser | Tyr<br>815 | Gly |
| Thr | Thr | Ile | Thr<br>820 | Phe | Ser | His | Pro | Ala<br>825 | Gly | Leu | Ser | Tyr | Arg<br>830 | Tyr | Val |
| Ala | Glu<br>835 | Gly | Gln | Lys | Gln | Gly<br>840 | Gln | Leu | Arg | Ser | Leu<br>845 | His | Leu | Thr | Cys |
| Cys | Ser<br>850 | Ala | Pro | Val | Gly | Ser<br>855 | Gln | Gly | Thr | Trp | Ser<br>860 | Thr | Ser | Cys | Arg |
| Ile<br>865 | Asn | His | Leu | Ile | Phe<br>870 | Arg | Gly | Gly | Ala | Gln<br>875 | Ile | Thr | Phe | Leu | Ala<br>880 |
| Thr | Phe | Asp | Val | Ser<br>885 | Pro | Lys | Ala | Val | Gly<br>890 | Leu | Asp | Arg | Leu | Leu<br>895 | Leu |
| Ile | Ala | Asn | Val | Ser | Ser | Glu | Asn | Asn | Ile | Pro | Arg | Thr | Ser | Lys | Thr |

|     |     |     |     |     |     |     |     |     |     |     |     |     |     |     |
|-----|-----|-----|-----|-----|-----|-----|-----|-----|-----|-----|-----|-----|-----|-----|
|     |     |     |     |     | 900 |     |     |     |     | 905 |     |     |     | 910 |
| Ile | Phe | Gln | Leu | Glu | Leu | Pro | Val | Lys | Tyr | Ala | Val | Tyr | Ile | Val | Val |
|     |     |     |     | 915 |     |     |     |     | 920 |     |     |     | 925 |     |
| Ser | Ser | His | Glu | Gln | Phe | Thr | Lys | Tyr | Leu | Asn | Phe | Ser | Glu | Ser | Glu |
|     |     |     | 930 |     |     |     | 935 |     |     |     |     | 940 |     |     |     |
| Glu | Lys | Glu | Ser | His | Val | Ala | Met | His | Arg | Tyr | Gln | Val | Asn | Asn | Leu |
| 945 |     |     |     |     | 950 |     |     |     |     | 955 |     |     |     |     | 960 |
| Gly | Gln | Arg | Asp | Leu | Pro | Val | Ser | Ile | Asn | Phe | Trp | Val | Pro | Val | Glu |
|     |     |     |     | 965 |     |     |     |     | 970 |     |     |     |     | 975 |     |
| Leu | Asn | Gln | Glu | Ala | Val | Trp | Met | Asp | Val | Glu | Val | Ser | His | Pro | Gln |
|     |     |     |     | 980 |     |     |     | 985 |     |     |     |     | 990 |     |     |
| Asn | Pro | Ser | Leu | Arg | Cys | Ser | Ser | Glu | Lys | Ile | Ala | Pro | Pro | Ala | Ser |
|     |     |     | 995 |     |     |     |     | 1000|     |     |     |     | 1005|     |     |
| Asp | Phe | Leu | Ala | His | Ile | Gln | Lys | Asn | Pro | Val | Leu | Asp | Cys | Ser | Ile |
|     |     |     | 1010|     |     |     | 1015|     |     |     |     | 1020|     |     |     |
| Ala | Gly | Cys | Leu | Arg | Phe | Arg | Cys | Asp | Val | Pro | Ser | Phe | Ser | Val | Gln |
| 1025|     |     |     |     | 1030|     |     |     |     | 1035|     |     |     |     | 1040|
| Glu | Glu | Leu | Asp | Phe | Thr | Leu | Lys | Gly | Asn | Leu | Ser | Phe | Gly | Trp | Val |
|     |     |     |     | 1045|     |     |     |     | 1050|     |     |     |     | 1055|     |
| Arg | Gln | Ile | Leu | Gln | Lys | Lys | Val | Ser | Val | Val | Ser | Val | Ala | Glu | Ile |
|     |     |     | 1060|     |     |     |     | 1065|     |     |     |     | 1070|     |     |
| Ile | Phe | Asp | Thr | Ser | Val | Tyr | Ser | Gln | Leu | Pro | Gly | Gln | Glu | Ala | Phe |
|     |     |     | 1075|     |     |     |     | 1080|     |     |     |     | 1085|     |     |
| Met | Arg | Ala | Gln | Thr | Ile | Thr | Val | Leu | Glu | Lys | Tyr | Lys | Val | His | Asn |
|     |     |     | 1090|     |     |     |     | 1095|     |     |     |     | 1100|     |     |
| Pro | Ile | Pro | Leu | Ile | Val | Gly | Ser | Ser | Ile | Gly | Gly | Leu | Leu | Leu | Leu |
| 1105|     |     |     |     | 1110|     |     |     |     | 1115|     |     |     |     | 1120|
| Ala | Leu | Ile | Thr | Ala | Val | Leu | Tyr | Lys | Val | Gly | Phe | Phe | Lys | Arg | Gln |
|     |     |     |     | 1125|     |     |     |     | 1130|     |     |     |     | 1135|     |
| Tyr | Lys | Glu | Met | Met | Glu | Glu | Ala | Asn | Gly | Gln | Ile | Ala | Pro | Glu | Asn |
|     |     |     |     | 1140|     |     |     |     | 1145|     |     |     |     | 1150|     |
| Gly | Thr | Gln | Thr | Pro | Ser | Pro | Pro | Ser | Glu | Lys |     |     |     |     |     |
|     |     |     | 1155|     |     |     |     | 1160|     |     |     |     |     |     |     |

( 2 ) INFORMATION FOR SEQ ID NO:5:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

| Phe | Asn | Leu | Asp | Val | Glu | Glu | Pro | Met | Val | Phe | Gln |
|-----|-----|-----|-----|-----|-----|-----|-----|-----|-----|-----|-----|
| 1   |     |     |     | 5   |     |     |     |     | 10  |     |     |

( 2 ) INFORMATION FOR SEQ ID NO:6:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:6:

TTYAAYYTGG AYGTNGARGA RCCNATGGTN TTYCA                                                35

( 2 ) INFORMATION FOR SEQ ID NO:7:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:7:

TTCAACCTGG ACGTGGAGGA GCCCATGGTG TTCCAA    36

( 2 ) INFORMATION FOR SEQ ID NO:8:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:8:

TTCAACCTGG ACGTNGAASA NCCCATGGTC TTCCAA    36

( 2 ) INFORMATION FOR SEQ ID NO:9:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:9:

TTYAAYYTNG AYGTNGARGA RCC    23

( 2 ) INFORMATION FOR SEQ ID NO:10:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:10:

TTYAAYYTGG ACGTNGAAGA    20

( 2 ) INFORMATION FOR SEQ ID NO:11:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:11:

TGRAANACCA TNGGYTC    17

( 2 ) INFORMATION FOR SEQ ID NO:12:

( i ) SEQUENCE CHARACTERISTICS:
    ( A ) LENGTH: 18 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

TTGGAAGACC ATNGGYTC    18

(2) INFORMATION FOR SEQ ID NO:13:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

ATTAACCCTC ACTAAAG    17

(2) INFORMATION FOR SEQ ID NO:14:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

AATACGACTC ACTATAG    17

(2) INFORMATION FOR SEQ ID NO:15:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:15:

Val Phe Gln Glu Xaa Gly Ala Gly Phe Gly Gln
 1               5                   10

(2) INFORMATION FOR SEQ ID NO:16:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:16:

Leu Tyr Asp Xaa Val Ala Ala Thr Gly Leu Xaa Gln Pro Ile
 1               5                   10

(2) INFORMATION FOR SEQ ID NO:17:

(i) SEQUENCE CHARACTERISTICS:
(A) LENGTH: 12 amino acids
(B) TYPE: amino acid
(D) TOPOLOGY: linear (ii) MOLECULE TYPE: peptide ( x i ) SEQUENCE DESCRIPTION: SEQ ID NO:17:

Pro Leu Glu Tyr Xaa Asp Val Ile Pro Gln Ala Glu
1               5                   10

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Phe Gln Glu Gly Phe Ser Xaa Val Leu Xaa
1               5                   10

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Thr Ser Pro Thr Phe Ile Xaa Met Ser Gln Glu Asn Val Asp
1               5                   10

( 2 ) INFORMATION FOR SEQ ID NO:20:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Leu Val Val Gly Ala Pro Leu Glu Val Val Ala Val Xaa Gln Thr Gly
1               5                   10                  15

Arg ( 2 ) INFORMATION FOR SEQ ID NO:21:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Leu Asp Xaa Lys Pro Xaa Asp Thr Ala
1               5

( 2 ) INFORMATION FOR SEQ ID NO:22:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Phe  Gly  Glu  Gln  Phe  Ser  Glu
 1              5
```

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

```
RAANCCYTCY  TGRAAACTYT  C                                            21
```

( 2 ) INFORMATION FOR SEQ ID NO:24:

( i ) SEQUENCE CHARACTERISTICS:
        ( A ) LENGTH: 1006 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
TTCAACCTGG  ACGTGGAGGA  GCCCATGGTG  TTCAAGAGGA  TGGAGCTGGC  TTTGGACAGA    60
GCGTGGCCCA  GCTTGGCGGA  TCTAGACTCG  TGGTGGGAGC  CCCCCTGGAG  GTGGTGGCGG   120
TCAACCAAAC  AGGAAGGTTG  TATGACTGTG  TGGCTGCCAC  TGGCCTTGTC  AACCCATACC   180
CCTGCACACA  CCCCCAGATG  CTGTGAACAT  GTCCCTGGGT  CTGTCCCTGT  CAGCCGCCGC   240
CAGTCGCCCC  TGGCTGCTGG  CCTGTGGCCC  AACCATGCAC  AGAGCCTGTG  GGGAGAATAT   300
GTATGCAGAA  GGCTTTTGCC  TCCTGTTGGA  CTCCCATCTG  CAGACCATTT  GGACAGTACC   360
TGCTGCCCTA  CCAGAGTGTC  CAAGTCAAGA  GATGGACATT  GTCTTCCTGA  TTGATGGTTC   420
TGGCAGTATG  AGCAAAGTGA  CTTTAAACAA  ATGAAGGATT  TGTGAGAGCT  GTGATGGGAC   480
AGTTTGAGGG  CACCCAAACC  CTGTTCTCAC  TGATACAGTA  TCCCACCTCC  CTGAAGATCC   540
ACTTCACCTT  CACGCAATTC  CAGAGCAGCT  GGAACCCTCT  GAGCCTGGTG  GATCCCATTG   600
TCCAACTGGA  CGGCCTGACA  TATACAGCCA  CGGGCATCCG  GAAAGTGGTG  GAGGAACTGT   660
TTCATAGTAA  GAATGGGGCC  CGTAAAAGTG  CCAAGAAGAT  CCTCATTGTC  ATCACAGATG   720
GCAAAAATAC  AAAGACCCCC  TGGAGTACGA  GGACGTATCC  CCAGGCAGAG  AGAGCGGATC   780
ATCCGCTATG  CCATTGGGGT  GGGAGATGCT  TTCTGGAAAC  CCAGTGCCAA  GCAGGAGCTG   840
GACAACATTG  CTCAGAGCC   GGCTCAGGAC  CATGTGTTCA  GGGTGGACAA  CTTTGCAGCA   900
CTCAGCAGCA  TCCAGGAGCA  GCTGCAGGAG  AAGATCTTTG  CACTCGAAGG  AACCCAGTCG   960
ACGACAAGTA  GCTCTTTCCA  ACATGAGATG  TTCCAAGAAG  GGTTCA                 1006
```

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

```
GTNTTYCARG  ARGAYGG                                                   17
```

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

CCACTGTCAG GATGCCCGTG        20

( 2 ) INFORMATION FOR SEQ ID NO:27:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

AGTTACGAAT TCGCCACCAT GGCTCTACGG GTGCTTCTTC TG        42

( 2 ) INFORMATION FOR SEQ ID NO:28:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

AGTTACGAAT TCGCCACCAT GACTCGGACT GTGCTTCTTC TG        42

( 2 ) INFORMATION FOR SEQ ID NO:29:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

AGTTACGAAT TCGCCACCAT GACCTTCGGC ACTGTG        36

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

TTGCTGACTG CCTGCAGTTC        20

( 2 ) INFORMATION FOR SEQ ID NO:31:

( i ) SEQUENCE CHARACTERISTICS:
        ( A ) LENGTH: 36 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:31:

GTTCTGACGC GTAATGGCAT TGTAGACCTC GTCTTC    36

(2) INFORMATION FOR SEQ ID NO:32:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:32:

ACGTATGCAG GATCCCATCA AGAGATGGAC ATCGCT    36

(2) INFORMATION FOR SEQ ID NO:33:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:33:

ACTGCATGTC TCGAGGCTGA AGCCTTCTTG GGACATC    37

(2) INFORMATION FOR SEQ ID NO:34:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:34:

TATAGACTGC TGGGTAGTCC CCAC    24

(2) INFORMATION FOR SEQ ID NO:35:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:35:

TGAAGATTGG GGGTAAATAA CAGA    24

(2) INFORMATION FOR SEQ ID NO:36:

(i) SEQUENCE CHARACTERISTICS:
(A) LENGTH: 3528 base pairs
(B) TYPE: nucleic acid
(C) STRANDEDNESS: single
(D) TOPOLOGY: linear (ii) MOLECULE TYPE: cDNA ( i x ) FEATURE:
    ( A ) NAME/KEY: CDS
    ( B ) LOCATION: 1..3456

( x i ) SEQUENCE DESCRIPTION: SEQ ID NO:36:

| | | | | | | | | | | | | | | | | |
|---|---|---|---|---|---|---|---|---|---|---|---|---|---|---|---|---|
| GGC | TGG | GCC | CTG | GCT | TCC | TGT | CAT | GGG | TCT | AAC | CTG | GAT | GTG | GAG | GAA | 48 |
| Gly | Trp | Ala | Leu | Ala | Ser | Cys | His | Gly | Ser | Asn | Leu | Asp | Val | Glu | Glu | |
| 1 | | | | 5 | | | | | 10 | | | | | 15 | | |
| CCC | ATC | GTG | TTC | AGA | GAG | GAT | GCA | GCC | AGC | TTT | GGA | CAG | ACT | GTG | GTG | 96 |
| Pro | Ile | Val | Phe | Arg | Glu | Asp | Ala | Ala | Ser | Phe | Gly | Gln | Thr | Val | Val | |
| | | | 20 | | | | | 25 | | | | | 30 | | | |
| CAG | TTT | GGT | GGA | TCT | CGA | CTC | GTG | GTG | GGA | GCC | CCT | CTG | GAG | GCG | GTG | 144 |
| Gln | Phe | Gly | Gly | Ser | Arg | Leu | Val | Val | Gly | Ala | Pro | Leu | Glu | Ala | Val | |
| | | | | 35 | | | | 40 | | | | | 45 | | | |
| GCA | GTC | AAC | CAA | ACA | GGA | CGG | TTG | TAT | GAC | TGT | GCA | CCT | GCC | ACT | GGC | 192 |
| Ala | Val | Asn | Gln | Thr | Gly | Arg | Leu | Tyr | Asp | Cys | Ala | Pro | Ala | Thr | Gly | |
| | | 50 | | | | | 55 | | | | | 60 | | | | |
| ATG | TGC | CAG | CCC | ATC | GTA | CTG | CGC | AGT | CCC | CTA | GAG | GCA | GTG | AAC | ATG | 240 |
| Met | Cys | Gln | Pro | Ile | Val | Leu | Arg | Ser | Pro | Leu | Glu | Ala | Val | Asn | Met | |
| 65 | | | | | 70 | | | | | 75 | | | | | 80 | |
| TCC | CTG | GGC | CTG | TCT | CTG | GTG | ACT | GCC | ACC | AAT | AAC | GCC | CAG | TTG | CTG | 288 |
| Ser | Leu | Gly | Leu | Ser | Leu | Val | Thr | Ala | Thr | Asn | Asn | Ala | Gln | Leu | Leu | |
| | | | | 85 | | | | | 90 | | | | | 95 | | |
| GCT | TGT | GGT | CCA | ACT | GCA | CAG | AGA | GCT | TGT | GTG | AAG | AAC | ATG | TAT | GCG | 336 |
| Ala | Cys | Gly | Pro | Thr | Ala | Gln | Arg | Ala | Cys | Val | Lys | Asn | Met | Tyr | Ala | |
| | | | 100 | | | | | 105 | | | | | 110 | | | |
| AAA | GGT | TCC | TGC | CTC | CTT | CTC | GGC | TCC | AGC | TTG | CAG | TTC | ATC | CAG | GCA | 384 |
| Lys | Gly | Ser | Cys | Leu | Leu | Leu | Gly | Ser | Ser | Leu | Gln | Phe | Ile | Gln | Ala | |
| | | 115 | | | | | 120 | | | | | 125 | | | | |
| GTC | CCT | GCC | TCC | ATG | CCA | GAG | TGT | CCA | AGA | CAA | GAG | ATG | GAC | ATT | GCT | 432 |
| Val | Pro | Ala | Ser | Met | Pro | Glu | Cys | Pro | Arg | Gln | Glu | Met | Asp | Ile | Ala | |
| | 130 | | | | | 135 | | | | | 140 | | | | | |
| TTC | CTG | ATT | GAT | GGT | TCT | GGC | AGC | ATT | AAC | CAA | AGG | GAC | TTT | GCC | CAG | 480 |
| Phe | Leu | Ile | Asp | Gly | Ser | Gly | Ser | Ile | Asn | Gln | Arg | Asp | Phe | Ala | Gln | |
| 145 | | | | | 150 | | | | | 155 | | | | | 160 | |
| ATG | AAG | GAC | TTT | GTC | AAA | GCT | TTG | ATG | GGA | GAG | TTT | GCG | AGC | ACC | AGC | 528 |
| Met | Lys | Asp | Phe | Val | Lys | Ala | Leu | Met | Gly | Glu | Phe | Ala | Ser | Thr | Ser | |
| | | | | 165 | | | | | 170 | | | | | 175 | | |
| ACC | TTG | TTC | TCC | CTG | ATG | CAA | TAC | TCG | AAC | ATC | CTG | AAG | ACC | CAT | TTT | 576 |
| Thr | Leu | Phe | Ser | Leu | Met | Gln | Tyr | Ser | Asn | Ile | Leu | Lys | Thr | His | Phe | |
| | | | 180 | | | | | 185 | | | | | 190 | | | |
| ACC | TTC | ACT | GAA | TTC | AAG | AAC | ATC | CTG | GAC | CCT | CAG | AGC | CTG | GTG | GAT | 624 |
| Thr | Phe | Thr | Glu | Phe | Lys | Asn | Ile | Leu | Asp | Pro | Gln | Ser | Leu | Val | Asp | |
| | | 195 | | | | | 200 | | | | | 205 | | | | |
| CCC | ATT | GTC | CAG | CTG | CAA | GGC | CTG | ACC | TAC | ACA | GCC | ACA | GGC | ATC | CGG | 672 |
| Pro | Ile | Val | Gln | Leu | Gln | Gly | Leu | Thr | Tyr | Thr | Ala | Thr | Gly | Ile | Arg | |
| | 210 | | | | | 215 | | | | | 220 | | | | | |
| ACA | GTG | ATG | GAA | GAG | CTA | TTT | CAT | AGC | AAG | AAT | GGG | TCC | CGT | AAA | AGT | 720 |
| Thr | Val | Met | Glu | Glu | Leu | Phe | His | Ser | Lys | Asn | Gly | Ser | Arg | Lys | Ser | |
| 225 | | | | | 230 | | | | | 235 | | | | | 240 | |
| GCC | AAG | AAG | ATC | CTC | CTT | GTC | ATC | ACA | GAT | GGG | CAG | AAA | TAC | AGA | GAC | 768 |
| Ala | Lys | Lys | Ile | Leu | Leu | Val | Ile | Thr | Asp | Gly | Gln | Lys | Tyr | Arg | Asp | |
| | | | | 245 | | | | | 250 | | | | | 255 | | |
| CCC | CTG | GAG | TAT | AGT | GAT | GTC | ATT | CCC | GCC | GCA | GAC | AAA | GCT | GGC | ATC | 816 |
| Pro | Leu | Glu | Tyr | Ser | Asp | Val | Ile | Pro | Ala | Ala | Asp | Lys | Ala | Gly | Ile | |
| | | | 260 | | | | | 265 | | | | | 270 | | | |
| ATT | CGT | TAT | GCT | ATT | GGG | GTG | GGA | GAT | GCC | TTC | CAG | GAG | CCC | ACT | GCC | 864 |
| Ile | Arg | Tyr | Ala | Ile | Gly | Val | Gly | Asp | Ala | Phe | Gln | Glu | Pro | Thr | Ala | |
| | | 275 | | | | | 280 | | | | | 285 | | | | |
| CTG | AAG | GAG | CTG | AAC | ACC | ATT | GGC | TCA | GCT | CCC | CCA | CAG | GAC | CAC | GTG | 912 |

-continued

| | | | | | | | | | | | | | | | |
|---|---|---|---|---|---|---|---|---|---|---|---|---|---|---|---|
| Leu | Lys | Glu | Leu | Asn | Thr | Ile | Gly | Ser | Ala | Pro | Pro | Gln | Asp | His | Val |
| | 290 | | | | 295 | | | | | 300 | | | | | |

| TTC | AAG | GTA | GGC | AAC | TTT | GCA | GCA | CTT | CGC | AGC | ATC | CAG | AGG | CAA | CTT | 960 |
|---|---|---|---|---|---|---|---|---|---|---|---|---|---|---|---|---|
| Phe | Lys | Val | Gly | Asn | Phe | Ala | Ala | Leu | Arg | Ser | Ile | Gln | Arg | Gln | Leu | |
| 305 | | | | | 310 | | | | | 315 | | | | | 320 | |

| CAG | GAG | AAA | ATC | TTC | GCC | ATT | GAG | GGA | ACT | CAA | TCA | AGG | TCA | AGT | AGT | 1008 |
|---|---|---|---|---|---|---|---|---|---|---|---|---|---|---|---|---|
| Gln | Glu | Lys | Ile | Phe | Ala | Ile | Glu | Gly | Thr | Gln | Ser | Arg | Ser | Ser | Ser | |
| | | | | 325 | | | | | 330 | | | | | 335 | | |

| TCC | TTT | CAG | CAC | GAG | ATG | TCA | CAA | GAA | GGT | TTC | AGT | TCA | GCT | CTC | ACA | 1056 |
|---|---|---|---|---|---|---|---|---|---|---|---|---|---|---|---|---|
| Ser | Phe | Gln | His | Glu | Met | Ser | Gln | Glu | Gly | Phe | Ser | Ser | Ala | Leu | Thr | |
| | | | 340 | | | | | 345 | | | | | 350 | | | |

| TCG | GAT | GGA | CCC | GTT | CTG | GGG | GCC | GYG | GGA | AGC | TTC | AGC | TGG | TCC | GGA | 1104 |
|---|---|---|---|---|---|---|---|---|---|---|---|---|---|---|---|---|
| Ser | Asp | Gly | Pro | Val | Leu | Gly | Ala | Xaa | Gly | Ser | Phe | Ser | Trp | Ser | Gly | |
| | | 355 | | | | | 360 | | | | | 365 | | | | |

| GGT | GCC | TTC | TTA | TAT | CCC | CCA | AAT | ACG | AGA | CCC | ACC | TTT | ATC | AAC | ATG | 1152 |
|---|---|---|---|---|---|---|---|---|---|---|---|---|---|---|---|---|
| Gly | Ala | Phe | Leu | Tyr | Pro | Pro | Asn | Thr | Arg | Pro | Thr | Phe | Ile | Asn | Met | |
| 370 | | | | | 375 | | | | | 380 | | | | | | |

| TCT | CAG | GAG | AAT | GTG | GAC | ATG | AGA | GAC | TCC | TAC | CTG | GGT | TAC | TCC | ACC | 1200 |
|---|---|---|---|---|---|---|---|---|---|---|---|---|---|---|---|---|
| Ser | Gln | Glu | Asn | Val | Asp | Met | Arg | Asp | Ser | Tyr | Leu | Gly | Tyr | Ser | Thr | |
| 385 | | | | | 390 | | | | | 395 | | | | | 400 | |

| GCA | GTG | GCC | TTT | TGG | AAG | GGG | GTT | CAC | AGC | CTG | ATC | CTG | GGG | GCC | CCG | 1248 |
|---|---|---|---|---|---|---|---|---|---|---|---|---|---|---|---|---|
| Ala | Val | Ala | Phe | Trp | Lys | Gly | Val | His | Ser | Leu | Ile | Leu | Gly | Ala | Pro | |
| | | | | 405 | | | | | 410 | | | | | 415 | | |

| CGT | CAC | CAG | CAC | ACG | GGG | AAG | GTT | GTC | ATC | TTT | ACC | CAG | GAA | GCC | AGG | 1296 |
|---|---|---|---|---|---|---|---|---|---|---|---|---|---|---|---|---|
| Arg | His | Gln | His | Thr | Gly | Lys | Val | Val | Ile | Phe | Thr | Gln | Glu | Ala | Arg | |
| | | | 420 | | | | | 425 | | | | | 430 | | | |

| CAT | TGG | AGG | CCC | AAG | TCT | GAA | GTC | AGA | GGG | ACA | CAG | ATC | GGC | TCC | TAC | 1344 |
|---|---|---|---|---|---|---|---|---|---|---|---|---|---|---|---|---|
| His | Trp | Arg | Pro | Lys | Ser | Glu | Val | Arg | Gly | Thr | Gln | Ile | Gly | Ser | Tyr | |
| | | 435 | | | | | 440 | | | | | 445 | | | | |

| TTC | GGG | GCC | TCT | CTC | TGT | TCT | GTG | GAC | GTG | GAT | AGA | GAT | GGC | AGC | ACY | 1392 |
|---|---|---|---|---|---|---|---|---|---|---|---|---|---|---|---|---|
| Phe | Gly | Ala | Ser | Leu | Cys | Ser | Val | Asp | Val | Asp | Arg | Asp | Gly | Ser | Xaa | |
| | 450 | | | | | 455 | | | | | 460 | | | | | |

| GAC | CTG | GTC | CTG | ATC | GGA | GCC | CCC | CAT | TAC | TAT | GAG | CAG | ACC | CGA | GGG | 1440 |
|---|---|---|---|---|---|---|---|---|---|---|---|---|---|---|---|---|
| Asp | Leu | Val | Leu | Ile | Gly | Ala | Pro | His | Tyr | Tyr | Glu | Gln | Thr | Arg | Gly | |
| 465 | | | | | 470 | | | | | 475 | | | | | 480 | |

| GGG | CAG | GTC | TCA | GTG | TKC | CCC | GTG | CCC | GGT | GTG | AGG | GGC | AGG | TGG | CAG | 1488 |
|---|---|---|---|---|---|---|---|---|---|---|---|---|---|---|---|---|
| Gly | Gln | Val | Ser | Val | Xaa | Pro | Val | Pro | Gly | Val | Arg | Gly | Arg | Trp | Gln | |
| | | | | 485 | | | | | 490 | | | | | 495 | | |

| TGT | GAG | GCC | ACC | CTC | CAC | GGG | GAG | CAG | GRC | CAT | CCT | TGG | GGC | CGC | TTT | 1536 |
|---|---|---|---|---|---|---|---|---|---|---|---|---|---|---|---|---|
| Cys | Glu | Ala | Thr | Leu | His | Gly | Glu | Gln | Xaa | His | Pro | Trp | Gly | Arg | Phe | |
| | | | 500 | | | | | 505 | | | | | 510 | | | |

| GGG | GTG | GCT | CTG | ACA | GTG | CTG | GGG | GAC | GTA | AAC | GGG | GAC | AAT | CTG | GCA | 1584 |
|---|---|---|---|---|---|---|---|---|---|---|---|---|---|---|---|---|
| Gly | Val | Ala | Leu | Thr | Val | Leu | Gly | Asp | Val | Asn | Gly | Asp | Asn | Leu | Ala | |
| | | | 515 | | | | | 520 | | | | | 525 | | | |

| GAC | GTG | GCT | ATT | GGT | GCC | CCT | GGA | GAG | GAG | GAG | AGC | AGA | GGT | GCT | GTC | 1632 |
|---|---|---|---|---|---|---|---|---|---|---|---|---|---|---|---|---|
| Asp | Val | Ala | Ile | Gly | Ala | Pro | Gly | Glu | Glu | Glu | Ser | Arg | Gly | Ala | Val | |
| | 530 | | | | | 535 | | | | | 540 | | | | | |

| TAC | ATA | TTT | CAT | GGA | GCC | TCG | AGA | CTG | GAG | ATC | ATG | CCC | TCA | CCC | AGC | 1680 |
|---|---|---|---|---|---|---|---|---|---|---|---|---|---|---|---|---|
| Tyr | Ile | Phe | His | Gly | Ala | Ser | Arg | Leu | Glu | Ile | Met | Pro | Ser | Pro | Ser | |
| 545 | | | | | 550 | | | | | 555 | | | | | 560 | |

| CAG | CGG | GTC | ACT | GGC | TCC | CAG | CTC | TCC | CTG | AGA | CTG | CAG | TAT | TTT | GGG | 1728 |
|---|---|---|---|---|---|---|---|---|---|---|---|---|---|---|---|---|
| Gln | Arg | Val | Thr | Gly | Ser | Gln | Leu | Ser | Leu | Arg | Leu | Gln | Tyr | Phe | Gly | |
| | | | | 565 | | | | | 570 | | | | | 575 | | |

| CAG | TCA | TTG | AGT | GGG | GGT | CAG | GAC | CTT | ACA | CAG | GAT | GGC | CTG | GTG | GAC | 1776 |
|---|---|---|---|---|---|---|---|---|---|---|---|---|---|---|---|---|
| Gln | Ser | Leu | Ser | Gly | Gly | Gln | Asp | Leu | Thr | Gln | Asp | Gly | Leu | Val | Asp | |
| | | | 580 | | | | | 585 | | | | | 590 | | | |

| CTG | GCC | GTG | GGA | GCC | CAG | GGG | CAC | GTA | CTG | CTG | CTC | AGG | AGT | CTG | CCT | 1824 |
|---|---|---|---|---|---|---|---|---|---|---|---|---|---|---|---|---|
| Leu | Ala | Val | Gly | Ala | Gln | Gly | His | Val | Leu | Leu | Leu | Arg | Ser | Leu | Pro | |
| | | 595 | | | | | 600 | | | | | 605 | | | | |

| CTG | CTG | AAA | GTG | GAG | CTC | TCC | ATA | AGA | TTC | GCC | CCC | ATG | GAG | GTG | GCA | 1872 |

```
                Leu   Leu   Lys   Val   Glu   Leu   Ser   Ile   Arg   Phe   Ala   Pro   Met   Glu   Val   Ala
                      610                     615                           620

AAG   GCT   GTG   TAC   CAG   TGC   TGG   GAA   AGG   ACT   CCC   ACT   GTC   CTC   GAA   GCT              1920
Lys   Ala   Val   Tyr   Gln   Cys   Trp   Glu   Arg   Thr   Pro   Thr   Val   Leu   Glu   Ala
625                     630                           635                           640

GGA   GAG   GCC   ACT   GTC   TGT   CTC   ACT   GTC   CAC   AAA   GGC   TCA   CCT   GAC   CTG              1968
Gly   Glu   Ala   Thr   Val   Cys   Leu   Thr   Val   His   Lys   Gly   Ser   Pro   Asp   Leu
                        645                           650                           655

TTA   GGT   AAT   GTC   CAA   GGC   TCT   GTC   AGG   TAT   GAT   CTG   GCG   TTA   GAT   CCG              2016
Leu   Gly   Asn   Val   Gln   Gly   Ser   Val   Arg   Tyr   Asp   Leu   Ala   Leu   Asp   Pro
                  660                           665                           670

GGC   CGC   CTG   ATT   TCT   CGT   GCC   ATT   TTT   GAT   GAG   ACT   AAG   AAC   TGC   ACT              2064
Gly   Arg   Leu   Ile   Ser   Arg   Ala   Ile   Phe   Asp   Glu   Thr   Lys   Asn   Cys   Thr
            675                           680                           685

TTG   ACG   GGA   AGG   AAG   ACT   CTG   GGG   CTT   GGT   GAT   CAC   TGC   GAA   ACA   GTG              2112
Leu   Thr   Gly   Arg   Lys   Thr   Leu   Gly   Leu   Gly   Asp   His   Cys   Glu   Thr   Val
      690                           695                           700

AAG   CTG   CTT   TTG   CCG   GAC   TGT   GTG   GAA   GAT   GCA   GTG   AGC   CCT   ATC   ATC              2160
Lys   Leu   Leu   Leu   Pro   Asp   Cys   Val   Glu   Asp   Ala   Val   Ser   Pro   Ile   Ile
705                     710                           715                           720

CTG   CGC   CTC   AAC   TTT   TCC   CTG   GTG   AGA   GAC   TCT   GCT   TCA   CCC   AGG   AAC              2208
Leu   Arg   Leu   Asn   Phe   Ser   Leu   Val   Arg   Asp   Ser   Ala   Ser   Pro   Arg   Asn
                        725                           730                           735

CTG   CAT   CCT   GTG   CTG   GCT   GTG   GGC   TCA   CAA   GAC   CAC   ATA   ACT   GCT   TCT              2256
Leu   His   Pro   Val   Leu   Ala   Val   Gly   Ser   Gln   Asp   His   Ile   Thr   Ala   Ser
                  740                           745                           750

CTG   CCG   TTT   GAG   AAG   AAC   TGT   AAG   CAA   GAA   CTC   CTG   TGT   GAG   GGG   GAC              2304
Leu   Pro   Phe   Glu   Lys   Asn   Cys   Lys   Gln   Glu   Leu   Leu   Cys   Glu   Gly   Asp
            755                           760                           765

CTG   GGC   ATC   AGC   TTT   AAC   TTC   TCA   GGC   CTG   CAG   GTC   TTG   GTG   GTG   GGA              2352
Leu   Gly   Ile   Ser   Phe   Asn   Phe   Ser   Gly   Leu   Gln   Val   Leu   Val   Val   Gly
      770                           775                           780

GGC   TCC   CCA   GAG   CTC   ACT   GTG   ACA   GTC   ACT   GTG   TGG   AAT   GAG   GGT   GAG              2400
Gly   Ser   Pro   Glu   Leu   Thr   Val   Thr   Val   Thr   Val   Trp   Asn   Glu   Gly   Glu
785                     790                           795                           800

GAC   AGC   TAT   GGA   ACT   TTA   GTC   AAG   TTC   TAC   TAC   CCA   GCA   GGG   CTA   TCT              2448
Asp   Ser   Tyr   Gly   Thr   Leu   Val   Lys   Phe   Tyr   Tyr   Pro   Ala   Gly   Leu   Ser
                        805                           810                           815

TAC   CGA   CGG   GTA   ACA   GGG   ACT   CAG   CAA   CCT   CAT   CAG   TAC   CCA   CTA   CGC              2496
Tyr   Arg   Arg   Val   Thr   Gly   Thr   Gln   Gln   Pro   His   Gln   Tyr   Pro   Leu   Arg
                  820                           825                           830

TTG   GCC   TGT   GAG   GCT   GAG   CCC   GCT   GCC   CAG   GAG   GAC   CTG   AGG   AGC   AGC              2544
Leu   Ala   Cys   Glu   Ala   Glu   Pro   Ala   Ala   Gln   Glu   Asp   Leu   Arg   Ser   Ser
            835                           840                           845

AGC   TGT   AGC   ATT   AAT   CAC   CCC   ATC   TTC   CGA   GAA   GGT   GCA   AAG   ACC   ACC              2592
Ser   Cys   Ser   Ile   Asn   His   Pro   Ile   Phe   Arg   Glu   Gly   Ala   Lys   Thr   Thr
      850                           855                           860

TTC   ATG   ATC   ACA   TTC   GAT   GTC   TCC   TAC   AAG   GCC   TTC   CTA   GGA   GAC   AGG              2640
Phe   Met   Ile   Thr   Phe   Asp   Val   Ser   Tyr   Lys   Ala   Phe   Leu   Gly   Asp   Arg
865                     870                           875                           880

TTG   CTT   CTG   AGG   GCC   AAA   GCC   AGC   AGT   GAG   AAT   AAT   AAG   CCT   GAT   ACC              2688
Leu   Leu   Leu   Arg   Ala   Lys   Ala   Ser   Ser   Glu   Asn   Asn   Lys   Pro   Asp   Thr
                        885                           890                           895

AAC   AAG   ACT   GCC   TTC   CAG   CTG   GAG   CTC   CCA   GTG   AAG   TAC   ACC   GTC   TAT              2736
Asn   Lys   Thr   Ala   Phe   Gln   Leu   Glu   Leu   Pro   Val   Lys   Tyr   Thr   Val   Tyr
                  900                           905                           910

ACC   CTG   ATC   AGT   AGG   CAA   GAA   GAT   TCC   ACC   AAC   CAT   GTC   AAC   TTT   TCA              2784
Thr   Leu   Ile   Ser   Arg   Gln   Glu   Asp   Ser   Thr   Asn   His   Val   Asn   Phe   Ser
            915                           920                           925

TCT   TCC   CAC   GGG   GGG   AGA   AGG   CAA   GAA   GCC   GCA   CAT   CGC   TAT   CGT   GTG              2832
```

|  |  |  |  |  |  |  |  |  |  |  |  |  |  |  |
|---|---|---|---|---|---|---|---|---|---|---|---|---|---|---|
| Ser | Ser | His | Gly | Gly | Arg | Arg | Gln | Glu | Ala | Ala | His | Arg | Tyr | Arg | Val |
|  | 930 |  |  |  | 935 |  |  |  |  | 940 |  |  |  |  |

| AAT | AAC | CTG | AGT | CCA | CTG | AAG | CTG | GCC | GTC | AGA | GTT | AAC | TTC | TGG | GTC | 2880 |
|-----|-----|-----|-----|-----|-----|-----|-----|-----|-----|-----|-----|-----|-----|-----|-----|------|
| Asn | Asn | Leu | Ser | Pro | Leu | Lys | Leu | Ala | Val | Arg | Val | Asn | Phe | Trp | Val |  |
| 945 |  |  |  |  | 950 |  |  |  |  | 955 |  |  |  |  | 960 |  |

| CCT | GTC | CTT | CTG | AAC | GGT | GTG | GCT | GTG | TGG | GAC | GTG | ACT | CTG | AGC | AGC | 2928 |
| Pro | Val | Leu | Leu | Asn | Gly | Val | Ala | Val | Trp | Asp | Val | Thr | Leu | Ser | Ser |  |
|  |  |  |  | 965 |  |  |  |  | 970 |  |  |  |  | 975 |  |  |

| CCA | GCA | CAG | GGT | GTC | TCC | TGC | GTG | TCC | CAG | ATG | AAA | CCT | CCT | CAG | AAT | 2976 |
| Pro | Ala | Gln | Gly | Val | Ser | Cys | Val | Ser | Gln | Met | Lys | Pro | Pro | Gln | Asn |  |
|  |  |  | 980 |  |  |  |  | 985 |  |  |  |  | 990 |  |  |  |

| CCC | GAC | TTT | CTG | ACC | CAG | ATT | CAG | AGA | CGT | TCT | GTG | CTG | GAC | TGC | TCC | 3024 |
| Pro | Asp | Phe | Leu | Thr | Gln | Ile | Gln | Arg | Arg | Ser | Val | Leu | Asp | Cys | Ser |  |
|  |  | 995 |  |  |  |  | 1000 |  |  |  |  | 1005 |  |  |  |  |

| ATT | GCT | GAC | TGC | CTG | CAC | TCC | CGC | TGT | GAC | ATC | CCC | TCC | TTG | GAC | ATC | 3072 |
| Ile | Ala | Asp | Cys | Leu | His | Ser | Arg | Cys | Asp | Ile | Pro | Ser | Leu | Asp | Ile |  |
|  | 1010 |  |  |  |  | 1015 |  |  |  |  | 1020 |  |  |  |  |  |

| CAG | GAT | GAA | CTT | GAC | TTC | ATT | CTG | AGG | GGC | AAC | CTC | AGC | TTC | GGC | TGG | 3120 |
| Gln | Asp | Glu | Leu | Asp | Phe | Ile | Leu | Arg | Gly | Asn | Leu | Ser | Phe | Gly | Trp |  |
| 1025 |  |  |  |  | 1030 |  |  |  |  | 1035 |  |  |  |  | 1040 |  |

| GTC | AGT | CAG | ACA | TTG | CAG | GAA | AAG | GTG | TTG | CTT | GTG | AGT | GAG | GCT | GAA | 3168 |
| Val | Ser | Gln | Thr | Leu | Gln | Glu | Lys | Val | Leu | Leu | Val | Ser | Glu | Ala | Glu |  |
|  |  |  |  | 1045 |  |  |  |  | 1050 |  |  |  |  | 1055 |  |  |

| ATC | ACT | TTC | GAC | ACA | TCT | GTG | TAC | TCC | CAG | CTG | CCA | GGA | CAG | GAG | GCA | 3216 |
| Ile | Thr | Phe | Asp | Thr | Ser | Val | Tyr | Ser | Gln | Leu | Pro | Gly | Gln | Glu | Ala |  |
|  |  |  | 1060 |  |  |  |  | 1065 |  |  |  |  | 1070 |  |  |  |

| TTT | CTG | AGA | GCC | CAG | GTG | GAG | ACA | ACG | TTA | GAA | GAA | TAC | GTG | GTC | TAT | 3264 |
| Phe | Leu | Arg | Ala | Gln | Val | Glu | Thr | Thr | Leu | Glu | Glu | Tyr | Val | Val | Tyr |  |
|  |  | 1075 |  |  |  |  | 1080 |  |  |  |  | 1085 |  |  |  |  |

| GAG | CCC | ATC | TTC | CTC | GTG | GCG | GGC | AGC | TCG | GTG | GGA | GGT | CTG | CTG | TTA | 3312 |
| Glu | Pro | Ile | Phe | Leu | Val | Ala | Gly | Ser | Ser | Val | Gly | Gly | Leu | Leu | Leu |  |
|  | 1090 |  |  |  |  | 1095 |  |  |  |  | 1100 |  |  |  |  |  |

| CTG | GCT | CTC | ATC | ACA | GTG | GTA | CTG | TAC | AAG | CTT | GGC | TYC | TYC | AAA | CGT | 3360 |
| Leu | Ala | Leu | Ile | Thr | Val | Val | Leu | Tyr | Lys | Leu | Gly | Xaa | Xaa | Lys | Arg |  |
| 1105 |  |  |  |  | 1110 |  |  |  |  | 1115 |  |  |  |  | 1120 |  |

| CAG | TAC | AAA | GAA | ATG | CTG | GAC | GGC | AAG | GCT | GCA | GAT | CCT | GTC | ACA | GCC | 3408 |
| Gln | Tyr | Lys | Glu | Met | Leu | Asp | Gly | Lys | Ala | Ala | Asp | Pro | Val | Thr | Ala |  |
|  |  |  |  | 1125 |  |  |  |  | 1130 |  |  |  |  | 1135 |  |  |

| GGC | CAG | GCA | GAT | TTC | GGC | TGT | GAG | ACT | CCT | CCA | TAT | CTC |  |  |  |  |
| Gly | Gln | Ala | Asp | Phe | Gly | Cys | Glu | Thr | Pro | Pro | Tyr | Leu |  |  |  |  |
|  |  |  | 1140 |  |  |  |  | 1145 |  |  |  |  |  |  |  |  |

|  |  |  |  |  |  |  |  |  |  | GTG | AGC | TAGGAATCCA | 3463 |
|  |  |  |  |  |  |  |  |  |  | Val | Ser |  |  |
|  |  |  |  |  |  |  |  |  |  | 1150 |  |  |  |

| CTCTCCTGCC | TATCTCTGNA | ATGAAGATTG | GTCCTGCCTA | TGAGTCTACT | GGCATGGGAA | 3523 |
| CGAGT |  |  |  |  |  | 3528 |

( 2 ) INFORMATION FOR SEQ ID NO:37:

( i ) SEQUENCE CHARACTERISTICS:
        ( A ) LENGTH: 1151 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

| Gly | Trp | Ala | Leu | Ala | Ser | Cys | His | Gly | Ser | Asn | Leu | Asp | Val | Glu | Glu |
| 1 |  |  |  | 5 |  |  |  |  | 10 |  |  |  |  | 15 |  |

| Pro | Ile | Val | Phe | Arg | Glu | Asp | Ala | Ala | Ser | Phe | Gly | Gln | Thr | Val | Val |
|  |  |  | 20 |  |  |  |  | 25 |  |  |  |  | 30 |  |  |

```
Gln  Phe  Gly  Gly  Ser  Arg  Leu  Val  Val  Gly  Ala  Pro  Leu  Glu  Ala  Val
          35                  40                      45

Ala  Val  Asn  Gln  Thr  Gly  Arg  Leu  Tyr  Asp  Cys  Ala  Pro  Ala  Thr  Gly
          50                  55                      60

Met  Cys  Gln  Pro  Ile  Val  Leu  Arg  Ser  Pro  Leu  Glu  Ala  Val  Asn  Met
 65                      70                      75                           80

Ser  Leu  Gly  Leu  Ser  Leu  Val  Thr  Ala  Thr  Asn  Asn  Ala  Gln  Leu  Leu
                    85                       90                           95

Ala  Cys  Gly  Pro  Thr  Ala  Gln  Arg  Ala  Cys  Val  Lys  Asn  Met  Tyr  Ala
               100                 105                      110

Lys  Gly  Ser  Cys  Leu  Leu  Leu  Gly  Ser  Ser  Leu  Gln  Phe  Ile  Gln  Ala
               115                 120                      125

Val  Pro  Ala  Ser  Met  Pro  Glu  Cys  Pro  Arg  Gln  Glu  Met  Asp  Ile  Ala
     130                      135                      140

Phe  Leu  Ile  Asp  Gly  Ser  Gly  Ser  Ile  Asn  Gln  Arg  Asp  Phe  Ala  Gln
145                           150                 155                      160

Met  Lys  Asp  Phe  Val  Lys  Ala  Leu  Met  Gly  Glu  Phe  Ala  Ser  Thr  Ser
                    165                 170                      175

Thr  Leu  Phe  Ser  Leu  Met  Gln  Tyr  Ser  Asn  Ile  Leu  Lys  Thr  His  Phe
               180                 185                      190

Thr  Phe  Thr  Glu  Phe  Lys  Asn  Ile  Leu  Asp  Pro  Gln  Ser  Leu  Val  Asp
          195                 200                      205

Pro  Ile  Val  Gln  Leu  Gln  Gly  Leu  Thr  Tyr  Thr  Ala  Thr  Gly  Ile  Arg
     210                      215                      220

Thr  Val  Met  Glu  Glu  Leu  Phe  His  Ser  Lys  Asn  Gly  Ser  Arg  Lys  Ser
225                      230                 235                           240

Ala  Lys  Lys  Ile  Leu  Leu  Val  Ile  Thr  Asp  Gly  Gln  Lys  Tyr  Arg  Asp
                    245                 250                      255

Pro  Leu  Glu  Tyr  Ser  Asp  Val  Ile  Pro  Ala  Ala  Asp  Lys  Ala  Gly  Ile
               260                 265                      270

Ile  Arg  Tyr  Ala  Ile  Gly  Val  Gly  Asp  Ala  Phe  Gln  Glu  Pro  Thr  Ala
          275                 280                      285

Leu  Lys  Glu  Leu  Asn  Thr  Ile  Gly  Ser  Ala  Pro  Pro  Gln  Asp  His  Val
     290                      295                      300

Phe  Lys  Val  Gly  Asn  Phe  Ala  Ala  Leu  Arg  Ser  Ile  Gln  Arg  Gln  Leu
305                      310                 315                           320

Gln  Glu  Lys  Ile  Phe  Ala  Ile  Glu  Gly  Thr  Gln  Ser  Arg  Ser  Ser  Ser
                    325                 330                      335

Ser  Phe  Gln  His  Glu  Met  Ser  Gln  Glu  Gly  Phe  Ser  Ser  Ala  Leu  Thr
               340                 345                      350

Ser  Asp  Gly  Pro  Val  Leu  Gly  Ala  Xaa  Gly  Ser  Phe  Ser  Trp  Ser  Gly
          355                 360                      365

Gly  Ala  Phe  Leu  Tyr  Pro  Pro  Asn  Thr  Arg  Pro  Thr  Phe  Ile  Asn  Met
     370                      375                      380

Ser  Gln  Glu  Asn  Val  Asp  Met  Arg  Asp  Ser  Tyr  Leu  Gly  Tyr  Ser  Thr
385                      390                      395                      400

Ala  Val  Ala  Phe  Trp  Lys  Gly  Val  His  Ser  Leu  Ile  Leu  Gly  Ala  Pro
                    405                 410                      415

Arg  His  Gln  His  Thr  Gly  Lys  Val  Val  Ile  Phe  Thr  Gln  Glu  Ala  Arg
               420                 425                      430

His  Trp  Arg  Pro  Lys  Ser  Glu  Val  Arg  Gly  Thr  Gln  Ile  Gly  Ser  Tyr
          435                 440                      445

Phe  Gly  Ala  Ser  Leu  Cys  Ser  Val  Asp  Val  Asp  Arg  Asp  Gly  Ser  Xaa
```

-continued

|  | 450 |  |  |  |  | 455 |  |  |  |  | 460 |  |  |  |
|---|---|---|---|---|---|---|---|---|---|---|---|---|---|---|
| Asp 465 | Leu | Val | Leu | Ile | Gly 470 | Ala | Pro | His | Tyr | Tyr 475 | Glu | Gln | Thr | Arg | Gly 480 |
| Gly | Gln | Val | Ser | Val 485 | Xaa | Pro | Val | Pro | Gly 490 | Val | Arg | Gly | Arg | Trp | Gln 495 |
| Cys | Glu | Ala | Thr 500 | Leu | His | Gly | Glu | Gln 505 | Xaa | His | Pro | Trp | Gly 510 | Arg | Phe |
| Gly | Val | Ala 515 | Leu | Thr | Val | Leu | Gly 520 | Asp | Val | Asn | Gly 525 | Asp | Asn | Leu | Ala |
| Asp | Val 530 | Ala | Ile | Gly | Ala | Pro 535 | Gly | Glu | Glu | Glu | Ser 540 | Arg | Gly | Ala | Val |
| Tyr 545 | Ile | Phe | His | Gly | Ala 550 | Ser | Arg | Leu | Glu | Ile 555 | Met | Pro | Ser | Pro | Ser 560 |
| Gln | Arg | Val | Thr | Gly 565 | Ser | Gln | Leu | Ser | Leu 570 | Arg | Leu | Gln | Tyr | Phe 575 | Gly |
| Gln | Ser | Leu | Ser 580 | Gly | Gly | Gln | Asp | Leu 585 | Thr | Gln | Asp | Gly | Leu 590 | Val | Asp |
| Leu | Ala | Val 595 | Gly | Ala | Gln | Gly | His 600 | Val | Leu | Leu | Arg | Ser 605 | Leu | Pro |
| Leu | Leu 610 | Lys | Val | Glu | Leu | Ser 615 | Ile | Arg | Phe | Ala | Pro 620 | Met | Glu | Val | Ala |
| Lys 625 | Ala | Val | Tyr | Gln | Cys 630 | Trp | Glu | Arg | Thr | Pro 635 | Thr | Val | Leu | Glu | Ala 640 |
| Gly | Glu | Ala | Thr | Val 645 | Cys | Leu | Thr | Val | His 650 | Lys | Gly | Ser | Pro | Asp 655 | Leu |
| Leu | Gly | Asn | Val 660 | Gln | Gly | Ser | Val | Arg 665 | Tyr | Asp | Leu | Ala | Leu 670 | Asp | Pro |
| Gly | Arg | Leu 675 | Ile | Ser | Arg | Ala | Ile 680 | Phe | Asp | Glu | Thr | Lys 685 | Asn | Cys | Thr |
| Leu | Thr 690 | Gly | Arg | Lys | Thr | Leu 695 | Gly | Leu | Gly | Asp | His 700 | Cys | Glu | Thr | Val |
| Lys 705 | Leu | Leu | Leu | Pro | Asp 710 | Cys | Val | Glu | Asp | Ala 715 | Val | Ser | Pro | Ile | Ile 720 |
| Leu | Arg | Leu | Asn | Phe 725 | Ser | Leu | Val | Arg | Asp 730 | Ser | Ala | Ser | Pro | Arg 735 | Asn |
| Leu | His | Pro | Val 740 | Leu | Ala | Val | Gly | Ser 745 | Gln | Asp | His | Ile | Thr 750 | Ala | Ser |
| Leu | Pro | Phe 755 | Glu | Lys | Asn | Cys | Lys 760 | Gln | Glu | Leu | Leu | Cys 765 | Glu | Gly | Asp |
| Leu | Gly 770 | Ile | Ser | Phe | Asn | Phe 775 | Ser | Gly | Leu | Gln | Val 780 | Leu | Val | Val | Gly |
| Gly 785 | Ser | Pro | Glu | Leu | Thr 790 | Val | Thr | Val | Thr | Val 795 | Trp | Asn | Glu | Gly | Glu 800 |
| Asp | Ser | Tyr | Gly | Thr 805 | Leu | Val | Lys | Phe | Tyr 810 | Tyr | Pro | Ala | Gly | Leu 815 | Ser |
| Tyr | Arg | Arg | Val 820 | Thr | Gly | Thr | Gln | Gln 825 | Pro | His | Gln | Tyr | Pro 830 | Leu | Arg |
| Leu | Ala | Cys 835 | Glu | Ala | Glu | Pro | Ala 840 | Ala | Gln | Glu | Asp | Leu 845 | Arg | Ser | Ser |
| Ser | Cys 850 | Ser | Ile | Asn | His | Pro 855 | Ile | Phe | Arg | Glu | Gly 860 | Ala | Lys | Thr | Thr |
| Phe 865 | Met | Ile | Thr | Phe | Asp 870 | Val | Ser | Tyr | Lys | Ala 875 | Phe | Leu | Gly | Asp | Arg 880 |

```
Leu  Leu  Leu  Arg  Ala  Lys  Ala  Ser  Ser  Glu  Asn  Asn  Lys  Pro  Asp  Thr
                    885                      890                      895

Asn  Lys  Thr  Ala  Phe  Gln  Leu  Glu  Leu  Pro  Val  Lys  Tyr  Thr  Val  Tyr
                    900                      905                      910

Thr  Leu  Ile  Ser  Arg  Gln  Glu  Asp  Ser  Thr  Asn  His  Val  Asn  Phe  Ser
                    915                      920                      925

Ser  Ser  His  Gly  Gly  Arg  Arg  Gln  Glu  Ala  Ala  His  Arg  Tyr  Arg  Val
                    930                      935                      940

Asn  Asn  Leu  Ser  Pro  Leu  Lys  Leu  Ala  Val  Arg  Val  Asn  Phe  Trp  Val
945                      950                      955                      960

Pro  Val  Leu  Leu  Asn  Gly  Val  Ala  Val  Trp  Asp  Val  Thr  Leu  Ser  Ser
                    965                      970                      975

Pro  Ala  Gln  Gly  Val  Ser  Cys  Val  Ser  Gln  Met  Lys  Pro  Pro  Gln  Asn
                    980                      985                      990

Pro  Asp  Phe  Leu  Thr  Gln  Ile  Gln  Arg  Arg  Ser  Val  Leu  Asp  Cys  Ser
                    995                     1000                     1005

Ile  Ala  Asp  Cys  Leu  His  Ser  Arg  Cys  Asp  Ile  Pro  Ser  Leu  Asp  Ile
                   1010                     1015                     1020

Gln  Asp  Glu  Leu  Asp  Phe  Ile  Leu  Arg  Gly  Asn  Leu  Ser  Phe  Gly  Trp
1025                     1030                     1035                     1040

Val  Ser  Gln  Thr  Leu  Gln  Glu  Lys  Val  Leu  Leu  Val  Ser  Glu  Ala  Glu
                   1045                     1050                     1055

Ile  Thr  Phe  Asp  Thr  Ser  Val  Tyr  Ser  Gln  Leu  Pro  Gly  Gln  Glu  Ala
                   1060                     1065                     1070

Phe  Leu  Arg  Ala  Gln  Val  Glu  Thr  Thr  Leu  Glu  Glu  Tyr  Val  Val  Tyr
                   1075                     1080                     1085

Glu  Pro  Ile  Phe  Leu  Val  Ala  Gly  Ser  Ser  Val  Gly  Gly  Leu  Leu  Leu
1090                     1095                     1100

Leu  Ala  Leu  Ile  Thr  Val  Val  Leu  Tyr  Lys  Leu  Gly  Xaa  Xaa  Lys  Arg
1105                     1110                     1115                     1120

Gln  Tyr  Lys  Glu  Met  Leu  Asp  Gly  Lys  Ala  Ala  Asp  Pro  Val  Thr  Ala
                   1125                     1130                     1135

Gly  Gln  Ala  Asp  Phe  Gly  Cys  Glu  Thr  Pro  Pro  Tyr  Leu  Val  Ser
                   1140                     1145                     1150
```

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

GTCCAAGCTG TCATGGGCCA G                                             21

( 2 ) INFORMATION FOR SEQ ID NO:39:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

GTCCAGCAGA CTGAAGAGCA CGG                                       23

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

TGTAAAACGA CGGCCAGT                                                18

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

GGAAACAGCT ATGACCATG                                            19

( 2 ) INFORMATION FOR SEQ ID NO:42:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

GGACATGTTC ACTGCCTCTA GG                                  22

( 2 ) INFORMATION FOR SEQ ID NO:43:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GGCGGACAGT CAGACGACTG TCCTG                              25

( 2 ) INFORMATION FOR SEQ ID NO:44:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CTGGTTCGGC CCACCTCTGA AGGTTCCAGA ATCGATAG                38

( 2 ) INFORMATION FOR SEQ ID NO:45:

( i ) SEQUENCE CHARACTERISTICS:

(A) LENGTH: 3519 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 52..3519

(xi) SEQUENCE DESCRIPTION: SEQ ID NO:45:

```
GCTTTCTGAA GGTTCCAGAA TCGATAGTGA ATTCGTGGGC ACTGCTCAGA T ATG GTC      57
                                                        Met Val
                                                          1

CGT GGA GTT GTG ATC CTC CTG TGT GGC TGG GCC CTG GCT TCC TGT CAT      105
Arg Gly Val Val Ile Leu Leu Cys Gly Trp Ala Leu Ala Ser Cys His
          5                   10                  15

GGG TCT AAC CTG GAT GTG GAG AAG CCC GTC GTG TTC AAA GAG GAT GCA      153
Gly Ser Asn Leu Asp Val Glu Lys Pro Val Val Phe Lys Glu Asp Ala
        20                  25                  30

GCC AGC TTC GGA CAG ACT GTG GTG CAG TTT GGT GGA TCT CGA CTC GTG      201
Ala Ser Phe Gly Gln Thr Val Val Gln Phe Gly Gly Ser Arg Leu Val
 35                  40                  45                  50

GTG GGA GCC CCT CTG GAG GCG GTG GCA GTC AAC CAA ACA GGA CAG TCG      249
Val Gly Ala Pro Leu Glu Ala Val Ala Val Asn Gln Thr Gly Gln Ser
                 55                  60                  65

TCT GAC TGT CCG CCT GCC ACT GGC GTG TGC CAG CCC ATC TTA CTG CAC      297
Ser Asp Cys Pro Pro Ala Thr Gly Val Cys Gln Pro Ile Leu Leu His
             70                  75                  80

ATT CCC CTA GAG GCA GTG AAC ATG TCC CTG GGC CTG TCT CTG GTG GCT      345
Ile Pro Leu Glu Ala Val Asn Met Ser Leu Gly Leu Ser Leu Val Ala
         85                  90                  95

GAC ACC AAT AAC TCC CAG TTG CTG GCT TGT GGT CCA ACT GCA CAG AGA      393
Asp Thr Asn Asn Ser Gln Leu Leu Ala Cys Gly Pro Thr Ala Gln Arg
     100                 105                 110

GCT TGT GCA AAG AAC ATG TAT GCA AAA GGT TCC TGC CTC CTT CTG GGC      441
Ala Cys Ala Lys Asn Met Tyr Ala Lys Gly Ser Cys Leu Leu Leu Gly
115                 120                 125                 130

TCC AGC TTG CAG TTC ATC CAG GCA ATC CCT GCT ACC ATG CCA GAG TGT      489
Ser Ser Leu Gln Phe Ile Gln Ala Ile Pro Ala Thr Met Pro Glu Cys
                135                 140                 145

CCA GGA CAA GAG ATG GAC ATT GCT TTC CTG ATT GAT GGC TCC GGC AGC      537
Pro Gly Gln Glu Met Asp Ile Ala Phe Leu Ile Asp Gly Ser Gly Ser
            150                 155                 160

ATT GAT CAA AGT GAC TTT ACC CAG ATG AAG GAC TTC GTC AAA GCT TTG      585
Ile Asp Gln Ser Asp Phe Thr Gln Met Lys Asp Phe Val Lys Ala Leu
        165                 170                 175

ATG GGC CAG TTG GCG AGC ACC AGC ACC TCG TTC TCC CTG ATG CAA TAC      633
Met Gly Gln Leu Ala Ser Thr Ser Thr Ser Phe Ser Leu Met Gln Tyr
    180                 185                 190

TCA AAC ATC CTG AAG ACT CAT TTT ACC TTC ACG GAA TTC AAG AGC AGC      681
Ser Asn Ile Leu Lys Thr His Phe Thr Phe Thr Glu Phe Lys Ser Ser
195                 200                 205                 210

CTG AGC CCT CAG AGC CTG GTG GAT GCC ATC GTC CAG CTC AAG GGC CTG      729
Leu Ser Pro Gln Ser Leu Val Asp Ala Ile Val Gln Leu Gln Gly Leu
                215                 220                 225

ACG TAC ACA GCC TCG GGC ATC CAG AAA GTG GTG AAA GAG CTA TTT CAT      777
Thr Tyr Thr Ala Ser Gly Ile Gln Lys Val Val Lys Glu Leu Phe His
            230                 235                 240

AGC AAG AAT GGG GCC CGA AAA AGT GCC AAG AAG ATA CTA ATT GTC ATC      825
Ser Lys Asn Gly Ala Arg Lys Ser Ala Lys Lys Ile Leu Ile Val Ile
        245                 250                 255
```

| | | | | | | | | | | | | | | | | |
|---|---|---|---|---|---|---|---|---|---|---|---|---|---|---|---|---|
| ACA | GAT | GGG | CAG | AAA | TTC | AGA | GAC | CCC | CTG | GAG | TAT | AGA | CAT | GTC | ATC | 873 |
| Thr | Asp | Gly | Gln | Lys | Phe | Arg | Asp | Pro | Leu | Glu | Tyr | Arg | His | Val | Ile | |
| 260 | | | | | 265 | | | | | 270 | | | | | | |
| CCT | GAA | GCA | GAG | AAA | GCT | GGG | ATC | ATT | CGC | TAT | GCT | ATA | GGG | GTG | GGA | 921 |
| Pro | Glu | Ala | Glu | Lys | Ala | Gly | Ile | Ile | Arg | Tyr | Ala | Ile | Gly | Val | Gly | |
| 275 | | | | 280 | | | | | 285 | | | | | | 290 | |
| GAT | GCC | TTC | CGG | GAA | CCC | ACT | GCC | CTA | CAG | GAG | CTG | AAC | ACC | ATT | GGC | 969 |
| Asp | Ala | Phe | Arg | Glu | Pro | Thr | Ala | Leu | Gln | Glu | Leu | Asn | Thr | Ile | Gly | |
| | | | | 295 | | | | | 300 | | | | | 305 | | |
| TCA | GCT | CCC | TCG | CAG | GAC | CAC | GTG | TTC | AAG | GTG | GGC | AAT | TTT | GTA | GCA | 1017 |
| Ser | Ala | Pro | Ser | Gln | Asp | His | Val | Phe | Lys | Val | Gly | Asn | Phe | Val | Ala | |
| | | | 310 | | | | | 315 | | | | | 320 | | | |
| CTT | CGC | AGC | ATC | CAG | CGG | CAA | ATT | CAG | GAG | AAA | ATC | TTT | GCC | ATT | GAA | 1065 |
| Leu | Arg | Ser | Ile | Gln | Arg | Gln | Ile | Gln | Glu | Lys | Ile | Phe | Ala | Ile | Glu | |
| | | 325 | | | | | 330 | | | | | 335 | | | | |
| GGA | ACC | GAA | TCA | AGG | TCA | AGT | AGT | TCC | TTT | CAG | CAC | GAG | ATG | TCA | CAA | 1113 |
| Gly | Thr | Glu | Ser | Arg | Ser | Ser | Ser | Ser | Phe | Gln | His | Glu | Met | Ser | Gln | |
| | 340 | | | | | 345 | | | | | 350 | | | | | |
| GAA | GGT | TTC | AGC | TCA | GCT | CTC | TCA | ATG | GAT | GGA | CCA | GTT | CTG | GGG | GCT | 1161 |
| Glu | Gly | Phe | Ser | Ser | Ala | Leu | Ser | Met | Asp | Gly | Pro | Val | Leu | Gly | Ala | |
| 355 | | | | | 360 | | | | | 365 | | | | | 370 | |
| GTG | GGA | GGC | TTC | AGC | TGG | TCT | GGA | GGT | GCC | TTG | TAC | CCC | TCA | AAT | | 1209 |
| Val | Gly | Gly | Phe | Ser | Trp | Ser | Gly | Gly | Ala | Phe | Leu | Tyr | Pro | Ser | Asn | |
| | | | | 375 | | | | | 380 | | | | | 385 | | |
| ATG | AGA | TCC | ACC | TTC | ATC | AAC | ATG | TCT | CAG | GAG | AAC | GAG | GAT | ATG | AGG | 1257 |
| Met | Arg | Ser | Thr | Phe | Ile | Asn | Met | Ser | Gln | Glu | Asn | Glu | Asp | Met | Arg | |
| | | | 390 | | | | | 395 | | | | | 400 | | | |
| GAC | GCT | TAC | CTG | GGT | TAC | TCC | ACC | GCA | CTG | GCC | TTT | TGG | AAG | GGG | GTC | 1305 |
| Asp | Ala | Tyr | Leu | Gly | Tyr | Ser | Thr | Ala | Leu | Ala | Phe | Trp | Lys | Gly | Val | |
| | | 405 | | | | | 410 | | | | | 415 | | | | |
| CAC | AGC | CTG | ATC | CTG | GGG | GCC | CCT | CGC | CAC | CAG | CAC | ACG | GGG | AAG | GTT | 1353 |
| His | Ser | Leu | Ile | Leu | Gly | Ala | Pro | Arg | His | Gln | His | Thr | Gly | Lys | Val | |
| | 420 | | | | | 425 | | | | | 430 | | | | | |
| GTC | ATC | TTT | ACC | CAG | GAA | TCC | AGG | CAC | TGG | AGG | CCC | AAG | TCT | GAA | GTC | 1401 |
| Val | Ile | Phe | Thr | Gln | Glu | Ser | Arg | His | Trp | Arg | Pro | Lys | Ser | Glu | Val | |
| 435 | | | | | 440 | | | | | 445 | | | | | 450 | |
| AGA | GGG | ACA | CAG | ATC | GGC | TCC | TAC | TTT | GGG | GCA | TCT | CTC | TGT | TCT | GTG | 1449 |
| Arg | Gly | Thr | Gln | Ile | Gly | Ser | Tyr | Phe | Gly | Ala | Ser | Leu | Cys | Ser | Val | |
| | | | | 455 | | | | | 460 | | | | | 465 | | |
| GAC | ATG | GAT | AGA | GAT | GGC | AGC | ACT | GAC | CTG | GTC | CTG | ATT | GGA | GTC | CCC | 1497 |
| Asp | Met | Asp | Arg | Asp | Gly | Ser | Thr | Asp | Leu | Val | Leu | Ile | Gly | Val | Pro | |
| | | | 470 | | | | | 475 | | | | | 480 | | | |
| CAT | TAC | TAT | GAG | CAC | ACC | CGA | GGG | GGG | CAG | GTG | TCG | GTG | TGC | CCC | ATG | 1545 |
| His | Tyr | Tyr | Glu | His | Thr | Arg | Gly | Gly | Gln | Val | Ser | Val | Cys | Pro | Met | |
| | | 485 | | | | | 490 | | | | | 495 | | | | |
| CCT | GGT | GTG | AGG | AGC | AGG | TGG | CAT | TGT | GGG | ACC | ACC | CTC | CAT | GGG | GAG | 1593 |
| Pro | Gly | Val | Arg | Ser | Arg | Trp | His | Cys | Gly | Thr | Thr | Leu | His | Gly | Glu | |
| | 500 | | | | | 505 | | | | | 510 | | | | | |
| CAG | GGC | CAT | CCT | TGG | GGC | CGC | TTT | GGG | GCG | GCT | CTG | ACA | GTG | CTA | GGG | 1641 |
| Gln | Gly | His | Pro | Trp | Gly | Arg | Phe | Gly | Ala | Ala | Leu | Thr | Val | Leu | Gly | |
| 515 | | | | 520 | | | | | 525 | | | | | 530 | | |
| GAC | GTG | AAT | GGG | GAC | AGT | CTG | GCG | GAT | GTG | GCT | ATT | GGT | GCA | CCC | GGA | 1689 |
| Asp | Val | Asn | Gly | Asp | Ser | Leu | Ala | Asp | Val | Ala | Ile | Gly | Ala | Pro | Gly | |
| | | | 535 | | | | | 540 | | | | | 545 | | | |
| GAG | GAG | GAG | AAC | AGA | GGT | GCT | GTC | TAC | ATA | TTT | CAT | GGA | GCC | TCG | AGA | 1737 |
| Glu | Glu | Glu | Asn | Arg | Gly | Ala | Val | Tyr | Ile | Phe | His | Gly | Ala | Ser | Arg | |
| | | | 550 | | | | | 555 | | | | | 560 | | | |
| CAG | GAC | ATC | GCT | CCC | TCG | CCT | AGC | CAG | CGG | GTC | ACT | GGC | TCC | CAG | CTC | 1785 |
| Gln | Asp | Ile | Ala | Pro | Ser | Pro | Ser | Gln | Arg | Val | Thr | Gly | Ser | Gln | Leu | |
| | | 565 | | | | | 570 | | | | | 575 | | | | |

| | | | | | | | | | | | | | | | | |
|---|---|---|---|---|---|---|---|---|---|---|---|---|---|---|---|---|
| TTC | CTG | AGG | CTC | CAA | TAT | TTT | GGG | CAG | TCA | TTA | AGT | GGG | GGT | CAG | GAC | 1833 |
| Phe | Leu | Arg | Leu | Gln | Tyr | Phe | Gly | Gln | Ser | Leu | Ser | Gly | Gly | Gln | Asp | |
| | 580 | | | | 585 | | | | | 590 | | | | | | |
| CTT | ACA | CAG | GAT | GGC | CTG | GTG | GAC | CTG | GCC | GTG | GGA | GCC | CAG | GGG | CAC | 1881 |
| Leu | Thr | Gln | Asp | Gly | Leu | Val | Asp | Leu | Ala | Val | Gly | Ala | Gln | Gly | His | |
| 595 | | | | | 600 | | | | | 605 | | | | | 610 | |
| GTG | CTG | CTG | CTT | AGG | AGT | CTG | CCT | TTG | CTG | AAA | GTG | GGG | ATC | TCC | ATT | 1929 |
| Val | Leu | Leu | Leu | Arg | Ser | Leu | Pro | Leu | Leu | Lys | Val | Gly | Ile | Ser | Ile | |
| | | | | 615 | | | | | 620 | | | | | 625 | | |
| AGA | TTT | GCC | CCC | TCA | GAG | GTG | GCA | AAG | ACT | GTG | TAC | CAG | TGC | TGG | GGA | 1977 |
| Arg | Phe | Ala | Pro | Ser | Glu | Val | Ala | Lys | Thr | Val | Tyr | Gln | Cys | Trp | Gly | |
| | | | 630 | | | | | 635 | | | | | | 640 | | |
| AGG | ACT | CCC | ACT | GTC | CTC | GAA | GCT | GGA | GAG | GCC | ACC | GTC | TGT | CTC | ACT | 2025 |
| Arg | Thr | Pro | Thr | Val | Leu | Glu | Ala | Gly | Glu | Ala | Thr | Val | Cys | Leu | Thr | |
| | | 645 | | | | | 650 | | | | | 655 | | | | |
| GTC | CGC | AAA | GGT | TCA | CCT | GAC | CTG | TTA | GGT | GAT | GTC | CAA | AGC | TCT | GTC | 2073 |
| Val | Arg | Lys | Gly | Ser | Pro | Asp | Leu | Leu | Gly | Asp | Val | Gln | Ser | Ser | Val | |
| | 660 | | | | | 665 | | | | | 670 | | | | | |
| AGG | TAT | GAT | CTG | GCG | TTG | GAT | CCG | GGC | CGT | CTG | ATT | TCT | CGT | GCC | ATT | 2121 |
| Arg | Tyr | Asp | Leu | Ala | Leu | Asp | Pro | Gly | Arg | Leu | Ile | Ser | Arg | Ala | Ile | |
| 675 | | | | | 680 | | | | | 685 | | | | | 690 | |
| TTT | GAT | GAG | ACG | AAG | AAC | TGC | ACT | TTG | ACC | CGA | AGG | AAG | ACT | CTG | GGG | 2169 |
| Phe | Asp | Glu | Thr | Lys | Asn | Cys | Thr | Leu | Thr | Arg | Arg | Lys | Thr | Leu | Gly | |
| | | | | | 695 | | | | | 700 | | | | | 705 | |
| CTT | GGT | GAT | CAC | TGC | GAA | ACA | ATG | AAG | CTG | CTT | TTG | CCA | GAC | TGT | GTG | 2217 |
| Leu | Gly | Asp | His | Cys | Glu | Thr | Met | Lys | Leu | Leu | Leu | Pro | Asp | Cys | Val | |
| | | | 710 | | | | | 715 | | | | | 720 | | | |
| GAG | GAT | GCA | GTG | ACC | CCT | ATC | ATC | CTG | CGC | CTT | AAC | TTA | TCC | CTG | GCA | 2265 |
| Glu | Asp | Ala | Val | Thr | Pro | Ile | Ile | Leu | Arg | Leu | Asn | Leu | Ser | Leu | Ala | |
| | | 725 | | | | | 730 | | | | | 735 | | | | |
| GGG | GAC | TCT | GCT | CCA | TCC | AGG | AAC | CTT | CGT | CCT | GTG | CTG | GCT | GTG | GGC | 2313 |
| Gly | Asp | Ser | Ala | Pro | Ser | Arg | Asn | Leu | Arg | Pro | Val | Leu | Ala | Val | Gly | |
| | 740 | | | | | 745 | | | | | 750 | | | | | |
| TCA | CAA | GAC | CAT | GTA | ACA | GCT | TCT | TTC | CCG | TTT | GAG | AAG | AAC | TGT | GAG | 2361 |
| Ser | Gln | Asp | His | Val | Thr | Ala | Ser | Phe | Pro | Phe | Glu | Lys | Asn | Cys | Glu | |
| 755 | | | | | 760 | | | | | 765 | | | | | 770 | |
| GGG | AAC | CTG | GGC | GTC | AGC | TTC | AAC | TTC | TCA | GGC | CTG | CAG | GTC | TTG | GAG | 2409 |
| Gly | Asn | Leu | Gly | Val | Ser | Phe | Asn | Phe | Ser | Gly | Leu | Gln | Val | Leu | Glu | |
| | | | | 775 | | | | | 780 | | | | | 785 | | |
| GTA | GGA | AGC | TCC | CCA | GAG | CTC | ACT | GTG | ACA | GTA | ACA | GTT | TGG | AAT | GAG | 2457 |
| Val | Gly | Ser | Ser | Pro | Glu | Leu | Thr | Val | Thr | Val | Thr | Val | Trp | Asn | Glu | |
| | | | 790 | | | | | 795 | | | | | 800 | | | |
| GGT | GAG | GAC | AGC | TAT | GGA | ACC | TTA | ATC | AAG | TTC | TAC | TAC | CCA | GCA | GAG | 2505 |
| Gly | Glu | Asp | Ser | Tyr | Gly | Thr | Leu | Ile | Lys | Phe | Tyr | Tyr | Pro | Ala | Glu | |
| | | 805 | | | | | 810 | | | | | 815 | | | | |
| CTA | TCT | TAC | CGA | CGG | GTG | ACA | AGA | GCC | CAG | CAA | CCT | CAT | CCG | TAC | CCA | 2553 |
| Leu | Ser | Tyr | Arg | Arg | Val | Thr | Arg | Ala | Gln | Gln | Pro | His | Pro | Tyr | Pro | |
| | 820 | | | | | 825 | | | | | 830 | | | | | |
| CTA | CGC | CTG | GCA | TGT | GAG | GCT | GAG | CCC | ACG | GGC | CAG | GAG | AGC | CTG | AGG | 2601 |
| Leu | Arg | Leu | Ala | Cys | Glu | Ala | Glu | Pro | Thr | Gly | Gln | Glu | Ser | Leu | Arg | |
| 835 | | | | | 840 | | | | | 845 | | | | | 850 | |
| AGC | AGC | AGC | TGT | AGC | ATC | AAT | CAC | CCC | ATC | TTC | CGA | GAA | GGT | GCC | AAG | 2649 |
| Ser | Ser | Ser | Cys | Ser | Ile | Asn | His | Pro | Ile | Phe | Arg | Glu | Gly | Ala | Lys | |
| | | | | 855 | | | | | 860 | | | | | 865 | | |
| GCC | ACC | TTC | ATG | ATC | ACA | TTT | GAT | GTC | TCC | TAC | AAG | GCC | TTC | CTG | GGA | 2697 |
| Ala | Thr | Phe | Met | Ile | Thr | Phe | Asp | Val | Ser | Tyr | Lys | Ala | Phe | Leu | Gly | |
| | | | 870 | | | | | 875 | | | | | 880 | | | |
| GAC | AGG | TTG | CTT | CTG | AGG | GCC | AGC | GCA | AGC | AGT | GAG | AAT | AAT | AAG | CCT | 2745 |
| Asp | Arg | Leu | Leu | Leu | Arg | Ala | Ser | Ala | Ser | Ser | Glu | Asn | Asn | Lys | Pro | |
| | | 885 | | | | | 890 | | | | | 895 | | | | |

| | | | | | | | | | | | | | | | | |
|---|---|---|---|---|---|---|---|---|---|---|---|---|---|---|---|---|
| GAA | ACC | AGC | AAG | ACT | GCC | TTC | CAG | CTG | GAG | CTT | CCG | GTG | AAG | TAC | ACG | 2793 |
| Glu | Thr | Ser | Lys | Thr | Ala | Phe | Gln | Leu | Glu | Leu | Pro | Val | Lys | Tyr | Thr | |
| 900 | | | | | 905 | | | | | 910 | | | | | | |
| GTC | TAT | ACC | GTG | ATC | AGT | AGG | CAG | GAA | GAT | TCT | ACC | AAG | CAT | TTC | AAC | 2841 |
| Val | Tyr | Thr | Val | Ile | Ser | Arg | Gln | Glu | Asp | Ser | Thr | Lys | His | Phe | Asn | |
| 915 | | | | | 920 | | | | | 925 | | | | | 930 | |
| TTC | TCA | TCT | TCC | CAC | GGG | GAG | AGA | CAG | AAA | GAG | GCC | GAA | CAT | CGA | TAT | 2889 |
| Phe | Ser | Ser | Ser | His | Gly | Glu | Arg | Gln | Lys | Glu | Ala | Glu | His | Arg | Tyr | |
| | | | | 935 | | | | | 940 | | | | | 945 | | |
| CGT | GTG | AAT | AAC | CTG | AGT | CCA | TTG | ACG | CTG | GCC | ATC | AGC | GTT | AAC | TTC | 2937 |
| Arg | Val | Asn | Asn | Leu | Ser | Pro | Leu | Thr | Leu | Ala | Ile | Ser | Val | Asn | Phe | |
| | | | 950 | | | | | 955 | | | | | 960 | | | |
| TGG | GTC | CCC | ATC | CTT | CTG | AAT | GGT | GTG | GCC | GTG | TGG | GAT | GTG | ACT | CTG | 2985 |
| Trp | Val | Pro | Ile | Leu | Leu | Asn | Gly | Val | Ala | Val | Trp | Asp | Val | Thr | Leu | |
| | | 965 | | | | | 970 | | | | | 975 | | | | |
| AGG | AGC | CCA | GCA | CAG | GGT | GTC | TCC | TGT | GTG | TCA | CAG | AGG | GAA | CCT | CCT | 3033 |
| Arg | Ser | Pro | Ala | Gln | Gly | Val | Ser | Cys | Val | Ser | Gln | Arg | Glu | Pro | Pro | |
| | 980 | | | | | 985 | | | | | 990 | | | | | |
| CAA | CAT | TCC | GAC | CTT | CTG | ACC | CAG | ATC | CAA | GGA | CGC | TCT | GTG | CTG | GAC | 3081 |
| Gln | His | Ser | Asp | Leu | Leu | Thr | Gln | Ile | Gln | Gly | Arg | Ser | Val | Leu | Asp | |
| 995 | | | | | 1000 | | | | | 1005 | | | | | 1010 | |
| TGC | GCC | ATC | GCC | GAC | TGC | CTG | CAC | CTC | CGC | TGT | GAC | ATC | CCC | TCC | TTG | 3129 |
| Cys | Ala | Ile | Ala | Asp | Cys | Leu | His | Leu | Arg | Cys | Asp | Ile | Pro | Ser | Leu | |
| | | | | 1015 | | | | | 1020 | | | | | 1025 | | |
| GGC | ACC | CTG | GAT | GAG | CTT | GAC | TTC | ATT | CTG | AAG | GGC | AAC | CTC | AGC | TTC | 3177 |
| Gly | Thr | Leu | Asp | Glu | Leu | Asp | Phe | Ile | Leu | Lys | Gly | Asn | Leu | Ser | Phe | |
| | | | 1030 | | | | | 1035 | | | | | 1040 | | | |
| GGC | TGG | ATC | AGT | CAG | ACA | TTG | CAG | AAA | AAG | GTG | TTG | CTC | CTG | AGT | GAG | 3225 |
| Gly | Trp | Ile | Ser | Gln | Thr | Leu | Gln | Lys | Lys | Val | Leu | Leu | Leu | Ser | Glu | |
| | | 1045 | | | | | 1050 | | | | | 1055 | | | | |
| GCT | GAA | ATC | ACA | TTC | AAC | ACA | TCT | GTG | TAT | TCC | CAG | CTG | CCG | GGA | CAG | 3273 |
| Ala | Glu | Ile | Thr | Phe | Asn | Thr | Ser | Val | Tyr | Ser | Gln | Leu | Pro | Gly | Gln | |
| | | 1060 | | | | | 1065 | | | | | 1070 | | | | |
| GAG | GCA | TTT | CTG | AGA | GCC | CAG | GTG | TCA | ACG | ATG | CTA | GAA | GAA | TAC | GTG | 3321 |
| Glu | Ala | Phe | Leu | Arg | Ala | Gln | Val | Ser | Thr | Met | Leu | Glu | Glu | Tyr | Val | |
| 1075 | | | | | 1080 | | | | | 1085 | | | | | 1090 | |
| GTC | TAT | GAG | CCC | GTC | TTC | CTC | ATG | GTG | TTC | AGC | TCA | GTG | GGA | GGT | CTG | 3369 |
| Val | Tyr | Glu | Pro | Val | Phe | Leu | Met | Val | Phe | Ser | Ser | Val | Gly | Gly | Leu | |
| | | | | 1095 | | | | | 1100 | | | | | 1105 | | |
| CTG | TTA | CTG | GCT | CTC | ATC | ACT | GTG | GCG | CTG | TAC | AAG | CTT | GGC | TTC | TTC | 3417 |
| Leu | Leu | Leu | Ala | Leu | Ile | Thr | Val | Ala | Leu | Tyr | Lys | Leu | Gly | Phe | Phe | |
| | | | | 1110 | | | | | 1115 | | | | | 1120 | | |
| AAA | CGT | CAG | TAT | AAA | GAG | ATG | CTG | GAT | CTA | CCA | TCT | GCA | GAT | CCT | GAC | 3465 |
| Lys | Arg | Gln | Tyr | Lys | Glu | Met | Leu | Asp | Leu | Pro | Ser | Ala | Asp | Pro | Asp | |
| | | | 1125 | | | | | 1130 | | | | | 1135 | | | |
| CCA | GCC | GGC | CAG | GCA | GAT | TCC | AAC | CAT | GAG | ACT | CCT | CCA | CAT | CTC | ACG | 3513 |
| Pro | Ala | Gly | Gln | Ala | Asp | Ser | Asn | His | Glu | Thr | Pro | Pro | His | Leu | Thr | |
| | | 1140 | | | | | 1145 | | | | | 1150 | | | | |
| TCC | TAG | | | | | | | | | | | | | | | 3519 |
| Ser | | | | | | | | | | | | | | | | |
| 1155 | | | | | | | | | | | | | | | | |

( 2 ) INFORMATION FOR SEQ ID NO:46:

( i ) SEQUENCE CHARACTERISTICS:
        ( A ) LENGTH: 1155 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

-continued

| Met | Val | Arg | Gly | Val | Val | Ile | Leu | Leu | Cys | Gly | Trp | Ala | Leu | Ala | Ser |
| 1 | | | | 5 | | | | | 10 | | | | | 15 | |

| Cys | His | Gly | Ser | Asn | Leu | Asp | Val | Glu | Lys | Pro | Val | Val | Phe | Lys | Glu |
| | | | | 20 | | | | 25 | | | | | 30 | | |

| Asp | Ala | Ala | Ser | Phe | Gly | Gln | Thr | Val | Val | Gln | Phe | Gly | Gly | Ser | Arg |
| | | | 35 | | | | 40 | | | | | 45 | | | |

| Leu | Val | Val | Gly | Ala | Pro | Leu | Glu | Ala | Val | Ala | Val | Asn | Gln | Thr | Gly |
| | 50 | | | | | 55 | | | | | 60 | | | | |

| Gln | Ser | Ser | Asp | Cys | Pro | Pro | Ala | Thr | Gly | Val | Cys | Gln | Pro | Ile | Leu |
| 65 | | | | | 70 | | | | 75 | | | | | | 80 |

| Leu | His | Ile | Pro | Leu | Glu | Ala | Val | Asn | Met | Ser | Leu | Gly | Leu | Ser | Leu |
| | | | | 85 | | | | | 90 | | | | | 95 | |

| Val | Ala | Asp | Thr | Asn | Asn | Ser | Gln | Leu | Leu | Ala | Cys | Gly | Pro | Thr | Ala |
| | | | 100 | | | | | 105 | | | | | 110 | | |

| Gln | Arg | Ala | Cys | Ala | Lys | Asn | Met | Tyr | Ala | Lys | Gly | Ser | Cys | Leu | Leu |
| | | | 115 | | | | 120 | | | | | 125 | | | |

| Leu | Gly | Ser | Ser | Leu | Gln | Phe | Ile | Gln | Ala | Ile | Pro | Ala | Thr | Met | Pro |
| | | 130 | | | | | 135 | | | | | 140 | | | |

| Glu | Cys | Pro | Gly | Gln | Glu | Met | Asp | Ile | Ala | Phe | Leu | Ile | Asp | Gly | Ser |
| 145 | | | | | 150 | | | | | 155 | | | | | 160 |

| Gly | Ser | Ile | Asp | Gln | Ser | Asp | Phe | Thr | Gln | Met | Lys | Asp | Phe | Val | Lys |
| | | | | 165 | | | | | 170 | | | | | 175 | |

| Ala | Leu | Met | Gly | Gln | Leu | Ala | Ser | Thr | Ser | Thr | Ser | Phe | Ser | Leu | Met |
| | | | 180 | | | | | 185 | | | | | 190 | | |

| Gln | Tyr | Ser | Asn | Ile | Leu | Lys | Thr | His | Phe | Thr | Phe | Thr | Glu | Phe | Lys |
| | | | 195 | | | | | 200 | | | | | 205 | | |

| Ser | Ser | Leu | Ser | Pro | Gln | Ser | Leu | Val | Asp | Ala | Ile | Val | Gln | Leu | Gln |
| | | 210 | | | | | 215 | | | | | 220 | | | |

| Gly | Leu | Thr | Tyr | Thr | Ala | Ser | Gly | Ile | Gln | Lys | Val | Val | Lys | Glu | Leu |
| 225 | | | | | 230 | | | | | 235 | | | | | 240 |

| Phe | His | Ser | Lys | Asn | Gly | Ala | Arg | Lys | Ser | Ala | Lys | Lys | Ile | Leu | Ile |
| | | | | 245 | | | | | 250 | | | | | 255 | |

| Val | Ile | Thr | Asp | Gly | Gln | Lys | Phe | Arg | Asp | Pro | Leu | Glu | Tyr | Arg | His |
| | | | 260 | | | | | 265 | | | | | 270 | | |

| Val | Ile | Pro | Glu | Ala | Glu | Lys | Ala | Gly | Ile | Ile | Arg | Tyr | Ala | Ile | Gly |
| | | 275 | | | | | 280 | | | | | 285 | | | |

| Val | Gly | Asp | Ala | Phe | Arg | Glu | Pro | Thr | Ala | Leu | Gln | Glu | Leu | Asn | Thr |
| | | 290 | | | | | 295 | | | | | 300 | | | |

| Ile | Gly | Ser | Ala | Pro | Ser | Gln | Asp | His | Val | Phe | Lys | Val | Gly | Asn | Phe |
| 305 | | | | | 310 | | | | | 315 | | | | | 320 |

| Val | Ala | Leu | Arg | Ser | Ile | Gln | Arg | Gln | Ile | Gln | Glu | Lys | Ile | Phe | Ala |
| | | | | 325 | | | | | 330 | | | | | 335 | |

| Ile | Glu | Gly | Thr | Glu | Ser | Arg | Ser | Ser | Ser | Ser | Phe | Gln | His | Glu | Met |
| | | | 340 | | | | | 345 | | | | | 350 | | |

| Ser | Gln | Glu | Gly | Phe | Ser | Ser | Ala | Leu | Ser | Met | Asp | Gly | Pro | Val | Leu |
| | | | 355 | | | | | 360 | | | | | 365 | | |

| Gly | Ala | Val | Gly | Gly | Phe | Ser | Trp | Ser | Gly | Gly | Ala | Phe | Leu | Tyr | Pro |
| | | 370 | | | | | 375 | | | | | 380 | | | |

| Ser | Asn | Met | Arg | Ser | Thr | Phe | Ile | Asn | Met | Ser | Gln | Glu | Asn | Glu | Asp |
| 385 | | | | | 390 | | | | | 395 | | | | | 400 |

| Met | Arg | Asp | Ala | Tyr | Leu | Gly | Tyr | Ser | Thr | Ala | Leu | Ala | Phe | Trp | Lys |
| | | | | 405 | | | | | 410 | | | | | 415 | |

| Gly | Val | His | Ser | Leu | Ile | Leu | Gly | Ala | Pro | Arg | His | Gln | His | Thr | Gly |

|     |     |     |     |     |     | 420 |     |     |     |     | 425 |     |     |     |     | 430 |     |     |     |
| --- | --- | --- | --- | --- | --- | --- | --- | --- | --- | --- | --- | --- | --- | --- | --- | --- | --- | --- | --- |
| Lys | Val | Val | Ile | Phe | Thr | Gln | Glu | Ser | Arg | His | Trp | Arg | Pro | Lys | Ser |
|     |     |     | 435 |     |     |     | 440 |     |     |     |     | 445 |     |     |     |
| Glu | Val | Arg | Gly | Thr | Gln | Ile | Gly | Ser | Tyr | Phe | Gly | Ala | Ser | Leu | Cys |
|     | 450 |     |     |     |     | 455 |     |     |     |     |     | 460 |     |     |     |
| Ser | Val | Asp | Met | Asp | Arg | Asp | Gly | Ser | Thr | Asp | Leu | Val | Leu | Ile | Gly |
| 465 |     |     |     |     | 470 |     |     |     |     | 475 |     |     |     |     | 480 |
| Val | Pro | His | Tyr | Tyr | Glu | His | Thr | Arg | Gly | Gly | Gln | Val | Ser | Val | Cys |
|     |     |     |     | 485 |     |     |     |     | 490 |     |     |     |     | 495 |     |
| Pro | Met | Pro | Gly | Val | Arg | Ser | Arg | Trp | His | Cys | Gly | Thr | Thr | Leu | His |
|     |     |     | 500 |     |     |     |     | 505 |     |     |     |     | 510 |     |     |
| Gly | Glu | Gln | Gly | His | Pro | Trp | Gly | Arg | Phe | Gly | Ala | Ala | Leu | Thr | Val |
|     |     | 515 |     |     |     |     | 520 |     |     |     |     |     | 525 |     |     |
| Leu | Gly | Asp | Val | Asn | Gly | Asp | Ser | Leu | Ala | Asp | Val | Ala | Ile | Gly | Ala |
|     | 530 |     |     |     |     | 535 |     |     |     |     |     | 540 |     |     |     |
| Pro | Gly | Glu | Glu | Glu | Asn | Arg | Gly | Ala | Val | Tyr | Ile | Phe | His | Gly | Ala |
| 545 |     |     |     |     | 550 |     |     |     |     | 555 |     |     |     |     | 560 |
| Ser | Arg | Gln | Asp | Ile | Ala | Pro | Ser | Pro | Ser | Gln | Arg | Val | Thr | Gly | Ser |
|     |     |     |     | 565 |     |     |     |     | 570 |     |     |     |     | 575 |     |
| Gln | Leu | Phe | Leu | Arg | Leu | Gln | Tyr | Phe | Gly | Gln | Ser | Leu | Ser | Gly | Gly |
|     |     |     | 580 |     |     |     |     | 585 |     |     |     |     | 590 |     |     |
| Gln | Asp | Leu | Thr | Gln | Asp | Gly | Leu | Val | Asp | Leu | Ala | Val | Gly | Ala | Gln |
|     |     | 595 |     |     |     |     | 600 |     |     |     |     |     | 605 |     |     |
| Gly | His | Val | Leu | Leu | Leu | Arg | Ser | Leu | Pro | Leu | Leu | Lys | Val | Gly | Ile |
|     |     | 610 |     |     |     |     | 615 |     |     |     |     | 620 |     |     |     |
| Ser | Ile | Arg | Phe | Ala | Pro | Ser | Glu | Val | Ala | Lys | Thr | Val | Tyr | Gln | Cys |
| 625 |     |     |     |     | 630 |     |     |     |     | 635 |     |     |     |     | 640 |
| Trp | Gly | Arg | Thr | Pro | Thr | Val | Leu | Glu | Ala | Gly | Glu | Ala | Thr | Val | Cys |
|     |     |     |     | 645 |     |     |     |     | 650 |     |     |     |     | 655 |     |
| Leu | Thr | Val | Arg | Lys | Gly | Ser | Pro | Asp | Leu | Leu | Gly | Asp | Val | Gln | Ser |
|     |     |     | 660 |     |     |     |     | 665 |     |     |     |     | 670 |     |     |
| Ser | Val | Arg | Tyr | Asp | Leu | Ala | Leu | Asp | Pro | Gly | Arg | Leu | Ile | Ser | Arg |
|     |     | 675 |     |     |     |     | 680 |     |     |     |     | 685 |     |     |     |
| Ala | Ile | Phe | Asp | Glu | Thr | Lys | Asn | Cys | Thr | Leu | Thr | Arg | Arg | Lys | Thr |
|     | 690 |     |     |     |     | 695 |     |     |     |     | 700 |     |     |     |     |
| Leu | Gly | Leu | Gly | Asp | His | Cys | Glu | Thr | Met | Lys | Leu | Leu | Leu | Pro | Asp |
| 705 |     |     |     |     | 710 |     |     |     |     | 715 |     |     |     |     | 720 |
| Cys | Val | Glu | Asp | Ala | Val | Thr | Pro | Ile | Ile | Leu | Arg | Leu | Asn | Leu | Ser |
|     |     |     |     | 725 |     |     |     |     | 730 |     |     |     |     | 735 |     |
| Leu | Ala | Gly | Asp | Ser | Ala | Pro | Ser | Arg | Asn | Leu | Arg | Pro | Val | Leu | Ala |
|     |     |     | 740 |     |     |     |     | 745 |     |     |     |     | 750 |     |     |
| Val | Gly | Ser | Gln | Asp | His | Val | Thr | Ala | Ser | Phe | Pro | Phe | Glu | Lys | Asn |
|     |     | 755 |     |     |     |     | 760 |     |     |     |     | 765 |     |     |     |
| Cys | Glu | Gly | Asn | Leu | Gly | Val | Ser | Phe | Asn | Phe | Ser | Gly | Leu | Gln | Val |
|     | 770 |     |     |     |     | 775 |     |     |     |     | 780 |     |     |     |     |
| Leu | Glu | Val | Gly | Ser | Ser | Pro | Glu | Leu | Thr | Val | Thr | Val | Thr | Val | Trp |
| 785 |     |     |     |     | 790 |     |     |     |     | 795 |     |     |     |     | 800 |
| Asn | Glu | Gly | Glu | Asp | Ser | Tyr | Gly | Thr | Leu | Ile | Lys | Phe | Tyr | Tyr | Pro |
|     |     |     |     | 805 |     |     |     |     | 810 |     |     |     |     | 815 |     |
| Ala | Glu | Leu | Ser | Tyr | Arg | Arg | Val | Thr | Arg | Ala | Gln | Gln | Pro | His | Pro |
|     |     |     | 820 |     |     |     |     | 825 |     |     |     |     | 830 |     |     |
| Tyr | Pro | Leu | Arg | Leu | Ala | Cys | Glu | Ala | Glu | Pro | Thr | Gly | Gln | Glu | Ser |
|     |     | 835 |     |     |     |     | 840 |     |     |     |     | 845 |     |     |     |

```
Leu  Arg  Ser  Ser  Ser  Cys  Ser  Ile  Asn  His  Pro  Ile  Phe  Arg  Glu  Gly
     850                 855                      860

Ala  Lys  Ala  Thr  Phe  Met  Ile  Thr  Phe  Asp  Val  Ser  Tyr  Lys  Ala  Phe
865                      870                 875                           880

Leu  Gly  Asp  Arg  Leu  Leu  Arg  Ala  Ala  Ser  Ser  Glu  Asn
                    885                 890                 895

Lys  Pro  Glu  Thr  Ser  Lys  Thr  Ala  Phe  Gln  Leu  Glu  Leu  Pro  Val  Lys
               900                      905                      910

Tyr  Thr  Val  Tyr  Thr  Val  Ile  Ser  Arg  Gln  Glu  Asp  Ser  Thr  Lys  His
          915                      920                      925

Phe  Asn  Phe  Ser  Ser  Ser  His  Gly  Glu  Arg  Gln  Lys  Glu  Ala  Glu  His
     930                      935                      940

Arg  Tyr  Arg  Val  Asn  Asn  Leu  Ser  Pro  Leu  Thr  Leu  Ala  Ile  Ser  Val
945                      950                      955                          960

Asn  Phe  Trp  Val  Pro  Ile  Leu  Leu  Asn  Gly  Val  Ala  Val  Trp  Asp  Val
                    965                      970                      975

Thr  Leu  Arg  Ser  Pro  Ala  Gln  Gly  Val  Ser  Cys  Val  Ser  Gln  Arg  Glu
               980                      985                      990

Pro  Pro  Gln  His  Ser  Asp  Leu  Leu  Thr  Gln  Ile  Gln  Gly  Arg  Ser  Val
               995                      1000                     1005

Leu  Asp  Cys  Ala  Ile  Ala  Asp  Cys  Leu  His  Leu  Arg  Cys  Asp  Ile  Pro
     1010                     1015                     1020

Ser  Leu  Gly  Thr  Leu  Asp  Glu  Leu  Asp  Phe  Ile  Leu  Lys  Gly  Asn  Leu
1025                     1030                     1035                         1040

Ser  Phe  Gly  Trp  Ile  Ser  Gln  Thr  Leu  Gln  Lys  Val  Leu  Leu  Leu
                    1045                     1050                     1055

Ser  Glu  Ala  Glu  Ile  Thr  Phe  Asn  Thr  Ser  Val  Tyr  Ser  Gln  Leu  Pro
               1060                     1065                     1070

Gly  Gln  Glu  Ala  Phe  Leu  Arg  Ala  Gln  Val  Ser  Thr  Met  Leu  Glu  Glu
               1075                     1080                     1085

Tyr  Val  Val  Tyr  Glu  Pro  Val  Phe  Leu  Met  Val  Phe  Ser  Ser  Val  Gly
     1090                     1095                     1100

Gly  Leu  Leu  Leu  Leu  Ala  Leu  Ile  Thr  Val  Ala  Leu  Tyr  Lys  Leu  Gly
1105                     1110                     1115                         1120

Phe  Phe  Lys  Arg  Gln  Tyr  Lys  Glu  Met  Leu  Asp  Leu  Pro  Ser  Ala  Asp
                    1125                     1130                     1135

Pro  Asp  Pro  Ala  Gly  Gln  Ala  Asp  Ser  Asn  His  Glu  Thr  Pro  Pro  His
                    1140                     1145                     1150

Leu  Thr  Ser
     1155
```

( 2 ) INFORMATION FOR SEQ ID NO:47:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

AGTTACGGAT CCGGCACCAT GACCTTCGGC ACTGTGATCC TCCTGTGTG    49

( 2 ) INFORMATION FOR SEQ ID NO:48:

( i ) SEQUENCE CHARACTERISTICS:
        ( A ) LENGTH: 19 base pairs (B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:48:

GCTGGACGAT GGCATCCAC  19

(2) INFORMATION FOR SEQ ID NO:49:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:49:

GTAGAGTTAC GGATCCGGCA CCAT  24

(2) INFORMATION FOR SEQ ID NO:50:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:50:

GCAGCCAGCT TCGGACAGAC  20

(2) INFORMATION FOR SEQ ID NO:51:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:51:

CCATGTCCAC AGAACAGAGA G  21

(2) INFORMATION FOR SEQ ID NO:52:

(i) SEQUENCE CHARACTERISTICS:
(A) LENGTH: 3803 base pairs
(B) TYPE: nucleic acid
(C) STRANDEDNESS: single
(D) TOPOLOGY: linear (i i) MOLECULE TYPE: cDNA (i x) FEATURE:
(A) NAME/KEY: CDS
(B) LOCATION: 1..3486

(x i) SEQUENCE DESCRIPTION: SEQ ID NO:52:

| ATG | GTC | CGT | GGA | GTT | GTG | ATC | CTC | CTG | TGT | GGC | TGG | GCC | CTG | GCT | TCC | 48 |
| Met | Val | Arg | Gly | Val | Val | Ile | Leu | Leu | Cys | Gly | Trp | Ala | Leu | Ala | Ser | |
| 1 | | | | 5 | | | | | 10 | | | | | 15 | | |

| TGT | CAT | GGG | TCT | AAC | CTG | GAT | GTG | GAG | AAG | CCC | GTC | GTG | TTC | AAA | GAG | 96 |
| Cys | His | Gly | Ser | Asn | Leu | Asp | Val | Glu | Lys | Pro | Val | Val | Phe | Lys | Glu | |
| | | | | 20 | | | | | 25 | | | | | 30 | | |

| | | | | | | | | | | | | | | | | |
|---|---|---|---|---|---|---|---|---|---|---|---|---|---|---|---|---|
| GAT | GCA | GCC | AGC | TTC | GGA | CAG | ACT | GTG | GTG | CAG | TTT | GGT | GGA | TCT | CGA | 144 |
| Asp | Ala | Ala | Ser | Phe | Gly | Gln | Thr | Val | Val | Gln | Phe | Gly | Gly | Ser | Arg | |
| | | 35 | | | | 40 | | | | | | 45 | | | | |
| CTC | GTG | GTG | GGA | GCC | CCT | CTG | GAG | GCG | GTG | GCA | GTC | AAC | CAA | ACA | GGA | 192 |
| Leu | Val | Val | Gly | Ala | Pro | Leu | Glu | Ala | Val | Ala | Val | Asn | Gln | Thr | Gly | |
| | 50 | | | | 55 | | | | | 60 | | | | | | |
| CAG | TCG | TCT | GAC | TGT | CCG | CCT | GCC | ACT | GGC | GTG | TGC | CAG | CCC | ATC | TTA | 240 |
| Gln | Ser | Ser | Asp | Cys | Pro | Pro | Ala | Thr | Gly | Val | Cys | Gln | Pro | Ile | Leu | |
| 65 | | | | 70 | | | | | 75 | | | | | | 80 | |
| CTG | CAC | ATT | CCC | CTA | GAG | GCA | GTG | AAC | ATG | TCC | CTG | GGC | CTG | TCT | CTG | 288 |
| Leu | His | Ile | Pro | Leu | Glu | Ala | Val | Asn | Met | Ser | Leu | Gly | Leu | Ser | Leu | |
| | | | | 85 | | | | | 90 | | | | | 95 | | |
| GTG | GCT | GAC | ACC | AAT | AAC | TCC | CAG | TTG | CTG | GCT | TGT | GGT | CCA | ACT | GCA | 336 |
| Val | Ala | Asp | Thr | Asn | Asn | Ser | Gln | Leu | Leu | Ala | Cys | Gly | Pro | Thr | Ala | |
| | | | 100 | | | | | 105 | | | | | 110 | | | |
| CAG | AGA | GCT | TGT | GCA | AAG | AAC | ATG | TAT | GCA | AAA | GGT | TCC | TGC | CTC | CTT | 384 |
| Gln | Arg | Ala | Cys | Ala | Lys | Asn | Met | Tyr | Ala | Lys | Gly | Ser | Cys | Leu | Leu | |
| | | 115 | | | | | 120 | | | | | 125 | | | | |
| CTG | GGC | TCC | AGC | TTG | CAG | TTC | ATC | CAG | GCA | ATC | CCT | GCT | ACC | ATG | CCA | 432 |
| Leu | Gly | Ser | Ser | Leu | Gln | Phe | Ile | Gln | Ala | Ile | Pro | Ala | Thr | Met | Pro | |
| | 130 | | | | | 135 | | | | | 140 | | | | | |
| GAG | TGT | CCA | GGA | CAA | GAG | ATG | GAC | ATT | GCT | TTC | CTG | ATT | GAT | GGC | TCC | 480 |
| Glu | Cys | Pro | Gly | Gln | Glu | Met | Asp | Ile | Ala | Phe | Leu | Ile | Asp | Gly | Ser | |
| 145 | | | | | 150 | | | | | 155 | | | | | 160 | |
| GGC | AGC | ATT | GAT | CAA | AGT | GAC | TTT | ACC | CAG | ATG | AAG | GAC | TTC | GTC | AAA | 528 |
| Gly | Ser | Ile | Asp | Gln | Ser | Asp | Phe | Thr | Gln | Met | Lys | Asp | Phe | Val | Lys | |
| | | | | 165 | | | | | 170 | | | | | 175 | | |
| GCT | TTG | ATG | GGC | CAG | TTG | GCG | AGC | ACC | AGC | ACC | TCG | TTC | TCC | CTG | ATG | 576 |
| Ala | Leu | Met | Gly | Gln | Leu | Ala | Ser | Thr | Ser | Thr | Ser | Phe | Ser | Leu | Met | |
| | | | 180 | | | | | 185 | | | | | 190 | | | |
| CAA | TAC | TCA | AAC | ATC | CTG | AAG | ACT | CAT | TTT | ACC | TTC | ACG | GAA | TTC | AAG | 624 |
| Gln | Tyr | Ser | Asn | Ile | Leu | Lys | Thr | His | Phe | Thr | Phe | Thr | Glu | Phe | Lys | |
| | | 195 | | | | | 200 | | | | | 205 | | | | |
| AGC | AGC | CTG | AGC | CCT | CAG | AGC | CTG | GTG | GAT | GCC | ATC | GTC | CAG | CTC | CAA | 672 |
| Ser | Ser | Leu | Ser | Pro | Gln | Ser | Leu | Val | Asp | Ala | Ile | Val | Gln | Leu | Gln | |
| | 210 | | | | | 215 | | | | | 220 | | | | | |
| GGC | CTG | ACG | TAC | ACA | GCC | TCG | GGC | ATC | CAG | AAA | GTG | GTG | AAA | GAG | CTA | 720 |
| Gly | Leu | Thr | Tyr | Thr | Ala | Ser | Gly | Ile | Gln | Lys | Val | Val | Lys | Glu | Leu | |
| 225 | | | | | 230 | | | | | 235 | | | | | 240 | |
| TTT | CAT | AGC | AAG | AAT | GGG | GCC | CGA | AAA | AGT | GCC | AAG | AAG | ATA | CTA | ATT | 768 |
| Phe | His | Ser | Lys | Asn | Gly | Ala | Arg | Lys | Ser | Ala | Lys | Lys | Ile | Leu | Ile | |
| | | | | 245 | | | | | 250 | | | | | 255 | | |
| GTC | ATC | ACA | GAT | GGG | CAG | AAA | TTC | AGA | GAC | CCC | CTG | GAG | TAT | AGA | CAT | 816 |
| Val | Ile | Thr | Asp | Gly | Gln | Lys | Phe | Arg | Asp | Pro | Leu | Glu | Tyr | Arg | His | |
| | | | 260 | | | | | 265 | | | | | 270 | | | |
| GTC | ATC | CCT | GAA | GCA | GAG | AAA | GCT | GGG | ATC | ATT | CGC | TAT | GCT | ATA | GGG | 864 |
| Val | Ile | Pro | Glu | Ala | Glu | Lys | Ala | Gly | Ile | Ile | Arg | Tyr | Ala | Ile | Gly | |
| | | 275 | | | | | 280 | | | | | 285 | | | | |
| GTG | GGA | GAT | GCC | TTC | CGG | GAA | CCC | ACT | GCC | CTA | CAG | GAG | CTG | AAC | ACC | 912 |
| Val | Gly | Asp | Ala | Phe | Arg | Glu | Pro | Thr | Ala | Leu | Gln | Glu | Leu | Asn | Thr | |
| | 290 | | | | | 295 | | | | | 300 | | | | | |
| ATT | GGC | TCA | GCT | CCC | TCG | CAG | GAC | CAC | GTG | TTC | AAG | GTG | GGC | AAT | TTT | 960 |
| Ile | Gly | Ser | Ala | Pro | Ser | Gln | Asp | His | Val | Phe | Lys | Val | Gly | Asn | Phe | |
| 305 | | | | 310 | | | | | 315 | | | | | | 320 | |
| GTA | GCA | CTT | CGC | AGC | ATC | CAG | CGG | CAA | ATT | CAG | GAG | AAA | ATC | TTT | GCC | 1008 |
| Val | Ala | Leu | Arg | Ser | Ile | Gln | Arg | Gln | Ile | Gln | Glu | Lys | Ile | Phe | Ala | |
| | | | | 325 | | | | | 330 | | | | | 335 | | |
| ATT | GAA | GGA | ACC | GAA | TCA | AGG | TCA | AGT | AGT | TCC | TTT | CAG | CAC | GAG | ATG | 1056 |
| Ile | Glu | Gly | Thr | Glu | Ser | Arg | Ser | Ser | Ser | Ser | Phe | Gln | His | Glu | Met | |
| | | | 340 | | | | | 345 | | | | | 350 | | | |

| | | | | | | | | | | | | | | | | |
|---|---|---|---|---|---|---|---|---|---|---|---|---|---|---|---|---|
| TCA | CAA | GAA | GGT | TTC | AGC | TCA | GCT | CTC | TCA | ATG | GAT | GGA | CCA | GTT | CTG | 1104 |
| Ser | Gln | Glu | Gly | Phe | Ser | Ser | Ala | Leu | Ser | Met | Asp | Gly | Pro | Val | Leu | |
| | | 355 | | | | 360 | | | | | | 365 | | | | |
| GGG | GCT | GTG | GGA | GGC | TTC | AGC | TGG | TCT | GGA | GGT | GCC | TTC | TTG | TAC | CCC | 1152 |
| Gly | Ala | Val | Gly | Gly | Phe | Ser | Trp | Ser | Gly | Gly | Ala | Phe | Leu | Tyr | Pro | |
| | 370 | | | | | 375 | | | | | 380 | | | | | |
| TCA | AAT | ATG | AGA | TCC | ACC | TTC | ATC | AAC | ATG | TCT | CAG | GAG | AAC | GAG | GAT | 1200 |
| Ser | Asn | Met | Arg | Ser | Thr | Phe | Ile | Asn | Met | Ser | Gln | Glu | Asn | Glu | Asp | |
| 385 | | | | | 390 | | | | | 395 | | | | | 400 | |
| ATG | AGG | GAC | GCT | TAC | CTG | GGT | TAC | TCC | ACC | GCA | CTG | GCC | TTT | TGG | AAG | 1248 |
| Met | Arg | Asp | Ala | Tyr | Leu | Gly | Tyr | Ser | Thr | Ala | Leu | Ala | Phe | Trp | Lys | |
| | | | | 405 | | | | 410 | | | | | 415 | | | |
| GGG | GTC | CAC | AGC | CTG | ATC | CTG | GGG | GCC | CCT | CGC | CAC | CAG | CAC | ACG | GGG | 1296 |
| Gly | Val | His | Ser | Leu | Ile | Leu | Gly | Ala | Pro | Arg | His | Gln | His | Thr | Gly | |
| | | | 420 | | | | | 425 | | | | | 430 | | | |
| AAG | GTT | GTC | ATC | TTT | ACC | CAG | GAA | TCC | AGG | CAC | TGG | AGG | CCC | AAG | TCT | 1344 |
| Lys | Val | Val | Ile | Phe | Thr | Gln | Glu | Ser | Arg | His | Trp | Arg | Pro | Lys | Ser | |
| | | 435 | | | | | 440 | | | | | 445 | | | | |
| GAA | GTC | AGA | GGG | ACA | CAG | ATC | GGC | TCC | TAC | TTT | GGG | GCA | TCT | CTC | TGT | 1392 |
| Glu | Val | Arg | Gly | Thr | Gln | Ile | Gly | Ser | Tyr | Phe | Gly | Ala | Ser | Leu | Cys | |
| | 450 | | | | | 455 | | | | | 460 | | | | | |
| TCT | GTG | GAC | ATG | GAT | AGA | GAT | GGC | AGC | ACT | GAC | CTG | GTC | CTG | ATT | GGA | 1440 |
| Ser | Val | Asp | Met | Asp | Arg | Asp | Gly | Ser | Thr | Asp | Leu | Val | Leu | Ile | Gly | |
| 465 | | | | | 470 | | | | | 475 | | | | | 480 | |
| GTC | CCC | CAT | TAC | TAT | GAG | CAC | ACC | CGA | GGG | GGG | CAG | GTG | TCG | GTG | TGC | 1488 |
| Val | Pro | His | Tyr | Tyr | Glu | His | Thr | Arg | Gly | Gly | Gln | Val | Ser | Val | Cys | |
| | | | | 485 | | | | 490 | | | | | 495 | | | |
| CCC | ATG | CCT | GGT | GTG | AGG | AGC | AGG | TGG | CAT | TGT | GGG | ACC | ACC | CTC | CAT | 1536 |
| Pro | Met | Pro | Gly | Val | Arg | Ser | Arg | Trp | His | Cys | Gly | Thr | Thr | Leu | His | |
| | | | 500 | | | | | 505 | | | | | 510 | | | |
| GGG | GAG | CAG | GGC | CAT | CCT | TGG | GGC | CGC | TTT | GGG | GCG | GCT | CTG | ACA | GTG | 1584 |
| Gly | Glu | Gln | Gly | His | Pro | Trp | Gly | Arg | Phe | Gly | Ala | Ala | Leu | Thr | Val | |
| | | 515 | | | | | 520 | | | | | 525 | | | | |
| CTA | GGG | GAC | GTG | AAT | GGG | GAC | AGT | CTG | GCG | GAT | GTG | GCT | ATT | GGT | GCA | 1632 |
| Leu | Gly | Asp | Val | Asn | Gly | Asp | Ser | Leu | Ala | Asp | Val | Ala | Ile | Gly | Ala | |
| | 530 | | | | | 535 | | | | | 540 | | | | | |
| CCC | GGA | GAG | GAG | GAG | AAC | AGA | GGT | GCT | GTC | TAC | ATA | TTT | CAT | GGA | GCC | 1680 |
| Pro | Gly | Glu | Glu | Glu | Asn | Arg | Gly | Ala | Val | Tyr | Ile | Phe | His | Gly | Ala | |
| 545 | | | | | 550 | | | | | 555 | | | | | 560 | |
| TCG | AGA | CAG | GAC | ATC | GCT | CCC | TCG | CCT | AGC | CAG | CGG | GTC | ACT | GGC | TCC | 1728 |
| Ser | Arg | Gln | Asp | Ile | Ala | Pro | Ser | Pro | Ser | Gln | Arg | Val | Thr | Gly | Ser | |
| | | | | 565 | | | | 570 | | | | | 575 | | | |
| CAG | CTC | TTC | CTG | AGG | CTC | CAA | TAT | TTT | GGG | CAG | TCA | TTA | AGT | GGG | GGT | 1776 |
| Gln | Leu | Phe | Leu | Arg | Leu | Gln | Tyr | Phe | Gly | Gln | Ser | Leu | Ser | Gly | Gly | |
| | | | 580 | | | | | 585 | | | | | 590 | | | |
| CAG | GAC | CTT | ACA | CAG | GAT | GGC | CTG | GTG | GAC | CTG | GCC | GTG | GGA | GCC | CAG | 1824 |
| Gln | Asp | Leu | Thr | Gln | Asp | Gly | Leu | Val | Asp | Leu | Ala | Val | Gly | Ala | Gln | |
| | | 595 | | | | | 600 | | | | | 605 | | | | |
| GGG | CAC | GTG | CTG | CTG | CTT | AGG | AGT | CTG | CCT | TTG | CTG | AAA | GTG | GGG | ATC | 1872 |
| Gly | His | Val | Leu | Leu | Leu | Arg | Ser | Leu | Pro | Leu | Leu | Lys | Val | Gly | Ile | |
| | 610 | | | | | 615 | | | | | 620 | | | | | |
| TCC | ATT | AGA | TTT | GCC | CCC | TCA | GAG | GTG | GCA | AAG | ACT | GTG | TAC | CAG | TGC | 1920 |
| Ser | Ile | Arg | Phe | Ala | Pro | Ser | Glu | Val | Ala | Lys | Thr | Val | Tyr | Gln | Cys | |
| 625 | | | | | 630 | | | | | 635 | | | | | 640 | |
| TGG | GGA | AGG | ACT | CCC | ACT | GTC | CTC | GAA | GCT | GGA | GAG | GCC | ACC | GTC | TGT | 1968 |
| Trp | Gly | Arg | Thr | Pro | Thr | Val | Leu | Glu | Ala | Gly | Glu | Ala | Thr | Val | Cys | |
| | | | | 645 | | | | 650 | | | | | 655 | | | |
| CTC | ACT | GTC | CGC | AAA | GGT | TCA | CCT | GAC | CTG | TTA | GGT | GAT | GTC | CAA | AGC | 2016 |
| Leu | Thr | Val | Arg | Lys | Gly | Ser | Pro | Asp | Leu | Leu | Gly | Asp | Val | Gln | Ser | |
| | | | 660 | | | | | 665 | | | | | 670 | | | |

| | | | | | | | | | | | | | | | | |
|---|---|---|---|---|---|---|---|---|---|---|---|---|---|---|---|---|
| TCT | GTC | AGG | TAT | GAT | CTG | GCG | TTG | GAT | CCG | GGC | CGT | CTG | ATT | TCT | CGT | 2064 |
| Ser | Val | Arg | Tyr | Asp | Leu | Ala | Leu | Asp | Pro | Gly | Arg | Leu | Ile | Ser | Arg | |
| | | 675 | | | 680 | | | | | 685 | | | | | | |
| GCC | ATT | TTT | GAT | GAG | ACG | AAG | AAC | TGC | ACT | TTG | ACC | CGA | AGG | AAG | ACT | 2112 |
| Ala | Ile | Phe | Asp | Glu | Thr | Lys | Asn | Cys | Thr | Leu | Thr | Arg | Arg | Lys | Thr | |
| 690 | | | | | 695 | | | | | 700 | | | | | | |
| CTG | GGG | CTT | GGT | GAT | CAC | TGC | GAA | ACA | ATG | AAG | CTG | CTT | TTG | CCA | GAC | 2160 |
| Leu | Gly | Leu | Gly | Asp | His | Cys | Glu | Thr | Met | Lys | Leu | Leu | Leu | Pro | Asp | |
| 705 | | | | 710 | | | | | 715 | | | | | | 720 | |
| TGT | GTG | GAG | GAT | GCA | GTG | ACC | CCT | ATC | ATC | CTG | CGC | CTT | AAC | TTA | TCC | 2208 |
| Cys | Val | Glu | Asp | Ala | Val | Thr | Pro | Ile | Ile | Leu | Arg | Leu | Asn | Leu | Ser | |
| | | | | 725 | | | | | 730 | | | | | 735 | | |
| CTG | GCA | GGG | GAC | TCT | GCT | CCA | TCC | AGG | AAC | CTT | CGT | CCT | GTG | CTG | GCT | 2256 |
| Leu | Ala | Gly | Asp | Ser | Ala | Pro | Ser | Arg | Asn | Leu | Arg | Pro | Val | Leu | Ala | |
| | | | 740 | | | | | 745 | | | | | 750 | | | |
| GTG | GGC | TCA | CAA | GAC | CAT | GTA | ACA | GCT | TCT | TTC | CCG | TTT | GAG | AAG | AAC | 2304 |
| Val | Gly | Ser | Gln | Asp | His | Val | Thr | Ala | Ser | Phe | Pro | Phe | Glu | Lys | Asn | |
| | | 755 | | | | | 760 | | | | | 765 | | | | |
| TGT | AAG | CAG | GAG | CTC | CTG | TGT | GAG | GGG | AAC | CTG | GGC | GTC | AGC | TTC | AAC | 2352 |
| Cys | Lys | Gln | Glu | Leu | Leu | Cys | Glu | Gly | Asn | Leu | Gly | Val | Ser | Phe | Asn | |
| | 770 | | | | | 775 | | | | | 780 | | | | | |
| TTC | TCA | GGC | CTG | CAG | GTC | TTG | GAG | GTA | GGA | AGC | TCC | CCA | GAG | CTC | ACT | 2400 |
| Phe | Ser | Gly | Leu | Gln | Val | Leu | Glu | Val | Gly | Ser | Ser | Pro | Glu | Leu | Thr | |
| 785 | | | | | 790 | | | | | 795 | | | | | 800 | |
| GTG | ACA | GTA | ACA | GTT | TGG | AAT | GAG | GGT | GAG | GAC | AGC | TAT | GGA | ACC | TTA | 2448 |
| Val | Thr | Val | Thr | Val | Trp | Asn | Glu | Gly | Glu | Asp | Ser | Tyr | Gly | Thr | Leu | |
| | | | | 805 | | | | | 810 | | | | | 815 | | |
| ATC | AAG | TTC | TAC | TAC | CCA | GCA | GAG | CTA | TCT | TAC | CGA | CGG | GTG | ACA | AGA | 2496 |
| Ile | Lys | Phe | Tyr | Tyr | Pro | Ala | Glu | Leu | Ser | Tyr | Arg | Arg | Val | Thr | Arg | |
| | | | 820 | | | | | 825 | | | | | 830 | | | |
| GCC | CAG | CAA | CCT | CAT | CCG | TAC | CCA | CTA | CGC | CTG | GCA | TGT | GAG | GCT | GAG | 2544 |
| Ala | Gln | Gln | Pro | His | Pro | Tyr | Pro | Leu | Arg | Leu | Ala | Cys | Glu | Ala | Glu | |
| | | 835 | | | | | 840 | | | | | 845 | | | | |
| CCC | ACG | GGC | CAG | GAG | AGC | CTG | AGG | AGC | AGC | TGT | AGC | ATC | AAT | CAC | | 2592 |
| Pro | Thr | Gly | Gln | Glu | Ser | Leu | Arg | Ser | Ser | Cys | Ser | Ile | Asn | His | | |
| | 850 | | | | | 855 | | | | | 860 | | | | | |
| CCC | ATC | TTC | CGA | GAA | GGT | GCC | AAG | GCC | ACC | TTC | ATG | ATC | ACA | TTT | GAT | 2640 |
| Pro | Ile | Phe | Arg | Glu | Gly | Ala | Lys | Ala | Thr | Phe | Met | Ile | Thr | Phe | Asp | |
| 865 | | | | | 870 | | | | | 875 | | | | | 880 | |
| GTC | TCC | TAC | AAG | GCC | TTC | CTG | GGA | GAC | AGG | TTG | CTT | CTG | AGG | GCC | AGC | 2688 |
| Val | Ser | Tyr | Lys | Ala | Phe | Leu | Gly | Asp | Arg | Leu | Leu | Leu | Arg | Ala | Ser | |
| | | | | 885 | | | | | 890 | | | | | 895 | | |
| GCA | AGC | AGT | GAG | AAT | AAT | AAG | CCT | GAA | ACC | AGC | AAG | ACT | GCC | TTC | CAG | 2736 |
| Ala | Ser | Ser | Glu | Asn | Asn | Lys | Pro | Glu | Thr | Ser | Lys | Thr | Ala | Phe | Gln | |
| | | | 900 | | | | | 905 | | | | | 910 | | | |
| CTG | GAG | CTT | CCG | GTG | AAG | TAC | ACG | GTC | TAT | ACC | GTG | ATC | AGT | AGG | CAG | 2784 |
| Leu | Glu | Leu | Pro | Val | Lys | Tyr | Thr | Val | Tyr | Thr | Val | Ile | Ser | Arg | Gln | |
| | | 915 | | | | | 920 | | | | | 925 | | | | |
| GAA | GAT | TCT | ACC | AAG | CAT | TTC | AAC | TTC | TCA | TCT | TCC | CAC | GGG | GAG | AGA | 2832 |
| Glu | Asp | Ser | Thr | Lys | His | Phe | Asn | Phe | Ser | Ser | Ser | His | Gly | Glu | Arg | |
| | 930 | | | | | 935 | | | | | 940 | | | | | |
| CAG | AAA | GAG | GCC | GAA | CAT | CGA | TAT | CGT | GTG | AAT | AAC | CTG | AGT | CCA | TTG | 2880 |
| Gln | Lys | Glu | Ala | Glu | His | Arg | Tyr | Arg | Val | Asn | Asn | Leu | Ser | Pro | Leu | |
| 945 | | | | | 950 | | | | | 955 | | | | | 960 | |
| ACG | CTG | GCC | ATC | AGC | GTT | AAC | TTC | TGG | GTC | CCC | ATC | CTT | CTG | AAT | GGT | 2928 |
| Thr | Leu | Ala | Ile | Ser | Val | Asn | Phe | Trp | Val | Pro | Ile | Leu | Leu | Asn | Gly | |
| | | | | 965 | | | | | 970 | | | | | 975 | | |
| GTG | GCC | GTG | TGG | GAT | GTG | ACT | CTG | AGG | AGC | CCA | GCA | CAG | GGT | GTC | TCC | 2976 |
| Val | Ala | Val | Trp | Asp | Val | Thr | Leu | Arg | Ser | Pro | Ala | Gln | Gly | Val | Ser | |
| | | | 980 | | | | | 985 | | | | | 990 | | | |

| | |
|---|---|
| TGT GTG TCA CAG AGG GAA CCT CCT CAA CAT TCC GAC CTT CTG ACC CAG<br>Cys Val Ser Gln Arg Glu Pro Pro Gln His Ser Asp Leu Leu Thr Gln<br>       995                          1000                          1005 | 3024 |
| ATC CAA GGA CGC TCT GTG CTG GAC TGC GCC ATC GCC GAC TGC CTG CAC<br>Ile Gln Gly Arg Ser Val Leu Asp Cys Ala Ile Ala Asp Cys Leu His<br>      1010                         1015                       1020 | 3072 |
| CTC CGC TGT GAC ATC CCC TCC TTG GGC ACC CTG GAT GAG CTT GAC TTC<br>Leu Arg Cys Asp Ile Pro Ser Leu Gly Thr Leu Asp Glu Leu Asp Phe<br>1025                       1030                     1035                   1040 | 3120 |
| ATT CTG AAG GGC AAC CTC AGC TTC GGC TGG ATC AGT CAG ACA TTG CAG<br>Ile Leu Lys Gly Asn Leu Ser Phe Gly Trp Ile Ser Gln Thr Leu Gln<br>                    1045                     1050                    1055 | 3168 |
| AAA AAG GTG TTG CTC CTG AGT GAG GCT GAA ATC ACA TTC AAC ACA TCT<br>Lys Lys Val Leu Leu Leu Ser Glu Ala Glu Ile Thr Phe Asn Thr Ser<br>              1060                     1065                     1070 | 3216 |
| GTG TAT TCC CAG CTG CCG GGA CAG GAG GCA TTT CTG AGA GCC CAG GTG<br>Val Tyr Ser Gln Leu Pro Gly Gln Glu Ala Phe Leu Arg Ala Gln Val<br>          1075                     1080                   1085 | 3264 |
| TCA ACG ATG CTA GAA GAA TAC GTG GTC TAT GAG CCC GTC TTC CTC ATG<br>Ser Thr Met Leu Glu Glu Tyr Val Val Tyr Glu Pro Val Phe Leu Met<br>    1090                     1095                     1100 | 3312 |
| GTG TTC AGC TCA GTG GGA GGT CTG CTG TTA CTG GCT CTC ATC ACT GTG<br>Val Phe Ser Ser Val Gly Gly Leu Leu Leu Leu Ala Leu Ile Thr Val<br>1105                     1110                     1115                   1120 | 3360 |
| GCG CTG TAC AAG CTT GGC TTC TTC AAA CGT CAG TAT AAA GAG ATG CTG<br>Ala Leu Tyr Lys Leu Gly Phe Phe Lys Arg Gln Tyr Lys Glu Met Leu<br>                    1125                     1130                   1135 | 3408 |
| GAT CTA CCA TCT GCA GAT CCT GAC CCA GCC GGC CAG GCA GAT TCC AAC<br>Asp Leu Pro Ser Ala Asp Pro Asp Pro Ala Gly Gln Ala Asp Ser Asn<br>              1140                     1145                     1150 | 3456 |
| CAT GAG ACT CCT CCA CAT CTC ACG TCC TAGGAATCTA CTTTCCTGTA<br>His Glu Thr Pro Pro His Leu Thr Ser<br>         1155                     1160 | 3503 |
| TATCTCCACA ATTACGAGAT TGGTTTTGCT TTTGCCTATG AATCTACTGG CATGGGAACA | 3563 |
| AGTTCTCTTC AGCTCTGGGC TAGCCTGGGA AACTTCCCAG AAATGATGCC CTACCTCCTG | 3623 |
| AGCTGGGAGA TTTTTATGGT TTGCCCATGT GTCAGATTTC AGTGCTGATC CACTTTTTTT | 3683 |
| GCAAGAGCAG GAATGGGGTC AGCATAAATT TACATATGGA TAAGAACTAA CACAAGACTG | 3743 |
| AGTAATATGC TCAATATTCA ATGTATTGCT TGTATAAATT TTTAAAAAAT AAAATGAAAN | 3803 |

( 2 ) INFORMATION FOR SEQ ID NO:53:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
Met Val Arg Gly Val Val Ile Leu Leu Cys Gly Trp Ala Leu Ala Ser
 1               5                  10                  15

Cys His Gly Ser Asn Leu Asp Val Glu Lys Pro Val Val Phe Lys Glu
                20                  25                  30

Asp Ala Ala Ser Phe Gly Gln Thr Val Val Gln Phe Gly Gly Ser Arg
            35                  40                  45

Leu Val Val Gly Ala Pro Leu Glu Ala Val Ala Val Asn Gln Thr Gly
        50                  55                  60

Gln Ser Ser Asp Cys Pro Pro Ala Thr Gly Val Cys Gln Pro Ile Leu
65                  70                  75                  80
```

| | | | | | | | | | | | | | | |
|---|---|---|---|---|---|---|---|---|---|---|---|---|---|---|
| Leu | His | Ile | Pro | Leu | Glu | Ala | Val | Asn | Met | Ser | Leu | Gly | Leu | Ser | Leu |
| | | | | 85 | | | | | 90 | | | | | 95 | |
| Val | Ala | Asp | Thr | Asn | Asn | Ser | Gln | Leu | Leu | Ala | Cys | Gly | Pro | Thr | Ala |
| | | | | 100 | | | | | 105 | | | | | 110 | |
| Gln | Arg | Ala | Cys | Ala | Lys | Asn | Met | Tyr | Ala | Lys | Gly | Ser | Cys | Leu | Leu |
| | | | | 115 | | | | | 120 | | | | | 125 | |
| Leu | Gly | Ser | Ser | Leu | Gln | Phe | Ile | Gln | Ala | Ile | Pro | Ala | Thr | Met | Pro |
| | | | | 130 | | | | | 135 | | | | | 140 | |
| Glu | Cys | Pro | Gly | Gln | Glu | Met | Asp | Ile | Ala | Phe | Leu | Ile | Asp | Gly | Ser |
| 145 | | | | | 150 | | | | | 155 | | | | | 160 |
| Gly | Ser | Ile | Asp | Gln | Ser | Asp | Phe | Thr | Gln | Met | Lys | Asp | Phe | Val | Lys |
| | | | | 165 | | | | | 170 | | | | | 175 | |
| Ala | Leu | Met | Gly | Gln | Leu | Ala | Ser | Thr | Ser | Thr | Ser | Phe | Ser | Leu | Met |
| | | | | 180 | | | | | 185 | | | | | 190 | |
| Gln | Tyr | Ser | Asn | Ile | Leu | Lys | Thr | His | Phe | Thr | Phe | Thr | Glu | Phe | Lys |
| | | | | 195 | | | | | 200 | | | | | 205 | |
| Ser | Ser | Leu | Ser | Pro | Gln | Ser | Leu | Val | Asp | Ala | Ile | Val | Gln | Leu | Gln |
| | 210 | | | | | 215 | | | | | 220 | | | | |
| Gly | Leu | Thr | Tyr | Thr | Ala | Ser | Gly | Ile | Gln | Lys | Val | Val | Lys | Glu | Leu |
| 225 | | | | | 230 | | | | | 235 | | | | | 240 |
| Phe | His | Ser | Lys | Asn | Gly | Ala | Arg | Lys | Ser | Ala | Lys | Lys | Ile | Leu | Ile |
| | | | | 245 | | | | | 250 | | | | | 255 | |
| Val | Ile | Thr | Asp | Gly | Gln | Lys | Phe | Arg | Asp | Pro | Leu | Glu | Tyr | Arg | His |
| | | | | 260 | | | | | 265 | | | | | 270 | |
| Val | Ile | Pro | Glu | Ala | Glu | Lys | Ala | Gly | Ile | Ile | Arg | Tyr | Ala | Ile | Gly |
| | | | | 275 | | | | | 280 | | | | | 285 | |
| Val | Gly | Asp | Ala | Phe | Arg | Glu | Pro | Thr | Ala | Leu | Gln | Glu | Leu | Asn | Thr |
| | | | | 290 | | | | | 295 | | | | | 300 | |
| Ile | Gly | Ser | Ala | Pro | Ser | Gln | Asp | His | Val | Phe | Lys | Val | Gly | Asn | Phe |
| 305 | | | | | 310 | | | | | 315 | | | | | 320 |
| Val | Ala | Leu | Arg | Ser | Ile | Gln | Arg | Gln | Ile | Gln | Glu | Lys | Ile | Phe | Ala |
| | | | | 325 | | | | | 330 | | | | | 335 | |
| Ile | Glu | Gly | Thr | Glu | Ser | Arg | Ser | Ser | Ser | Phe | Gln | His | Glu | Met | |
| | | | | 340 | | | | | 345 | | | | | 350 | |
| Ser | Gln | Glu | Gly | Phe | Ser | Ser | Ala | Leu | Ser | Met | Asp | Gly | Pro | Val | Leu |
| | | | | 355 | | | | | 360 | | | | | 365 | |
| Gly | Ala | Val | Gly | Gly | Phe | Ser | Trp | Ser | Gly | Gly | Ala | Phe | Leu | Tyr | Pro |
| | | | | 370 | | | | | 375 | | | | | 380 | |
| Ser | Asn | Met | Arg | Ser | Thr | Phe | Ile | Asn | Met | Ser | Gln | Glu | Asn | Glu | Asp |
| 385 | | | | | 390 | | | | | 395 | | | | | 400 |
| Met | Arg | Asp | Ala | Tyr | Leu | Gly | Tyr | Ser | Thr | Ala | Leu | Ala | Phe | Trp | Lys |
| | | | | 405 | | | | | 410 | | | | | 415 | |
| Gly | Val | His | Ser | Leu | Ile | Leu | Gly | Ala | Pro | Arg | His | Gln | His | Thr | Gly |
| | | | | 420 | | | | | 425 | | | | | 430 | |
| Lys | Val | Val | Ile | Phe | Thr | Gln | Glu | Ser | Arg | His | Trp | Arg | Pro | Lys | Ser |
| | | | | 435 | | | | | 440 | | | | | 445 | |
| Glu | Val | Arg | Gly | Thr | Gln | Ile | Gly | Ser | Tyr | Phe | Gly | Ala | Ser | Leu | Cys |
| | | | | 450 | | | | | 455 | | | | | 460 | |
| Ser | Val | Asp | Met | Asp | Arg | Asp | Gly | Ser | Thr | Asp | Leu | Val | Leu | Ile | Gly |
| 465 | | | | | 470 | | | | | 475 | | | | | 480 |
| Val | Pro | His | Tyr | Tyr | Glu | His | Thr | Arg | Gly | Gly | Gln | Val | Ser | Val | Cys |
| | | | | 485 | | | | | 490 | | | | | 495 | |
| Pro | Met | Pro | Gly | Val | Arg | Ser | Arg | Trp | His | Cys | Gly | Thr | Thr | Leu | His |

-continued

|     |     |     | 500 |     |     |     | 505 |     |     |     | 510 |     |     |     |
|---|---|---|---|---|---|---|---|---|---|---|---|---|---|---|

Gly Glu Gln Gly His Pro Trp Arg Phe Gly Ala Ala Leu Thr Val
            515                 520                 525

Leu Gly Asp Val Asn Gly Asp Ser Leu Ala Asp Val Ala Ile Gly Ala
    530                 535                 540

Pro Gly Glu Glu Glu Asn Arg Gly Ala Val Tyr Ile Phe His Gly Ala
545                 550                 555                 560

Ser Arg Gln Asp Ile Ala Pro Ser Pro Ser Gln Arg Val Thr Gly Ser
                565                 570                 575

Gln Leu Phe Leu Arg Leu Gln Tyr Phe Gly Gln Ser Leu Ser Gly Gly
            580                 585                 590

Gln Asp Leu Thr Gln Asp Gly Leu Val Asp Leu Ala Val Gly Ala Gln
            595                 600                 605

Gly His Val Leu Leu Leu Arg Ser Leu Pro Leu Leu Lys Val Gly Ile
    610                 615                 620

Ser Ile Arg Phe Ala Pro Ser Glu Val Ala Lys Thr Val Tyr Gln Cys
625                 630                 635                 640

Trp Gly Arg Thr Pro Thr Val Leu Glu Ala Gly Glu Ala Thr Val Cys
                645                 650                 655

Leu Thr Val Arg Lys Gly Ser Pro Asp Leu Leu Gly Asp Val Gln Ser
            660                 665                 670

Ser Val Arg Tyr Asp Leu Ala Leu Asp Pro Gly Arg Leu Ile Ser Arg
            675                 680                 685

Ala Ile Phe Asp Glu Thr Lys Asn Cys Thr Leu Thr Arg Arg Lys Thr
    690                 695                 700

Leu Gly Leu Gly Asp His Cys Glu Thr Met Lys Leu Leu Leu Pro Asp
705                 710                 715                 720

Cys Val Glu Asp Ala Val Thr Pro Ile Ile Leu Arg Leu Asn Leu Ser
                725                 730                 735

Leu Ala Gly Asp Ser Ala Pro Ser Arg Asn Leu Arg Pro Val Leu Ala
            740                 745                 750

Val Gly Ser Gln Asp His Val Thr Ala Ser Phe Pro Phe Glu Lys Asn
        755                 760                 765

Cys Lys Gln Glu Leu Leu Cys Glu Gly Asn Leu Gly Val Ser Phe Asn
770                 775                 780

Phe Ser Gly Leu Gln Val Leu Glu Val Gly Ser Ser Pro Glu Leu Thr
785                 790                 795                 800

Val Thr Val Thr Val Trp Asn Glu Gly Glu Asp Ser Tyr Gly Thr Leu
                805                 810                 815

Ile Lys Phe Tyr Tyr Pro Ala Glu Leu Ser Tyr Arg Arg Val Thr Arg
                820                 825                 830

Ala Gln Gln Pro His Pro Tyr Pro Leu Arg Leu Ala Cys Glu Ala Glu
            835                 840                 845

Pro Thr Gly Gln Glu Ser Leu Arg Ser Ser Ser Cys Ser Ile Asn His
    850                 855                 860

Pro Ile Phe Arg Glu Gly Ala Lys Ala Thr Phe Met Ile Thr Phe Asp
865                 870                 875                 880

Val Ser Tyr Lys Ala Phe Leu Gly Asp Arg Leu Leu Leu Arg Ala Ser
                885                 890                 895

Ala Ser Ser Glu Asn Asn Lys Pro Glu Thr Ser Lys Thr Ala Phe Gln
            900                 905                 910

Leu Glu Leu Pro Val Lys Tyr Thr Val Tyr Thr Val Ile Ser Arg Gln
            915                 920                 925

```
Glu  Asp  Ser  Thr  Lys  His  Phe  Asn  Phe  Ser  Ser  Ser  His  Gly  Glu  Arg
     930                      935                      940
Gln  Lys  Glu  Ala  Glu  His  Arg  Tyr  Arg  Val  Asn  Asn  Leu  Ser  Pro  Leu
945                           950                      955                      960
Thr  Leu  Ala  Ile  Ser  Val  Asn  Phe  Trp  Pro  Ile  Leu  Leu  Asn  Gly
               965                      970                           975
Val  Ala  Val  Trp  Asp  Val  Thr  Leu  Arg  Ser  Pro  Ala  Gln  Gly  Val  Ser
               980                      985                      990
Cys  Val  Ser  Gln  Arg  Glu  Pro  Pro  Gln  His  Ser  Asp  Leu  Leu  Thr  Gln
          995                      1000                     1005
Ile  Gln  Gly  Arg  Ser  Val  Leu  Asp  Cys  Ala  Ile  Ala  Asp  Cys  Leu  His
          1010                     1015                     1020
Leu  Arg  Cys  Asp  Ile  Pro  Ser  Leu  Gly  Thr  Leu  Asp  Glu  Leu  Asp  Phe
1025                     1030                     1035                     1040
Ile  Leu  Lys  Gly  Asn  Leu  Ser  Phe  Gly  Trp  Ile  Ser  Gln  Thr  Leu  Gln
                    1045                     1050                     1055
Lys  Lys  Val  Leu  Leu  Leu  Ser  Glu  Ala  Glu  Ile  Thr  Phe  Asn  Thr  Ser
                    1060                     1065                     1070
Val  Tyr  Ser  Gln  Leu  Pro  Gly  Gln  Glu  Ala  Phe  Leu  Arg  Ala  Gln  Val
          1075                     1080                     1085
Ser  Thr  Met  Leu  Glu  Glu  Tyr  Val  Val  Tyr  Glu  Pro  Val  Phe  Leu  Met
     1090                     1095                     1100
Val  Phe  Ser  Ser  Val  Gly  Gly  Leu  Leu  Leu  Leu  Ala  Leu  Ile  Thr  Val
1105                     1110                     1115                     1120
Ala  Leu  Tyr  Lys  Leu  Gly  Phe  Phe  Lys  Arg  Gln  Tyr  Lys  Glu  Met  Leu
                    1125                     1130                     1135
Asp  Leu  Pro  Ser  Ala  Asp  Pro  Asp  Pro  Ala  Gly  Gln  Ala  Asp  Ser  Asn
                    1140                     1145                     1150
His  Glu  Thr  Pro  Pro  His  Leu  Thr  Ser
                    1155                     1160
```

(2) INFORMATION FOR SEQ ID NO:54:

(i) SEQUENCE CHARACTERISTICS:
        (A) LENGTH: 3597 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 40..3525

(xi) SEQUENCE DESCRIPTION: SEQ ID NO:54:

```
AGCTTTACAG  CTCTCTACTT  CTCAGTGCAC  TGCTCAGTG  ATG  GCC  GGT  GGA  GTT        54
                                               Met  Ala  Gly  Gly  Val
                                                1                    5

GTG  ATC  CTC  CTG  TGT  GGC  TGG  GTC  CTG  GCT  TCC  TGT  CAT  GGG  TCT  AAC    102
Val  Ile  Leu  Leu  Cys  Gly  Trp  Val  Leu  Ala  Ser  Cys  His  Gly  Ser  Asn
               10                       15                       20

CTG  GAT  GTG  GAG  GAA  CCC  ATC  GTG  TTC  AGA  GAG  GAT  GCA  GCC  AGC  TTT    150
Leu  Asp  Val  Glu  Glu  Pro  Ile  Val  Phe  Arg  Glu  Asp  Ala  Ala  Ser  Phe
               25                       30                       35

GGA  CAG  ACT  GTG  GTG  CAG  TTT  GGT  GGA  TCT  CGA  CTC  GTG  GTG  GGA  GCC    198
Gly  Gln  Thr  Val  Val  Gln  Phe  Gly  Gly  Ser  Arg  Leu  Val  Val  Gly  Ala
          40                       45                       50

CCT  CTG  GAG  GCG  GTG  GCA  GTC  AAC  CAA  ACA  GGA  CGG  TTG  TAT  GAC  TGT    246
Pro  Leu  Glu  Ala  Val  Ala  Val  Asn  Gln  Thr  Gly  Arg  Leu  Tyr  Asp  Cys
```

-continued

```
                 55                            60                            65
GCA  CCT  GCC  ACT  GGC  ATG  TGC  CAG  CCC  ATC  GTA  CTG  CGC  AGT  CCC  CTA        294
Ala  Pro  Ala  Thr  Gly  Met  Cys  Gln  Pro  Ile  Val  Leu  Arg  Ser  Pro  Leu
70                       75                       80                         85

GAG  GCA  GTG  AAC  ATG  TCC  CTG  GGC  CTG  TCT  CTG  GTG  ACT  GCC  ACC  AAT        342
Glu  Ala  Val  Asn  Met  Ser  Leu  Gly  Leu  Ser  Leu  Val  Thr  Ala  Thr  Asn
                         90                       95                        100

AAC  GCC  CAG  TTG  CTG  GCT  TGT  GGT  CCA  ACT  GCA  CAG  AGA  GCT  TGT  GTG        390
Asn  Ala  Gln  Leu  Leu  Ala  Cys  Gly  Pro  Thr  Ala  Gln  Arg  Ala  Cys  Val
               105                      110                      115

AAG  AAC  ATG  TAT  GCG  AAA  GGT  TCC  TGC  CTC  CTT  CTC  GGC  TCC  AGC  TTG        438
Lys  Asn  Met  Tyr  Ala  Lys  Gly  Ser  Cys  Leu  Leu  Leu  Gly  Ser  Ser  Leu
               120                      125                      130

CAG  TTC  ATC  CAG  GCA  GTC  CCT  GCC  TCC  ATG  CCA  GAG  TGT  CCA  AGA  CAA        486
Gln  Phe  Ile  Gln  Ala  Val  Pro  Ala  Ser  Met  Pro  Glu  Cys  Pro  Arg  Gln
     135                      140                      145

GAG  ATG  GAC  ATT  GCT  TTC  CTG  ATT  GAT  GGT  TCT  GGC  AGC  ATT  AAC  CAA        534
Glu  Met  Asp  Ile  Ala  Phe  Leu  Ile  Asp  Gly  Ser  Gly  Ser  Ile  Asn  Gln
150                      155                      160                      165

AGG  GAC  TTT  GCC  CAG  ATG  AAG  GAC  TTT  GTC  AAA  GCT  TTG  ATG  GGA  GAG        582
Arg  Asp  Phe  Ala  Gln  Met  Lys  Asp  Phe  Val  Lys  Ala  Leu  Met  Gly  Glu
                         170                      175                      180

TTT  GCG  AGC  ACC  AGC  ACC  TTG  TTC  TCC  CTG  ATG  CAA  TAC  TCG  AAC  ATC        630
Phe  Ala  Ser  Thr  Ser  Thr  Leu  Phe  Ser  Leu  Met  Gln  Tyr  Ser  Asn  Ile
               185                      190                      195

CTG  AAG  ACC  CAT  TTT  ACC  TTC  ACT  GAA  TTC  AAG  AAC  ATC  CTG  GAC  CCT        678
Leu  Lys  Thr  His  Phe  Thr  Phe  Thr  Glu  Phe  Lys  Asn  Ile  Leu  Asp  Pro
               200                      205                      210

CAG  AGC  CTG  GTG  GAT  CCC  ATT  GTC  CAG  CTG  CAA  GGC  CTG  ACC  TAC  ACA        726
Gln  Ser  Leu  Val  Asp  Pro  Ile  Val  Gln  Leu  Gln  Gly  Leu  Thr  Tyr  Thr
     215                      220                      225

GCC  ACA  GGC  ATC  CGG  ACA  GTG  ATG  GAA  GAG  CTA  TTT  CAT  AGC  AAG  AAT        774
Ala  Thr  Gly  Ile  Arg  Thr  Val  Met  Glu  Glu  Leu  Phe  His  Ser  Lys  Asn
230                      235                      240                      245

GGG  TCC  CGT  AAA  AGT  GCC  AAG  AAG  ATC  CTC  CTT  GTC  ATC  ACA  GAT  GGG        822
Gly  Ser  Arg  Lys  Ser  Ala  Lys  Lys  Ile  Leu  Leu  Val  Ile  Thr  Asp  Gly
                         250                      255                      260

CAG  AAA  TAC  AGA  GAC  CCC  CTG  GAG  TAT  AGT  GAT  GTC  ATT  CCC  GCC  GCA        870
Gln  Lys  Tyr  Arg  Asp  Pro  Leu  Glu  Tyr  Ser  Asp  Val  Ile  Pro  Ala  Ala
               265                      270                      275

GAC  AAA  GCT  GGC  ATC  ATT  CGT  TAT  GCT  ATT  GGG  GTG  GGA  GAT  GCC  TTC        918
Asp  Lys  Ala  Gly  Ile  Ile  Arg  Tyr  Ala  Ile  Gly  Val  Gly  Asp  Ala  Phe
               280                      285                      290

CAG  GAG  CCC  ACT  GCC  CTG  AAG  GAG  CTG  AAC  ACC  ATT  GGC  TCA  GCT  CCC        966
Gln  Glu  Pro  Thr  Ala  Leu  Lys  Glu  Leu  Asn  Thr  Ile  Gly  Ser  Ala  Pro
     295                      300                      305

CCA  CAG  GAC  CAC  GTG  TTC  AAG  GTA  GGC  AAC  TTT  GCA  GCA  CTT  CGC  AGC       1014
Pro  Gln  Asp  His  Val  Phe  Lys  Val  Gly  Asn  Phe  Ala  Ala  Leu  Arg  Ser
310                      315                      320                      325

ATC  CAG  AGG  CAA  CTT  CAG  GAG  AAA  ATC  TTC  GCC  ATT  GAG  GGA  ACT  CAA       1062
Ile  Gln  Arg  Gln  Leu  Gln  Glu  Lys  Ile  Phe  Ala  Ile  Glu  Gly  Thr  Gln
                         330                      335                      340

TCA  AGG  TCA  AGT  AGT  TCC  TTT  CAG  CAC  GAG  ATG  TCA  CAA  GAA  GGT  TTC       1110
Ser  Arg  Ser  Ser  Ser  Ser  Phe  Gln  His  Glu  Met  Ser  Gln  Glu  Gly  Phe
               345                      350                      355

AGT  TCA  GCT  CTC  ACA  TCG  GAT  GGA  CCC  GTT  CTG  GGG  GCC  GTG  GGA  AGC       1158
Ser  Ser  Ala  Leu  Thr  Ser  Asp  Gly  Pro  Val  Leu  Gly  Ala  Val  Gly  Ser
               360                      365                      370

TTC  AGC  TGG  TCC  GGA  GGT  GCC  TTC  TTA  TAT  CCC  CCA  AAT  ACG  AGA  CCC       1206
Phe  Ser  Trp  Ser  Gly  Gly  Ala  Phe  Leu  Tyr  Pro  Pro  Asn  Thr  Arg  Pro
```

```
                    375                         380                          385
ACC  TTT  ATC  AAC  ATG  TCT  CAG  GAG  AAT  GTG  GAC  ATG  AGA  GAC  TCC  TAC    1254
Thr  Phe  Ile  Asn  Met  Ser  Gln  Glu  Asn  Val  Asp  Met  Arg  Asp  Ser  Tyr
390            395                      400                           405

CTG  GGT  TAC  TCC  ACC  GCA  GTG  GCC  TTT  TGG  AAG  GGG  GTT  CAC  AGC  CTG    1302
Leu  Gly  Tyr  Ser  Thr  Ala  Val  Ala  Phe  Trp  Lys  Gly  Val  His  Ser  Leu
                    410                      415                           420

ATC  CTG  GGG  GCC  CCG  CGT  CAC  CAG  CAC  ACG  GGG  AAG  GTT  GTC  ATC  TTT    1350
Ile  Leu  Gly  Ala  Pro  Arg  His  Gln  His  Thr  Gly  Lys  Val  Val  Ile  Phe
               425                      430                      435

ACC  CAG  GAA  GCC  AGG  CAT  TGG  AGG  CCC  AAG  TCT  GAA  GTC  AGA  GGG  ACA    1398
Thr  Gln  Glu  Ala  Arg  His  Trp  Arg  Pro  Lys  Ser  Glu  Val  Arg  Gly  Thr
          440                      445                      450

CAG  ATC  GGC  TCC  TAC  TTC  GGG  GCC  TCT  CTC  TGT  TCT  GTG  GAC  GTG  GAT    1446
Gln  Ile  Gly  Ser  Tyr  Phe  Gly  Ala  Ser  Leu  Cys  Ser  Val  Asp  Val  Asp
     455                      460                      465

AGA  GAT  GGC  AGC  ACY  GAC  CTG  GTC  CTG  ATC  GGA  GCC  CCC  CAT  TAC  TAT    1494
Arg  Asp  Gly  Ser  Xaa  Asp  Leu  Val  Leu  Ile  Gly  Ala  Pro  His  Tyr  Tyr
470                 475                      480                           485

GAG  CAG  ACC  CGA  GGG  GGG  CAG  GTC  TCA  GTG  TTC  CCC  GTG  CCC  GGT  GTG    1542
Glu  Gln  Thr  Arg  Gly  Gly  Gln  Val  Ser  Val  Phe  Pro  Val  Pro  Gly  Val
                    490                      495                      500

AGG  GGC  AGG  TGG  CAG  TGT  GAG  GCC  ACC  CTC  CAC  GGG  GAG  CAG  GGC  CAT    1590
Arg  Gly  Arg  Trp  Gln  Cys  Glu  Ala  Thr  Leu  His  Gly  Glu  Gln  Gly  His
               505                      510                      515

CCT  TGG  GGC  CGC  TTT  GGG  GTG  GCT  CTG  ACA  GTG  CTG  GGG  GAC  GTA  AAC    1638
Pro  Trp  Gly  Arg  Phe  Gly  Val  Ala  Leu  Thr  Val  Leu  Gly  Asp  Val  Asn
          520                      525                      530

GGG  GAC  AAT  CTG  GCA  GAC  GTG  GCT  ATT  GGT  GCC  CCT  GGA  GAG  GAG  GAG    1686
Gly  Asp  Asn  Leu  Ala  Asp  Val  Ala  Ile  Gly  Ala  Pro  Gly  Glu  Glu  Glu
     535                      540                      545

AGC  AGA  GGT  GCT  GTC  TAC  ATA  TTT  CAT  GGA  GCC  TCG  AGA  CTG  GAG  ATC    1734
Ser  Arg  Gly  Ala  Val  Tyr  Ile  Phe  His  Gly  Ala  Ser  Arg  Leu  Glu  Ile
550                 555                      560                           565

ATG  CCC  TCA  CCC  AGC  CAG  CGG  GTC  ACT  GGC  TCC  CAG  CTC  TCC  CTG  AGA    1782
Met  Pro  Ser  Pro  Ser  Gln  Arg  Val  Thr  Gly  Ser  Gln  Leu  Ser  Leu  Arg
                    570                      575                      580

CTG  CAG  TAT  TTT  GGG  CAG  TCA  TTG  AGT  GGG  GGT  CAG  GAC  CTT  ACA  CAG    1830
Leu  Gln  Tyr  Phe  Gly  Gln  Ser  Leu  Ser  Gly  Gly  Gln  Asp  Leu  Thr  Gln
               585                      590                      595

GAT  GGC  CTG  GTG  GAC  CTG  GCC  GTG  GGA  GCC  CAG  GGG  CAC  GTA  CTG  CTG    1878
Asp  Gly  Leu  Val  Asp  Leu  Ala  Val  Gly  Ala  Gln  Gly  His  Val  Leu  Leu
          600                      605                      610

CTC  AGG  AGT  CTG  CCT  CTG  CTG  AAA  GTG  GAG  CTC  TCC  ATA  AGA  TTC  GCC    1926
Leu  Arg  Ser  Leu  Pro  Leu  Leu  Lys  Val  Glu  Leu  Ser  Ile  Arg  Phe  Ala
     615                      620                      625

CCC  ATG  GAG  GTG  GCA  AAG  GCT  GTG  TAC  CAG  TGC  TGG  GAA  AGG  ACT  CCC    1974
Pro  Met  Glu  Val  Ala  Lys  Ala  Val  Tyr  Gln  Cys  Trp  Glu  Arg  Thr  Pro
630                 635                      640                           645

ACT  GTC  CTC  GAA  GCT  GGA  GAG  GCC  ACT  GTC  TGT  CTC  ACT  GTC  CAC  AAA    2022
Thr  Val  Leu  Glu  Ala  Gly  Glu  Ala  Thr  Val  Cys  Leu  Thr  Val  His  Lys
                    650                      655                      660

GGC  TCA  CCT  GAC  CTG  TTA  GGT  AAT  GTC  CAA  GGC  TCT  GTC  AGG  TAT  GAT    2070
Gly  Ser  Pro  Asp  Leu  Leu  Gly  Asn  Val  Gln  Gly  Ser  Val  Arg  Tyr  Asp
               665                      670                      675

CTG  GCG  TTA  GAT  CCG  GGC  CGC  CTG  ATT  TCT  CGT  GCC  ATT  TTT  GAT  GAG    2118
Leu  Ala  Leu  Asp  Pro  Gly  Arg  Leu  Ile  Ser  Arg  Ala  Ile  Phe  Asp  Glu
          680                      685                      690

ACT  AAG  AAC  TGC  ACT  TTG  ACG  GGA  AGG  AAG  ACT  CTG  GGG  CTT  GGT  GAT    2166
Thr  Lys  Asn  Cys  Thr  Leu  Thr  Gly  Arg  Lys  Thr  Leu  Gly  Leu  Gly  Asp
```

|  |  |  |  |  |  |  |  |  |  |  |  |  |  |  |  |  |
|---|---|---|---|---|---|---|---|---|---|---|---|---|---|---|---|---|
| | 695 | | | | | 700 | | | | | | 705 | | | | |
| CAC | TGC | GAA | ACA | GTG | AAG | CTG | CTT | TTG | CCG | GAC | TGT | GTG | GAA | GAT | GCA | 2214 |
| His | Cys | Glu | Thr | Val | Lys | Leu | Leu | Leu | Pro | Asp | Cys | Val | Glu | Asp | Ala | |
| 710 | | | | 715 | | | | | 720 | | | | | | 725 | |
| GTG | AGC | CCT | ATC | ATC | CTG | CGC | CTC | AAC | TTT | TCC | CTG | GTG | AGA | GAC | TCT | 2262 |
| Val | Ser | Pro | Ile | Ile | Leu | Arg | Leu | Asn | Phe | Ser | Leu | Val | Arg | Asp | Ser | |
| | | | | 730 | | | | | 735 | | | | | 740 | | |
| GCT | TCA | CCC | AGG | AAC | CTG | CAT | CCT | GTG | CTG | GCT | GTG | GGC | TCA | CAA | GAC | 2310 |
| Ala | Ser | Pro | Arg | Asn | Leu | His | Pro | Val | Leu | Ala | Val | Gly | Ser | Gln | Asp | |
| | | | 745 | | | | | 750 | | | | | 755 | | | |
| CAC | ATA | ACT | GCT | TCT | CTG | CCG | TTT | GAG | AAG | AAC | TGT | AAG | CAA | GAA | CTC | 2358 |
| His | Ile | Thr | Ala | Ser | Leu | Pro | Phe | Glu | Lys | Asn | Cys | Lys | Gln | Glu | Leu | |
| | | 760 | | | | | 765 | | | | | 770 | | | | |
| CTG | TGT | GAG | GGG | GAC | CTG | GGC | ATC | AGC | TTT | AAC | TTC | TCA | GGC | CTG | CAG | 2406 |
| Leu | Cys | Glu | Gly | Asp | Leu | Gly | Ile | Ser | Phe | Asn | Phe | Ser | Gly | Leu | Gln | |
| | 775 | | | | | 780 | | | | | 785 | | | | | |
| GTC | TTG | GTG | GTG | GGA | GGC | TCC | CCA | GAG | CTC | ACT | GTG | ACA | GTC | ACT | GTG | 2454 |
| Val | Leu | Val | Val | Gly | Gly | Ser | Pro | Glu | Leu | Thr | Val | Thr | Val | Thr | Val | |
| 790 | | | | | 795 | | | | | 800 | | | | | 805 | |
| TGG | AAT | GAG | GGT | GAG | GAC | AGC | TAT | GGA | ACT | TTA | GTC | AAG | TTC | TAC | TAC | 2502 |
| Trp | Asn | Glu | Gly | Glu | Asp | Ser | Tyr | Gly | Thr | Leu | Val | Lys | Phe | Tyr | Tyr | |
| | | | | 810 | | | | | 815 | | | | | 820 | | |
| CCA | GCA | GGG | CTA | TCT | TAC | CGA | CGG | GTA | ACA | GGG | ACT | CAG | CAA | CCT | CAT | 2550 |
| Pro | Ala | Gly | Leu | Ser | Tyr | Arg | Arg | Val | Thr | Gly | Thr | Gln | Gln | Pro | His | |
| | | | 825 | | | | | 830 | | | | | 835 | | | |
| CAG | TAC | CCA | CTA | CGC | TTG | GCC | TGT | GAG | GCT | GAG | CCC | GCT | GCC | CAG | GAG | 2598 |
| Gln | Tyr | Pro | Leu | Arg | Leu | Ala | Cys | Glu | Ala | Glu | Pro | Ala | Ala | Gln | Glu | |
| | | 840 | | | | | 845 | | | | | 850 | | | | |
| GAC | CTG | AGG | AGC | AGC | AGC | TGT | AGC | ATT | AAT | CAC | CCC | ATC | TTC | CGA | GAA | 2646 |
| Asp | Leu | Arg | Ser | Ser | Ser | Cys | Ser | Ile | Asn | His | Pro | Ile | Phe | Arg | Glu | |
| | 855 | | | | | 860 | | | | | 865 | | | | | |
| GGT | GCA | AAG | ACC | ACC | TTC | ATG | ATC | ACA | TTC | GAT | GTC | TCC | TAC | AAG | GCC | 2694 |
| Gly | Ala | Lys | Thr | Thr | Phe | Met | Ile | Thr | Phe | Asp | Val | Ser | Tyr | Lys | Ala | |
| 870 | | | | | 875 | | | | | 880 | | | | | 885 | |
| TTC | CTA | GGA | GAC | AGG | TTG | CTT | CTG | AGG | GCC | AAA | GCC | AGC | AGT | GAG | AAT | 2742 |
| Phe | Leu | Gly | Asp | Arg | Leu | Leu | Leu | Arg | Ala | Lys | Ala | Ser | Ser | Glu | Asn | |
| | | | | 890 | | | | | 895 | | | | | 900 | | |
| AAT | AAG | CCT | GAT | ACC | AAC | AAG | ACT | GCC | TTC | CAG | CTG | GAG | CTC | CCA | GTG | 2790 |
| Asn | Lys | Pro | Asp | Thr | Asn | Lys | Thr | Ala | Phe | Gln | Leu | Glu | Leu | Pro | Val | |
| | | | 905 | | | | | 910 | | | | | 915 | | | |
| AAG | TAC | ACC | GTC | TAT | ACC | CTG | ATC | AGT | AGG | CAA | GAA | GAT | TCC | ACC | AAC | 2838 |
| Lys | Tyr | Thr | Val | Tyr | Thr | Leu | Ile | Ser | Arg | Gln | Glu | Asp | Ser | Thr | Asn | |
| | | 920 | | | | | 925 | | | | | 930 | | | | |
| CAT | GTC | AAC | TTT | TCA | TCT | TCC | CAC | GGG | GGG | AGA | AGG | CAA | GAA | GCC | GCA | 2886 |
| His | Val | Asn | Phe | Ser | Ser | Ser | His | Gly | Gly | Arg | Arg | Gln | Glu | Ala | Ala | |
| | 935 | | | | | 940 | | | | | 945 | | | | | |
| CAT | CGC | TAT | CGT | GTG | AAT | AAC | CTG | AGT | CCA | CTG | AAG | CTG | GCC | GTC | AGA | 2934 |
| His | Arg | Tyr | Arg | Val | Asn | Asn | Leu | Ser | Pro | Leu | Lys | Leu | Ala | Val | Arg | |
| 950 | | | | | 955 | | | | | 960 | | | | | 965 | |
| GTT | AAC | TTC | TGG | GTC | CCT | GTC | CTT | CTG | AAC | GGT | GTG | GCT | GTG | TGG | GAC | 2982 |
| Val | Asn | Phe | Trp | Val | Pro | Val | Leu | Leu | Asn | Gly | Val | Ala | Val | Trp | Asp | |
| | | | | 970 | | | | | 975 | | | | | 980 | | |
| GTG | ACT | CTG | AGC | AGC | CCA | GCA | CAG | GGT | GTC | TCC | TGC | GTG | TCC | CAG | ATG | 3030 |
| Val | Thr | Leu | Ser | Ser | Pro | Ala | Gln | Gly | Val | Ser | Cys | Val | Ser | Gln | Met | |
| | | | 985 | | | | | 990 | | | | | 995 | | | |
| AAA | CCT | CCT | CAG | AAT | CCC | GAC | TTT | CTG | ACC | CAG | ATT | CAG | AGA | CGT | TCT | 3078 |
| Lys | Pro | Pro | Gln | Asn | Pro | Asp | Phe | Leu | Thr | Gln | Ile | Gln | Arg | Arg | Ser | |
| | | | 1000 | | | | | 1005 | | | | | 1010 | | | |
| GTG | CTG | GAC | TGC | TCC | ATT | GCT | GAC | TGC | CTG | CAC | TTC | CGC | TGT | GAC | ATC | 3126 |
| Val | Leu | Asp | Cys | Ser | Ile | Ala | Asp | Cys | Leu | His | Phe | Arg | Cys | Asp | Ile | |

-continued

```
              1015                    1020                        1025
CCC  TCC  TTG  GAC  ATC  CAG  GAT  GAA  CTT  GAC  TTC  ATT  CTG  AGG  GGC  AAC      3174
Pro  Ser  Leu  Asp  Ile  Gln  Asp  Glu  Leu  Asp  Phe  Ile  Leu  Arg  Gly  Asn
1030                1035                     1040                      1045

CTC  AGC  TTC  GGC  TGG  GTC  AGT  CAG  ACA  TTG  CAG  GAA  AAG  GTG  TTG  CTT      3222
Leu  Ser  Phe  Gly  Trp  Val  Ser  Gln  Thr  Leu  Gln  Glu  Lys  Val  Leu  Leu
                         1050                     1055                1060

GTG  AGT  GAG  GCT  GAA  ATC  ACT  TTC  GAC  ACA  TCT  GTG  TAC  TCC  CAG  CTG      3270
Val  Ser  Glu  Ala  Glu  Ile  Thr  Phe  Asp  Thr  Ser  Val  Tyr  Ser  Gln  Leu
               1065                     1070                     1075

CCA  GGA  CAG  GAG  GCA  TTT  CTG  AGA  GCC  CAG  GTG  GAG  ACA  ACG  TTA  GAA      3318
Pro  Gly  Gln  Glu  Ala  Phe  Leu  Arg  Ala  Gln  Val  Glu  Thr  Thr  Leu  Glu
          1080                     1085                     1090

GAA  TAC  GTG  GTC  TAT  GAG  CCC  ATC  TTC  CTC  GTG  GCG  GGC  AGC  TCG  GTG      3366
Glu  Tyr  Val  Val  Tyr  Glu  Pro  Ile  Phe  Leu  Val  Ala  Gly  Ser  Ser  Val
     1095                     1100                     1105

GGA  GGT  CTG  CTG  TTA  CTG  GCT  CTC  ATC  ACA  GTG  GTA  CTG  TAC  AAG  CTT      3414
Gly  Gly  Leu  Leu  Leu  Leu  Ala  Leu  Ile  Thr  Val  Val  Leu  Tyr  Lys  Leu
1110                     1115                     1120                     1125

GGC  TTC  TYC  AAA  CGT  CAG  TAC  AAA  GAA  ATG  CTG  GAC  GGC  AAG  GCT  GCA      3462
Gly  Phe  Xaa  Lys  Arg  Gln  Tyr  Lys  Glu  Met  Leu  Asp  Gly  Lys  Ala  Ala
                    1130                     1135                     1140

GAT  CCT  GTC  ACA  GCC  GGC  CAG  GCA  GAT  TTC  GGC  TGT  GAG  ACT  CCT  CCA      3510
Asp  Pro  Val  Thr  Ala  Gly  Gln  Ala  Asp  Phe  Gly  Cys  Glu  Thr  Pro  Pro
               1145                     1150                     1155

TAT  CTC  GTG  AGC  TAGGAATCCA  CTCTCCTGCC  TATCTCTGCA  ATGAAGATTG                   3562
Tyr  Leu  Val  Ser
               1160

GTCCTGCCTA  TGAGTCTACT  GGCATGGGAA  CGAGT                                            3597
```

( 2 ) INFORMATION FOR SEQ ID NO:55:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:55:

```
Met  Ala  Gly  Gly  Val  Val  Ile  Leu  Leu  Cys  Gly  Trp  Val  Leu  Ala  Ser
1                   5                        10                       15

Cys  His  Gly  Ser  Asn  Leu  Asp  Val  Glu  Glu  Pro  Ile  Val  Phe  Arg  Glu
               20                       25                       30

Asp  Ala  Ala  Ser  Phe  Gly  Gln  Thr  Val  Val  Gln  Phe  Gly  Gly  Ser  Arg
          35                       40                       45

Leu  Val  Val  Gly  Ala  Pro  Leu  Glu  Ala  Val  Ala  Val  Asn  Gln  Thr  Gly
     50                       55                       60

Arg  Leu  Tyr  Asp  Cys  Ala  Pro  Ala  Thr  Gly  Met  Cys  Gln  Pro  Ile  Val
65                       70                       75                       80

Leu  Arg  Ser  Pro  Leu  Glu  Ala  Val  Asn  Met  Ser  Leu  Gly  Leu  Ser  Leu
                    85                       90                       95

Val  Thr  Ala  Thr  Asn  Asn  Ala  Gln  Leu  Leu  Ala  Cys  Gly  Pro  Thr  Ala
               100                      105                      110

Gln  Arg  Ala  Cys  Val  Lys  Asn  Met  Tyr  Ala  Lys  Gly  Ser  Cys  Leu  Leu
          115                      120                      125

Leu  Gly  Ser  Ser  Leu  Gln  Phe  Ile  Gln  Ala  Val  Pro  Ala  Ser  Met  Pro
     130                      135                      140

Glu  Cys  Pro  Arg  Gln  Glu  Met  Asp  Ile  Ala  Phe  Leu  Ile  Asp  Gly  Ser
```

-continued

```
145                 150                 155                 160
Gly Ser Ile Asn Gln Arg Asp Phe Ala Gln Met Lys Asp Phe Val Lys
                165                 170                 175
Ala Leu Met Gly Glu Phe Ala Ser Thr Ser Thr Leu Phe Ser Leu Met
            180                 185                 190
Gln Tyr Ser Asn Ile Leu Lys Thr His Phe Thr Phe Thr Glu Phe Lys
        195                 200                 205
Asn Ile Leu Asp Pro Gln Ser Leu Val Asp Pro Ile Val Gln Leu Gln
    210                 215                 220
Gly Leu Thr Tyr Thr Ala Thr Gly Ile Arg Thr Val Met Glu Glu Leu
225                 230                 235                 240
Phe His Ser Lys Asn Gly Ser Arg Lys Ser Ala Lys Lys Ile Leu Leu
                245                 250                 255
Val Ile Thr Asp Gly Gln Lys Tyr Arg Asp Pro Leu Glu Tyr Ser Asp
            260                 265                 270
Val Ile Pro Ala Ala Asp Lys Ala Gly Ile Ile Arg Tyr Ala Ile Gly
        275                 280                 285
Val Gly Asp Ala Phe Gln Glu Pro Thr Ala Leu Lys Glu Leu Asn Thr
    290                 295                 300
Ile Gly Ser Ala Pro Pro Gln Asp His Val Phe Lys Val Gly Asn Phe
305                 310                 315                 320
Ala Ala Leu Arg Ser Ile Gln Arg Gln Leu Gln Glu Lys Ile Phe Ala
                325                 330                 335
Ile Glu Gly Thr Gln Ser Arg Ser Ser Ser Phe Gln His Glu Met
            340                 345                 350
Ser Gln Glu Gly Phe Ser Ser Ala Leu Thr Ser Asp Gly Pro Val Leu
        355                 360                 365
Gly Ala Val Gly Ser Phe Ser Trp Ser Gly Gly Ala Phe Leu Tyr Pro
    370                 375                 380
Pro Asn Thr Arg Pro Thr Phe Ile Asn Met Ser Gln Glu Asn Val Asp
385                 390                 395                 400
Met Arg Asp Ser Tyr Leu Gly Tyr Ser Thr Ala Val Ala Phe Trp Lys
                405                 410                 415
Gly Val His Ser Leu Ile Leu Gly Ala Pro Arg His Gln His Thr Gly
            420                 425                 430
Lys Val Val Ile Phe Thr Gln Glu Ala Arg His Trp Arg Pro Lys Ser
        435                 440                 445
Glu Val Arg Gly Thr Gln Ile Gly Ser Tyr Phe Gly Ala Ser Leu Cys
    450                 455                 460
Ser Val Asp Val Asp Arg Asp Gly Ser Xaa Asp Leu Val Leu Ile Gly
465                 470                 475                 480
Ala Pro His Tyr Tyr Glu Gln Thr Arg Gly Gly Gln Val Ser Val Phe
                485                 490                 495
Pro Val Pro Gly Val Arg Gly Arg Trp Gln Cys Glu Ala Thr Leu His
            500                 505                 510
Gly Glu Gln Gly His Pro Trp Gly Arg Phe Gly Val Ala Leu Thr Val
        515                 520                 525
Leu Gly Asp Val Asn Gly Asp Asn Leu Ala Asp Val Ala Ile Gly Ala
    530                 535                 540
Pro Gly Glu Glu Glu Ser Arg Gly Ala Val Tyr Ile Phe His Gly Ala
545                 550                 555                 560
Ser Arg Leu Glu Ile Met Pro Ser Pro Ser Gln Arg Val Thr Gly Ser
                565                 570                 575
```

-continued

| Gln | Leu | Ser | Leu | Arg | Leu | Gln | Tyr | Phe | Gly | Gln | Ser | Leu | Ser | Gly | Gly |
|  |  |  | 580 |  |  |  | 585 |  |  |  |  |  | 590 |  |  |

| Gln | Asp | Leu | Thr | Gln | Asp | Gly | Leu | Val | Asp | Leu | Ala | Val | Gly | Ala | Gln |
|  |  | 595 |  |  |  | 600 |  |  |  |  | 605 |  |  |  |  |

| Gly | His | Val | Leu | Leu | Leu | Arg | Ser | Leu | Pro | Leu | Lys | Val | Glu | Leu |
|  | 610 |  |  |  |  | 615 |  |  |  |  | 620 |  |  |  |

| Ser | Ile | Arg | Phe | Ala | Pro | Met | Glu | Val | Ala | Lys | Ala | Val | Tyr | Gln | Cys |
| 625 |  |  |  |  | 630 |  |  |  |  | 635 |  |  |  |  | 640 |

| Trp | Glu | Arg | Thr | Pro | Thr | Val | Leu | Glu | Ala | Gly | Glu | Ala | Thr | Val | Cys |
|  |  |  |  | 645 |  |  |  |  | 650 |  |  |  |  | 655 |  |

| Leu | Thr | Val | His | Lys | Gly | Ser | Pro | Asp | Leu | Leu | Gly | Asn | Val | Gln | Gly |
|  |  |  | 660 |  |  |  |  | 665 |  |  |  |  | 670 |  |  |

| Ser | Val | Arg | Tyr | Asp | Leu | Ala | Leu | Asp | Pro | Gly | Arg | Leu | Ile | Ser | Arg |
|  |  | 675 |  |  |  |  |  | 680 |  |  |  |  | 685 |  |  |

| Ala | Ile | Phe | Asp | Glu | Thr | Lys | Asn | Cys | Thr | Leu | Thr | Gly | Arg | Lys | Thr |
|  | 690 |  |  |  |  | 695 |  |  |  |  | 700 |  |  |  |  |

| Leu | Gly | Leu | Gly | Asp | His | Cys | Glu | Thr | Val | Lys | Leu | Leu | Leu | Pro | Asp |
| 705 |  |  |  |  | 710 |  |  |  |  | 715 |  |  |  |  | 720 |

| Cys | Val | Glu | Asp | Ala | Val | Ser | Pro | Ile | Ile | Leu | Arg | Leu | Asn | Phe | Ser |
|  |  |  |  | 725 |  |  |  |  | 730 |  |  |  |  | 735 |  |

| Leu | Val | Arg | Asp | Ser | Ala | Ser | Pro | Arg | Asn | Leu | His | Pro | Val | Leu | Ala |
|  |  |  | 740 |  |  |  |  | 745 |  |  |  |  | 750 |  |  |

| Val | Gly | Ser | Gln | Asp | His | Ile | Thr | Ala | Ser | Leu | Pro | Phe | Glu | Lys | Asn |
|  |  | 755 |  |  |  |  | 760 |  |  |  |  | 765 |  |  |  |

| Cys | Lys | Gln | Glu | Leu | Leu | Cys | Glu | Gly | Asp | Leu | Gly | Ile | Ser | Phe | Asn |
|  | 770 |  |  |  |  | 775 |  |  |  |  | 780 |  |  |  |  |

| Phe | Ser | Gly | Leu | Gln | Val | Leu | Val | Val | Gly | Gly | Ser | Pro | Glu | Leu | Thr |
| 785 |  |  |  |  | 790 |  |  |  |  | 795 |  |  |  |  | 800 |

| Val | Thr | Val | Thr | Val | Trp | Asn | Glu | Gly | Glu | Asp | Ser | Tyr | Gly | Thr | Leu |
|  |  |  |  | 805 |  |  |  |  | 810 |  |  |  |  | 815 |  |

| Val | Lys | Phe | Tyr | Tyr | Pro | Ala | Gly | Leu | Ser | Tyr | Arg | Arg | Val | Thr | Gly |
|  |  |  | 820 |  |  |  |  | 825 |  |  |  |  | 830 |  |  |

| Thr | Gln | Gln | Pro | His | Gln | Tyr | Pro | Leu | Arg | Leu | Ala | Cys | Glu | Ala | Glu |
|  |  | 835 |  |  |  |  | 840 |  |  |  |  | 845 |  |  |  |

| Pro | Ala | Ala | Gln | Glu | Asp | Leu | Arg | Ser | Ser | Ser | Cys | Ser | Ile | Asn | His |
| 850 |  |  |  |  | 855 |  |  |  |  | 860 |  |  |  |  |  |

| Pro | Ile | Phe | Arg | Glu | Gly | Ala | Lys | Thr | Thr | Phe | Met | Ile | Thr | Phe | Asp |
| 865 |  |  |  |  | 870 |  |  |  |  | 875 |  |  |  |  | 880 |

| Val | Ser | Tyr | Lys | Ala | Phe | Leu | Gly | Asp | Arg | Leu | Leu | Leu | Arg | Ala | Lys |
|  |  |  |  | 885 |  |  |  |  | 890 |  |  |  |  | 895 |  |

| Ala | Ser | Ser | Glu | Asn | Asn | Lys | Pro | Asp | Thr | Asn | Lys | Thr | Ala | Phe | Gln |
|  |  |  | 900 |  |  |  |  | 905 |  |  |  |  | 910 |  |  |

| Leu | Glu | Leu | Pro | Val | Lys | Tyr | Thr | Val | Tyr | Thr | Leu | Ile | Ser | Arg | Gln |
|  |  | 915 |  |  |  |  | 920 |  |  |  |  | 925 |  |  |  |

| Glu | Asp | Ser | Thr | Asn | His | Val | Asn | Phe | Ser | Ser | His | Gly | Gly | Arg |
|  | 930 |  |  |  |  | 935 |  |  |  |  | 940 |  |  |  |

| Arg | Gln | Glu | Ala | Ala | His | Arg | Tyr | Arg | Val | Asn | Asn | Leu | Ser | Pro | Leu |
| 945 |  |  |  |  | 950 |  |  |  |  | 955 |  |  |  |  | 960 |

| Lys | Leu | Ala | Val | Arg | Val | Asn | Phe | Trp | Val | Pro | Val | Leu | Leu | Asn | Gly |
|  |  |  |  | 965 |  |  |  |  | 970 |  |  |  |  | 975 |  |

| Val | Ala | Val | Trp | Asp | Val | Thr | Leu | Ser | Ser | Pro | Ala | Gln | Gly | Val | Ser |
|  |  |  | 980 |  |  |  |  | 985 |  |  |  |  | 990 |  |  |

| Cys | Val | Ser | Gln | Met | Lys | Pro | Pro | Gln | Asn | Pro | Asp | Phe | Leu | Thr | Gln |
|  |  | 995 |  |  |  |  | 1000 |  |  |  |  | 1005 |  |  |  |

Ile Gln Arg Arg Ser Val Leu Asp Cys Ser Ile Ala Asp Cys Leu His
    1010                1015                1020

Phe Arg Cys Asp Ile Pro Ser Leu Asp Ile Gln Asp Glu Leu Asp Phe
1025            1030                1035                    1040

Ile Leu Arg Gly Asn Leu Ser Phe Gly Trp Val Ser Gln Thr Leu Gln
            1045                1050                1055

Glu Lys Val Leu Leu Val Ser Glu Ala Glu Ile Thr Phe Asp Thr Ser
        1060                1065                1070

Val Tyr Ser Gln Leu Pro Gly Gln Glu Ala Phe Leu Arg Ala Gln Val
    1075                1080                1085

Glu Thr Thr Leu Glu Glu Tyr Val Val Tyr Glu Pro Ile Phe Leu Val
    1090                1095                1100

Ala Gly Ser Ser Val Gly Gly Leu Leu Leu Leu Ala Leu Ile Thr Val
1105            1110                1115                    1120

Val Leu Tyr Lys Leu Gly Xaa Xaa Lys Arg Gln Tyr Lys Glu Met Leu
            1125                1130                1135

Asp Gly Lys Ala Ala Asp Pro Val Thr Xaa Gly Gln Ala Asp Phe Gly
            1140            1145                1150

Cys Glu Thr Pro Pro Tyr Leu Val Ser
        1155                1160

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

CCTGTCATGG GTCTAACCTG        20

( 2 ) INFORMATION FOR SEQ ID NO:57:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

AGGTTAGACC CATGACAGG        19

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

GGCCTTGCAG CTGGACAATG        20

( 2 ) INFORMATION FOR SEQ ID NO:59:

( i ) SEQUENCE CHARACTERISTICS:

(A) LENGTH: 22 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:59:

CCAAAGCTGG CTGCATCCTC TC 22

(2) INFORMATION FOR SEQ ID NO:60:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:60:

CCGCCTGCCA CTGGCGTGTG C 21

(2) INFORMATION FOR SEQ ID NO:61:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:61:

CCCAGATGAA GGACTTCGTC AA 22

(2) INFORMATION FOR SEQ ID NO:62:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:62:

GCTGGGATCA TTCGCTATGC 20

(2) INFORMATION FOR SEQ ID NO:63:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:63:

CAATGGATGG ACCAGTTCTG G 21

(2) INFORMATION FOR SEQ ID NO:64:

(i) SEQUENCE CHARACTERISTICS:
(A) LENGTH: 20 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:64:

CAGATCGGCT CCTACTTTGG 20

( 2 ) INFORMATION FOR SEQ ID NO:65:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:65:

CATGGAGCCT CGAGACAGG 19

( 2 ) INFORMATION FOR SEQ ID NO:66:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:66:

CCACTGTCCT CGAAGCTGGA G 21

( 2 ) INFORMATION FOR SEQ ID NO:67:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:67:

CTTCGTCCTG TGCTGGCTGT GGGCTC 26

( 2 ) INFORMATION FOR SEQ ID NO:68:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:68:

CGCCTGGCAT GTGAGGCTGA G 21

( 2 ) INFORMATION FOR SEQ ID NO:69:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:69:

CCGTGATCAG TAGGCAGGAA G 21

( 2 ) INFORMATION FOR SEQ ID NO:70:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:70:

GTCACAGAGG GAACCTCC                                                    18

( 2 ) INFORMATION FOR SEQ ID NO:71:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:71:

GCTCCTGAGT GAGGCTGAAA TCA                                     23

( 2 ) INFORMATION FOR SEQ ID NO:72:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:72:

GAGATGCTGG ATCTACCATC TGC                                     23

( 2 ) INFORMATION FOR SEQ ID NO:73:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:73:

CTGAGCTGGG AGATTTTTAT GG                                      22

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:74:

GTGGATCAGC ACTGAAATCT G                                        21

( 2 ) INFORMATION FOR SEQ ID NO:75:

( i ) SEQUENCE CHARACTERISTICS:

(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:75:

CGTTTGAAGA AGCCAAGCTT G 21

(2) INFORMATION FOR SEQ ID NO:76:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:76:

CACAGCGGAG GTGCAGGCAG 20

(2) INFORMATION FOR SEQ ID NO:77:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:77:

CTCACTGCTT GCGCTGGC 18

(2) INFORMATION FOR SEQ ID NO:78:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:78:

CGGTAAGATA GCTCTGCTGG 20

(2) INFORMATION FOR SEQ ID NO:79:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:79:

GAGCCCACAG CCAGCACAGG 20

(2) INFORMATION FOR SEQ ID NO:80:

(i) SEQUENCE CHARACTERISTICS:
(A) LENGTH: 21 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:80:

GATCCAACGC CAGATCATAC C           21

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:81:

CACGGCCAGG TCCACCAGGC           20

( 2 ) INFORMATION FOR SEQ ID NO:82:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:82:

CACGTCCCCT AGCACTGTCA G           21

( 2 ) INFORMATION FOR SEQ ID NO:83:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:83:

TTGACGAAGT CCTTCATCTG GG           22

( 2 ) INFORMATION FOR SEQ ID NO:84:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:84:

GAACTGCAAG CTGGAGCCCA G           21

( 2 ) INFORMATION FOR SEQ ID NO:85:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:85:

CTGGATGCTG CGAAGTGCTA C           21

( 2 ) INFORMATION FOR SEQ ID NO:86:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:86:

GCCTTGGAGC TGGACGATGG C            21

( 2 ) INFORMATION FOR SEQ ID NO:87:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:87:

GTAAGATCTC CAGAGTGTCC AAGACAAGAG ATG      33

( 2 ) INFORMATION FOR SEQ ID NO:88:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:88:

CTTCTCGAGT GTGAGAGCTG AACTGAAACC TTC      33

( 2 ) INFORMATION FOR SEQ ID NO:89:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:89:

CGCTGTGACG TCAGAGTTGA GTCCAAATAT GG       32

( 2 ) INFORMATION FOR SEQ ID NO:90:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:90:

GGTGACACTA TAGAATAGGG C           21

( 2 ) INFORMATION FOR SEQ ID NO:91:

( i ) SEQUENCE CHARACTERISTICS:

( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:91:

AAGCAGGAGCTCCTGTGT                                                                                                18

( 2 ) INFORMATION FOR SEQ ID NO:92:

( i ) SEQUENCE CHARACTERISTICS:
            ( A ) LENGTH: 852 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: CDS
            ( B ) LOCATION: 61..852

( x i ) SEQUENCE DESCRIPTION: SEQ ID NO:92:

| TGATCTCCCT | CCAGGCCACT | GTTCCCTCTC | CACTTCCCCT | CACCGCTGCA | CTGCTCAGAG | 60 |

| ATG | GCC | CTT | GGG | GCT | GTG | GTC | CTC | CTT | GGG | GTC | CTG | GCT | TCT | TAC | CAC | 108 |
| Met | Ala | Leu | Gly | Ala | Val | Val | Leu | Leu | Gly | Val | Leu | Ala | Ser | Tyr | His | |
| 1 | | | | 5 | | | | | 10 | | | | | 15 | | |

| GGA | TTC | AAC | TTG | GAC | GTG | ATG | AGC | GGT | GAT | CTT | CCA | GGA | AGA | CGC | AGC | 156 |
| Gly | Phe | Asn | Leu | Asp | Val | Met | Ser | Gly | Asp | Leu | Pro | Gly | Arg | Arg | Ser | |
| | | | 20 | | | | | 25 | | | | | 30 | | | |

| GGG | CTT | CGG | GCA | GAG | CGT | GAT | GCA | GTT | TGG | GGA | TCT | CGA | CTC | GTG | GTG | 204 |
| Gly | Leu | Arg | Ala | Glu | Arg | Asp | Ala | Val | Trp | Gly | Ser | Arg | Leu | Val | Val | |
| | | 35 | | | | | 40 | | | | | 45 | | | | |

| GGA | GCC | CCC | CTG | GCG | GTG | GTG | TCG | GCC | AAC | CAC | ACA | GGA | CGG | CTG | TAC | 252 |
| Gly | Ala | Pro | Leu | Ala | Val | Val | Ser | Ala | Asn | His | Thr | Gly | Arg | Leu | Tyr | |
| | 50 | | | | | 55 | | | | | 60 | | | | | |

| GAG | TGT | GCG | CCT | GCC | TCC | GGC | ACC | TGC | ACG | CCC | ATT | TTC | CCA | TTC | ATG | 300 |
| Glu | Cys | Ala | Pro | Ala | Ser | Gly | Thr | Cys | Thr | Pro | Ile | Phe | Pro | Phe | Met | |
| 65 | | | | | 70 | | | | | 75 | | | | | 80 | |

| CCC | CCC | GAA | GCC | GTG | AAC | ATG | TCC | CTG | GGC | CTG | TCC | CTG | GCA | GCC | TCC | 348 |
| Pro | Pro | Glu | Ala | Val | Asn | Met | Ser | Leu | Gly | Leu | Ser | Leu | Ala | Ala | Ser | |
| | | | | 85 | | | | | 90 | | | | | 95 | | |

| CCC | AAC | CAT | TCC | CAG | CTG | CTG | GCT | TGT | GGC | CCG | ACC | GTG | CAT | AGA | GCC | 396 |
| Pro | Asn | His | Ser | Gln | Leu | Leu | Ala | Cys | Gly | Pro | Thr | Val | His | Arg | Ala | |
| | | | 100 | | | | | 105 | | | | | 110 | | | |

| TGC | GGG | GAG | GAC | GTG | TAC | GCC | CAG | GGT | TTC | TGT | GTG | CTG | CTG | GAT | GCC | 444 |
| Cys | Gly | Glu | Asp | Val | Tyr | Ala | Gln | Gly | Phe | Cys | Val | Leu | Leu | Asp | Ala | |
| | | 115 | | | | | 120 | | | | | 125 | | | | |

| CAC | GCA | CAG | CCC | ATC | GGG | ACT | GTG | CCA | GCT | GCC | CTG | CCC | GAG | TGC | CCA | 492 |
| His | Ala | Gln | Pro | Ile | Gly | Thr | Val | Pro | Ala | Ala | Leu | Pro | Glu | Cys | Pro | |
| | 130 | | | | | 135 | | | | | 140 | | | | | |

| GAT | CAA | GAG | ATG | GAC | ATT | GTC | TTC | CTG | ATT | GAC | GGC | TCT | GGC | AGC | ATT | 540 |
| Asp | Gln | Glu | Met | Asp | Ile | Val | Phe | Leu | Ile | Asp | Gly | Ser | Gly | Ser | Ile | |
| 145 | | | | | 150 | | | | | 155 | | | | | 160 | |

| AGC | TCA | AAT | GAC | TTC | CGC | AAG | ATG | AAG | GAC | TTT | GTC | AGA | GCT | GTG | ATG | 588 |
| Ser | Ser | Asn | Asp | Phe | Arg | Lys | Met | Lys | Asp | Phe | Val | Arg | Ala | Val | Met | |
| | | | | 165 | | | | | 170 | | | | | 175 | | |

| GAC | CAG | TTC | AAG | GAC | ACC | AAC | ACC | CAG | TTC | TCG | CTG | ATG | CAG | TAC | TCC | 636 |
| Asp | Gln | Phe | Lys | Asp | Thr | Asn | Thr | Gln | Phe | Ser | Leu | Met | Gln | Tyr | Ser | |
| | | | 180 | | | | | 185 | | | | | 190 | | | |

| AAT | GTG | CTG | GTG | ACA | CAT | TTC | ACC | TTC | AGC | AGC | TTC | CGG | AAC | AGC | TCC | 684 |
| Asn | Val | Leu | Val | Thr | His | Phe | Thr | Phe | Ser | Ser | Phe | Arg | Asn | Ser | Ser | |

|     |     |     |     | 195 |     |     |     | 200 |     |     |     | 205 |     |     |     |     |
|-----|-----|-----|-----|-----|-----|-----|-----|-----|-----|-----|-----|-----|-----|-----|-----|-----|
| AAT | CCT | CAG | GGC | CTA | GTG | GAG | CCC | ATT | GTG | CAG | CTG | ACA | GGC | CTC | ACG | 732 |
| Asn | Pro | Gln | Gly | Leu | Val | Glu | Pro | Ile | Val | Gln | Leu | Thr | Gly | Leu | Thr |     |
|     | 210 |     |     |     |     | 215 |     |     |     | 220 |     |     |     |     |     |     |
| TTC | ACG | GCC | ACA | GGG | ATC | CTG | AAA | GTG | GTG | ACA | GAG | CTG | TTT | CAA | ACC | 780 |
| Phe | Thr | Ala | Thr | Gly | Ile | Leu | Lys | Val | Val | Thr | Glu | Leu | Phe | Gln | Thr |     |
| 225 |     |     |     |     | 230 |     |     |     |     | 235 |     |     |     |     | 240 |     |
| AAG | AAC | GGG | GCC | CGC | GAA | AGT | GCC | AAG | AAG | ATC | CTC | ATC | GTC | ATC | ACA | 828 |
| Lys | Asn | Gly | Ala | Arg | Glu | Ser | Ala | Lys | Lys | Ile | Leu | Ile | Val | Ile | Thr |     |
|     |     |     |     | 245 |     |     |     |     | 250 |     |     |     |     | 255 |     |     |
| GAT | GGG | CAG | AAG | TAC | AAA | GCG | GCA |     |     |     |     |     |     |     |     | 852 |
| Asp | Gly | Gln | Lys | Tyr | Lys | Ala | Ala |     |     |     |     |     |     |     |     |     |
|     |     |     |     | 260 |     |     |     |     |     |     |     |     |     |     |     |     |

( 2 ) INFORMATION FOR SEQ ID NO:93:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:93:

| Met | Ala | Leu | Gly | Ala | Val | Val | Leu | Leu | Gly | Val | Leu | Ala | Ser | Tyr | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Phe | Asn | Leu | Asp | Val | Met | Ser | Gly | Asp | Leu | Pro | Gly | Arg | Arg | Ser |
|     |     |     | 20  |     |     |     |     | 25  |     |     |     |     | 30  |     |     |
| Gly | Leu | Arg | Ala | Glu | Arg | Asp | Ala | Val | Trp | Gly | Ser | Arg | Leu | Val | Val |
|     |     |     | 35  |     |     |     |     | 40  |     |     |     |     | 45  |     |     |
| Gly | Ala | Pro | Leu | Ala | Val | Val | Ser | Ala | Asn | His | Thr | Gly | Arg | Leu | Tyr |
|     | 50  |     |     |     |     | 55  |     |     |     |     | 60  |     |     |     |     |
| Glu | Cys | Ala | Pro | Ala | Ser | Gly | Thr | Cys | Thr | Pro | Ile | Phe | Pro | Phe | Met |
| 65  |     |     |     |     | 70  |     |     |     |     | 75  |     |     |     |     | 80  |
| Pro | Pro | Glu | Ala | Val | Asn | Met | Ser | Leu | Gly | Leu | Ser | Leu | Ala | Ala | Ser |
|     |     |     |     | 85  |     |     |     |     | 90  |     |     |     |     | 95  |     |
| Pro | Asn | His | Ser | Gln | Leu | Leu | Ala | Cys | Gly | Pro | Thr | Val | His | Arg | Ala |
|     |     |     | 100 |     |     |     |     | 105 |     |     |     |     | 110 |     |     |
| Cys | Gly | Glu | Asp | Val | Tyr | Ala | Gln | Gly | Phe | Cys | Val | Leu | Leu | Asp | Ala |
|     |     |     | 115 |     |     |     |     | 120 |     |     |     |     | 125 |     |     |
| His | Ala | Gln | Pro | Ile | Gly | Thr | Val | Pro | Ala | Ala | Leu | Pro | Glu | Cys | Pro |
|     | 130 |     |     |     |     | 135 |     |     |     |     | 140 |     |     |     |     |
| Asp | Gln | Glu | Met | Asp | Ile | Val | Phe | Leu | Ile | Asp | Gly | Ser | Gly | Ser | Ile |
| 145 |     |     |     |     | 150 |     |     |     |     | 155 |     |     |     |     | 160 |
| Ser | Ser | Asn | Asp | Phe | Arg | Lys | Met | Lys | Asp | Phe | Val | Arg | Ala | Val | Met |
|     |     |     |     | 165 |     |     |     |     | 170 |     |     |     |     | 175 |     |
| Asp | Gln | Phe | Lys | Asp | Thr | Asn | Thr | Gln | Phe | Ser | Leu | Met | Gln | Tyr | Ser |
|     |     |     | 180 |     |     |     |     | 185 |     |     |     |     | 190 |     |     |
| Asn | Val | Leu | Val | Thr | His | Phe | Thr | Phe | Ser | Ser | Phe | Arg | Asn | Ser | Ser |
|     |     |     | 195 |     |     |     |     | 200 |     |     |     |     | 205 |     |     |
| Asn | Pro | Gln | Gly | Leu | Val | Glu | Pro | Ile | Val | Gln | Leu | Thr | Gly | Leu | Thr |
|     |     |     |     | 210 |     |     |     |     | 215 |     |     |     |     | 220 |     |
| Phe | Thr | Ala | Thr | Gly | Ile | Leu | Lys | Val | Val | Thr | Glu | Leu | Phe | Gln | Thr |
| 225 |     |     |     |     | 230 |     |     |     |     | 235 |     |     |     |     | 240 |
| Lys | Asn | Gly | Ala | Arg | Glu | Ser | Ala | Lys | Lys | Ile | Leu | Ile | Val | Ile | Thr |
|     |     |     |     | 245 |     |     |     |     | 250 |     |     |     |     | 255 |     |
| Asp | Gly | Gln | Lys | Tyr | Lys | Ala | Ala |     |     |     |     |     |     |     |     |
|     |     |     | 260 |     |     |     |     |     |     |     |     |     |     |     |     |

( 2 ) INFORMATION FOR SEQ ID NO:94:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:94:

```
CTGGTCTGGA GGTGCCTTCC TG                                                    22
```

( 2 ) INFORMATION FOR SEQ ID NO:95:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:95:

```
CCTGAGCAGG AGCACCTGGC C                                                     21
```

( 2 ) INFORMATION FOR SEQ ID NO:96:

( i ) SEQUENCE CHARACTERISTICS:
        ( A ) LENGTH: 2499 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:96:

```
ATGACCTTCG GCACTGTGCT TCTTCTGAGT GTCCTGGCTT CTTATCATGG ATTCAACCTG           60
GATGTGGAGG AGCCTACGAT CTTCCAGGAG GATGCAGGCG GCTTTGGGCA GAGCGTGGTG          120
CAGTTCGGTG GATCTCGACT CGTGGTGGGA GCACCCCTGG AGGTGGTGGC GGCCAACCAG          180
ACGGGACGGC TGTATGACTG CGCAGCTGCC ACCGGCATGT GCCAGCCCAT CCCGCTGCAC          240
ATCCGCCCTG AGGCCGTGAA CATGTCCTTG GGCCTGACCC TGGCAGCCTC CACCAACGGC          300
TCCCGGCTCC TGGCCTGTGG CCCGACCCTG CACAGAGTCT GTGGGGAGAA CTCATACTCA          360
AAGGGTTCCT GCCTCCTGCT GGGCTCGCGC TGGGAGATCA TCCAGACAGT CCCCGACGCC          420
ACGCCAGAGT GTCCACATCA AGAGATGGAC ATCGTCTTCC TGATTGACGG CTCTGGAAGC          480
ATTGACCAAA ATGACTTTAA CCAGATGAAG GGCTTTGTCC AAGCTGTCAT GGGCCAGTTT          540
GAGGGCACTG ACACCCTGTT TGCACTGATG CAGTACTCAA ACCTCCTGAA GATCCACTTC          600
ACCTTCACCC AATTCCGGAC CAGCCCGAGC CAGCAGAGCC TGGTGGATCC CATCGTCCAA          660
CTGAAAGGCC TGACGTTCAC GGCCACGGGC ATCCTGACAG TGGTGACACA GCTATTTCAT          720
CATAAGAATG GGCCCGAAA AAGTGCCAAG AAGATCCTCA TTGTCATCAC AGATGGGCAG           780
AAGTACAAAG ACCCCCTGGA ATACAGTGAT GTCATCCCCC AGGCAGAGAA GGCTGGCATC          840
ATCCGCTACG CTATCGGGGT GGGACACGCT TTCAGGGAC CCACTGCCAG GCAGGAGCTG           900
AATACCATCA GCTCAGCGCC TCCGCAGGAC CACGTGTTCA AGGTGGACAA CTTTGCAGCC          960
CTTGGCAGCA TCCAGAAGCA GCTGCAGGAG AAGATCTATG CAGTTGAGGG AACCCAGTCC         1020
AGGGCAAGCA GCTCCTTCCA GCACGAGATG TCCCAAGAAG GCTTCAGCAC AGCCCTCACA         1080
```

| | | | | | | |
|---|---|---|---|---|---|---|
| ATGGATGGCC | TCTTCCTGGG | GGCTGTGGGG | AGCTTTAGCT | GGTCTGGAGG | TGCCTTCCTG | 1140 |
| TATCCCCCAA | ATATGAGCCC | CACCTTCATC | AACATGTCTC | AGGAGAATGT | GGACATGAGG | 1200 |
| GACTCTTACC | TGGGTTACTC | CACCGAGCTA | GCCCTGTGGA | AGGGGGTACA | GAACCTGGTC | 1260 |
| CTGGGGGCCC | CCCGCTACCA | GCATACCGGG | AAGGCTGTCA | TCTTCACCCA | GGTGTCCAGG | 1320 |
| CAATGGAGGA | AGAAGGCCGA | AGTCACAGGG | ACGCAGATCG | GCTCCTACTT | CGGGGCCTCC | 1380 |
| CTCTGCTCCG | TGGATGTGGA | CAGCGATGGC | AGCACCGACC | TGATCCTCAT | TGGGGCCCCC | 1440 |
| CATTACTATG | AGCAGACCCG | AGGGGGCCAG | GTGTCCGTGT | GTCCCTTGCC | TAGGGGGAGG | 1500 |
| GTGCAGTGGC | AGTGTGACGC | TGTTCTCCGT | GGTGAGCAGG | GCCACCCCTG | GGGCCGCTTT | 1560 |
| GGGGCAGCCC | TGACAGTGTT | GGGGGATGTG | AATGAGGACA | AGCTGATAGA | CGTGGCCATT | 1620 |
| GGGGCCCCGG | GAGAGCAGGA | GAACCGGGGT | GCTGTCTACC | TGTTTCACGG | AGCCTCAGAA | 1680 |
| TCCGGCATCA | GCCCCTCCCA | CAGCCAGCGG | ATTGCCAGCT | CCAGCTCTC | CCCCAGGCTG | 1740 |
| CAGTATTTTG | GGCAGGCGCT | GAGTGGGGGT | CAGGACCTCA | CCCAGGATGG | ACTGATGGAC | 1800 |
| CTGGCCGTGG | GGGCCCGGGG | CCAGGTGCTC | CTGCTCAGGA | GTCTGCCGGT | GCTGAAAGTG | 1860 |
| GGGGTGGCCA | TGAGATTCAG | CCCTGTGGAG | GTGGCCAAGG | CTGTGTACCG | GTGCTGGGAA | 1920 |
| GAGAAGCCCA | GTGCCCTGGA | AGCTGGGGAC | GCCACCGTCT | GTCTCACCAT | CCAGAAAAGC | 1980 |
| TCACTGGACC | AGCTAGGTGA | CATCCAAAGC | TCTGTCAGGT | TTGATCTGGC | ACTGGACCCA | 2040 |
| GGTCGTCTGA | CTTCTCGTGC | CATTTTCAAT | GAAACCAAGA | ACCCACTTT | GACTCGAAGA | 2100 |
| AAAACCCTGG | GACTGGGGAT | TCACTGTGAA | ACCCTGAAGC | TGCTTTTGCC | AGTGAGGACT | 2160 |
| TTGGGTTCTG | GGAAGGGGGA | GAGAGGAGGA | GCCCAAGGCT | GGCCTGGAGC | ACCCCCGTTC | 2220 |
| TCTGCTGAGC | GAGGTGGGAA | GGGTTAGGAT | GTTGGGGCTG | GAGAGAGGGA | CATTAGGGCA | 2280 |
| GGAGAACCTG | GCTCCACGGC | TTGGAGGGAG | CACTGTCAGG | GCAGTGGGGA | GTGGATGCAG | 2340 |
| TGGAGGAGGA | CTTGTGGTGG | AGCGTAGAGA | GGACAGCAGG | TTCTTGAAAG | CCTGTTCTCT | 2400 |
| CTCAGGATTG | TGTGGAGGAT | GTGGTGAGCC | CCATCATTCT | GCACCTCAAC | TTCTCACTGG | 2460 |
| TGAGAGAGCC | CATCCCCTCC | CCCCAGAACC | TGCGTCCTG | | | 2499 |

(2) INFORMATION FOR SEQ ID NO:97:

(i) SEQUENCE CHARACTERISTICS:
        (A) LENGTH: 3956 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:97:

| | | | | | | |
|---|---|---|---|---|---|---|
| TTTAACTGCA | CCAACTTTAA | AATACGCTAT | TGGAGCTGGA | ATTACCGCGG | CTGCTGGCAC | 60 |
| CAGACTTGCC | CTCCAATGGA | TCCTCGTTAA | AGGATTTAAA | GTGGACTCAT | TCCAATTACA | 120 |
| GGGCCTCGAA | AGAGTCCTGT | ATTGTTATTT | TTCGTCACTA | CCTCCCCGGG | TCGGGAGTGG | 180 |
| GTAATTTGCG | CGCCTGCTGC | CTTCCTTGGA | TGTGGTAGCC | GTTTCTCAGG | CTCCCTCTCC | 240 |
| GGAATCGAAC | CCTGATTCCC | CGTCACCCGT | GGTCACCATG | GTAGGCACGT | GCAGTTCGGT | 300 |
| GGATCTCGAC | TCGTGGTGGG | AGCACCCCTG | GAGGTGGTGG | CGGCCAACCA | GACGGGACGG | 360 |
| CTGTATGACT | GCGCAGCTGC | CACCGGCATG | TGCCAGCCCA | TCCCGCTGCA | CATCCGCCCT | 420 |
| GAGGCCGTGA | ACATGTCCTT | GGGCCTGACC | CTGGCAGCCT | CCACCAACGG | CTCCCGGCTC | 480 |
| CTGGCCTGTG | GCCCGACCCT | GCACAGAGTC | TGTGGGGAGA | ACTCATACTC | AAAGGGTTCC | 540 |
| TGCCTCCTGC | TGGGCTCGCG | CTGGGAGATC | ATCCAGACAG | TCCCCGACGC | CACGCCAGAG | 600 |

| | | | | | |
|---|---|---|---|---|---|
|TGTCCACATC|AAGAGATGGA|CATCGTCTTC|CTGATTGACG|GCTCTGGAAG|CATTGACCAA  660|
|AATGACTTTA|ACCAGATGAA|GGGCTTTGTC|CAAGCTGTCA|TGGGCCAGTT|TGAGGGCACT  720|
|GACACCCTGT|TTGCACTGAT|GCAGTACTCA|AACCTCCTGA|AGATCCACTT|CACCTTCACC  780|
|CAATTCCGGA|CCAGCCCGAG|CCAGCAGAGC|CTGGTGGATC|CCATCGTCCA|ACTGAAAGGC  840|
|CTGACGTTCA|CGGCCACGGG|CATCCTGACA|GTGGTGACAC|AGCTATTTCA|TCATAAGAAT  900|
|GGGGCCCGAA|AAAGTGCCAA|GAAGATCCTC|ATTGTCATCA|CAGATGGGCA|GAAGTACAAA  960|
|GACCCCCTGG|AATACAGTGA|TGTCATCCCC|CAGGCAGAGA|AGGCTGGCAT|CATCCGCTAC 1020|
|GCTATCGGGG|TGGGACACGC|TTTCCAGGGA|CCCACTGCCA|GGCAGGAGCT|GAATACCATC 1080|
|AGCTCAGCGC|CTCCGCAGGA|CCACGTGTTC|AAGGTGGACA|ACTTTGCAGC|CCTTGGCAGC 1140|
|ATCCAGAAGC|AGCTGCAGGA|GAAGATCTAT|GCAGTTGAGG|GAACCCAGTC|CAGGGCAAGC 1200|
|AGCTCCTTCC|AGCACGAGAT|GTCCAAGAA|GGCTTCAGCA|CAGCCCTCAC|AATGGATGGC 1260|
|CTCTTCCTGG|GGGCTGTGGG|GAGCTTTAGC|TGGTCTGGAG|GTGCCTTCCT|GTATCCCCCA 1320|
|AATATGAGCC|CCACCTTCAT|CAACATGTCT|CAGGAGAATG|TGGACATGAG|GGACTCTTAC 1380|
|CTGGGTTACT|CCACCGAGCT|AGCCCTGTGG|AAGGGGGTAC|AGAACCTGGT|CCTGGGGGCC 1440|
|CCCCGCTACC|AGCATACCGG|GAAGGCTGTC|ATCTTCACCC|AGGTGTCCAG|GCAATGGAGG 1500|
|AAGAAGGCCG|AAGTCACAGG|GACGCAGATC|GGCTCCTACT|TCGGGGCCTC|CCTCTGCTCC 1560|
|GTGGATGTGG|ACAGCGATGG|CAGCACCGAC|CTGATCCTCA|TTGGGGCCCC|CCATTACTAT 1620|
|GAGCAGACCC|GAGGGGGCCA|GGTGTCCGTG|TGTCCCTTGC|CTAGGGGGAG|GGTGCAGTGG 1680|
|CAGTGTGACG|CTGTTCTCCG|TGGTGAGCAG|GGCCACCCCT|GGGGCCGCTT|TGGGGCAGCC 1740|
|CTGACAGTGT|TGGGGGATGT|GAATGAGGAC|AAGCTGATAG|ACGTGGCCAT|TGGGGCCCCG 1800|
|GGAGAGCAGG|AGAACCGGGG|TGCTGTCTAC|CTGTTTCACG|GAGCCTCAGA|ATCCGGCATC 1860|
|AGCCCCTCCC|ACAGCCAGCG|GATTGCCAGC|TCCCAGCTCT|CCCCCAGGCT|GCAGTATTTT 1920|
|GGGCAGGCGC|TGAGTGGGGG|TCAGGACCTC|ACCCAGGATG|GACTGATGGA|CCTGGCCGTG 1980|
|GGGGCCCGGG|GCCAGGTGCT|CCTGCTCAGG|AGTCTGCCGG|TGCTGAAAGT|GGGGGTGGCC 2040|
|ATGAGATTCA|GCCCTGTGGA|GGTGGCCAAG|GCTGTGTACC|GGTGCTGGGA|AGAGAAGCCC 2100|
|AGTGCCCTGG|AAGCTGGGGA|CGCCACCGTC|TGTCTCACCA|TCCAGAAAAG|CTCACTGGAC 2160|
|CAGCTAGGTG|ACATCCAAAG|CTCTGTCAGG|TTTGATCTGG|CACTGGACCC|AGGTCGTCTG 2220|
|ACTTCTCGTG|CCATTTTCAA|TGAAACCAAG|AACCCCACTT|TGACTCGAAG|AAAAACCCTG 2280|
|GGACTGGGGA|TTCACTGTGA|AACCCTGAAG|CTGCTTTTGC|CAGATTGTGT|GGAGGATGTG 2340|
|GTGAGCCCCA|TCATTCTGCA|CCTCAACTTC|TCACTGGTGA|GAGAGCCCAT|CCCCTCCCCC 2400|
|CAGAACCTGC|GTCCTGTGCT|GGCCGTGGGC|TCACAAGACC|TCTTCACTGC|TTCTCTCCCC 2460|
|TTCGAGAAGA|ACTGTGGGCA|AGATGGCCTC|TGTGAAGGGG|ACCTGGGTGT|CACCCTCAGC 2520|
|TTCTCAGGCC|TGCAGACCCT|GACCGTGGGG|AGCTCCCTGG|AGCTCAACGT|GATTGTGACT 2580|
|GTGTGGAACG|CAGGTGAGGA|TTCCTACGGA|ACCGTGGTCA|GCCTCTACTA|TCCAGCAGGG 2640|
|CTGTCGCACC|GACGGGTGTC|AGGAGCCCAG|AAGCAGCCCC|ATCAGAGTGC|CCTGCGCCTG 2700|
|GCATGTGAGA|CAGTGCCCAC|TGAGGATGAG|GGCCTAAGAA|GCAGCCGCTG|CAGTGTCAAC 2760|
|CACCCCATCT|TCCATGAGGG|CTCTAACGGC|ACCTTCATAG|TCACATTCGA|TGTCTCCTAC 2820|
|AAGGCCACCC|TGGGAGACAG|GATGCTTATG|AGGGCCAGTG|CAAGCAGTGA|GAACAATAAG 2880|
|GCTTCAAGCA|GCAAGGCCAC|CTTCCAGCTG|GAGCTCCCGG|TGAAGTATGC|AGTCTACACC 2940|
|ATGATCAGCA|GGCAGGAAGA|ATCCACCAAG|TACTTCAACT|TTGCAACCTC|CGATGAGAAG 3000|

| | | | | | |
|---|---|---|---|---|---|
| AAAATGAAAG | AGGCTGAGCA | TCGATACCGT | GTGAATAACC | TCAGCCAGCG | AGATCTGGCC | 3060 |
| ATCAGCATTA | ACTTCTGGGT | TCCTGTCCTG | CTGAACGGGG | TGGCTGTGTG | GGATGTGGTC | 3120 |
| ATGGAGGCCC | CATCTCAGAG | TCTCCCCTGT | GTTCAGAGA | GAAAACCTCC | CCAGCATTCT | 3180 |
| GACTTCCTGA | CCCAGATTTC | AAGAAGTCCC | ATGCTGGACT | GCTCCATTGC | TGACTGCCTG | 3240 |
| CAGTTCCGCT | GTGACGTCCC | CTCCTTCAGC | GTCCAGGAGG | AGCTGGATTT | CACCCTGAAG | 3300 |
| GGCAATCTCA | GTTTCGGCTG | GGTCCGCGAG | ACATTGCAGA | AGAAGGTGTT | GGTCGTGAGT | 3360 |
| GTGGCTGAAA | TTACGTTCGA | CACATCCGTG | TACTCCCAGC | TTCCAGGACA | GGAGGCATTT | 3420 |
| ATGAGAGCTC | AGATGGAGAT | GGTGCTAGAA | GAAGACGAGG | TCTACAATGC | CATTCCCATC | 3480 |
| ATCATGGGCA | GCTCTGTGGG | GGCTCTGCTA | CTGCTGGCGC | TCATCACAGC | CACACTGTAC | 3540 |
| AAGCTTGGCT | TCTTCAAACG | CCACTACAAG | GAAATGCTGG | AGGACAAGCC | TGAAGACACT | 3600 |
| GCCACATTCA | GTGGGGACGA | TTTCAGCTGT | GTGGCCCCAA | ATGTGCCTTT | GTCCTAATAA | 3660 |
| TCCACTTTCC | TGTTTATCTC | TACCACTGTG | GGCTGGACTT | GCTTGCAACC | ATAAATCAAC | 3720 |
| TTACATGGAA | ACAACTTCTG | CATAGATCTG | CACTGGCCTA | AGCAACCTAC | CAGGTGCTAA | 3780 |
| GCACCTTCTC | GGAGAGATAG | AGATTGTCAA | TGTTTTACA | TATCTGTCCA | TCTTTTTCAG | 3840 |
| CAATGACCCA | CTTTTTACAG | AAGCAGGCAT | GGTGCCAGCA | TAAATTTTCA | TATGCTTAAG | 3900 |
| AATTGTCACA | TGAAAAAAAA | AAAAAAAAA | AAAAAAAAAA | AAAAAAAAA | CTTTAG | 3956 |

(2) INFORMATION FOR SEQ ID NO:98:

(i) SEQUENCE CHARACTERISTICS:
        (A) LENGTH: 3785 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..3486

(xi) SEQUENCE DESCRIPTION: SEQ ID NO:98:

```
ATG  ACC  TTC  GGC  ACT  GTG  CTT  CTT  CTG  AGT  GTC  CTG  GCT  TCT  TAT  CAT        48
Met  Thr  Phe  Gly  Thr  Val  Leu  Leu  Leu  Ser  Val  Leu  Ala  Ser  Tyr  His
 1                    5                        10                       15

GGA  TTC  AAC  CTG  GAT  GTG  GAG  GAG  CCT  ACG  ATC  TTC  CAG  GAG  GAT  GCA        96
Gly  Phe  Asn  Leu  Asp  Val  Glu  Glu  Pro  Thr  Ile  Phe  Gln  Glu  Asp  Ala
               20                        25                       30

GGC  GGC  TTT  GGG  CAG  AGC  GTG  GTG  CAG  TTC  GGT  GGA  TCT  CGA  CTC  GTG       144
Gly  Gly  Phe  Gly  Gln  Ser  Val  Val  Gln  Phe  Gly  Gly  Ser  Arg  Leu  Val
         35                        40                       45

GTG  GGA  GCA  CCC  CTG  GAG  GTG  GTG  GCG  GCC  AAC  CAG  ACG  GGA  CGG  CTG       192
Val  Gly  Ala  Pro  Leu  Glu  Val  Val  Ala  Ala  Asn  Gln  Thr  Gly  Arg  Leu
     50                        55                       60

TAT  GAC  TGC  GCA  GCT  GCC  ACC  GGC  ATG  TGC  CAG  CCC  ATC  CCG  CTG  CAC       240
Tyr  Asp  Cys  Ala  Ala  Ala  Thr  Gly  Met  Cys  Gln  Pro  Ile  Pro  Leu  His
 65                   70                        75                             80

ATC  CGC  CCT  GAG  GCC  GTG  AAC  ATG  TCC  TTG  GGC  CTG  ACC  CTG  GCA  GCC       288
Ile  Arg  Pro  Glu  Ala  Val  Asn  Met  Ser  Leu  Gly  Leu  Thr  Leu  Ala  Ala
                     85                        90                       95

TCC  ACC  AAC  GGC  TCC  CGG  CTC  CTG  GCC  TGT  GGC  CCG  ACC  CTG  CAC  AGA       336
Ser  Thr  Asn  Gly  Ser  Arg  Leu  Leu  Ala  Cys  Gly  Pro  Thr  Leu  His  Arg
              100                       105                     110

GTC  TGT  GGG  GAG  AAC  TCA  TAC  TCA  AAG  GGT  TCC  TGC  CTC  CTG  CTG  GGC       384
Val  Cys  Gly  Glu  Asn  Ser  Tyr  Ser  Lys  Gly  Ser  Cys  Leu  Leu  Leu  Gly
```

```
                115                         120                              125
TCG CGC TGG GAG ATC ATC CAG ACA GTC CCC GAC GCC ACG CCA GAG TGT        432
Ser Arg Trp Glu Ile Ile Gln Thr Val Pro Asp Ala Thr Pro Glu Cys
    130                 135                     140

CCA CAT CAA GAG ATG GAC ATC GTC TTC CTG ATT GAC GGC TCT GGA AGC        480
Pro His Gln Glu Met Asp Ile Val Phe Leu Ile Asp Gly Ser Gly Ser
145                     150                     155                 160

ATT GAC CAA AAT GAC TTT AAC CAG ATG AAG GGC TTT GTC CAA GCT GTC        528
Ile Asp Gln Asn Asp Phe Asn Gln Met Lys Gly Phe Val Gln Ala Val
                    165                     170                 175

ATG GGC CAG TTT GAG GGC ACT GAC ACC CTG TTT GCA CTG ATG CAG TAC        576
Met Gly Gln Phe Glu Gly Thr Asp Thr Leu Phe Ala Leu Met Gln Tyr
            180                     185                 190

TCA AAC CTC CTG AAG ATC CAC TTC ACC TTC ACC CAA TTC CGG ACC AGC        624
Ser Asn Leu Leu Lys Ile His Phe Thr Phe Thr Gln Phe Arg Thr Ser
        195                     200                 205

CCG AGC CAG CAG AGC CTG GTG GAT CCC ATC GTC CAA CTG AAA GGC CTG        672
Pro Ser Gln Gln Ser Leu Val Asp Pro Ile Val Gln Leu Lys Gly Leu
    210                     215                 220

ACG TTC ACG GCC ACG GGC ATC CTG ACA GTG GTG ACA CAG CTA TTT CAT        720
Thr Phe Thr Ala Thr Gly Ile Leu Thr Val Val Thr Gln Leu Phe His
225                     230                     235                 240

CAT AAG AAT GGG GCC CGA AAA AGT GCC AAG AAG ATC CTC ATT GTC ATC        768
His Lys Asn Gly Ala Arg Lys Ser Ala Lys Lys Ile Leu Ile Val Ile
                    245                     250                 255

ACA GAT GGG CAG AAG TAC AAA GAC CCC CTG GAA TAC AGT GAT GTC ATC        816
Thr Asp Gly Gln Lys Tyr Lys Asp Pro Leu Glu Tyr Ser Asp Val Ile
            260                     265                 270

CCC CAG GCA GAG AAG GCT GGC ATC ATC CGC TAC GCT ATC GGG GTG GGA        864
Pro Gln Ala Glu Lys Ala Gly Ile Ile Arg Tyr Ala Ile Gly Val Gly
        275                     280                 285

CAC GCT TTC CAG GGA CCC ACT GCC AGG CAG GAG CTG AAT ACC ATC AGC        912
His Ala Phe Gln Gly Pro Thr Ala Arg Gln Glu Leu Asn Thr Ile Ser
    290                     295                 300

TCA GCG CCT CCG CAG GAC CAC GTG TTC AAG GTG GAC AAC TTT GCA GCC        960
Ser Ala Pro Pro Gln Asp His Val Phe Lys Val Asp Asn Phe Ala Ala
305                     310                     315                 320

CTT GGC AGC ATC CAG AAG CAG CTG CAG GAG AAG ATC TAT GCA GTT GAG       1008
Leu Gly Ser Ile Gln Lys Gln Leu Gln Glu Lys Ile Tyr Ala Val Glu
                    325                     330                 335

GGA ACC CAG TCC AGG GCA AGC AGC TCC TTC CAG CAC GAG ATG TCC CAA       1056
Gly Thr Gln Ser Arg Ala Ser Ser Ser Phe Gln His Glu Met Ser Gln
            340                     345                 350

GAA GGC TTC AGC ACA GCC CTC ACA ATG GAT GGC CTC TTC CTG GGG GCT       1104
Glu Gly Phe Ser Thr Ala Leu Thr Met Asp Gly Leu Phe Leu Gly Ala
        355                     360                 365

GTG GGG AGC TTT AGC TGG TCT GGA GGT GCC TTC CTG TAT CCC CCA AAT       1152
Val Gly Ser Phe Ser Trp Ser Gly Gly Ala Phe Leu Tyr Pro Pro Asn
    370                     375                 380

ATG AGC CCC ACC TTC ATC AAC ATG TCT CAG GAG AAT GTG GAC ATG AGG       1200
Met Ser Pro Thr Phe Ile Asn Met Ser Gln Glu Asn Val Asp Met Arg
385                     390                     395                 400

GAC TCT TAC CTG GGT TAC TCC ACC GAG CTA GCC CTG TGG AAG GGG GTA       1248
Asp Ser Tyr Leu Gly Tyr Ser Thr Glu Leu Ala Leu Trp Lys Gly Val
                    405                     410                 415

CAG AAC CTG GTC CTG GGG GCC CCC CGC TAC CAG CAT ACC GGG AAG GCT       1296
Gln Asn Leu Val Leu Gly Ala Pro Arg Tyr Gln His Thr Gly Lys Ala
            420                     425                 430

GTC ATC TTC ACC CAG GTG TCC AGG CAA TGG AGG AAG AAG GCC GAA GTC       1344
Val Ile Phe Thr Gln Val Ser Arg Gln Trp Arg Lys Lys Ala Glu Val
```

|   |   |   |   |   |   |   |   |   |   |   |   |   |   |   |   |      |
|---|---|---|---|---|---|---|---|---|---|---|---|---|---|---|---|------|
|   |   |   |   | 435 |   |   |   |   | 440 |   |   |   |   | 445 |   |      |
| ACA | GGG | ACG | CAG | ATC | GGC | TCC | TAC | TTC | GGG | GCC | TCC | CTC | TGC | TCC | GTG | 1392 |
| Thr | Gly | Thr | Gln | Ile | Gly | Ser | Tyr | Phe | Gly | Ala | Ser | Leu | Cys | Ser | Val |      |
|     | 450 |     |     |     | 455 |     |     |     |     | 460 |     |     |     |     |     |      |
| GAT | GTG | GAC | AGC | GAT | GGC | AGC | ACC | GAC | CTG | ATC | CTC | ATT | GGG | GCC | CCC | 1440 |
| Asp | Val | Asp | Ser | Asp | Gly | Ser | Thr | Asp | Leu | Ile | Leu | Ile | Gly | Ala | Pro |      |
| 465 |     |     |     |     | 470 |     |     |     |     | 475 |     |     |     |     | 480 |      |
| CAT | TAC | TAT | GAG | CAG | ACC | CGA | GGG | GGC | CAG | GTG | TCC | GTG | TGT | CCC | TTG | 1488 |
| His | Tyr | Tyr | Glu | Gln | Thr | Arg | Gly | Gly | Gln | Val | Ser | Val | Cys | Pro | Leu |      |
|     |     |     |     | 485 |     |     |     |     | 490 |     |     |     |     | 495 |     |      |
| CCT | AGG | GGG | AGG | GTG | CAG | TGG | CAG | TGT | GAC | GCT | GTT | CTC | CGT | GGT | GAG | 1536 |
| Pro | Arg | Gly | Arg | Val | Gln | Trp | Gln | Cys | Asp | Ala | Val | Leu | Arg | Gly | Glu |      |
|     |     |     | 500 |     |     |     |     | 505 |     |     |     |     | 510 |     |     |      |
| CAG | GGC | CAC | CCC | TGG | GGC | CGC | TTT | GGG | GCA | GCC | CTG | ACA | GTG | TTG | GGG | 1584 |
| Gln | Gly | His | Pro | Trp | Gly | Arg | Phe | Gly | Ala | Ala | Leu | Thr | Val | Leu | Gly |      |
|     |     | 515 |     |     |     |     | 520 |     |     |     |     | 525 |     |     |     |      |
| GAT | GTG | AAT | GAG | GAC | AAG | CTG | ATA | GAC | GTG | GCC | ATT | GGG | GCC | CCG | GGA | 1632 |
| Asp | Val | Asn | Glu | Asp | Lys | Leu | Ile | Asp | Val | Ala | Ile | Gly | Ala | Pro | Gly |      |
|     | 530 |     |     |     | 535 |     |     |     |     | 540 |     |     |     |     |     |      |
| GAG | CAG | GAG | AAC | CGG | GGT | GCT | GTC | TAC | CTG | TTT | CAC | GGA | GCC | TCA | GAA | 1680 |
| Glu | Gln | Glu | Asn | Arg | Gly | Ala | Val | Tyr | Leu | Phe | His | Gly | Ala | Ser | Glu |      |
| 545 |     |     |     |     | 550 |     |     |     |     | 555 |     |     |     |     | 560 |      |
| TCC | GGC | ATC | AGC | CCC | TCC | CAC | AGC | CAG | CGG | ATT | GCC | AGC | TCC | CAG | CTC | 1728 |
| Ser | Gly | Ile | Ser | Pro | Ser | His | Ser | Gln | Arg | Ile | Ala | Ser | Ser | Gln | Leu |      |
|     |     |     |     | 565 |     |     |     |     | 570 |     |     |     |     | 575 |     |      |
| TCC | CCC | AGG | CTG | CAG | TAT | TTT | GGG | CAG | GCG | CTG | AGT | GGG | GGT | CAG | GAC | 1776 |
| Ser | Pro | Arg | Leu | Gln | Tyr | Phe | Gly | Gln | Ala | Leu | Ser | Gly | Gly | Gln | Asp |      |
|     |     |     | 580 |     |     |     |     | 585 |     |     |     |     | 590 |     |     |      |
| CTC | ACC | CAG | GAT | GGA | CTG | ATG | GAC | CTG | GCC | GTG | GGG | GCC | CGG | GGC | CAG | 1824 |
| Leu | Thr | Gln | Asp | Gly | Leu | Met | Asp | Leu | Ala | Val | Gly | Ala | Arg | Gly | Gln |      |
|     |     | 595 |     |     |     |     | 600 |     |     |     |     | 605 |     |     |     |      |
| GTG | CTC | CTG | CTC | AGG | AGT | CTG | CCG | GTG | CTG | AAA | GTG | GGG | GTG | GCC | ATG | 1872 |
| Val | Leu | Leu | Leu | Arg | Ser | Leu | Pro | Val | Leu | Lys | Val | Gly | Val | Ala | Met |      |
|     |     | 610 |     |     |     |     | 615 |     |     |     |     | 620 |     |     |     |      |
| AGA | TTC | AGC | CCT | GTG | GAG | GTG | GCC | AAG | GCT | GTG | TAC | CGG | TGC | TGG | GAA | 1920 |
| Arg | Phe | Ser | Pro | Val | Glu | Val | Ala | Lys | Ala | Val | Tyr | Arg | Cys | Trp | Glu |      |
| 625 |     |     |     |     | 630 |     |     |     |     | 635 |     |     |     |     | 640 |      |
| GAG | AAG | CCC | AGT | GCC | CTG | GAA | GCT | GGG | GAC | GCC | ACC | GTC | TGT | CTC | ACC | 1968 |
| Glu | Lys | Pro | Ser | Ala | Leu | Glu | Ala | Gly | Asp | Ala | Thr | Val | Cys | Leu | Thr |      |
|     |     |     |     | 645 |     |     |     |     | 650 |     |     |     |     | 655 |     |      |
| ATC | CAG | AAA | AGC | TCA | CTG | GAC | CAG | CTA | GGT | GAC | ATC | CAA | AGC | TCT | GTC | 2016 |
| Ile | Gln | Lys | Ser | Ser | Leu | Asp | Gln | Leu | Gly | Asp | Ile | Gln | Ser | Ser | Val |      |
|     |     |     | 660 |     |     |     |     | 665 |     |     |     |     | 670 |     |     |      |
| AGG | TTT | GAT | CTG | GCA | CTG | GAC | CCA | GGT | CGT | CTG | ACT | TCT | CGT | GCC | ATT | 2064 |
| Arg | Phe | Asp | Leu | Ala | Leu | Asp | Pro | Gly | Arg | Leu | Thr | Ser | Arg | Ala | Ile |      |
|     |     | 675 |     |     |     |     | 680 |     |     |     |     | 685 |     |     |     |      |
| TTC | AAT | GAA | ACC | AAG | AAC | CCC | ACT | TTG | ACT | CGA | AGA | AAA | ACC | CTG | GGA | 2112 |
| Phe | Asn | Glu | Thr | Lys | Asn | Pro | Thr | Leu | Thr | Arg | Arg | Lys | Thr | Leu | Gly |      |
|     |     | 690 |     |     |     |     | 695 |     |     |     |     | 700 |     |     |     |      |
| CTG | GGG | ATT | CAC | TGT | GAA | ACC | CTG | AAG | CTG | CTT | TTG | CCA | GAT | TGT | GTG | 2160 |
| Leu | Gly | Ile | His | Cys | Glu | Thr | Leu | Lys | Leu | Leu | Leu | Pro | Asp | Cys | Val |      |
| 705 |     |     |     |     | 710 |     |     |     |     | 715 |     |     |     |     | 720 |      |
| GAG | GAT | GTG | GTG | AGC | CCC | ATC | ATT | CTG | CAC | CTC | AAC | TTC | TCA | CTG | GTG | 2208 |
| Glu | Asp | Val | Val | Ser | Pro | Ile | Ile | Leu | His | Leu | Asn | Phe | Ser | Leu | Val |      |
|     |     |     |     | 725 |     |     |     |     | 730 |     |     |     |     | 735 |     |      |
| AGA | GAG | CCC | ATC | CCC | TCC | CCC | CAG | AAC | CTG | CGT | CCT | GTG | CTG | GCC | GTG | 2256 |
| Arg | Glu | Pro | Ile | Pro | Ser | Pro | Gln | Asn | Leu | Arg | Pro | Val | Leu | Ala | Val |      |
|     |     |     | 740 |     |     |     |     | 745 |     |     |     |     | 750 |     |     |      |
| GGC | TCA | CAA | GAC | CTC | TTC | ACT | GCT | TCT | CTC | CCC | TTC | GAG | AAG | AAC | TGT | 2304 |
| Gly | Ser | Gln | Asp | Leu | Phe | Thr | Ala | Ser | Leu | Pro | Phe | Glu | Lys | Asn | Cys |      |

-continued

|  |  |  | 755 |  |  |  |  | 760 |  |  |  |  | 765 |  |  |  |
|---|---|---|---|---|---|---|---|---|---|---|---|---|---|---|---|---|
| GGG | CAA | GAT | GGC | CTC | TGT | GAA | GGG | GAC | CTG | GGT | GTC | ACC | CTC | AGC | TTC | 2352 |
| Gly | Gln | Asp | Gly | Leu | Cys | Glu | Gly | Asp | Leu | Gly | Val | Thr | Leu | Ser | Phe |  |
|  | 770 |  |  |  | 775 |  |  |  |  | 780 |  |  |  |  |  |  |
| TCA | GGC | CTG | CAG | ACC | CTG | ACC | GTG | GGG | AGC | TCC | CTG | GAG | CTC | AAC | GTG | 2400 |
| Ser | Gly | Leu | Gln | Thr | Leu | Thr | Val | Gly | Ser | Ser | Leu | Glu | Leu | Asn | Val |  |
| 785 |  |  |  |  | 790 |  |  |  |  | 795 |  |  |  |  | 800 |  |
| ATT | GTG | ACT | GTG | TGG | AAC | GCA | GGT | GAG | GAT | TCC | TAC | GGA | ACC | GTG | GTC | 2448 |
| Ile | Val | Thr | Val | Trp | Asn | Ala | Gly | Glu | Asp | Ser | Tyr | Gly | Thr | Val | Val |  |
|  |  |  |  | 805 |  |  |  |  | 810 |  |  |  |  | 815 |  |  |
| AGC | CTC | TAC | TAT | CCA | GCA | GGG | CTG | TCG | CAC | CGA | CGG | GTG | TCA | GGA | GCC | 2496 |
| Ser | Leu | Tyr | Tyr | Pro | Ala | Gly | Leu | Ser | His | Arg | Arg | Val | Ser | Gly | Ala |  |
|  |  |  | 820 |  |  |  |  | 825 |  |  |  |  | 830 |  |  |  |
| CAG | AAG | CAG | CCC | CAT | CAG | AGT | GCC | CTG | CGC | CTG | GCA | TGT | GAG | ACA | GTG | 2544 |
| Gln | Lys | Gln | Pro | His | Gln | Ser | Ala | Leu | Arg | Leu | Ala | Cys | Glu | Thr | Val |  |
|  |  | 835 |  |  |  |  | 840 |  |  |  |  | 845 |  |  |  |  |
| CCC | ACT | GAG | GAT | GAG | GGC | CTA | AGA | AGC | AGC | CGC | TGC | AGT | GTC | AAC | CAC | 2592 |
| Pro | Thr | Glu | Asp | Glu | Gly | Leu | Arg | Ser | Ser | Arg | Cys | Ser | Val | Asn | His |  |
|  | 850 |  |  |  |  | 855 |  |  |  |  | 860 |  |  |  |  |  |
| CCC | ATC | TTC | CAT | GAG | GGC | TCT | AAC | GGC | ACC | TTC | ATA | GTC | ACA | TTC | GAT | 2640 |
| Pro | Ile | Phe | His | Glu | Gly | Ser | Asn | Gly | Thr | Phe | Ile | Val | Thr | Phe | Asp |  |
| 865 |  |  |  |  | 870 |  |  |  |  | 875 |  |  |  |  | 880 |  |
| GTC | TCC | TAC | AAG | GCC | ACC | CTG | GGA | GAC | AGG | ATG | CTT | ATG | AGG | GCC | AGT | 2688 |
| Val | Ser | Tyr | Lys | Ala | Thr | Leu | Gly | Asp | Arg | Met | Leu | Met | Arg | Ala | Ser |  |
|  |  |  |  | 885 |  |  |  |  | 890 |  |  |  |  | 895 |  |  |
| GCA | AGC | AGT | GAG | AAC | AAT | AAG | GCT | TCA | AGC | AGC | AAG | GCC | ACC | TTC | CAG | 2736 |
| Ala | Ser | Ser | Glu | Asn | Asn | Lys | Ala | Ser | Ser | Ser | Lys | Ala | Thr | Phe | Gln |  |
|  |  |  | 900 |  |  |  |  | 905 |  |  |  |  | 910 |  |  |  |
| CTG | GAG | CTC | CCG | GTG | AAG | TAT | GCA | GTC | TAC | ACC | ATG | ATC | AGC | AGG | CAG | 2784 |
| Leu | Glu | Leu | Pro | Val | Lys | Tyr | Ala | Val | Tyr | Thr | Met | Ile | Ser | Arg | Gln |  |
|  |  | 915 |  |  |  |  | 920 |  |  |  |  | 925 |  |  |  |  |
| GAA | GAA | TCC | ACC | AAG | TAC | TTC | AAC | TTT | GCA | ACC | TCC | GAT | GAG | AAG | AAA | 2832 |
| Glu | Glu | Ser | Thr | Lys | Tyr | Phe | Asn | Phe | Ala | Thr | Ser | Asp | Glu | Lys | Lys |  |
|  | 930 |  |  |  |  | 935 |  |  |  |  | 940 |  |  |  |  |  |
| ATG | AAA | GAG | GCT | GAG | CAT | CGA | TAC | CGT | GTG | AAT | AAC | CTC | AGC | CAG | CGA | 2880 |
| Met | Lys | Glu | Ala | Glu | His | Arg | Tyr | Arg | Val | Asn | Asn | Leu | Ser | Gln | Arg |  |
| 945 |  |  |  |  | 950 |  |  |  |  | 955 |  |  |  |  | 960 |  |
| GAT | CTG | GCC | ATC | AGC | ATT | AAC | TTC | TGG | GTT | CCT | GTC | CTG | CTG | AAC | GGG | 2928 |
| Asp | Leu | Ala | Ile | Ser | Ile | Asn | Phe | Trp | Val | Pro | Val | Leu | Leu | Asn | Gly |  |
|  |  |  |  | 965 |  |  |  |  | 970 |  |  |  |  | 975 |  |  |
| GTG | GCT | GTG | TGG | GAT | GTG | GTC | ATG | GAG | GCC | CCA | TCT | CAG | AGT | CTC | CCC | 2976 |
| Val | Ala | Val | Trp | Asp | Val | Val | Met | Glu | Ala | Pro | Ser | Gln | Ser | Leu | Pro |  |
|  |  |  | 980 |  |  |  |  | 985 |  |  |  |  | 990 |  |  |  |
| TGT | GTT | TCA | GAG | AGA | AAA | CCT | CCC | CAG | CAT | TCT | GAC | TTC | CTG | ACC | CAG | 3024 |
| Cys | Val | Ser | Glu | Arg | Lys | Pro | Pro | Gln | His | Ser | Asp | Phe | Leu | Thr | Gln |  |
|  |  | 995 |  |  |  |  | 1000 |  |  |  |  | 1005 |  |  |  |  |
| ATT | TCA | AGA | AGT | CCC | ATG | CTG | GAC | TGC | TCC | ATT | GCT | GAC | TGC | CTG | CAG | 3072 |
| Ile | Ser | Arg | Ser | Pro | Met | Leu | Asp | Cys | Ser | Ile | Ala | Asp | Cys | Leu | Gln |  |
|  | 1010 |  |  |  |  | 1015 |  |  |  |  | 1020 |  |  |  |  |  |
| TTC | CGC | TGT | GAC | GTC | CCC | TCC | TTC | AGC | GTC | CAG | GAG | GAG | CTG | GAT | TTC | 3120 |
| Phe | Arg | Cys | Asp | Val | Pro | Ser | Phe | Ser | Val | Gln | Glu | Glu | Leu | Asp | Phe |  |
| 1025 |  |  |  |  | 1030 |  |  |  |  | 1035 |  |  |  |  | 1040 |  |
| ACC | CTG | AAG | GGC | AAT | CTC | AGT | TTC | GGC | TGG | GTC | CGC | GAG | ACA | TTG | CAG | 3168 |
| Thr | Leu | Lys | Gly | Asn | Leu | Ser | Phe | Gly | Trp | Val | Arg | Glu | Thr | Leu | Gln |  |
|  |  |  |  | 1045 |  |  |  |  | 1050 |  |  |  |  | 1055 |  |  |
| AAG | AAG | GTG | TTG | GTC | GTG | AGT | GTG | GCT | GAA | ATT | ACG | TTC | GAC | ACA | TCC | 3216 |
| Lys | Lys | Val | Leu | Val | Val | Ser | Val | Ala | Glu | Ile | Thr | Phe | Asp | Thr | Ser |  |
|  |  |  | 1060 |  |  |  |  | 1065 |  |  |  |  | 1070 |  |  |  |
| GTG | TAC | TCC | CAG | CTT | CCA | GGA | CAG | GAG | GCA | TTT | ATG | AGA | GCT | CAG | ATG | 3264 |
| Val | Tyr | Ser | Gln | Leu | Pro | Gly | Gln | Glu | Ala | Phe | Met | Arg | Ala | Gln | Met |  |

```
                            1075                       1080                        1085
GAG  ATG  GTG  CTA  GAA  GAA  GAC  GAG  GTC  TAC  AAT  GCC  ATT  CCC  ATC  ATC         3312
Glu  Met  Val  Leu  Glu  Glu  Asp  Glu  Val  Tyr  Asn  Ala  Ile  Pro  Ile  Ile
     1090                     1095                     1100

ATG  GGC  AGC  TCT  GTG  GGG  GCT  CTG  CTA  CTG  CTG  GCG  CTC  ATC  ACA  GCC         3360
Met  Gly  Ser  Ser  Val  Gly  Ala  Leu  Leu  Leu  Leu  Ala  Leu  Ile  Thr  Ala
1105                     1110                     1115                     1120

ACA  CTG  TAC  AAG  CTT  GGC  TTC  TTC  AAA  CGC  CAC  TAC  AAG  GAA  ATG  CTG         3408
Thr  Leu  Tyr  Lys  Leu  Gly  Phe  Phe  Lys  Arg  His  Tyr  Lys  Glu  Met  Leu
               1125                     1130                     1135

GAG  GAC  AAG  CCT  GAA  GAC  ACT  GCC  ACA  TTC  AGT  GGG  GAC  GAT  TTC  AGC         3456
Glu  Asp  Lys  Pro  Glu  Asp  Thr  Ala  Thr  Phe  Ser  Gly  Asp  Asp  Phe  Ser
               1140                     1145                     1150

TGT  GTG  GCC  CCA  AAT  GTG  CCT  TTG  TCC  TAATAATCCA  CTTTCCTGTT                    3503
Cys  Val  Ala  Pro  Asn  Val  Pro  Leu  Ser
          1155                     1160

TATCTCTACC  ACTGTGGGCT  GGACTTGCTT  GCAACCATAA  ATCAACTTAC  ATGGAAACAA                 3563

CTTCTGCATA  GATCTGCACT  GGCCTAAGCA  ACCTACCAGG  TGCTAAGCAC  CTTCTCGGAG                 3623

AGATAGAGAT  TGTCAATGTT  TTTACATATC  TGTCCATCTT  TTTCAGCAAT  GACCCACTTT                 3683

TTACAGAAGC  AGGCATGGTG  CCAGCATAAA  TTTTCATATG  CTTAAGAATT  GTCACATGAA                 3743

AAAAAAAAAA  AAAAAAAAAA  AAAAAAAAAA  AAAAAACTTT  AG                                     3785
```

( 2 ) INFORMATION FOR SEQ ID NO:99:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:99:

```
Met  Thr  Phe  Gly  Thr  Val  Leu  Leu  Leu  Ser  Val  Leu  Ala  Ser  Tyr  His
 1                  5                        10                       15

Gly  Phe  Asn  Leu  Asp  Val  Glu  Glu  Pro  Thr  Ile  Phe  Gln  Glu  Asp  Ala
               20                       25                       30

Gly  Gly  Phe  Gly  Gln  Ser  Val  Val  Gln  Phe  Gly  Gly  Ser  Arg  Leu  Val
               35                       40                       45

Val  Gly  Ala  Pro  Leu  Glu  Val  Val  Ala  Ala  Asn  Gln  Thr  Gly  Arg  Leu
     50                       55                       60

Tyr  Asp  Cys  Ala  Ala  Ala  Thr  Gly  Met  Cys  Gln  Pro  Ile  Pro  Leu  His
 65                           70                       75                       80

Ile  Arg  Pro  Glu  Ala  Val  Asn  Met  Ser  Leu  Gly  Leu  Thr  Leu  Ala  Ala
                    85                       90                       95

Ser  Thr  Asn  Gly  Ser  Arg  Leu  Leu  Ala  Cys  Gly  Pro  Thr  Leu  His  Arg
                    100                      105                      110

Val  Cys  Gly  Glu  Asn  Ser  Tyr  Ser  Lys  Gly  Ser  Cys  Leu  Leu  Leu  Gly
          115                      120                      125

Ser  Arg  Trp  Glu  Ile  Ile  Gln  Thr  Val  Pro  Asp  Ala  Thr  Pro  Glu  Cys
     130                      135                      140

Pro  His  Gln  Glu  Met  Asp  Ile  Val  Phe  Leu  Ile  Asp  Gly  Ser  Gly  Ser
145                      150                      155                      160

Ile  Asp  Gln  Asn  Asp  Phe  Asn  Gln  Met  Lys  Gly  Phe  Val  Gln  Ala  Val
                    165                      170                      175

Met  Gly  Gln  Phe  Glu  Gly  Thr  Asp  Thr  Leu  Phe  Ala  Leu  Met  Gln  Tyr
                    180                      185                      190
```

```
Ser  Asn  Leu  Leu  Lys  Ile  His  Phe  Thr  Phe  Thr  Gln  Phe  Arg  Thr  Ser
          195                      200                      205

Pro  Ser  Gln  Gln  Ser  Leu  Val  Asp  Pro  Ile  Val  Gln  Leu  Lys  Gly  Leu
     210                      215                      220

Thr  Phe  Thr  Ala  Thr  Gly  Ile  Leu  Thr  Val  Val  Thr  Gln  Leu  Phe  His
225                           230                 235                           240

His  Lys  Asn  Gly  Ala  Arg  Lys  Ser  Ala  Lys  Lys  Ile  Leu  Ile  Val  Ile
                    245                      250                      255

Thr  Asp  Gly  Gln  Lys  Tyr  Lys  Asp  Pro  Leu  Glu  Tyr  Ser  Asp  Val  Ile
               260                      265                      270

Pro  Gln  Ala  Glu  Lys  Ala  Gly  Ile  Ile  Arg  Tyr  Ala  Ile  Gly  Val  Gly
               275                      280                      285

His  Ala  Phe  Gln  Gly  Pro  Thr  Ala  Arg  Gln  Glu  Leu  Asn  Thr  Ile  Ser
     290                      295                      300

Ser  Ala  Pro  Pro  Gln  Asp  His  Val  Phe  Lys  Val  Asp  Asn  Phe  Ala  Ala
305                      310                      315                           320

Leu  Gly  Ser  Ile  Gln  Lys  Gln  Leu  Gln  Glu  Lys  Ile  Tyr  Ala  Val  Glu
                    325                      330                      335

Gly  Thr  Gln  Ser  Arg  Ala  Ser  Ser  Ser  Phe  Gln  His  Glu  Met  Ser  Gln
               340                      345                      350

Glu  Gly  Phe  Ser  Thr  Ala  Leu  Thr  Met  Asp  Gly  Leu  Phe  Leu  Gly  Ala
          355                      360                      365

Val  Gly  Ser  Phe  Ser  Trp  Ser  Gly  Ala  Phe  Leu  Tyr  Pro  Pro  Asn
     370                      375                      380

Met  Ser  Pro  Thr  Phe  Ile  Asn  Met  Ser  Gln  Glu  Asn  Val  Asp  Met  Arg
385                           390                 395                           400

Asp  Ser  Tyr  Leu  Gly  Tyr  Ser  Thr  Glu  Leu  Ala  Leu  Trp  Lys  Gly  Val
               405                      410                      415

Gln  Asn  Leu  Val  Leu  Gly  Ala  Pro  Arg  Tyr  Gln  His  Thr  Gly  Lys  Ala
               420                      425                      430

Val  Ile  Phe  Thr  Gln  Val  Ser  Arg  Gln  Trp  Arg  Lys  Lys  Ala  Glu  Val
          435                      440                      445

Thr  Gly  Thr  Gln  Ile  Gly  Ser  Tyr  Phe  Gly  Ala  Ser  Leu  Cys  Ser  Val
     450                      455                      460

Asp  Val  Asp  Ser  Asp  Gly  Ser  Thr  Asp  Leu  Ile  Leu  Ile  Gly  Ala  Pro
465                      470                      475                           480

His  Tyr  Tyr  Glu  Gln  Thr  Arg  Gly  Gly  Gln  Val  Ser  Val  Cys  Pro  Leu
               485                      490                      495

Pro  Arg  Gly  Arg  Val  Gln  Trp  Gln  Cys  Asp  Ala  Val  Leu  Arg  Gly  Glu
               500                      505                      510

Gln  Gly  His  Pro  Trp  Gly  Arg  Phe  Gly  Ala  Ala  Leu  Thr  Val  Leu  Gly
          515                      520                      525

Asp  Val  Asn  Glu  Asp  Lys  Leu  Ile  Asp  Val  Ala  Ile  Gly  Ala  Pro  Gly
     530                      535                      540

Glu  Gln  Glu  Asn  Arg  Gly  Ala  Val  Tyr  Leu  Phe  His  Gly  Ala  Ser  Glu
545                      550                      555                           560

Ser  Gly  Ile  Ser  Pro  Ser  His  Ser  Gln  Arg  Ile  Ala  Ser  Ser  Gln  Leu
                    565                      570                      575

Ser  Pro  Arg  Leu  Gln  Tyr  Phe  Gly  Gln  Ala  Leu  Ser  Gly  Gly  Gln  Asp
               580                      585                      590

Leu  Thr  Gln  Asp  Gly  Leu  Met  Asp  Leu  Ala  Val  Gly  Ala  Arg  Gly  Gln
          595                      600                      605

Val  Leu  Leu  Leu  Arg  Ser  Leu  Pro  Val  Leu  Lys  Val  Gly  Val  Ala  Met
610                      615                      620
```

| | | | | | | | | | | | | | | |
|---|---|---|---|---|---|---|---|---|---|---|---|---|---|---|
| Arg | Phe | Ser | Pro | Val | Glu | Val | Ala | Lys | Ala | Val | Tyr | Arg | Cys | Trp | Glu |
| 625 | | | | | 630 | | | | 635 | | | | | | 640 |
| Glu | Lys | Pro | Ser | Ala | Leu | Glu | Ala | Gly | Asp | Ala | Thr | Val | Cys | Leu | Thr |
| | | | | 645 | | | | | 650 | | | | | 655 | |
| Ile | Gln | Lys | Ser | Ser | Leu | Asp | Gln | Leu | Gly | Asp | Ile | Gln | Ser | Ser | Val |
| | | | 660 | | | | | 665 | | | | | 670 | | |
| Arg | Phe | Asp | Leu | Ala | Leu | Asp | Pro | Gly | Arg | Leu | Thr | Ser | Arg | Ala | Ile |
| | | 675 | | | | | 680 | | | | | 685 | | | |
| Phe | Asn | Glu | Thr | Lys | Asn | Pro | Thr | Leu | Thr | Arg | Arg | Lys | Thr | Leu | Gly |
| | 690 | | | | | 695 | | | | | 700 | | | | |
| Leu | Gly | Ile | His | Cys | Glu | Thr | Leu | Lys | Leu | Leu | Leu | Pro | Asp | Cys | Val |
| 705 | | | | | 710 | | | | 715 | | | | | | 720 |
| Glu | Asp | Val | Val | Ser | Pro | Ile | Ile | Leu | His | Leu | Asn | Phe | Ser | Leu | Val |
| | | | | 725 | | | | | 730 | | | | | 735 | |
| Arg | Glu | Pro | Ile | Pro | Ser | Pro | Gln | Asn | Leu | Arg | Pro | Val | Leu | Ala | Val |
| | | | 740 | | | | | 745 | | | | | 750 | | |
| Gly | Ser | Gln | Asp | Leu | Phe | Thr | Ala | Ser | Leu | Pro | Phe | Glu | Lys | Asn | Cys |
| | | 755 | | | | | 760 | | | | | 765 | | | |
| Gly | Gln | Asp | Gly | Leu | Cys | Glu | Gly | Asp | Leu | Gly | Val | Thr | Leu | Ser | Phe |
| | 770 | | | | | 775 | | | | | 780 | | | | |
| Ser | Gly | Leu | Gln | Thr | Leu | Thr | Val | Gly | Ser | Ser | Leu | Glu | Leu | Asn | Val |
| 785 | | | | | 790 | | | | 795 | | | | | | 800 |
| Ile | Val | Thr | Val | Trp | Asn | Ala | Gly | Glu | Asp | Ser | Tyr | Gly | Thr | Val | Val |
| | | | | 805 | | | | | 810 | | | | | 815 | |
| Ser | Leu | Tyr | Tyr | Pro | Ala | Gly | Leu | Ser | His | Arg | Arg | Val | Ser | Gly | Ala |
| | | | 820 | | | | | 825 | | | | | 830 | | |
| Gln | Lys | Gln | Pro | His | Gln | Ser | Ala | Leu | Arg | Leu | Ala | Cys | Glu | Thr | Val |
| | | 835 | | | | | 840 | | | | | 845 | | | |
| Pro | Thr | Glu | Asp | Glu | Gly | Leu | Arg | Ser | Ser | Arg | Cys | Ser | Val | Asn | His |
| | 850 | | | | | 855 | | | | | 860 | | | | |
| Pro | Ile | Phe | His | Glu | Gly | Ser | Asn | Gly | Thr | Phe | Ile | Val | Thr | Phe | Asp |
| 865 | | | | | 870 | | | | 875 | | | | | | 880 |
| Val | Ser | Tyr | Lys | Ala | Thr | Leu | Gly | Asp | Arg | Met | Leu | Met | Arg | Ala | Ser |
| | | | | 885 | | | | | 890 | | | | | 895 | |
| Ala | Ser | Ser | Glu | Asn | Asn | Lys | Ala | Ser | Ser | Lys | Ala | Thr | Phe | Gln |
| | | | 900 | | | | | 905 | | | | | 910 | | |
| Leu | Glu | Leu | Pro | Val | Lys | Tyr | Ala | Val | Tyr | Thr | Met | Ile | Ser | Arg | Gln |
| | | | 915 | | | | | 920 | | | | | 925 | | |
| Glu | Glu | Ser | Thr | Lys | Tyr | Phe | Asn | Phe | Ala | Thr | Ser | Asp | Glu | Lys | Lys |
| | 930 | | | | | 935 | | | | | 940 | | | | |
| Met | Lys | Glu | Ala | Glu | His | Arg | Tyr | Arg | Val | Asn | Asn | Leu | Ser | Gln | Arg |
| 945 | | | | | 950 | | | | 955 | | | | | | 960 |
| Asp | Leu | Ala | Ile | Ser | Ile | Asn | Phe | Trp | Val | Pro | Val | Leu | Leu | Asn | Gly |
| | | | | 965 | | | | | 970 | | | | | 975 | |
| Val | Ala | Val | Trp | Asp | Val | Val | Met | Glu | Ala | Pro | Ser | Gln | Ser | Leu | Pro |
| | | | 980 | | | | | 985 | | | | | 990 | | |
| Cys | Val | Ser | Glu | Arg | Lys | Pro | Pro | Gln | His | Ser | Asp | Phe | Leu | Thr | Gln |
| | | 995 | | | | | 1000 | | | | | 1005 | | | |
| Ile | Ser | Arg | Ser | Pro | Met | Leu | Asp | Cys | Ser | Ile | Ala | Asp | Cys | Leu | Gln |
| | 1010 | | | | | 1015 | | | | | 1020 | | | | |
| Phe | Arg | Cys | Asp | Val | Pro | Ser | Phe | Ser | Val | Gln | Glu | Glu | Leu | Asp | Phe |
| 1025 | | | | | 1030 | | | | 1035 | | | | | | 1040 |
| Thr | Leu | Lys | Gly | Asn | Leu | Ser | Phe | Gly | Trp | Val | Arg | Glu | Thr | Leu | Gln |

|   |   |   |   |   |   |   |   |   |   |   |   |   |   |   |
|---|---|---|---|---|---|---|---|---|---|---|---|---|---|---|
|   |   |   | 1045 |   |   |   |   | 1050 |   |   |   |   | 1055 |   |
| Lys | Lys | Val | Leu | Val | Val | Ser | Val | Ala | Glu | Ile | Thr | Phe | Asp | Thr | Ser |
|   |   |   | 1060 |   |   |   |   | 1065 |   |   |   |   | 1070 |   |
| Val | Tyr | Ser | Gln | Leu | Pro | Gly | Gln | Glu | Ala | Phe | Met | Arg | Ala | Gln | Met |
|   |   |   | 1075 |   |   |   |   | 1080 |   |   |   |   | 1085 |   |
| Glu | Met | Val | Leu | Glu | Glu | Asp | Glu | Val | Tyr | Asn | Ala | Ile | Pro | Ile | Ile |
|   |   |   | 1090 |   |   |   |   | 1095 |   |   |   |   | 1100 |   |
| Met | Gly | Ser | Ser | Val | Gly | Ala | Leu | Leu | Leu | Leu | Ala | Leu | Ile | Thr | Ala |
| 1105 |   |   |   |   | 1110 |   |   |   |   | 1115 |   |   |   |   | 1120 |
| Thr | Leu | Tyr | Lys | Leu | Gly | Phe | Phe | Lys | Arg | His | Tyr | Lys | Glu | Met | Leu |
|   |   |   |   | 1125 |   |   |   |   | 1130 |   |   |   |   | 1135 |   |
| Glu | Asp | Lys | Pro | Glu | Asp | Thr | Ala | Thr | Phe | Ser | Gly | Asp | Asp | Phe | Ser |
|   |   |   | 1140 |   |   |   |   | 1145 |   |   |   |   | 1150 |   |
| Cys | Val | Ala | Pro | Asn | Val | Pro | Leu | Ser |
|   |   |   | 1155 |   |   |   |   | 1160 |

( 2 ) INFORMATION FOR SEQ ID NO:100:

( i ) SEQUENCE CHARACTERISTICS:
        ( A ) LENGTH: 1318 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 17..1255

( x i ) SEQUENCE DESCRIPTION: SEQ ID NO:100:

| AATTCGGCAC | GAGCTT | GGG | GCT | GTG | GTC | CTC | CTT | GGG | GTC | CTG | GCT | TCT | 49 |
|---|---|---|---|---|---|---|---|---|---|---|---|---|---|
|   |   | Gly | Ala | Val | Val | Leu | Leu | Gly | Val | Leu | Ala | Ser |   |
|   |   | 1 |   |   |   | 5 |   |   |   |   | 10 |   |   |

| TAC | CAC | GGA | TTC | AAC | TTG | GAC | GTG | GAT | GAG | CCG | GTG | ATC | TTC | CAG | GAA | 97 |
|---|---|---|---|---|---|---|---|---|---|---|---|---|---|---|---|---|
| Tyr | His | Gly | Phe | Asn | Leu | Asp | Val | Asp | Glu | Pro | Val | Ile | Phe | Gln | Glu |   |
|   |   |   | 15 |   |   |   | 20 |   |   |   |   | 25 |   |   |   |   |

| GAC | GCA | GCG | GGC | TTC | GGG | CAG | AGC | GTG | ATG | CAG | TTT | GGA | GGA | TCT | CGA | 145 |
|---|---|---|---|---|---|---|---|---|---|---|---|---|---|---|---|---|
| Asp | Ala | Ala | Gly | Phe | Gly | Gln | Ser | Val | Met | Gln | Phe | Gly | Gly | Ser | Arg |   |
|   |   | 30 |   |   |   | 35 |   |   |   |   | 40 |   |   |   |   |   |

| CTC | GTG | GTG | GGA | GCC | CCC | CTG | GCG | GTG | GTG | TCG | GCC | AAC | CAC | ACA | GGA | 193 |
|---|---|---|---|---|---|---|---|---|---|---|---|---|---|---|---|---|
| Leu | Val | Val | Gly | Ala | Pro | Leu | Ala | Val | Val | Ser | Ala | Asn | His | Thr | Gly |   |
|   | 45 |   |   |   |   | 50 |   |   |   |   | 55 |   |   |   |   |   |

| CGG | CTG | TAC | GAG | TGT | GCG | CCT | GCC | TCC | GGC | ACC | TGC | ACG | CCC | ATT | TTC | 241 |
|---|---|---|---|---|---|---|---|---|---|---|---|---|---|---|---|---|
| Arg | Leu | Tyr | Glu | Cys | Ala | Pro | Ala | Ser | Gly | Thr | Cys | Thr | Pro | Ile | Phe |   |
| 60 |   |   |   |   | 65 |   |   |   |   | 70 |   |   |   |   | 75 |   |

| CCA | TTC | ATG | CCC | CCC | GAA | GCC | GTG | AAC | ATG | TCC | CTG | GGC | CTG | TCC | CTG | 289 |
|---|---|---|---|---|---|---|---|---|---|---|---|---|---|---|---|---|
| Pro | Phe | Met | Pro | Pro | Glu | Ala | Val | Asn | Met | Ser | Leu | Gly | Leu | Ser | Leu |   |
|   |   |   | 80 |   |   |   |   | 85 |   |   |   |   | 90 |   |   |   |

| GCA | GCC | TCC | CCC | AAC | CAT | TCC | CAG | CTG | CTG | GCT | TGT | GGC | CCG | ACC | GTG | 337 |
|---|---|---|---|---|---|---|---|---|---|---|---|---|---|---|---|---|
| Ala | Ala | Ser | Pro | Asn | His | Ser | Gln | Leu | Leu | Ala | Cys | Gly | Pro | Thr | Val |   |
|   |   |   | 95 |   |   |   |   | 100 |   |   |   |   | 105 |   |   |   |

| CAT | AGA | GCC | TGC | GGG | GAG | GAC | GTG | TAC | GCC | CAG | GGT | TTC | TGT | GTG | CTG | 385 |
|---|---|---|---|---|---|---|---|---|---|---|---|---|---|---|---|---|
| His | Arg | Ala | Cys | Gly | Glu | Asp | Val | Tyr | Ala | Gln | Gly | Phe | Cys | Val | Leu |   |
|   |   | 110 |   |   |   |   | 115 |   |   |   |   | 120 |   |   |   |   |

| CTG | GAT | GCC | CAC | GCA | CAG | CCC | ATC | GGG | ACT | GTG | CCA | GCT | GCC | CTG | CCC | 433 |
|---|---|---|---|---|---|---|---|---|---|---|---|---|---|---|---|---|
| Leu | Asp | Ala | His | Ala | Gln | Pro | Ile | Gly | Thr | Val | Pro | Ala | Ala | Leu | Pro |   |
|   | 125 |   |   |   |   | 130 |   |   |   |   | 135 |   |   |   |   |   |

| GAG | TGC | CCA | GAT | CAA | GAG | ATG | GAC | ATT | GTC | TTC | CTG | ATT | GAC | GGC | TCT | 481 |
|---|---|---|---|---|---|---|---|---|---|---|---|---|---|---|---|---|
| Glu | Cys | Pro | Asp | Gln | Glu | Met | Asp | Ile | Val | Phe | Leu | Ile | Asp | Gly | Ser |   |
| 140 |   |   |   |   | 145 |   |   |   |   | 150 |   |   |   |   | 155 |   |

| | | | | | | | | | | | | | | | | |
|---|---|---|---|---|---|---|---|---|---|---|---|---|---|---|---|---|
| GGC | AGC | ATT | AGC | TCA | AAT | GAC | TTC | CGC | AAG | ATG | AAG | GAC | TTT | GTC | AGA | 529 |
| Gly | Ser | Ile | Ser | Ser | Asn | Asp | Phe | Arg | Lys | Met | Lys | Asp | Phe | Val | Arg | |
| | | | 160 | | | | | 165 | | | | | 170 | | | |
| GCT | GTG | ATG | GAC | CAG | TTC | AAG | GAC | ACC | AAC | ACC | CAG | TTC | TCG | CTG | ATG | 577 |
| Ala | Val | Met | Asp | Gln | Phe | Lys | Asp | Thr | Asn | Thr | Gln | Phe | Ser | Leu | Met | |
| | | | 175 | | | | | 180 | | | | | 185 | | | |
| CAG | TAC | TCC | AAT | GTG | CTG | GTG | ACA | CAT | TTC | ACC | TTC | AGC | AGC | TTC | CGG | 625 |
| Gln | Tyr | Ser | Asn | Val | Leu | Val | Thr | His | Phe | Thr | Phe | Ser | Ser | Phe | Arg | |
| | | 190 | | | | | 195 | | | | | 200 | | | | |
| AAC | AGC | TCC | AAT | CCT | CAG | GGC | CTA | GTG | GAG | CCC | ATT | GTG | CAG | CTG | ACA | 673 |
| Asn | Ser | Ser | Asn | Pro | Gln | Gly | Leu | Val | Glu | Pro | Ile | Val | Gln | Leu | Thr | |
| | 205 | | | | | 210 | | | | | 215 | | | | | |
| GGC | CTC | ACG | TTC | ACG | GCC | ACA | GGG | ATC | CTG | AAA | GTG | GTG | ACA | GAG | CTG | 721 |
| Gly | Leu | Thr | Phe | Thr | Ala | Thr | Gly | Ile | Leu | Lys | Val | Val | Thr | Glu | Leu | |
| 220 | | | | | 225 | | | | | 230 | | | | | 235 | |
| TTT | CAA | ACC | AAG | AAC | GGG | GCC | CGC | GAA | AGT | GCC | AAG | AAG | ATC | CTC | ATC | 769 |
| Phe | Gln | Thr | Lys | Asn | Gly | Ala | Arg | Glu | Ser | Ala | Lys | Lys | Ile | Leu | Ile | |
| | | | | 240 | | | | | 245 | | | | | 250 | | |
| GTC | ATC | ACA | GAT | GGG | CAG | AAG | TAC | AAA | GAC | CCC | CTG | CAC | TAC | AGT | GCT | 817 |
| Val | Ile | Thr | Asp | Gly | Gln | Lys | Tyr | Lys | Asp | Pro | Leu | His | Tyr | Ser | Ala | |
| | | | 255 | | | | | 260 | | | | | 265 | | | |
| GTC | ATC | CCA | CAG | GCA | GAG | CAG | GCG | GGC | ATC | ATC | CGC | TAC | GCC | ATC | GGG | 865 |
| Val | Ile | Pro | Gln | Ala | Glu | Gln | Ala | Gly | Ile | Ile | Arg | Tyr | Ala | Ile | Gly | |
| | | 270 | | | | | 275 | | | | | 280 | | | | |
| GTG | GGG | GAC | GCG | TTC | CAG | AAA | CCC | ACA | GCC | AGG | CAG | GAG | CTG | GAC | ACC | 913 |
| Val | Gly | Asp | Ala | Phe | Gln | Lys | Pro | Thr | Ala | Arg | Gln | Glu | Leu | Asp | Thr | |
| | 285 | | | | | 290 | | | | | 295 | | | | | |
| ATC | GCC | TCC | GAG | CCG | CCC | GAC | GCC | CAC | GTG | TTC | CAG | GTG | GAC | AAT | TTC | 961 |
| Ile | Ala | Ser | Glu | Pro | Pro | Asp | Ala | His | Val | Phe | Gln | Val | Asp | Asn | Phe | |
| 300 | | | | | 305 | | | | | 310 | | | | | 315 | |
| TCA | GCA | CTC | AGC | AGC | ATC | CAA | AAG | CAG | CTG | TAT | GAC | AGG | ATC | TTT | GCC | 1009 |
| Ser | Ala | Leu | Ser | Ser | Ile | Gln | Lys | Gln | Leu | Tyr | Asp | Arg | Ile | Phe | Ala | |
| | | | | 320 | | | | | 325 | | | | | 330 | | |
| GTC | GAG | GGA | ACC | CTG | TCA | TCG | GCA | AGC | ACC | TCC | TTC | CAG | CAT | GAG | ATG | 1057 |
| Val | Glu | Gly | Thr | Leu | Ser | Ser | Ala | Ser | Thr | Ser | Phe | Gln | His | Glu | Met | |
| | | | 335 | | | | | 340 | | | | | 345 | | | |
| TCC | CAA | GAG | GGC | TTC | AGC | TCA | CTT | CTC | ACC | ACG | GAA | GGA | CCG | GTG | CTG | 1105 |
| Ser | Gln | Glu | Gly | Phe | Ser | Ser | Leu | Leu | Thr | Thr | Glu | Gly | Pro | Val | Leu | |
| | | 350 | | | | | 355 | | | | | 360 | | | | |
| GGG | GCT | GTG | GGC | AGC | TTC | GAT | TGG | TCC | GGG | GGT | GCT | TTC | CTG | TAC | CCC | 1153 |
| Gly | Ala | Val | Gly | Ser | Phe | Asp | Trp | Ser | Gly | Gly | Ala | Phe | Leu | Tyr | Pro | |
| | 365 | | | | | 370 | | | | | 375 | | | | | |
| CCC | GGC | GGG | AGC | CCC | ACC | TTC | ATC | AAC | ATG | TCT | CAG | CAG | AAC | GTG | GAC | 1201 |
| Pro | Gly | Gly | Ser | Pro | Thr | Phe | Ile | Asn | Met | Ser | Gln | Gln | Asn | Val | Asp | |
| 380 | | | | | 385 | | | | | 390 | | | | | 395 | |
| ATG | AGG | GAC | TCC | TAC | CTG | GGT | GAG | GAA | GGG | GTG | GGG | GTG | GGG | ACA | GGT | 1249 |
| Met | Arg | Asp | Ser | Tyr | Leu | Gly | Glu | Glu | Gly | Val | Gly | Val | Gly | Thr | Gly | |
| | | | | 400 | | | | | 405 | | | | | 410 | | |
| GGG | AGC | TGAGGCTTGG | | GGTGGGGTGG | | GGCTGGGCTG | | GGAGGGGAGG | | GAAGAGGAGG | | | | | | 1305 |
| Gly | Ser | | | | | | | | | | | | | | | |
| GGAGAGGCAA | AGA | | | | | | | | | | | | | | | 1318 |

( 2 ) INFORMATION FOR SEQ ID NO:101:

( i ) SEQUENCE CHARACTERISTICS:
        ( A ) LENGTH: 413 amino acids
        ( B ) TYPE: amino acid
        ( D ) TOPOLOGY: linear ( i i ) MOLECULE TYPE: protein ( x i ) SEQUENCE DESCRIPTION: SEQ ID NO:101:

| | | | | | | | | | | | | | | |
|---|---|---|---|---|---|---|---|---|---|---|---|---|---|---|
| Gly | Ala | Val | Val | Leu | Leu | Gly | Val | Leu | Ala | Ser | Tyr | His | Gly | Phe | Asn |
| 1 | | | | 5 | | | | | 10 | | | | | 15 |
| Leu | Asp | Val | Asp | Glu | Pro | Val | Ile | Phe | Gln | Glu | Asp | Ala | Ala | Gly | Phe |
| | | | 20 | | | | | 25 | | | | | 30 | | |
| Gly | Gln | Ser | Val | Met | Gln | Phe | Gly | Ser | Arg | Leu | Val | Val | Gly | Ala |
| | | 35 | | | | 40 | | | | | 45 | | | |
| Pro | Leu | Ala | Val | Val | Ser | Ala | Asn | His | Thr | Gly | Arg | Leu | Tyr | Glu | Cys |
| | 50 | | | | | 55 | | | | | 60 | | | | |
| Ala | Pro | Ala | Ser | Gly | Thr | Cys | Thr | Pro | Ile | Phe | Pro | Phe | Met | Pro | Pro |
| 65 | | | | | 70 | | | | | 75 | | | | | 80 |
| Glu | Ala | Val | Asn | Met | Ser | Leu | Gly | Leu | Ser | Leu | Ala | Ala | Ser | Pro | Asn |
| | | | | 85 | | | | | 90 | | | | | 95 | |
| His | Ser | Gln | Leu | Leu | Ala | Cys | Gly | Pro | Thr | Val | His | Arg | Ala | Cys | Gly |
| | | | 100 | | | | | 105 | | | | | 110 | | |
| Glu | Asp | Val | Tyr | Ala | Gln | Gly | Phe | Cys | Val | Leu | Leu | Asp | Ala | His | Ala |
| | | | 115 | | | | | 120 | | | | | 125 | | |
| Gln | Pro | Ile | Gly | Thr | Val | Pro | Ala | Ala | Leu | Pro | Glu | Cys | Pro | Asp | Gln |
| | | 130 | | | | 135 | | | | | 140 | | | | |
| Glu | Met | Asp | Ile | Val | Phe | Leu | Ile | Asp | Gly | Ser | Gly | Ser | Ile | Ser | Ser |
| 145 | | | | | 150 | | | | | 155 | | | | | 160 |
| Asn | Asp | Phe | Arg | Lys | Met | Lys | Asp | Phe | Val | Arg | Ala | Val | Met | Asp | Gln |
| | | | | 165 | | | | | 170 | | | | | 175 | |
| Phe | Lys | Asp | Thr | Asn | Thr | Gln | Phe | Ser | Leu | Met | Gln | Tyr | Ser | Asn | Val |
| | | | | 180 | | | | | 185 | | | | | 190 | |
| Leu | Val | Thr | His | Phe | Thr | Phe | Ser | Ser | Phe | Arg | Asn | Ser | Ser | Asn | Pro |
| | | | 195 | | | | | 200 | | | | | 205 | | |
| Gln | Gly | Leu | Val | Glu | Pro | Ile | Val | Gln | Leu | Thr | Gly | Leu | Thr | Phe | Thr |
| | | 210 | | | | | 215 | | | | | 220 | | | |
| Ala | Thr | Gly | Ile | Leu | Lys | Val | Val | Thr | Glu | Leu | Phe | Gln | Thr | Lys | Asn |
| 225 | | | | | 230 | | | | | 235 | | | | | 240 |
| Gly | Ala | Arg | Glu | Ser | Ala | Lys | Lys | Ile | Leu | Ile | Val | Ile | Thr | Asp | Gly |
| | | | | 245 | | | | | 250 | | | | | 255 | |
| Gln | Lys | Tyr | Lys | Asp | Pro | Leu | His | Tyr | Ser | Ala | Val | Ile | Pro | Gln | Ala |
| | | | 260 | | | | | 265 | | | | | 270 | | |
| Glu | Gln | Ala | Gly | Ile | Ile | Arg | Tyr | Ala | Ile | Gly | Val | Gly | Asp | Ala | Phe |
| | | 275 | | | | | 280 | | | | | 285 | | | |
| Gln | Lys | Pro | Thr | Ala | Arg | Gln | Glu | Leu | Asp | Thr | Ile | Ala | Ser | Glu | Pro |
| | | | 290 | | | | | 295 | | | | | 300 | | |
| Pro | Asp | Ala | His | Val | Phe | Gln | Val | Asp | Asn | Phe | Ser | Ala | Leu | Ser | Ser |
| 305 | | | | | 310 | | | | | 315 | | | | | 320 |
| Ile | Gln | Lys | Gln | Leu | Tyr | Asp | Arg | Ile | Phe | Ala | Val | Glu | Gly | Thr | Leu |
| | | | | 325 | | | | | 330 | | | | | 335 | |
| Ser | Ser | Ala | Ser | Thr | Ser | Phe | Gln | His | Glu | Met | Ser | Gln | Glu | Gly | Phe |
| | | | 340 | | | | | 345 | | | | | 350 | | |
| Ser | Ser | Leu | Leu | Thr | Thr | Glu | Gly | Pro | Val | Leu | Gly | Ala | Val | Gly | Ser |
| | | | 355 | | | | | 360 | | | | | 365 | | |
| Phe | Asp | Trp | Ser | Gly | Gly | Ala | Phe | Leu | Tyr | Pro | Pro | Gly | Gly | Ser | Pro |
| | | 370 | | | | 375 | | | | | 380 | | | | |
| Thr | Phe | Ile | Asn | Met | Ser | Gln | Gln | Asn | Val | Asp | Met | Arg | Asp | Ser | Tyr |
| 385 | | | | | 390 | | | | | 395 | | | | | 400 |
| Leu | Gly | Glu | Glu | Gly | Val | Gly | Val | Gly | Thr | Gly | Gly | Ser | | | |
| | | | | 405 | | | | | 410 | | | | | | |

( 2 ) INFORMATION FOR SEQ ID NO:102:

( i ) SEQUENCE CHARACTERISTICS:
        ( A ) LENGTH: 1484 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1482

( x i ) SEQUENCE DESCRIPTION: SEQ ID NO:102:

```
GAT  GTC  CAG  AGC  TCC  ATC  AGC  TAT  GAT  CTG  GCA  CTG  GAC  CCA  GGC  CGC        48
Asp  Val  Gln  Ser  Ser  Ile  Ser  Tyr  Asp  Leu  Ala  Leu  Asp  Pro  Gly  Arg
 1                    5                    10                       15

CTG  GTC  TCT  CGG  GCC  ATT  TTT  CAA  GAG  ACC  CAG  AAC  CAG  ACT  TTA  ACT        96
Leu  Val  Ser  Arg  Ala  Ile  Phe  Gln  Glu  Thr  Gln  Asn  Gln  Thr  Leu  Thr
                20                        25                       30

CGA  AGG  AAG  ACC  CTG  GGG  CTG  GGG  CGT  CAC  TGT  GAA  ACC  ATG  AGG  CTA       144
Arg  Arg  Lys  Thr  Leu  Gly  Leu  Gly  Arg  His  Cys  Glu  Thr  Met  Arg  Leu
           35                        40                        45

CTT  TTG  CCA  GAC  TGC  GTA  GAG  GAC  GTG  GTG  AAC  CCC  ATC  GTC  CTG  CAC       192
Leu  Leu  Pro  Asp  Cys  Val  Glu  Asp  Val  Val  Asn  Pro  Ile  Val  Leu  His
      50                        55                        60

CTC  AAC  TTC  TCC  CTG  GAG  GGA  CAG  CCA  ATC  CTC  TCA  TCC  CAG  AAT  CTG       240
Leu  Asn  Phe  Ser  Leu  Glu  Gly  Gln  Pro  Ile  Leu  Ser  Ser  Gln  Asn  Leu
 65                        70                        75                       80

CGC  CCT  GTG  CTG  GCC  ACG  GGC  TCG  CAG  GAC  CAC  TTC  ATT  GCC  TCC  CTC       288
Arg  Pro  Val  Leu  Ala  Thr  Gly  Ser  Gln  Asp  His  Phe  Ile  Ala  Ser  Leu
                85                        90                       95

CCC  TTT  GAG  AAG  AAC  TGC  GGA  CAA  GAT  CGC  CTG  TGT  GAG  GGG  GAC  CTG       336
Pro  Phe  Glu  Lys  Asn  Cys  Gly  Gln  Asp  Arg  Leu  Cys  Glu  Gly  Asp  Leu
          100                       105                      110

AGC  ATC  AGC  TTC  AAC  TTC  TCG  GGC  TTG  AAT  ACC  CTG  CTG  GTG  GGG  CTC       384
Ser  Ile  Ser  Phe  Asn  Phe  Ser  Gly  Leu  Asn  Thr  Leu  Leu  Val  Gly  Leu
               115                       120                      125

TCC  CTG  GAG  CTC  ACA  GTG  ACA  GTG  ACC  GTG  CGG  AAT  GAG  GGC  GAG  GAC       432
Ser  Leu  Glu  Leu  Thr  Val  Thr  Val  Thr  Val  Arg  Asn  Glu  Gly  Glu  Asp
     130                       135                       140

TCC  TAT  GGG  ACC  GCC  ATC  ACC  CTC  TAC  TAC  CCA  GCA  GGG  CTA  TCC  TAC       480
Ser  Tyr  Gly  Thr  Ala  Ile  Thr  Leu  Tyr  Tyr  Pro  Ala  Gly  Leu  Ser  Tyr
145                       150                       155                      160

AGG  CGG  GTG  TCG  GGC  CAG  ACA  CAA  CCC  TGG  CAG  CGC  CCC  CTG  CAC  CTC       528
Arg  Arg  Val  Ser  Gly  Gln  Thr  Gln  Pro  Trp  Gln  Arg  Pro  Leu  His  Leu
               165                       170                      175

GCA  TGT  GAG  GCT  GTA  CCT  ACC  GAG  AGC  GAG  GGC  TTG  AGG  AGT  ACC  AGC       576
Ala  Cys  Glu  Ala  Val  Pro  Thr  Glu  Ser  Glu  Gly  Leu  Arg  Ser  Thr  Ser
               180                       185                      190

TGC  AGC  GTC  AAC  CAC  CCC  ATC  TTC  CAA  GGG  GGT  GCT  CAG  GGC  ACT  TTC       624
Cys  Ser  Val  Asn  His  Pro  Ile  Phe  Gln  Gly  Gly  Ala  Gln  Gly  Thr  Phe
          195                       200                      205

GTA  GTC  AAG  TTC  GAT  GTC  TCC  TCC  AAG  GCC  AGC  CTG  GGT  GAC  AGG  TTG       672
Val  Val  Lys  Phe  Asp  Val  Ser  Ser  Lys  Ala  Ser  Leu  Gly  Asp  Arg  Leu
     210                       215                       220

CTC  ATG  GGG  GCC  AGT  GCC  AGC  AGT  GAG  AAT  AAT  AAG  CCT  GCG  AGC  AAC       720
Leu  Met  Gly  Ala  Ser  Ala  Ser  Ser  Glu  Asn  Asn  Lys  Pro  Ala  Ser  Asn
225                       230                       235                     240

AAG  ACC  TCC  TTT  GAG  CTG  GAA  CTG  CCA  GTG  AAA  TAC  GCT  GTC  TAC  ATG       768
Lys  Thr  Ser  Phe  Glu  Leu  Glu  Leu  Pro  Val  Lys  Tyr  Ala  Val  Tyr  Met
                         245                       250                      255
```

| | | | | | | | | | | | | | | | | |
|---|---|---|---|---|---|---|---|---|---|---|---|---|---|---|---|---|
| ATG | ATC | ACA | AGG | CAC | GAA | GGC | TCC | ACC | AGG | TTC | TTC | AAC | TTT | TCC | ACT | 816 |
| Met | Ile | Thr | Arg 260 | His | Glu | Gly | Ser | Thr 265 | Arg | Phe | Phe | Asn | Phe 270 | Ser | Thr | |
| TCC | GCT | GAG | AAG | AGC | AGC | AAA | GAG | GCC | GAG | CAC | CGC | TAT | CGG | GTG | AAC | 864 |
| Ser | Ala | Glu 275 | Lys | Ser | Ser | Lys | Glu 280 | Ala | Glu | His | Arg | Tyr 285 | Arg | Val | Asn | |
| AAC | CTG | AGT | CTG | CGA | GAT | GTG | GCC | GTC | AGC | GTG | GAC | TTC | TGG | GCC | CCC | 912 |
| Asn | Leu 290 | Ser | Leu | Arg | Asp | Val 295 | Ala | Val | Ser | Val | Asp 300 | Phe | Trp | Ala | Pro | |
| GTG | CAG | CTG | AAC | GGA | GCA | GCT | GTG | TGG | GAC | GTG | GCG | GTG | GAG | GCC | CCT | 960 |
| Val 305 | Gln | Leu | Asn | Gly | Ala 310 | Ala | Val | Trp | Asp | Val 315 | Ala | Val | Glu | Ala | Pro 320 | |
| GCC | CAG | AGC | CTG | CCC | TGT | GCG | CGG | GAG | AGG | GAA | CCT | CCG | AGG | ACC | TCT | 1008 |
| Ala | Gln | Ser | Leu | Pro 325 | Cys | Ala | Arg | Glu | Arg 330 | Glu | Pro | Pro | Arg | Thr 335 | Ser | |
| GAC | CTG | AGC | CGG | GTC | CCG | GGG | AGT | CCC | GTG | CTG | GAC | TGC | AGC | GTT | GCG | 1056 |
| Asp | Leu | Ser | Arg 340 | Val | Pro | Gly | Ser | Pro 345 | Val | Leu | Asp | Cys | Ser 350 | Val | Ala | |
| CAC | TGC | CTG | AGG | TTC | CGC | TGC | CAC | ATC | CCC | TCC | TTC | AGC | GCC | AAG | GAG | 1104 |
| His | Cys | Leu 355 | Arg | Phe | Arg | Cys | His 360 | Ile | Pro | Ser | Phe | Ser 365 | Ala | Lys | Glu | |
| GAG | CTC | CAC | TTC | ACC | CTG | AAG | GGC | AAC | CTC | AGC | TTC | GCC | TGG | GTC | AGC | 1152 |
| Glu | Leu 370 | His | Phe | Thr | Leu | Lys 375 | Gly | Asn | Leu | Ser | Phe 380 | Ala | Trp | Val | Ser | |
| CAG | ATG | CTG | CAA | AAG | AAG | GTG | TCG | GTG | GTG | AGT | GTG | GCC | GAG | ATC | ACC | 1200 |
| Gln | Met | Leu | Gln | Lys | Lys 390 | Val | Ser | Val | Val | Ser 395 | Val | Ala | Glu | Ile | Thr 400 | |
| | | | | | | | | | | | | | | | | |
| | | | 385 | | | | | | | | | | | | | |
| TTC | AAC | AGG | GCC | GTG | TAC | TCC | CAA | GTT | CCG | GGC | GAG | GAG | CCC | TTT | ATG | 1248 |
| Phe | Asn | Arg | Ala | Val 405 | Tyr | Ser | Gln | Val | Pro 410 | Gly | Glu | Glu | Pro | Phe 415 | Met | |
| AGA | GCC | CAG | GTG | GAG | ACG | GTG | CTG | GAG | GAG | TAT | GAG | GAG | CAC | GAC | CCC | 1296 |
| Arg | Ala | Gln | Val 420 | Glu | Thr | Val | Leu | Glu 425 | Glu | Tyr | Glu | Glu | His 430 | Asp | Pro | |
| GTC | CCC | CTG | GTG | GTG | GGC | AGC | TGT | GTG | GGC | GGC | CTG | CTG | CTG | CTG | GCT | 1344 |
| Val | Pro | Leu 435 | Val | Val | Gly | Ser | Cys 440 | Val | Gly | Gly | Leu | Leu 445 | Leu | Leu | Ala | |
| CTC | ATC | TCA | GCC | ACC | CTG | TAC | AAG | CTT | GGC | TTC | TTC | AAG | CGC | CGG | TAC | 1392 |
| Leu | Ile 450 | Ser | Ala | Thr | Leu | Tyr 455 | Lys | Leu | Gly | Phe | Phe 460 | Lys | Arg | Arg | Tyr | |
| AAG | GAG | ATG | CTG | GGC | GAG | AAA | CCG | GGA | GAC | GCG | GCC | ACC | TTC | CCC | GGG | 1440 |
| Lys 465 | Glu | Met | Leu | Gly | Glu 470 | Lys | Pro | Gly | Asp | Ala 475 | Ala | Thr | Phe | Pro | Gly 480 | |
| GAG | GAC | GCC | AGC | TGC | GGG | GCT | TCA | GAT | TTG | CCT | TTG | TCC | CAG | | | 1482 |
| Glu | Asp | Ala | Ser | Cys 485 | Gly | Ala | Ser | Asp | Leu 490 | Pro | Leu | Ser | Gln | | | |
| TG | | | | | | | | | | | | | | | | 1484 |

( 2 ) INFORMATION FOR SEQ ID NO:103:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:103:

| | | | | | | | | | | | | | | | |
|---|---|---|---|---|---|---|---|---|---|---|---|---|---|---|---|
| Asp 1 | Val | Gln | Ser | Ser 5 | Ile | Ser | Tyr | Asp | Leu 10 | Ala | Leu | Asp | Pro | Gly 15 | Arg |
| Leu | Val | Ser | Arg 20 | Ala | Ile | Phe | Gln | Glu 25 | Thr | Gln | Asn | Gln | Thr 30 | Leu | Thr |

```
Arg  Arg  Lys  Thr  Leu  Gly  Leu  Gly  Arg  His  Cys  Glu  Thr  Met  Arg  Leu
          35                  40                       45

Leu  Leu  Pro  Asp  Cys  Val  Glu  Asp  Val  Val  Asn  Pro  Ile  Val  Leu  His
     50                       55                       60

Leu  Asn  Phe  Ser  Leu  Glu  Gly  Gln  Pro  Ile  Leu  Ser  Ser  Gln  Asn  Leu
65                       70                       75                       80

Arg  Pro  Val  Leu  Ala  Thr  Gly  Ser  Gln  Asp  His  Phe  Ile  Ala  Ser  Leu
                    85                       90                       95

Pro  Phe  Glu  Lys  Asn  Cys  Gly  Gln  Asp  Arg  Leu  Cys  Glu  Gly  Asp  Leu
               100                      105                      110

Ser  Ile  Ser  Phe  Asn  Phe  Ser  Gly  Leu  Asn  Thr  Leu  Leu  Val  Gly  Leu
          115                      120                      125

Ser  Leu  Glu  Leu  Thr  Val  Thr  Val  Thr  Val  Arg  Asn  Glu  Gly  Glu  Asp
     130                      135                      140

Ser  Tyr  Gly  Thr  Ala  Ile  Thr  Leu  Tyr  Tyr  Pro  Ala  Gly  Leu  Ser  Tyr
145                      150                      155                      160

Arg  Arg  Val  Ser  Gly  Gln  Thr  Gln  Pro  Trp  Gln  Arg  Pro  Leu  His  Leu
                    165                      170                      175

Ala  Cys  Glu  Ala  Val  Pro  Thr  Glu  Ser  Gly  Leu  Arg  Ser  Thr  Ser
               180                      185                      190         Ser

Cys  Ser  Val  Asn  His  Pro  Ile  Phe  Gln  Gly  Gly  Ala  Gln  Gly  Thr  Phe
          195                      200                      205

Val  Val  Lys  Phe  Asp  Val  Ser  Ser  Lys  Ala  Ser  Leu  Gly  Asp  Arg  Leu
     210                      215                      220

Leu  Met  Gly  Ala  Ser  Ala  Ser  Ser  Glu  Asn  Asn  Lys  Pro  Ala  Ser  Asn
225                      230                      235                      240

Lys  Thr  Ser  Phe  Glu  Leu  Glu  Leu  Pro  Val  Lys  Tyr  Ala  Val  Tyr  Met
                    245                      250                      255

Met  Ile  Thr  Arg  His  Glu  Gly  Ser  Thr  Arg  Phe  Phe  Asn  Phe  Ser  Thr
               260                      265                      270

Ser  Ala  Glu  Lys  Ser  Ser  Lys  Glu  Ala  Glu  His  Arg  Tyr  Arg  Val  Asn
          275                      280                      285

Asn  Leu  Ser  Leu  Arg  Asp  Val  Ala  Val  Ser  Val  Asp  Phe  Trp  Ala  Pro
     290                      295                      300

Val  Gln  Leu  Asn  Gly  Ala  Ala  Val  Trp  Asp  Val  Ala  Val  Glu  Ala  Pro
305                      310                      315                      320

Ala  Gln  Ser  Leu  Pro  Cys  Ala  Arg  Glu  Arg  Glu  Pro  Pro  Arg  Thr  Ser
                    325                      330                      335

Asp  Leu  Ser  Arg  Val  Pro  Gly  Ser  Pro  Val  Leu  Asp  Cys  Ser  Val  Ala
               340                      345                      350

His  Cys  Leu  Arg  Phe  Arg  Cys  His  Ile  Pro  Ser  Phe  Ser  Ala  Lys  Glu
          355                      360                      365

Glu  Leu  His  Phe  Thr  Leu  Lys  Gly  Asn  Leu  Ser  Phe  Ala  Trp  Val  Ser
     370                      375                      380

Gln  Met  Leu  Gln  Lys  Lys  Val  Ser  Val  Val  Ser  Val  Ala  Glu  Ile  Thr
385                      390                      395                      400

Phe  Asn  Arg  Ala  Val  Tyr  Ser  Gln  Val  Pro  Gly  Glu  Glu  Pro  Phe  Met
                    405                      410                      415

Arg  Ala  Gln  Val  Glu  Thr  Val  Leu  Glu  Glu  Tyr  Glu  Glu  His  Asp  Pro
               420                      425                      430

Val  Pro  Leu  Val  Val  Gly  Ser  Cys  Val  Gly  Gly  Leu  Leu  Leu  Leu  Ala
          435                      440                      445

Leu  Ile  Ser  Ala  Thr  Leu  Tyr  Lys  Leu  Gly  Phe  Phe  Lys  Arg  Arg  Tyr
450                      455                      460
```

-continued

```
Lys  Glu  Met  Leu  Gly  Glu  Lys  Pro  Gly  Asp  Ala  Ala  Thr  Phe  Pro  Gly
465                 470                 475                           480

Glu  Asp  Ala  Ser  Cys  Gly  Ala  Ser  Asp  Leu  Pro  Leu  Ser  Gln
                    485                 490
```